US011358948B2

(12) United States Patent
Mainolfi et al.

(10) Patent No.: US 11,358,948 B2
(45) Date of Patent: Jun. 14, 2022

(54) CRBN LIGANDS AND USES THEREOF

(71) Applicant: Kymera Therapeutics, Inc., Cambridge, MA (US)

(72) Inventors: Nello Mainolfi, Belmont, MA (US); Nan Ji, Arlington, MA (US); Yi Zhang, Belmont, MA (US); Matthew M. Weiss, Boston, MA (US)

(73) Assignee: KYMERA THERAPEUTICS, INC., Watertown, MA (US)

( * ) Notice: Subject to any disclaimer, the term of this patent is extended or adjusted under 35 U.S.C. 154(b) by 24 days.

(21) Appl. No.: 16/649,717

(22) PCT Filed: Sep. 21, 2018

(86) PCT No.: PCT/US2018/052181
§ 371 (c)(1),
(2) Date: Mar. 23, 2020

(87) PCT Pub. No.: WO2019/060693
PCT Pub. Date: Mar. 28, 2019

(65) Prior Publication Data
US 2020/0377469 A1  Dec. 3, 2020

Related U.S. Application Data

(60) Provisional application No. 62/610,410, filed on Dec. 26, 2017, provisional application No. 62/563,689, filed on Sep. 27, 2017, provisional application No. 62/562,126, filed on Sep. 22, 2017.

(51) Int. Cl.
*C07D 401/04* (2006.01)
*C07D 401/14* (2006.01)
*C07D 413/04* (2006.01)

(52) U.S. Cl.
CPC ......... *C07D 401/04* (2013.01); *C07D 401/14* (2013.01); *C07D 413/04* (2013.01)

(58) Field of Classification Search
CPC ... C07D 401/04; C07D 401/14; C07D 413/04
See application file for complete search history.

(56) References Cited

U.S. PATENT DOCUMENTS

| 4,650,750 | A | 3/1987 | Giese |
| 4,709,016 | A | 11/1987 | Giese |
| 5,217,866 | A | 6/1993 | Summerton et al. |
| 5,360,811 | A | 11/1994 | Tegeler et al. |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 5,721,246 | A | 2/1998 | Yoshino et al. |
| 6,306,663 | B1 | 10/2001 | Kenten et al. |
| 6,552,065 | B2 | 4/2003 | Remiszewski et al. |
| 6,559,280 | B2 | 5/2003 | Kenten et al. |
| 6,627,754 | B2 | 9/2003 | Blumenkopf et al. |
| 6,949,537 | B2 | 9/2005 | Garlich et al. |
| 7,041,298 | B2 | 5/2006 | Deshaies et al. |
| 7,071,189 | B2 | 7/2006 | Kawashima et al. |
| 7,074,620 | B2 | 7/2006 | Kenten et al. |
| 7,173,015 | B2 | 2/2007 | Schreiber et al. |
| 7,208,157 | B2 | 4/2007 | Deshaies et al. |
| 7,273,920 | B2 | 9/2007 | Kenten et al. |
| 7,307,077 | B2 | 12/2007 | Kawashima et al. |
| 7,390,799 | B2 | 6/2008 | Bruncko et al. |
| 7,402,325 | B2 | 7/2008 | Addington |
| 7,449,458 | B2 | 11/2008 | Bhamidipati et al. |
| 7,501,496 | B1 | 3/2009 | Endl et al. |
| 7,514,444 | B2 | 4/2009 | Honigberg et al. |
| 7,528,143 | B2 | 5/2009 | Noronha et al. |
| 7,557,210 | B2 | 7/2009 | Singh et al. |
| 7,598,257 | B2 | 10/2009 | Rodgers et al. |
| 7,622,496 | B2 | 11/2009 | Larsen et al. |
| 7,667,039 | B2 | 2/2010 | Garcia-Echeverria et al. |
| 7,713,943 | B2 | 5/2010 | Klippel-Giese et al. |
| 7,781,433 | B2 | 8/2010 | Chuckowree et al. |
| 7,932,260 | B2 | 4/2011 | Fowler et al. |
| 7,989,622 | B2 | 8/2011 | Bajjalieh et al. |
| 8,138,347 | B2 | 3/2012 | Knight et al. |
| 8,185,616 | B2 | 5/2012 | Nagata et al. |
| 8,217,035 | B2 | 7/2012 | Burger et al. |
| 8,338,439 | B2 | 12/2012 | Singh et al. |
| 8,486,941 | B2 | 7/2013 | Burns et al. |
| 8,906,682 | B2 | 12/2014 | June et al. |
| 9,500,653 | B2 | 11/2016 | Crews et al. |

(Continued)

FOREIGN PATENT DOCUMENTS

CN  105085620  5/2018
WO  WO2001042246  6/2001

(Continued)

OTHER PUBLICATIONS

Matyskiela et al., "A Cereblon Modulator (CC-220) with Improved Degradation of Ikaros and Aiolos," J Med Chem. 2018;61(2):535-542.
Xia and Chen, "Iron-catalyzed N-alkylation of azoles via cleavage of an sp3 C-H bond adjacent to a nitrogen atom," J Org Chem. 2012;77(20):9366-73.
U.S. Appl. No. 62/847,413, filed May 14, 2019, Nello Mainolfi.
U.S. Appl. No. 62/832,103, filed Apr. 10, 2019, Nello Mainolfi.
U.S. Appl. No. 62/888,234, filed Aug. 16, 2019, Nan Ji.
U.S. Appl. No. 62/859,325, filed Jun. 10, 2019, Nan Ji.
U.S. Appl. No. 62/912,252, filed Oct. 8, 2019, Nello Mainolfi.
U.S. Appl. No. 16/701,077, filed Dec. 2, 2019, Nello Mainolfi.
U.S. Appl. No. 62/948,936, filed Dec. 17, 2019, Nello Mainolfi.
U.S. Appl. No. 62/948,992, filed Dec. 17, 2019, Yi Zhang.

(Continued)

*Primary Examiner* — Samira J Jean-Louis
(74) *Attorney, Agent, or Firm* — Dechert LLP; Andrea L. C. Reid; Todd K. Macklin

(57) ABSTRACT

The present invention provides compounds, compositions thereof, and methods of using the same for the inhibition of CRBN, and the treatment of CRBN-mediated disorders.

16 Claims, No Drawings

(56) References Cited

U.S. PATENT DOCUMENTS

| | | |
|---|---|---|
| 9,632,089 B2 | 4/2017 | Crews et al. |
| 9,694,084 B2 | 4/2017 | Bradner et al. |
| 9,750,816 B2 | 9/2017 | Bradner et al. |
| 9,770,512 B2 | 9/2017 | Bradner et al. |
| 9,821,068 B2 | 11/2017 | Bradner et al. |
| 9,969,710 B2 | 5/2018 | Jorand-Lebrun et al. |
| 10,125,114 B2 | 11/2018 | Bradner et al. |
| 10,336,744 B2 | 7/2019 | Harling et al. |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2004/0029902 A1 | 2/2004 | Singh et al. |
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel et al. |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | Mcelroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crews et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0256468 A1 | 9/2016 | Schafer et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Li et al. |
| 2016/0326151 A1 | 11/2016 | Gummadi et al. |
| 2016/0340366 A1 | 11/2016 | Gummadi et al. |
| 2017/0001990 A1 | 1/2017 | Chen et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0065719 A1 | 3/2017 | Qian et al. |
| 2017/0121321 A1 | 5/2017 | Crews et al. |
| 2017/0152263 A1 | 6/2017 | Gummadi et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 5/2018 | Harling et al. |
| 2018/0134684 A1 | 5/2018 | Bradner et al. |
| 2018/0147202 A1 | 5/2018 | Crew et al. |
| 2018/0186799 A1 | 7/2018 | Gardner et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0151457 A1 | 5/2019 | Bradner et al. |
| 2019/0192668 A1 | 6/2019 | Mainolfi et al. |
| 2019/0276474 A1 | 9/2019 | Chan et al. |
| 2020/0010468 A1 | 1/2020 | Ji et al. |

FOREIGN PATENT DOCUMENTS

| | | |
|---|---|---|
| WO | WO2002020740 | 3/2002 |
| WO | WO2002088112 | 11/2002 |
| WO | WO2003063794 | 8/2003 |
| WO | WO2004019973 | 3/2004 |
| WO | WO2004089925 | 10/2004 |
| WO | WO2004106328 | 12/2004 |
| WO | WO2005007623 | 1/2005 |
| WO | WO2005113554 | 12/2005 |
| WO | WO2006029879 | 3/2006 |

(56) References Cited

FOREIGN PATENT DOCUMENTS

| | | |
|---|---|---|
| WO | WO2006078846 | 7/2006 |
| WO | WO2006105021 | 10/2006 |
| WO | WO2006122806 | 11/2006 |
| WO | WO2007005874 | 1/2007 |
| WO | WO2007016176 | 2/2007 |
| WO | WO2007044729 | 4/2007 |
| WO | WO2007053452 | 5/2007 |
| WO | WO2007070514 | 6/2007 |
| WO | WO2007084786 | 7/2007 |
| WO | WO2007129161 | 11/2007 |
| WO | WO2008039218 | 4/2008 |
| WO | WO2008109943 | 9/2008 |
| WO | WO2008118802 | 10/2008 |
| WO | WO2008132601 | 11/2008 |
| WO | WO2009009116 | 1/2009 |
| WO | WO2009044273 | 4/2009 |
| WO | WO2009073620 | 6/2009 |
| WO | WO2009114512 | 9/2009 |
| WO | WO2009132238 | 10/2009 |
| WO | WO2010019570 | 2/2010 |
| WO | WO2010077634 | 7/2010 |
| WO | WO2011028683 | 3/2011 |
| WO | WO2011043371 | 4/2011 |
| WO | WO2011056652 | 5/2011 |
| WO | WO2011070024 | 6/2011 |
| WO | WO2011090760 | 7/2011 |
| WO | WO2011107553 | 9/2011 |
| WO | WO2011109400 | 9/2011 |
| WO | WO2011131407 | 10/2011 |
| WO | WO2011140249 | 11/2011 |
| WO | WO2012003281 | 1/2012 |
| WO | WO2012007375 | 1/2012 |
| WO | WO2012032433 | 3/2012 |
| WO | WO2012145493 | 4/2012 |
| WO | WO2012068546 | 5/2012 |
| WO | WO2012078559 | 6/2012 |
| WO | WO2012084704 | 6/2012 |
| WO | WO2012097013 | 7/2012 |
| WO | WO2012129258 | 9/2012 |
| WO | WO2012142237 | 10/2012 |
| WO | WO2013042137 | 3/2013 |
| WO | WO2013066729 | 5/2013 |
| WO | WO2013079174 | 6/2013 |
| WO | WO2013087699 | 6/2013 |
| WO | WO2013106535 | 7/2013 |
| WO | WO2013106612 | 7/2013 |
| WO | WO2013106614 | 7/2013 |
| WO | WO2013106641 | 7/2013 |
| WO | WO2013106643 | 7/2013 |
| WO | WO2013106646 | 7/2013 |
| WO | WO2013119716 | 8/2013 |
| WO | WO2013132044 | 9/2013 |
| WO | WO2013169264 | 11/2013 |
| WO | WO2014008218 | 1/2014 |
| WO | WO2014008992 | 1/2014 |
| WO | WO2014011902 | 1/2014 |
| WO | WO2014011911 | 1/2014 |
| WO | WO2014036357 | 3/2014 |
| WO | WO2014044622 | 3/2014 |
| WO | WO2014058685 | 4/2014 |
| WO | WO2014058691 | 4/2014 |
| WO | WO2014063061 | 4/2014 |
| WO | WO2014074675 | 5/2014 |
| WO | WO2014108452 | 7/2014 |
| WO | WO2014121931 | 8/2014 |
| WO | WO2014121942 | 8/2014 |
| WO | WO2014143672 | 9/2014 |
| WO | WO2015048281 | 4/2015 |
| WO | WO2015068856 | 5/2015 |
| WO | WO2015071393 | 5/2015 |
| WO | WO2015091426 | 6/2015 |
| WO | WO2015103453 | 7/2015 |
| WO | WO2015104662 | 7/2015 |
| WO | WO2015104688 | 7/2015 |
| WO | WO2015150995 | 10/2015 |
| WO | WO2015160845 | 10/2015 |
| WO | WO2015164374 | 10/2015 |
| WO | WO2015193846 | 12/2015 |
| WO | WO2016011390 | 1/2016 |
| WO | WO2016053769 | 4/2016 |
| WO | WO2016053770 | 4/2016 |
| WO | WO2016053771 | 4/2016 |
| WO | WO2016053772 | 4/2016 |
| WO | WO2016081679 | 5/2016 |
| WO | WO2016105518 | 6/2016 |
| WO | WO2016118666 | 7/2016 |
| WO | WO2016144844 | 9/2016 |
| WO | WO2016144846 | 9/2016 |
| WO | WO2016144847 | 9/2016 |
| WO | WO2016144848 | 9/2016 |
| WO | WO2016144849 | 9/2016 |
| WO | WO2016149668 | 9/2016 |
| WO | WO2016169989 | 10/2016 |
| WO | WO2016172560 | 10/2016 |
| WO | WO2016174183 | 11/2016 |
| WO | WO2016197032 | 12/2016 |
| WO | WO2016197114 | 12/2016 |
| WO | WO2016210034 | 12/2016 |
| WO | WO2017004133 | 1/2017 |
| WO | WO2017004134 | 1/2017 |
| WO | WO2017007612 | 1/2017 |
| WO | WO2017009798 | 1/2017 |
| WO | WO2017009806 | 1/2017 |
| WO | WO2017011371 | 1/2017 |
| WO | WO2017011590 | 1/2017 |
| WO | WO2017030814 | 2/2017 |
| WO | WO2017033093 | 3/2017 |
| WO | WO2017049068 | 3/2017 |
| WO | WO2017059280 | 4/2017 |
| WO | WO2017079267 | 5/2017 |
| WO | WO2017108723 | 6/2017 |
| WO | WO2017117473 | 7/2017 |
| WO | WO2017117474 | 7/2017 |
| WO | WO2017127430 | 7/2017 |
| WO | WO2017161119 | 9/2017 |
| WO | WO2017176708 | 10/2017 |
| WO | WO2017176957 | 10/2017 |
| WO | WO2017176958 | 10/2017 |
| WO | WO2017197036 | 11/2017 |
| WO | WO2017197046 | 11/2017 |
| WO | WO2017197051 | 11/2017 |
| WO | WO2017197055 | 11/2017 |
| WO | WO2017197056 | 11/2017 |
| WO | WO2017201449 | 11/2017 |
| WO | WO2017205762 | 11/2017 |
| WO | WO2017205766 | 11/2017 |
| WO | WO2017207385 | 12/2017 |
| WO | WO2017211924 | 12/2017 |
| WO | WO2018052058 | 3/2018 |
| WO | WO2018089736 | 5/2018 |
| WO | WO2018098367 | 5/2018 |
| WO | WO2018144649 | 8/2018 |
| WO | WO2018209012 | 11/2018 |
| WO | WO2018237026 | 12/2018 |
| WO | WO2019043214 | 3/2019 |
| WO | WO2019060742 | 3/2019 |
| WO | WO2019084026 | 5/2019 |
| WO | WO2019084030 | 5/2019 |
| WO | WO2019099868 | 5/2019 |
| WO | WO2019099926 | 5/2019 |
| WO | WO2019140380 | 7/2019 |
| WO | WO2019140387 | 7/2019 |
| WO | WO2019165229 | 8/2019 |
| WO | WO2020010210 | 1/2020 |
| WO | WO2020010227 | 1/2020 |

OTHER PUBLICATIONS

U.S. Appl. No. 62/949,195, filed Dec. 17, 2019, Nello Mainolfi.
U.S. Appl. No. 62/949,298, filed Dec. 17, 2019, Matthew M. Weiss.
U.S. Appl. No. 62/949,320, filed Dec. 17, 2019, Matthew M. Weiss.
U.S. Appl. No. 62/950,507, filed Dec. 19, 2019, Matthew M. Weiss.
U.S. Appl. No. 62/952,561, filed Dec. 23, 2019, Yi Zhang.
U.S. Appl. No. 62/952,578, filed Dec. 23, 2019, Yi Zhang.

(56) References Cited

OTHER PUBLICATIONS

U.S. Appl. No. 62/955,143, filed Dec. 30, 2019, Nan Ji.
U.S. Appl. No. 62/955,152, filed Dec. 30, 2019, Nan Ji.
U.S. Appl. No. 62/959,302, filed Jan. 10, 2020, Nan Ji.
U.S. Appl. No. 62/959,316, filed Jan. 10, 2020, Nan Ji.
U.S. Appl. No. 62/959,332, filed Jan. 10, 2020, Nan Ji.
U.S. Appl. No. 62/959,342, filed Jan. 10, 2020, Nan Ji.
U.S. Appl. No. 62/964,955, filed Jan. 23, 2020, Nello Mainolfi.
U.S. Appl. No. 62/969,418, filed Feb. 3, 2020, Matthew M. Weiss.
U.S. Appl. No. 62/990,555, filed Mar. 17, 2020, Nan Ji.
U.S. Appl. No. 62/991,763, filed Mar. 19, 2020, Nan Ji.
U.S. Appl. No. 16/841,095, filed Apr. 6, 2020, Nello Mainolfi.
Adams et al., 2015, "Big opportunities for small molecules in immuno-oncology," Nature Reviews: Drug Discovery 14 (9): 603-622.
Aruri et al., 2016, "Metal-free Cross-Dehydrogenative Coupling of HN-azoles with a-C(sp3)-H Amides via C-H Activation and Its Mechanistic and Application Studies," The Journal of Organic Chemistry 82(2): 1000-1012.
Aurigene Discovery Tech. Ltd. Presentation, 2015, "Novel IRAK-4 Inhibitors exhibit highly potent anti-proliferative activity in DLBCL cell lines with activation MYD88 L264P mutation" (2 pages).
Berge et al., 1977, "Pharmaceutical Salts," Journal of Pharmaceutical Sciences 66 (1): 1-19.
Berndsen et al., 2014, "New insights into ubiquitin E3 ligase mechanism," Nature Structural and Molecular Biology 21(4): 301-307.
Boichenko et al., 2016, "A FRET-Based Assay for the Identification and Characterization of Cereblon Ligands," Journal of Medicinal Chemistry 59(2): 770-774.
Buckley et al., 2008, "IRAK-4 inhibitors. Part 1: a series of amides," Bioorganic & Medicinal Chemistry Letters 11: 3211-3214.
Buckley et al., 2008, "IRAK-4 inhibitors. Part II: a structure-based assessment of imidazo[1,2-a]pyridine binding," Bioorganic & Medicinal Chemistry Letters 18: 3291-3295.
Buckley et al., 2008, "IRAK-4 inhibitors. Part III: A series of imidazo[1,2-a]pyridines," Bioorganic & Medicinal Chemistry Letters 18: 3656-3660.
Cameron et al., 2012, "Loss of Interleukin Receptor-Associated Kinase 4 Signaling Suppresses Amyloid Pathology and Alters Microglial Phenotype in a Mouse Model of Alzheimer's Disease" Journal of Neuroscience 32(43): 15112-15123.
Cario, E., 2008, "Therapeutic Impact of Toll-like Receptors on Inflammatory Bowel Diseases: A Multiple-edged Sword," Inflammatory Bowel Diseases 14(3): 411-421.
Chang et al., 2011, "What is the functional role of the thalidomide binding protein cereblon?", International Journal of Biochemistry and Molecular Biology 2(3): 287-294.
Chaudhary et al., 2015, "Recent Advances in the Discovery of Small Molecule Inhibitors of Interleukin-1 Receptor-Associated Kinase 4 (IRAK4) as a Therapeutic Target for Inflammation and Oncology Disorders," Journal of Medicinal Chemistry 58(1): 96-110.
Chiang, E.Y. et al., 2011, "Immune Complex-Mediated Cell Activation from Systemic Lupus Erythematosus and Rheumatoid Arthritis Patients Elaborate Different Requirements for IRAK1/4 Kinase Activity across human Cell Types," The Journal of Immunology 186(2): 1279-88.
Cohen et al., 2009, "Targeting protein kinases for the development of anti-inflammatory drugs," Current Opinion Cell Biology 21(2): 317-324.
Connolly et al., 2012, "Complexities of TGF-β Targeted Cancer Therapy," International Journal of Biological Sciences 8: 964-978.
Contino-Pepin et al., 2009, "Preliminary biological evaluations of new thalidomide analogues for multiple sclerosis application," Bioorganic & Medicinal Chemistry Letters 19(2): 878-881.
Crews et al., 2010, "Targeting the Undruggable Proteome: The Small Molecules of My Dreams," Chemistry & Biology 17(6): 551-555.

Cushing et al., 2017, "IRAK4 kinase controls Toll-like receptor induced inflammation through the transcription factor IRF5 in primary human monocytes," Journal of Biological Chemistry 292(45): 689-698.
Dalbeth et al., 2010, "Hyperuricaemia and gout: state of the art and future perspectives," Annals of Rheumatic Diseases 69(10): 1738-1743.
Degorce et al., 2018, "Optimization of permeability in a series of pyrrolotriazine inhibitors of IRAK4," Bioorganic and Medicinal Chemistry 26(4): 913-924.
Deshaies et al., 2009, "RING domain E3 ubiquitin ligases," Annual Review of Biochemistry 78: 399-434.
Dinarello, C., 2006, "Interleukin 1 and interleukin 18 as mediators of inflammation and the aging process," The American Journal of Clinical Nutrition 83: 447S-455S.
Dinarello, C., 2007, "Interleukin-18 and the Pathogenesis of Inflammatory Diseases," Seminars in Nephrology 27(1): 98-114.
Dinarello, C., 2010, "IL-1: Discoveries, controversies and future directions," European Journal of Immunology 40: 595-653.
Dudhgaonkar et al., 2017, "Selective IRAK4 Inhibition Attenuates Disease in Murine Lupus Models and Demonstrates Steroid Sparing Activity," Journal of Immunology 198:(3): 1308-19.
Dunne et al., 2010, "IRAK1 and IRAK4 Promote Phosphorylation, Ubiquitation, and Degradation of MyD88 Adaptor-like (Mal)," The Journal of Biological Chemistry 2010, 285(24): 18276-18282.
Fischer et al., 2014, "Structure of the DDB1-CRBN E3 ubiquitin ligase in complex with thalidomide," Nature 512(7512): 49-53.
Flannery et al., 2010, "The interleukin-1 receptor-associated kinases: Critical regulators of innate immune signaling" Biochemical Pharmacology 80(12): 1981-1991.
Gearing, A., 2007, "Targeting toll-like receptors for drug development: a summary of commercial approaches," Immunology and Cell Biology 85(6): 490-494.
Geyer, M. et al., 2010, "Actual status of antiinterleukin-1 therapies in rheumatic diseases," Current Opinion in Rheumatology 22(3): 246-251.
Gottipati et al., 2008, "IRAK1: A critical signaling mediator of innate immunity," Cellular Signaling 20:(2): 269-276.
Hagner et al., 2015, "CC-122, a pleiotropic pathway modifier, mimics an interferon response and has antitumor activity in DLBCL," Blood 126: 779-789.
Hennessy et al., 2010, "Targeting Toll-like receptors, emerging therapeutics?" Nature Reviews Drug Discovery 9: 293-307.
Hines et al., 2019, "MDM2-Recruiting PROTAC Offers Superior, Synergistic Antiproliferative Activity via Simultaneous Degradation of BRD4 and Stabilization of p. 53," Cancer Research 79(1): 251-262.
Hoffman, H. et al., 2008, "Efficacy and Safety of Rilonacept (Interleukin-1 Trap) in Patients with Cryopyrin-Associated Periodic Syndromes," Arthritis & Rheumatism 58(8): 2443-2452.
Iannello et al., 2009, "Role of Interleukin-18 in the Development and Pathogenesis of AIDS," AIDS Reviews 11(3): 115-125.
Iconomou et al., 2016, "Systematic approaches to identify E3 ligase substrates," Biochemical Journal 473: 4083-4101.
Iriyama et al., 2011, "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011.
Ito et al., 2010, "Identification of a primary target of thalidomide teratogenicity," Science 327(5971): 1345-1350.
Kelly et al., 2015, "Selective interleukin-1 receptor-associated kinase 4 inhibitors for the treatment of autoimmune disorders and lymphoid malignancy," Journal of Experimental Medicine 212(13): 2189-2201.
Kester et al., 2013, "Optimization of Benzodiazepinones as Selective Inhibitors of the X-Linked Inhibitor of Apoptosis Protein (XIAP) Second Baculovirus IAP Repeat (BIR2) Domain," Journal of Medicinal Chemistry 56(20): 7788-7803.
Kim et al., 2007, "A critical role for IRAK4 kinase activity in Toll-like receptor-mediated innate immunity," Journal of Experimental Medicine 204(5): 1025-1036.
Kondo et al., 2014, "Renoprotective effects of novel interleukin-1 receptor-associated kinase 4 inhibitor AS2444697 through anti-

(56) References Cited

OTHER PUBLICATIONS inflammatory action in 5/6 nephrectomized rats," Naunyn-Schmiedeberg's Archives of Pharmacology 387(10): 909-919.
Kou et al., 2015, "Effects of RuPeng15 Powder (RPP15) on Monosodium Urate Crystal-Induced Gouty Arthritis in Rats," Evidence-Based Complementary and Alternative Medicine 2015, art. 527019.
Koziczak-Holbro et al., 2007, "IRAK-4 Kinase Activity Is Required for Interleukin-1 (IL-1) Receptor- and Toll-like Receptor 7-mediated Signaling and Gene Expression," Journal of Biological Chemistry 282(18): 13552-13560.
Krönke et al., 2014, "Lenalidomide causes selective degradation of IKZF1 and IKZF3 in multiple myeloma cells" Science 343(6168): 301-305.
Ku et al., 2007, "Selective predisposition to bacterial infections in IRAK-4-deficient children: IRAK-4-dependent TLRs are otherwise redundant in protective immunity," Journal of Experimental Medicine 204(10): 2407-2422.
Kubo-Murai et al., 2008, "IRAK-4-dependent Degradation of IRAK-1 is a Negative Feedback Signal for TLR-mediated NF-kB Activation," Journal of Biochemistry 143: 295-302.
Küppers R., 2015, IRAK inhibition to shut down TLR signaling in autoimmunity and MyD88-dependent lymphomas, Journal of Experimental Medicine 212(13): 2184-2188.
Lebakken et al., 2007, "A Fluorescence Lifetime Based Binding Assay to Characterize Kinase Inhibitors," Journal of Biomedical Screening 12(6): 828-841.
Lee et al., 2017, "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," Journal of Medicinal Chemistry 60(13): 5521-5542.
Li et al., 2002, "IRAK-4: A novel member of the IRAK family with the properties of an IRAK-kinase," PNAS 99(8):5567-5572.
Li et al., 2008, "Genome-wide and functional annotation of human E3 ubiquitin ligases identifies MULAN, a mitochondrial E3 that regulates the organelle's dynamics and signaling," PLoS ONE 3(1): e1487, 1-14.
Li, 2008, "IRAK4 in TLR/IL-1R signaling: Possible clinical applications," European Journal of Immunology 38: 614-618.
Li, N. et al., 2016, "Targeting interleukin-1 receptor-associated kinase for human hepatocellular carcinoma," Journal of Experimental and Clinical Cancer Research 35(1): 140-150.
Lim et al., 2015, "Discovery of 5-Amino-N-(1H-pyrazol-4-yl)pyrazolo[1,5-a]pyrimidine-3-carboxamide Inhibitors of IRAK4," ACS Medicinal Chemistry Letters 6(6): 683-688.
Lin et al., 2010, "Helical assembly in the MyD88-IRAK4-IRAK2 complex in TLR /IL-1R signalling," Nature 465(17): 885-891.
Lu et al., 2014, "The myeloma drug lenalidomide promotes the cereblon-dependent destruction of Ikaros proteins," Science 343(6168): 305-309.
Lu et al., 2015, "Hijacking the E3 Ubiquitin Ligase Cereblon to Efficiently Target BRD4," Chemistry & Biology 22(6): 755-763.
Lust et al., 2009, "Induction of a Chronic Disease State in patients With Smoldering of Indolent Multiple Myeloma by Targeting Interleukin Iβ-Induced Interleukin 6 Production and the Myeloma Proliferative Component," Mayo Clinic Proceedings 84(2): 114-122.
Martinon et al., 2006, "Gout-associated uric acid crystals activate the NALP3 inflammasome," Nature 440: 237-241.
Maschera et al., 1999, "Overexpression of an enzymatically inactive interleukin-1-receptor-associated kinase activates nuclear factor-kB," Biochemical Journal 339: 227-231.
McElroy et al., 2015, "Discovery and hit-to-lead optimization of 2,6-diaminopyrimidine Inhibitors of interleukin-1 receptor-associated kinase 4," Bioorganic and Medicinal Chemistry Letters 25(9): 1836-1841.
McElroy et al., 2015, "Potent and Selective Amidopyrazole Inhibitors of IRAK4 That Are Efficacious in a Rodent Model of Inflammation," ACS Medicinal Chemistry Letters 6(6): 677-682.

Muller et al., 1999, "Amino-Substituted Thalidomide Analogs: Potent Inhibitors of TNF-α Production," Bioorganic & Medicinal Chemistry Letters 9: 1625-1630.
Ngo et al., 2011, "Oncogenically active MYD88 mutations in human lymphoma," Nature 470(7332): 115-119.
Ohoka et al., 2017, "In Vivo Knockdown of Pathogenic Proteins via Specific and Nongenetic Inhibitor of Apoptosis Protein (IAP)-dependent Protein Erasers (SNIPERs)," Journal of Biological Chemistry 292(11): 4556-4570.
Okazaki, et al., 2013, "A rheostat for immune responses: the unique properties of PD-1 and their advantages for clinical application," Nature Immunology 14(12): 1212-1218.
PCT International Search Report and Written Opinion from PCT/US2018/052181, dated Feb. 26, 2019.
PCT International Search Report and Written Opinion from PCT/US2018/052242, dated Jan. 30, 2019.
PCT International Search Report and Written Opinion from PCT/US2018/067304, dated Apr. 30, 2019.
PCT International Search Report and Written Opinion from PCT/US2019/013481, dated Mar. 15, 2019.
PCT International Search Report and Written Opinion from PCT/US2019/013491, dated Mar. 18, 2019.
PCT International Search Report and Written Opinion from PCT/US2019/040462, dated Sep. 20, 2019.
PCT International Search Report and Written Opinion from PCT/US2019/040520, dated Nov. 13, 2019.
PCT International Search Report and Written Opinion from PCT/US2019/040545, dated Oct. 21, 2019.
PCT International Search Report and Written Opinion from PCT/US2019/064070, dated Apr. 6, 2020.
Picard et al., 2007, "Inherited human IRAK-4 deficiency: an update," Immunologic Research 2007, 38(1-3): 347-352.
Picard et al., 2010, "Clinical features and outcome of patients with IRAK-4 and MyD88 deficiency," Medicine (Baltimore) 89(6): 403-425.
Piya et al., 2015, "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood, American Society of Hematology 126(23): 675-676.
Powers et al., 2006, "Discovery and initial SAR of inhibitors of interleukin-1 receptor-associated kinase-4," Bioorganic & Medicinal Chemistry Letters 16(11): 2842-45.
Priyadarshini et al., 2014, "Copper catalyzed oxidative cross-coupling of aromatic amines with 2-pyrrolidinone: a facile synthesis of N-aryl-r-amino-r-lactams," Tetrahedron 70(36): 6068-6074.
Pubmed Compound Summary for CID 101524675, "(2R)-3-Fluoro-2-(2-methylpropyl)-3-phenyl-1,3-azasilinan-6-one," U.S. National Library of Medicine, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 110491408, 3-(5-Amino-2-oxo-3H-benzimidazol-1-yl)piperidine-2,6-dione, U.S. Library of Medicine, created Jan. 18, 2016, https://pubchem.ncbi.nlm.nih.gov/compound/110491408. Date Accessed: Feb. 25, 2020 (7 pages).
Pubmed Compound Summary for CID 110491555, 3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Jan. 29, 2016, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).

(56) References Cited

OTHER PUBLICATIONS

Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 63661260,"5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," U.S. National Library of Medicine, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-yl)ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," U.S. National Library of Medicine, created Oct. 20, 2014, https://pubchem.ncbi.nlm.nih.gov/compound/83543479. Date Accessed: Feb. 25, 2020 (6 pages).
Pubmed Compound Summary for CID 84036945, 1-Piperidin-3-yl-3H-indol-2-one, U.S. Library of Medicine, created Oct. 20, 2014, https://pubchem.ncbi.nlm.nih.gov/compound/84036945. Date Accessed: Feb. 25, 2020 (7 pages).
Raina et al., 2010, "Chemical Inducers of Targeted Protein Degradation," Journal of Biological Chemistry 285(15): 11057-11060.
Ramirez, et al., 2012, "Defining causative factors contributing in the activation of hedgehog signaling in diffuse large B-cell lymphoma" Leukemia Research 36(10): 1267-1273.
Rokosz et al., 2008, "Kinase inhibitors as drugs for chronic inflammatory and immunological diseases: progress and challenges," Expert Opinions on Therapeutic Targets 12(7): 883-903.
Ronnebaum et al., 2016, "Synthesis of 1, 2, 3-triazole 'click' analogues of thalidomide," Tetrahedron 72(40): 6136-6141.
Ross et al., 2017, "Bispecific T cell engager (BiTE® ) antibody constructs can mediate bystander tumor cell killing", PLoS ONE vol. 12, No. 8, (e0183390), , https://doi.org/10.1371/journal.pone.0183390. Date Accessed: Feb. 12, 2020.
Rostovtsev et al., 2002, "A Stepwise Huisgen Cycloaddition Process: Copper(I)-Catalyzed Regioselective "Ligation" of Azides and Terminal Alkynes," Angewandte Chemie International Edition 41(14): 2596-2599.
Schnnekloth et al., 2005, "Chemical approaches to controlling intracellular protein degradation," Chembiochem: a European Journal of Chemical Biology 6(1): 40-46.
Scott et al., 2017, "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," Journal of Medicinal Chemistry 2017, 60(24): 10071-10091.
Seganish et al., 2015, "Discovery and Structure Enabled Synthesis of 2,6-diaminopyrimidine-4-one IRAK4 Inhibitors," ACS Medicinal Chemistry Letters 6(8): 942-947.
Seganish et al., 2015, "Initial optimization and series evolution of diaminopyrimidine inhibitors of interleukin-1 receptor associated kinase 4," Bioorganic and Medicinal Chemistry Letters 25(16): 3203-3207.
Sen et al., 2005, "Transcriptional signaling by double-standed RNA: role of TLR3," Cytokine & Growth Factor Reviews 16(1): 1-14.
Shanmugasundaram, K. et al., 2019, "A modular PROTAC design for target destruction using a degradation signal based on a single amino acid," Journal of Biochemical Chemistry, https://www.jbc.org/content/early/2019/09/11/jbc.AC119.010790.full.pdf. Date Accessed: Feb. 11, 2020.
Smith et al., 2017, "Identification of quinazoline based inhibitors of IRAK4 for the treatment of inflammation," Bioorganic and Medicinal Chemistry Letters 27(12): 2721-2726.
So et al., 2007, "A pilot study of IL-1 inhibition by anakinra in acute gout," Arthritis Research & Therapy 9(2): 1-6.
Song et al., 2009, "The kinase activities of interleukin-e receptor associated kinase (IRAK)-1 and 4 are redundant in the contiol of inflammatory cytokine expression in human cells," Molecular Immunology 46(7): 1458-1466.
Spradin et al., 2018, "Harnessing the Anti-Cancer Natural Product Nimbolide for Targeted Protein Degradation," bioRxiv.org, https://www.biorxiv.org/content/biorxiv/early/2019/04/09/436998.full.pdf. Date Accessed, Oct. 3, 2019.
Spratt et al., 2014, "RBR E3 ubiquitin ligases: new structures, new insights, new question," Biochemical Journal 458(Pt. 3): 421-437.
Stewart et al., 2010, "Efforts toward elucidating Thalidomide's molecular target: an expedient synthesis of the first Thalidomide biotin analogue," Organic & Biomolecular Chemisty 8(18): 4059-4062.
Sun et al., 2006, "Carbohydrate and protein immobilization onto solid surfaces by sequential Diels-Alder and azide-alkyne cycloadditions," Bioconjugate Chemistry 17(1): 52-57.
Suzuki et al., 2002, "IRAK-4 as the central TIR signaling mediator in innate immunity," TRENDS in Immunology 23(10): 503-506.
Suzuki et al., 2002, "Severe impairment of interleukin-1 and Toll-like receptor signalling in mice lacking IRAK-4," Nature 416(6882): 750-756.
Swantek et al., 2000, "IL-1 Receptor-Associated Kinase Modulates Host Responsiveness to Endotoxin," Journal of Immunology 164: 4301-4306.
Terkeltaub et al., 2009, "The interleukin 1 inhibitor rilonacept in treatment of chronic gouty arthritis: results of a placebo-controlled, monosequence crossover, non-randomised, single-blind pilot study," Annals of Rheumatic Diseases 68(10): 1613-1617.
Terkeltaub, R., 2010, "Update on gout: new therapeutic strategies and options," Nature 6: 30-38.
Toogood, P., 2017, "Small molecule immuno-oncology therapeutic agents," Bioorganic & Medicinal Chemistry Letters 28(3): 319-329.
Torres et al., 2009, "Hyperalgesia, synovitis and multiple biomarkers of inflammation are suppressed by interleukin 1 inhibition in a novel animal model of gouty arthritis," Annals of Rheumatic Diseases vol. 68: 1602-1608.
Toure et al., 2016, "Small-Molecule PROTACS: New Approaches to Protein Degradation," Angewandte Chemie International Edition 55(6): 1966-1973.
Treon et al., 2011, "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract].
Troseid, M., 2009, "The role of interleukin-18 in the metabolic syndrome," Cardiovascular Diabetology 9(11): 1-8.
Tumey et al., 2014, "Identification and optimization of indolo[2,3-c]quinoline inhibitors of IRAK4," Bioorganic and Medicinal Chemistry Letters 24(9): 2066-2072.
Uehara et al., 2017, "Selective degradation of splicing factor CAPERα by anticancer sulfonamides," Nature Chemical Biology 13(6): 675-680.
Varfolomeev et al., 2007, "IAP antagonists induce autoubiquitination of c-IAPs, NF-kappaB activation, and TNFalpha-dependent apoptosis," Cell 131(4): 669-681.
Vollmer, S., 2017, "The mechanism of activation of IRAK1 and IRAK4 by interleukin-1 and Toll-like receptor agonists," The Biochemical Journal 474(12): 2027-2038.
Wang et al., 2006, "Crystal Structure of IRAK-4 Kinase in Complex with Inhibitors: Serine/Threonine Kinase with Tyrosine as a Gatekeeper," Structure 14(12): 1835-1844.
Wang et al., 2009, "IRAK-4 Inhibitors for Inflammation," Current Topics in Medicinal Chemistry 9(8): 724-737.

(56) References Cited

OTHER PUBLICATIONS

Wang et al., 2014, "Roles of F-box proteins in cancer," Nature Reviews. Cancer 14(4): 233-247.
Wang et al., 2015, "Discovery of potent, selective, and orally bioavailable inhibitors of interleukin-1 receptor-associated kinase 4," Bioorganic & Medicinal Chemistry Letters 25(23): 5546-5550).
Ward et al., 2018, "Covalent Ligand Screening Uncovers a RNF4 E3 Ligase Recruiter for Targeted Protein Degradation Applications," bioRxiv.org, https://www.biorxiv.org/content/biorxiv/early/2018/11/16/439125.full.pdf. Date Accessed, Oct. 3, 2019 (24 pages).
Weaver, A., 2008, "Epidemiology of gout," Cleveland Clinic Journal of Medicine 75, suppl. 5: S9-S12.
Winter et al., 2015, "Selective Target Protein Degradation via Phthalimide Conjugation," Science 348(6241): 1376-1381.
Xu, et al., 2011, "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011.
Yang et al., 2011, "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53rd ASH Annual Meeting, San Diego, California, Dec. 10-13, 2011.
Yang et al., 2012, "Exploiting synthetic lethality for the therapy of ABC diffuse large B cell lymphoma" Cancer Cell 21(6): 723-737.
Zhang et al., 2017, "Constitutive IRAK4 Activation Underlies Poor Prognosis and Chemoresistance in Pancreatic Ductal Adenocarcinoma," Clinical Cancer Research: an Official Journal of the American Association for Cancer Research 23(7): 1748-1759.
Zhang et al., 2018, "Electrophilic PROTACs that degrade nuclear proteins by engaging DCAF16," bioRxiv.org, https://www.biorxiv.org/content/biorxiv/early/2018/10/15/443804.full.pdf. Date Accessed, Oct. 3, 2019.
Zhou et al., 2011, "Targets of curcumin," Current Drug Targets 12(3): 332-347.
Zou et al., 2016, "PD-L1 (B7-H1) and PD-1 Pathway Blockade for Cancer Therapy: Mechanisms, Response Biomarkers and Combinations," Science Translatonal Medicine 8(328): 1-34.

CRBN LIGANDS AND USES THEREOF

TECHNICAL FIELD OF THE INVENTION

The present invention relates to compounds and methods useful for binding and modulating the activity of cereblon (CRBN). The invention also provides pharmaceutically acceptable compositions comprising compounds of the present invention and methods of using said compositions in the treatment of various disorders.

BACKGROUND OF THE INVENTION

The Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases. These ligases comprise over 500 different proteins and are categorized into multiple classes defined by the structural element of their E3 functional activity.

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

Cereblon (CRBN) interacts with damaged DNA binding protein 1 and forms an E3 ubiquitin ligase complex with Cullin 4 where it functions as a substrate receptor in which the proteins recognized by CRBN might be ubiquitinated and degraded by proteasomes.

A new role for CRBN has been identified; i.e., the binding of immunomodulatory drugs (IMiDs), e.g. thalidomide, to CRBN has now been associated with teratogenicity and also the cytotoxicity of IMiDs, including lenalidomide, which are widely used to treat multiple myeloma patients. CRBN is likely a key player in the binding, ubiquitination and degradation of factors involved in maintaining function of myeloma cells. These new findings regarding the role of CRBN in IMiD action stimulated intense investigation of CRBN's downstream factors involved in maintaining regular function of a cell (Chang and Stewart Int J Biochem Mol Biol. 2011; 2(3): 287-294).

Accordingly, there remains a need to find CRBN ligands useful as therapeutic agents.

SUMMARY OF THE INVENTION

It has now been found that compounds of this invention, and pharmaceutically acceptable compositions thereof, are effective as CRBN ligands. Such compounds have the general formula I:

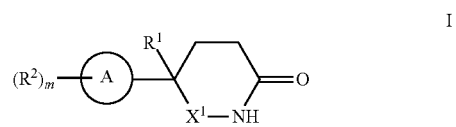

I or a pharmaceutically acceptable salt thereof, wherein each variable is as defined and described herein.

It has also been found that other compounds of this invention, and pharmaceutically acceptable compositions thereof, are effective as CRBN ligands. Such compounds have the general formula I':

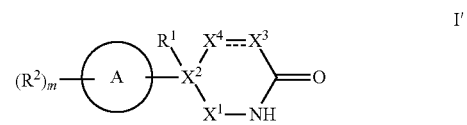

I' or a pharmaceutically acceptable salt thereof, wherein each variable is as defined and described herein.

It has also been found that other compounds of this invention, and pharmaceutically acceptable compositions thereof, are effective as CRBN ligands. Such compounds have the general formula II:

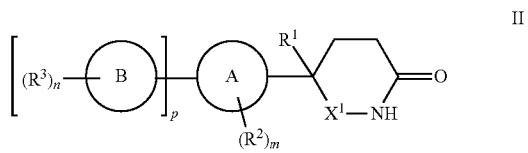

II or a pharmaceutically acceptable salt thereof, wherein each variable is as defined and described herein.

It has also been found that other compounds of this invention, and pharmaceutically acceptable compositions thereof, are effective as CRBN ligands. Such compounds have the general formula II':

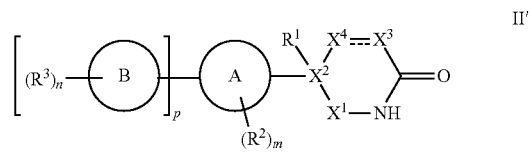

II' or a pharmaceutically acceptable salt thereof, wherein each variable is as defined and described herein.

Compounds of the present invention, and pharmaceutically acceptable compositions thereof, are useful for treating a variety of diseases, disorders or conditions, associated with CRBN. Such diseases, disorders, or conditions include those described herein.

Compounds provided by this invention are also useful for the study of CRBN and associated proteins in biological and pathological phenomena; the study of CRBN occurring in bodily tissues; and the comparative evaluation of new CRBN ligands or other regulators of CRBN in vitro or in vivo.

DETAILED DESCRIPTION OF CERTAIN EMBODIMENTS

1. General Description of Certain Embodiments of the Invention

Compounds of the present invention, and compositions thereof, are useful as CRBN ligands.

As defined herein, the terms "binder," "modulator," and "ligand" are used interchangeably and describe a compound that binds to, modulates or is a ligand for CRBN.

Without being bound by any particular theory, it is believed that the compounds of the present invention exert their effects by binding to CRBN, recruiting a protein substrate which results in ubiquitination by the E3 complex and subsequent degradation of the protein by the proteosome. This results in phenotypes such as, for example, decreased viability of cancer cells.

In certain embodiments, the present invention provides a compound of formula I:

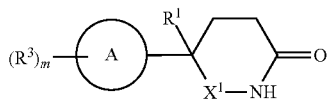

I or a pharmaceutically acceptable salt thereof, wherein:

$X^1$ is a bivalent moiety selected from a covalent bond —CH—, —C(O)—, —C(S)—, or

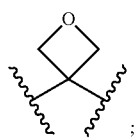

;

$R^1$ is hydrogen, deuterium, halogen, —CN, —OR, —SR, —S(O)R, —S(O)$_2$R, —NR$_2$, or an optionally substituted $C_{1-4}$ aliphatic;

each $R^2$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

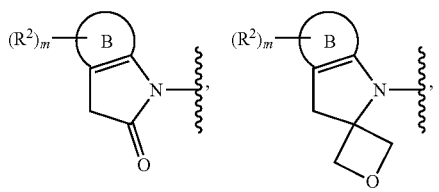

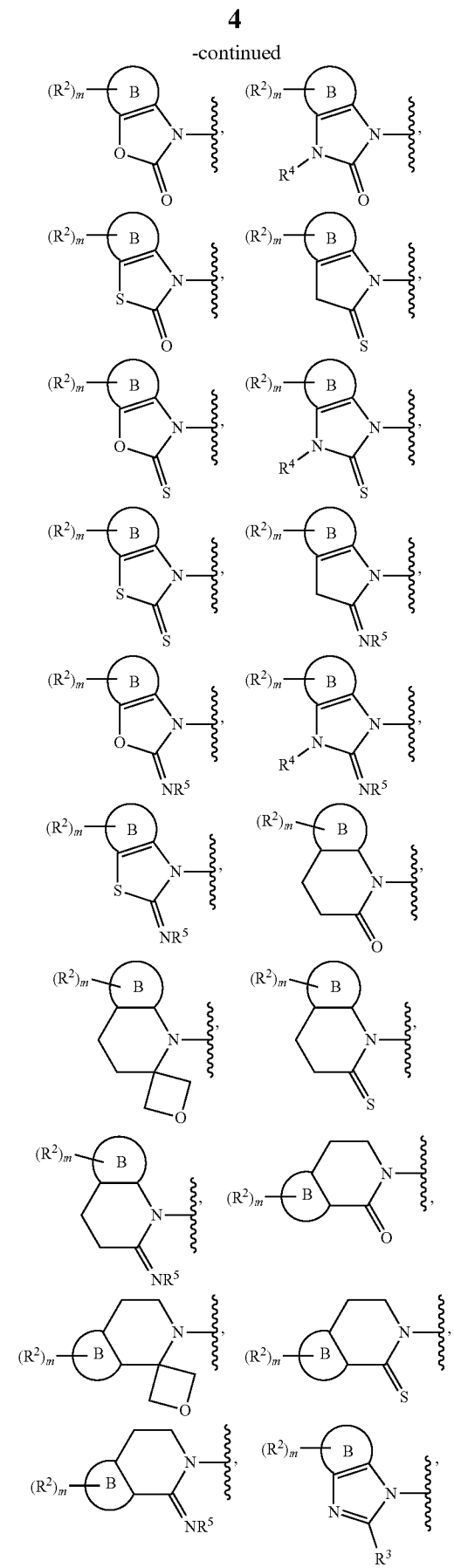

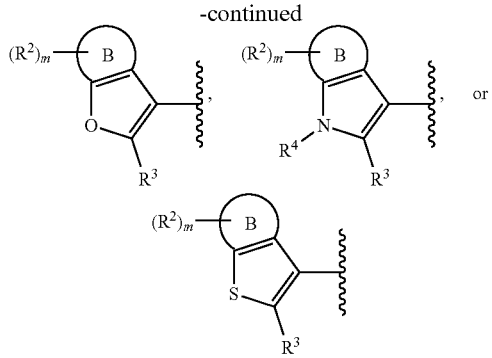

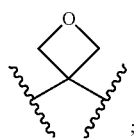 [SMILES: *C1(*)COC1]

wherein
Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I':

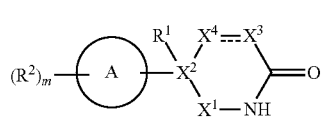

or a pharmaceutically acceptable salt thereof, wherein:
$X^1$ is a bivalent moiety selected from a covalent bond, —C(R)$_2$—, —C(O)—, —C(S)—, —P(O)(OR)—, —P(O)(R)—, —P(O)(NR$_2$)—, —S(O)—, —S(O)$_2$—, or $X^2$ is a carbon atom or silicon atom;
$X^3$ is a bivalent moiety selected from —C(R)$_2$—, —N(R)—, —CF$_2$—, —CHF—, —S—, or —O—;
$X^4$ is a bivalent moiety selected from a covalent bond or —C(R)$_2$—;
═══ is a single bond or double bond;
$R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, an optionally substituted $C_{1-4}$ aliphatic, or:
  $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur;

each $R^2$ is independently hydrogen, deuterium, —R$^6$, halogen, —CN, —NO$_2$, —OR, —SR, —NR$_2$, —Si(OH)$_2$R, —Si(OH)(R)$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N(R)S(O)$_2$NR$_2$, —P(O)(OR)$_2$, —P(O)(NR$_2$)OR, or —P(O)(NR$_2$)$_2$;

Ring A is a bi- or tricyclic ring selected from wherein
Ring B is a fused ring selected from 6-membered aryl containing 0-3 nitrogen atoms, 5 to 7-membered partially saturated carbocyclyl, 5 to 7-membered partially saturated heterocyclyl with 1-3 heteroatoms independently selected from boron, nitrogen, oxygen, silicon, or sulfur, or 5-membered heteroaryl with 1-3 heteroatoms independently selected from boron, nitrogen, oxygen, silicon, or sulfur;

$R^3$ is selected from hydrogen, deuterium, halogen, —CN, —NO$_2$, —OR, —NR$_2$, —SR, —S(O)$_2$R, —S(O)$_2$NR$_2$, —S(O)R, —C(O)R, —C(O)OR, —C(O)NR$_2$, —C(O)NR(OR), —OC(O)R, —OC(O)NR$_2$, —OP(O)(OR)$_2$, —OP(O)(NR$_2$)$_2$, —OP(O)(OR)NR$_2$, —N(R)C(O)R, —N(R)C(O)OR, —N(R)C(O)NR$_2$, —N(R)S(O)$_2$R, —N(R)S(O)$_2$NR$_2$, —N(R)P(O)(OR)$_2$, —N(R)P(O)(OR)NR$_2$, —P(O)(OR)$_2$, —P(O)(NR$_2$)OR, —P(O)(NR$_2$)$_2$, —Si(OH)$_2$R, —Si(OH)(R)$_2$, or —Si(R)$_3$;

each $R^4$ is independently hydrogen, deuterium, —$R^6$, halogen, —S(O)$_2$R, —S(O)$_2$NR$_2$, —S(O)R, —C(O)R, —C(O)OR, —C(O)NR$_2$, —C(O)N(R)OR, —P(O)(OR)$_2$, —P(O)(NR$_2$)OR, or —P(O)(NR$_2$)$_2$;

$R^5$ is hydrogen, deuterium, an optionally substituted $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-3 heteroatoms independently selected from boron, nitrogen, oxygen, silicon, or sulfur, and a 5-6 membered heteroaryl ring having 1-4 heteroatoms independently selected from boron, nitrogen, oxygen, silicon, or sulfur;

m is 0, 1, 2, 3 or 4; and each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)n is depicted on Ring B, it is intended, and one of ordinary skill in the art would appreciate, that the point of attachment of —(R$^2$)n may be on Ring A and may also be at any available boron, carbon, nitrogen, or silicon atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In certain embodiments, the present invention provides a compound of Formula II:

II or a pharmaceutically acceptable salt thereof, wherein:

$X^1$ is a bivalent moiety selected from a covalent bond, —CH$_2$—, —C(O)—, —C(S)—, or $R^1$ is hydrogen, deuterium, halogen, —CN, —OR, —SR, —S(O)R, —S(O)$_2$R, —NR$_2$, or an optionally substituted $C_{1-4}$ aliphatic;

Ring A is a mono- or bicyclic ring selected from

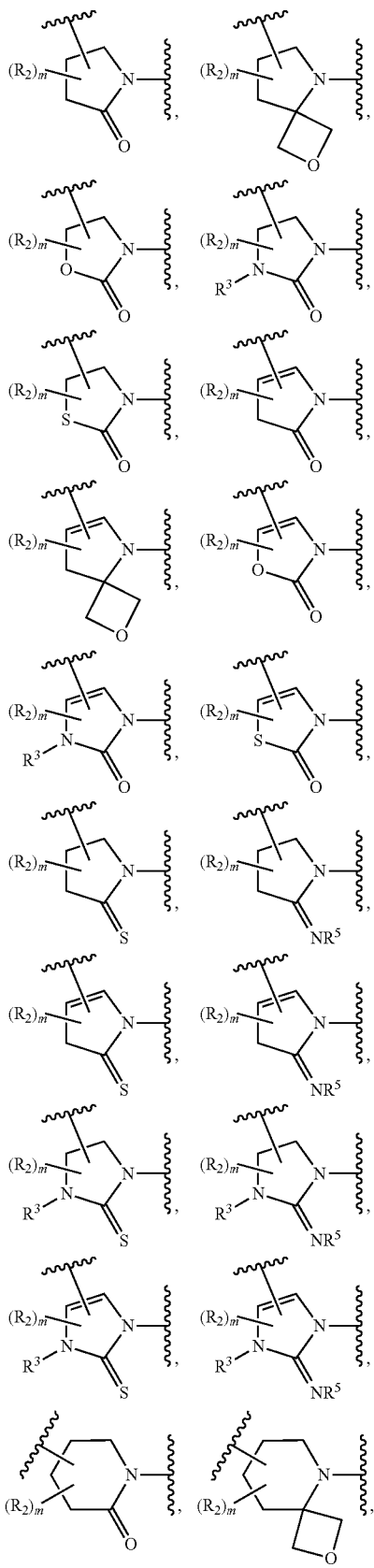

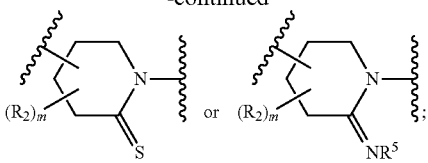

each $R^2$ is independently hydrogen, —$R^4$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

Ring B is selected from a 6-membered aryl containing 0-2 nitrogen atoms or a 5-membered heteroaryl with 1-3 heteroatoms independently selected from nitrogen, oxygen or sulfur;

each $R^3$ is independently hydrogen, —$R^4$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^5$ is hydrogen, $C_{1-4}$ aliphatic, or —CN;

m is 0, 1, or 2;

n is 0, 1, 2, 3, 4 or 5;

p is 0 or 1, wherein when p is 0, the bond connecting Ring A and Ring B terminates in a hydrogen; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of Formula II':

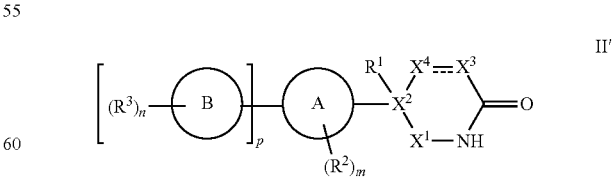

or a pharmaceutically acceptable salt thereof, wherein:

$X^1$ is a bivalent moiety selected from a covalent bond, —$C(R)_2$—, —C(O)—, —C(S)—, —P(O)(OR)—, —P(O)(R)—, —P(O)($NR_2$)—, —S(O)—, —$S(O)_2$—, or

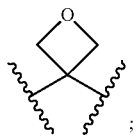 [SMILES: *C1(*)COC1]

$X^2$ is a carbon atom or silicon atom;

$X^3$ is a bivalent moiety selected from —C(R)$_2$—, —N(R)—, —CF$_2$—, —CHF—, —S—, or —O—;

$X^4$ is a bivalent moiety selected from a covalent bond or —C(R)$_2$—;

--- is a single bond or double bond;

$R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, an optionally substituted C$_{1-4}$ aliphatic, or:

$R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur;

Ring A is a mono- or bicyclic ring selected from

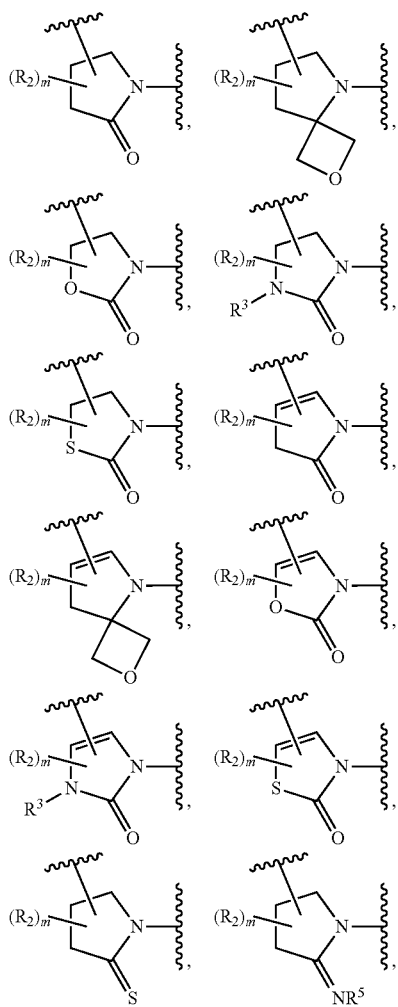

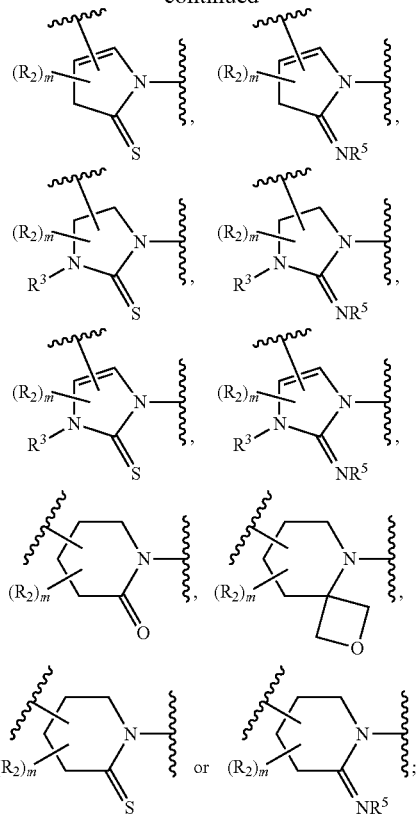

each $R^2$ is independently hydrogen, deuterium, —R$^6$, halogen, —CN, —NO$_2$, —OR, —SR, —NR$_2$, —Si(OH)$_2$R, —Si(OH)(R)$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N(R)S(O)$_2$NR$_2$, —P(O)(OR)$_2$, —P(O)(NR$_2$)OR, or —P(O)(NR$_2$)$_2$;

Ring B is selected from a 6-membered aryl containing 0-3 nitrogen atoms or a 5-membered heteroaryl with 1-3 heteroatoms independently selected from boron, nitrogen, oxygen, silicon, or sulfur;

each $R^3$ is selected from hydrogen, deuterium, halogen, —CN, —NO$_2$, —OR, —NR$_2$, —SR, —S(O)$_2$R, —S(O)$_2$NR$_2$, —S(O)R, —C(O)R, —C(O)OR, —C(O)NR$_2$, —C(O)NR(OR), —OC(O)R, —OC(O)NR$_2$, —OP(O)(OR)$_2$, —OP(O)(NR$_2$)$_2$, —OP(O)(OR)NR$_2$, —N(R)C(O)R, —N(R)C(O)OR, —N(R)C(O)NR$_2$, —N(R)S(O)$_2$R, —N(R)S(O)$_2$NR$_2$, —N(R)P(O)(OR)$_2$, —N(R)P(O)(OR)NR$_2$, —P(O)(OR)$_2$, —P(O)(NR$_2$)OR, —P(O)(NR$_2$)$_2$, —Si(OH)$_2$R, —Si(OH)(R)$_2$, or —Si(R)$_3$;

each $R^4$ is independently an optionally substituted group selected from C$_{1-6}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from nitrogen, oxygen, and sulfur;

$R^5$ is hydrogen, deuterium, an optionally substituted C$_{1-4}$ aliphatic, or —CN;

m is 0, 1, or 2;

n is 0, 1, 2, 3, 4 or 5;

p is 0 or 1, wherein when p is 0, the bond connecting Ring A and Ring B terminates in a hydrogen; and each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

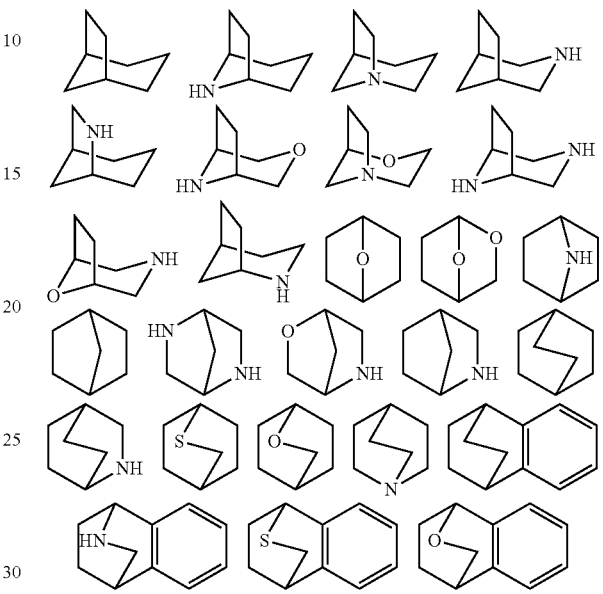

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

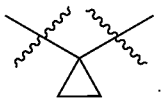 [SMILES: *C1(*)CC1]

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$R°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$C(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —(CH$_2$)$_{0-4}$C(O)NR°$_2$; —C(O)N (OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^●$, -(haloR$^●$), —(CH$_2$)$_{0-2}$OH, —(CH$_2$)$_{0-2}$OR$^●$, —(CH$_2$)$_{0-2}$CH(OR$^●$)$_2$; —O(haloR$^●$), —CN, —N$_3$, —(CH$_2$)$_{0-2}$C(O)R$^●$, —(CH$_2$)$_{0-2}$C(O)OH, —(CH$_2$)$_{0-2}$C(O)OR$^●$, —(CH$_2$)$_{0-2}$SR$^●$, —(CH$_2$)$_{0-2}$SH, —(CH$_2$)$_{0-2}$NH$_2$, —(CH$_2$)$_{0-2}$NHR$^●$, —(CH$_2$)$_{0-2}$NR$^●_2$, —NO$_2$, —SiR$^●_3$, —OSiR$^●_3$, —C(O)SR$^●$, —(C$_{1-4}$ straight or branched alkylene)C(O)OR$^●$, or —SSR$^●$ wherein each R$^●$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R are independently halogen, —R$^●$, -(haloR$^●$), —OH, —OR$^●$, —O(haloR$^●$), —CN, —C(O)OH, —C(O)OR$^●$, —NH$_2$, —NHR$^●$, —NR$^●_2$, or —NO$_2$, wherein each R$^●$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a provided compound may be substituted with one or more deuterium atoms.

As used herein, the term "binder" or "ligand" is defined as a compound that binds to CRBN with measurable affinity. In certain embodiments, a compound has a binding constant of less than about 50 µM, less than about 1 µM, less than about 500 nM, less than about 100 nM, less than about 10 nM, or less than about 1 nM.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}$P $^{33}$P, $^{35}$S, or $^{14}$C), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably modulate," as used herein, means a measurable change in a CRBN activity between a sample comprising a compound of the present invention, or composition thereof, and CRBN, and an equivalent sample comprising CRBN, in the absence of said compound, or composition thereof.

3. Description of Exemplary Embodiments

As described above, in certain embodiments, the present invention provides a compound of formula I:

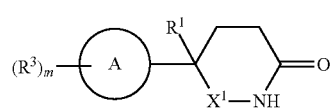

or a pharmaceutically acceptable salt thereof, wherein:

$X^1$ is a bivalent moiety selected from a covalent bond, —CH$_2$—, —C(O)—, —C(S)—, or

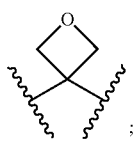 [SMILES: *C1(*)COC1]

R¹ is hydrogen, deuterium, halogen, —CN, —OR, —SR, —S(O)R, —S(O)₂R, —NR₂, or an optionally substituted C₁₋₄ aliphatic;

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring A is a bi- or tricyclic ring selected from

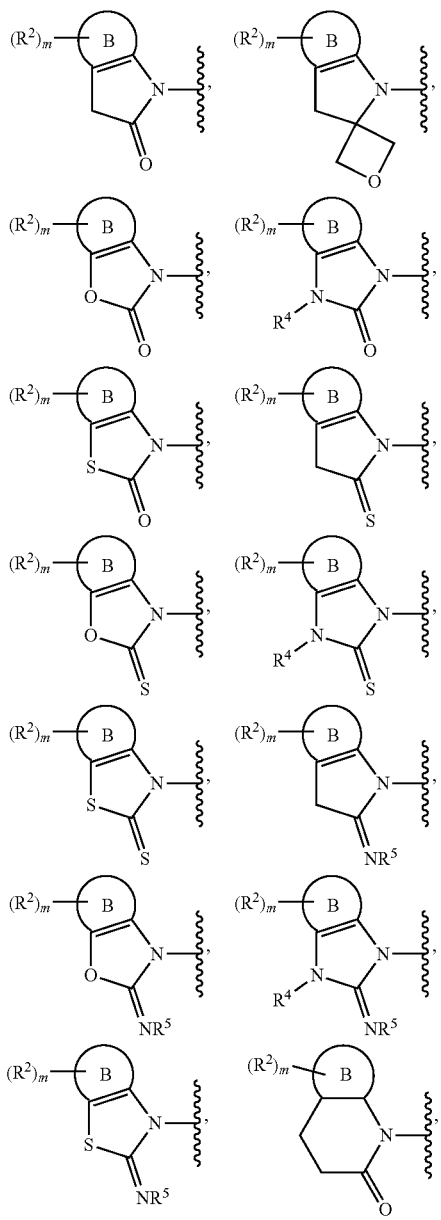

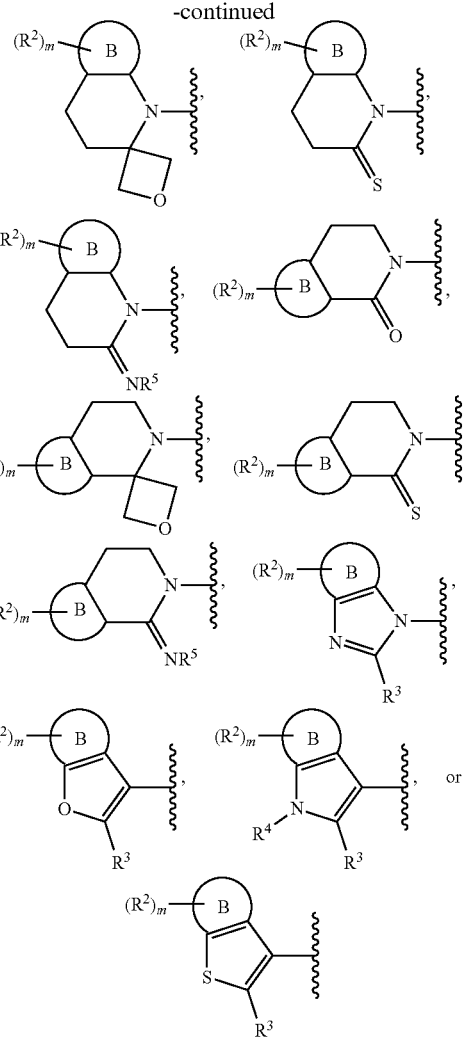

wherein

Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

R³ is selected from hydrogen, halogen, —OR, —N(R)₂, or —SR;

each R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

As described above, in certain embodiments, the present invention provides a compound of formula I':

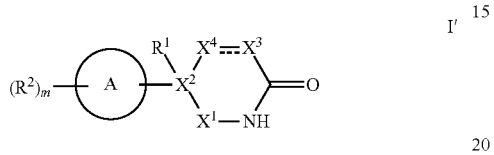

or a pharmaceutically acceptable salt thereof, wherein:

$X^1$ is a bivalent moiety selected from a covalent bond, —C(R)$_2$—, —C(O)—, —C(S)—, —P(O)(OR)—, —P(O)(R)—, —P(O)(NR$_2$)—, —S(O)—, —S(O)$_2$—, or

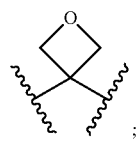 [SMILES: *C1(*)COC1]

$X^2$ is a carbon atom or silicon atom;
$X^3$ is a bivalent moiety selected from —C(R)$_2$—, —N(R)—, —CF$_2$—, —CHF—, —S—, or —O—;
$X^4$ is a bivalent moiety selected from a covalent bond or —C(R)$_2$—;
--- is a single bond or double bond;
$R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, an optionally substituted $C_{1-4}$ aliphatic, or:

$R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur;

each $R^2$ is independently hydrogen, deuterium, —R$^6$, halogen, —CN, —NO$_2$, —OR, —SR, —NR$_2$, —Si(OH)$_2$R, —Si(OH)(R)$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N(R)S(O)$_2$NR$_2$, —P(O)(OR)$_2$, —P(O)(NR$_2$)OR, or —P(O)(NR$_2$)$_2$;

Ring A is a bi- or tricyclic ring selected from

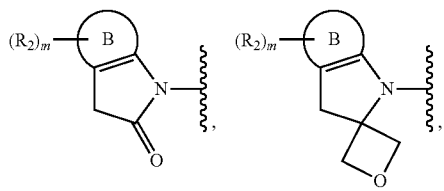

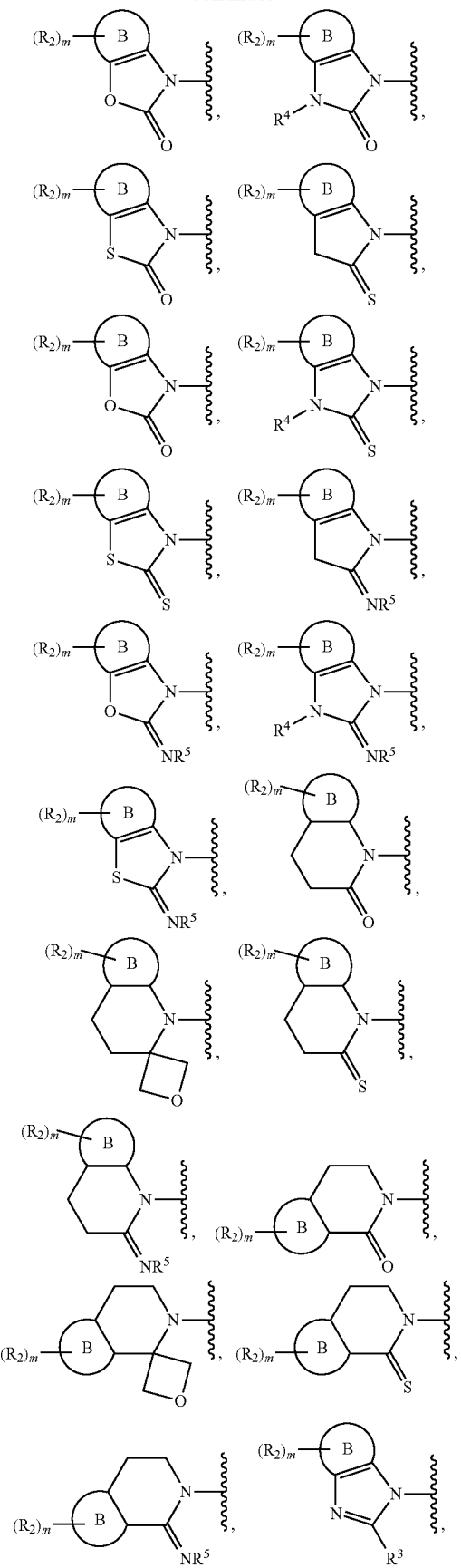

-continued

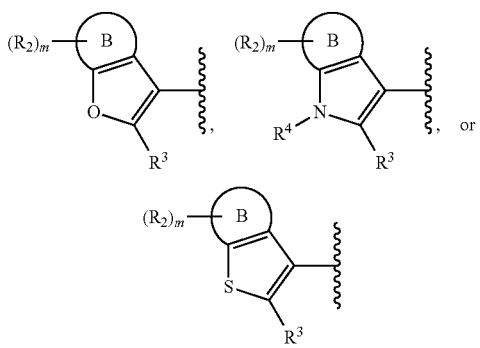

wherein

Ring B is a fused ring selected from 6-membered aryl containing 0-3 nitrogen atoms, 5 to 7-membered partially saturated carbocyclyl, 5 to 7-membered partially saturated heterocyclyl with 1-3 heteroatoms independently selected from boron, nitrogen, oxygen, silicon, or sulfur, or 5-membered heteroaryl with 1-3 heteroatoms independently selected from boron, nitrogen, oxygen, silicon, or sulfur;

$R^3$ is selected from hydrogen, deuterium, halogen, —CN, —NO$_2$, —OR, —NR$_2$, —SR, —S(O)$_2$R, —S(O)$_2$NR$_2$, —S(O)R, —C(O)R, —C(O)OR, —C(O)NR$_2$, —C(O)NR(OR), —OC(O)R, —OC(O)NR$_2$, —OP(O)(OR)$_2$, —OP(O)(NR$_2$)$_2$, —OP(O)(OR)NR$_2$, —N(R)C(O)R, —N(R)C(O)OR, —N(R)C(O)NR$_2$, —N(R)S(O)$_2$R, —N(R)S(O)$_2$NR$_2$, —N(R)P(O)(OR)$_2$, —N(R)P(O)(OR)NR$_2$, —P(O)(OR)$_2$, —P(O)(NR$_2$)OR, —P(O)(NR$_2$)$_2$, —Si(OH)$_2$R, —Si(OH)(R)$_2$, or —Si(R)$_3$;

each $R^4$ is independently hydrogen, deuterium, —$R^6$, halogen, —S(O)$_2$R, —S(O)$_2$NR$_2$, —S(O)R, —C(O)R, —C(O)OR, —C(O)NR$_2$, —C(O)N(R)OR, —P(O)(OR)$_2$, —P(O)(NR$_2$)OR, or —P(O)(NR$_2$)$_2$;

$R^5$ is hydrogen, deuterium, an optionally substituted $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-3 heteroatoms independently selected from boron, nitrogen, oxygen, silicon, or sulfur, and a 5-6 membered heteroaryl ring having 1-4 heteroatoms independently selected from boron, nitrogen, oxygen, silicon, or sulfur;

m is 0, 1, 2, 3 or 4; and each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

As described above, in certain embodiments, the present invention provides a compound of formula II:

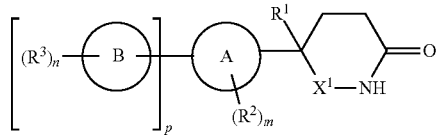

or a pharmaceutically acceptable salt thereof, wherein:

$X^1$ is a bivalent moiety selected from a covalent bond, —CH$_2$—, —C(O)—, —C(S)—, or

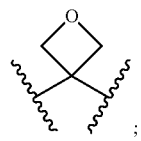 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

Ring A is a mono- or bicyclic ring selected from

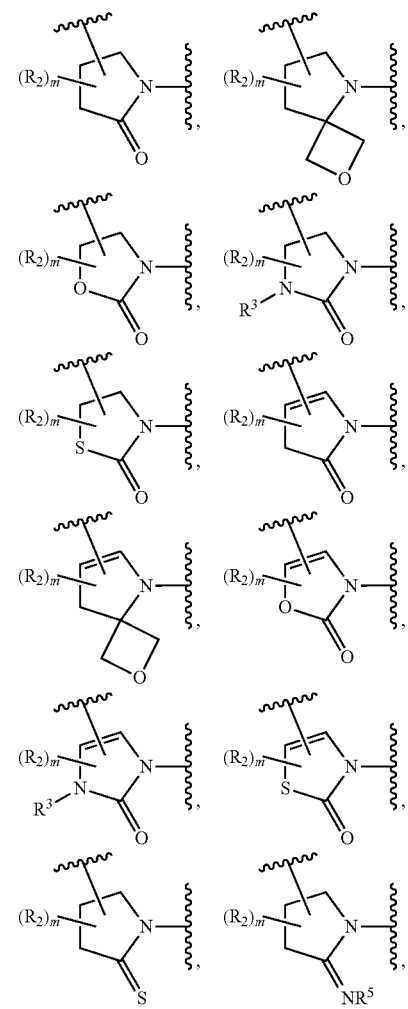

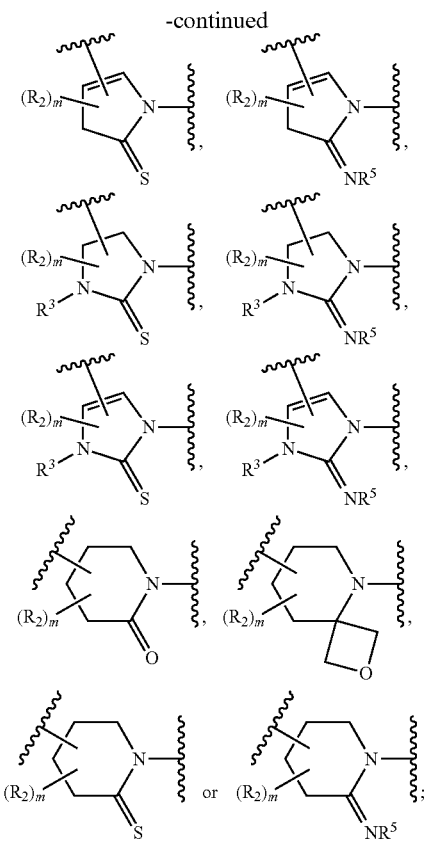

each R² is independently hydrogen, —R⁴, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each R³ is independently hydrogen, —R⁴, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

each R⁴ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

R⁵ is hydrogen, C₁₋₄ aliphatic, or —CN;
m is 0, 1, or 2;
n is 0, 1, 2, 3, 4 or 5;
p is 0 or 1, wherein when p is 0, the bond connecting Ring A and Ring B terminates in a hydrogen; and
each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

As describe above, in certain embodiments, the present invention provides a compound of Formula II':

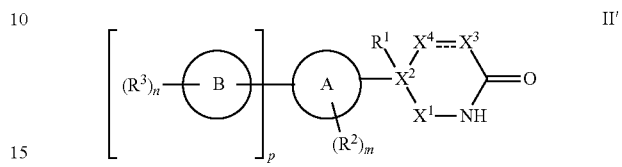

or a pharmaceutically acceptable salt thereof, wherein:

X¹ is a bivalent moiety selected from a covalent bond, —C(R)₂—, —C(O)—, —C(S)—, —P(O)(OR)—, —P(O)(R)—, —P(O)(NR₂)—, —S(O)—, —S(O)₂—, or

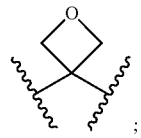 [SMILES: *C1(*)COC1]

X² is a carbon atom or silicon atom;
X³ is a bivalent moiety selected from —C(R)₂—, —N(R)—, —CF₂—, —CHF—, —S—, or —O—;
X⁴ is a bivalent moiety selected from a covalent bond or —C(R)₂—;
⸗ is a single bond or double bond;
R¹ is hydrogen, deuterium, halogen, —CN, —OR, —SR, —S(O)R, —S(O)₂R, —NR₂, —P(O)(OR)₂, —P(O)(NR₂)OR, —P(O)(NR₂)₂, —Si(OH)₂R, —Si(OH)(R)₂, —Si(R)₃, an optionally substituted C₁₋₄ aliphatic, or:

R¹ and X¹ or X⁴ are taken together with their intervening atoms to form a 5-7 membered saturated, partially unsaturated, carbocyclic ring or heterocyclic ring having 1-3 heteroatoms, independently selected from nitrogen, oxygen, or sulfur;

Ring A is a mono- or bicyclic ring selected from

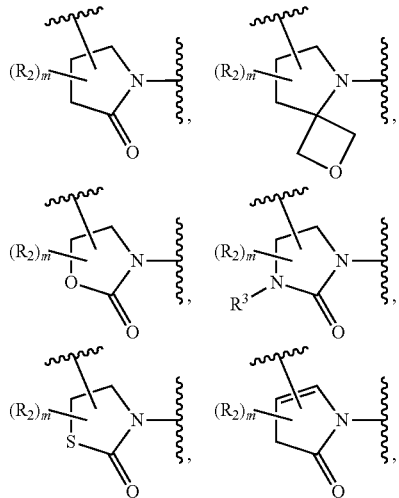

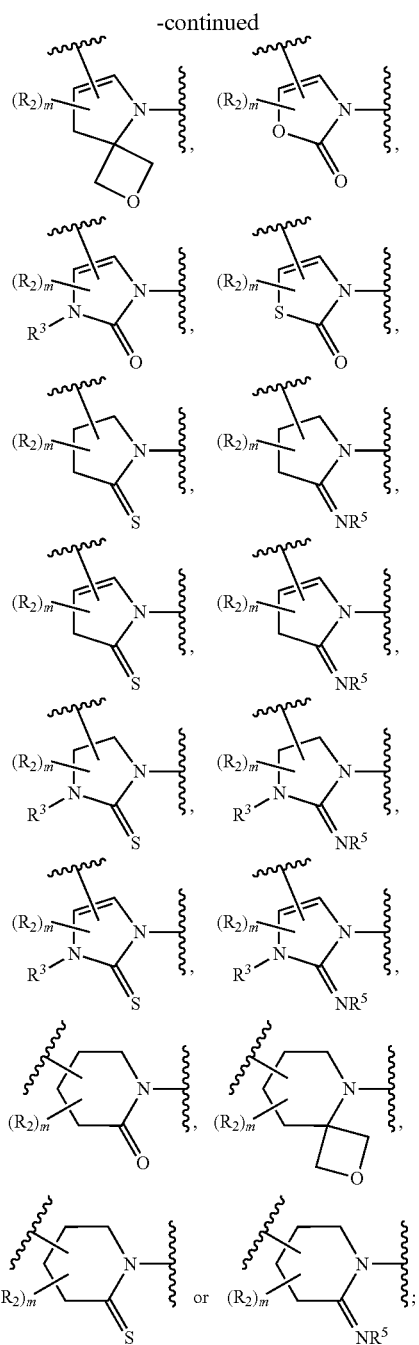

each R² is independently hydrogen, deuterium, —R⁶, halogen, —CN, —NO₂, —OR, —SR, —NR₂, —Si(OH)₂R, —Si(OH)(R)₂, —Si(R)₃, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, —N(R)S(O)₂R, —N(R)S(O)₂NR₂, —P(O)(OR)₂, —P(O)(NR₂)OR, or —P(O)(NR₂)₂;

Ring B is selected from a 6-membered aryl containing 0-3 nitrogen atoms or a 5-membered heteroaryl with 1-3 heteroatoms independently selected from boron, nitrogen, oxygen, silicon, or sulfur;

R³ is selected from hydrogen, deuterium, halogen, —CN, —NO₂, —OR, —NR₂, —SR, —S(O)₂R, —S(O)₂NR₂, —S(O)R, —C(O)R, —C(O)OR, —C(O)NR₂, —C(O)NR(OR), —OC(O)R, —OC(O)NR₂, —OP(O)(OR)₂, —OP(O)(NR₂)₂, —OP(O)(OR)NR₂, —N(R)C(O)R, —N(R)C(O)OR, —N(R)C(O)NR₂, —N(R)S(O)₂R, —N(R)S(O)₂NR₂, —N(R)P(O)(OR)₂, —N(R)P(O)(OR)NR₂, —P(O)(OR)₂, —P(O)(NR₂)OR, —P(O)(NR₂)₂, —Si(OH)₂R, —Si(OH)(R)₂, or —Si(R)₃;

each R⁴ is independently an optionally substituted group selected from C₁₋₆ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from nitrogen, oxygen, and sulfur;

R⁵ is hydrogen, deuterium, an optionally substituted C₁₋₄ aliphatic, or —CN;

m is 0, 1, or 2;

n is 0, 1, 2, 3, 4 or 5;

p is 0 or 1, wherein when p is 0, the bond connecting Ring A and Ring B terminates in a hydrogen; and each R is independently hydrogen, deuterium, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

As defined above and described herein, X¹ is a bivalent moiety selected from a covalent bond, —CH₂—, —C(R)₂—, —C(O)—, —C(S)—, —CH(R)—, —CH(CF₃)—, —P(O)(OR)—, —P(O)(R)—, —P(O)(NR₂)—, —S(O)—, —S(O)₂—, or

In some embodiments, X is a covalent bond. In some embodiments, X¹ is —CH₂—. In some embodiments, X¹ is —C(R)₂—. In some embodiments, X¹ is —C(O)—. In some embodiments, X¹ is —C(S)—. In some embodiments, X¹ is —CH(R)—. In some embodiments, X¹ is —CH(CF₃)—. In some embodiments, X¹ is —P(O)(OR)—. In some embodiments, X¹ is —P(O)(R)—. In some embodiments, X¹ is —P(O)(NR₂)—. In some embodiments, X¹ is —S(O)—. In some embodiments, X¹ is —S(O)₂—. In some embodiments, X¹ is

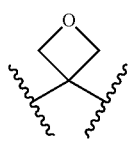

In some embodiments, X¹ is selected from those depicted in Table 1, below.

As defined above and described herein, $X^2$ is a carbon atom or silicon atom.

In some embodiments, $X^2$ is a carbon atom. In some embodiments, $X^2$ is a silicon atom.

In some embodiments, $X^2$ is selected from those depicted in Table 1, below.

As defined above and described herein, $X^3$ is a bivalent moiety selected from —CH$_2$—, —C(R)$_2$—, —N(R)—, —CF$_2$—, —CHF—, —S—, —CH(R)—, or —O—.

In some embodiments, $X^3$ is —CH$_2$—. In some embodiments, $X^1$ is —C(R)$_2$—. In some embodiments, $X^3$ is —N(R)—. In some embodiments, $X^3$ is —CF$_2$—. In some embodiments, $X^3$ is —CHF—. In some embodiments, $X^3$ is —S—. In some embodiments, $X^3$ is —CH(R)—. In some embodiments, $X^3$ is —O—.

In some embodiments, $X^3$ is selected from those depicted in Table 1, below.

As defined above and described herein, $X^4$ is a bivalent moiety selected from a covalent bond, —CH$_2$—, or —C(R)$_2$—.

In some embodiments, $X^4$ is a covalent bond. In some embodiments, $X^4$ is —CH$_2$—. In some embodiments, $X^4$ is —C(R)$_2$—.

In some embodiments, $X^4$ is selected from those depicted in Table 1, below.

As defined above and described herein, $R^1$ is hydrogen, deuterium, halogen, —CN, —OR, —SR, —S(O)R, —S(O)$_2$R, —NR$_2$, —P(O)(OR)$_2$, —P(O)(NR$_2$)OR, —P(O)(NR$_2$)$_2$, —Si(OH)$_2$R, —Si(OH)(R)$_2$, —Si(R)$_3$, an optionally substituted $C_{1-4}$ aliphatic, or $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is hydrogen. In some embodiments, $R^1$ is deuterium. In some embodiments, $R^1$ is halogen. In some embodiments, $R^1$ is —CN. In some embodiments, $R^1$ is —OR. In some embodiments, $R^1$ is —SR. In some embodiments, $R^1$ is —S(O)R. In some embodiments, $R^1$ is —S(O)$_2$R. In some embodiments, $R^1$ is —NR$_2$. In some embodiments, $R^1$ is —P(O)(OR)$_2$. In some embodiments, $R^1$ is —P(O)(NR$_2$)OR. In some embodiments, $R^1$ is —P(O)(NR$_2$)$_2$. In some embodiments, $R^1$ is —Si(OH)$_2$R. In some embodiments, $R^1$ is —Si(OH)(R)$_2$. In some embodiments, $R^1$ is —Si(R)$_3$. In some embodiments, $R^1$ is an optionally substituted $C_{1-4}$ aliphatic. In some embodiments, $R^1$ and $X^1$ or $X^4$ are taken together with their intervening atoms to form a 5-7 membered saturated, partially unsaturated, carbocyclic ring or heterocyclic ring having 1-3 heteroatoms, independently selected from nitrogen, oxygen, or sulfur.

In some embodiments, $R^1$ is selected from those depicted in Table 1, below.

As defined above and described herein, each $R^2$ is independently hydrogen, deuterium, —$R^6$, halogen, —CN, —NO$_2$, —OR, —SR, —NR$_2$, —Si(OH)$_2$R, —Si(OH)(R)$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N(R)S(O)$_2$NR$_2$, —P(O)(OR)$_2$, —P(O)(NR$_2$)OR, or —P(O)(NR$_2$)$_2$.

In some embodiments, $R^2$ is hydrogen. In some embodiments, $R^2$ is deuterium. In some embodiments, $R^2$ is —$R^6$. In some embodiments, $R^2$ is halogen. In some embodiments, $R^2$ is —CN. In some embodiments, $R^2$ is —NO$_2$. In some embodiments, $R^2$ is —OR. In some embodiments, $R^2$ is —Si(OH)$_2$R. In some embodiments, $R^2$ is —Si(OH)(R)$_2$. In some embodiments, $R^2$ is —SR. In some embodiments, $R^2$ is —NR$_2$. In some embodiments, $R^2$ is —Si(R)$_3$. In some embodiments, $R^2$ is —S(O)$_2$R. In some embodiments, $R^2$ is —S(O)$_2$NR$_2$. In some embodiments, $R^2$ is-S(O)R. In some embodiments, $R^2$ is-C(O)R. In some embodiments, $R^2$ is —C(O)OR. In some embodiments, $R^2$ is —C(O)NR$_2$. In some embodiments, $R^2$ is —C(O)N(R)OR. In some embodiments, $R^2$ is —OC(O)R. In some embodiments, $R^2$ is —OC(O)NR$_2$. In some embodiments, $R^2$ is —N(R)C(O)OR. In some embodiments, $R^2$ is —N(R)C(O)R. In some embodiments, $R^2$ is —N(R)C(O)NR$_2$. In some embodiments, $R^2$ is —N(R)S(O)$_2$R. In some embodiments, $R^2$ is —P(O)(OR)$_2$. In some embodiments, $R^2$ is —P(O)(NR$_2$)OR. In some embodiments, $R^2$ is —P(O)(NR$_2$)$_2$.

In some embodiments, $R^2$ is —OH. In some embodiments, $R^2$ is —NH$_2$.

In some embodiments, $R^2$ is selected from those depicted in Table 1, below.

As defined above and described herein, Ring A is a bi- or tricyclic ring selected from

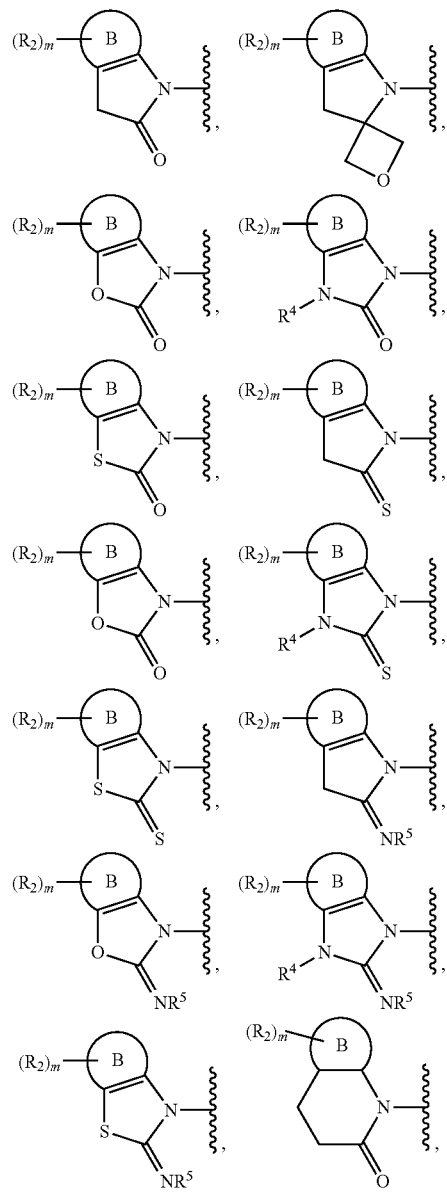

-continued
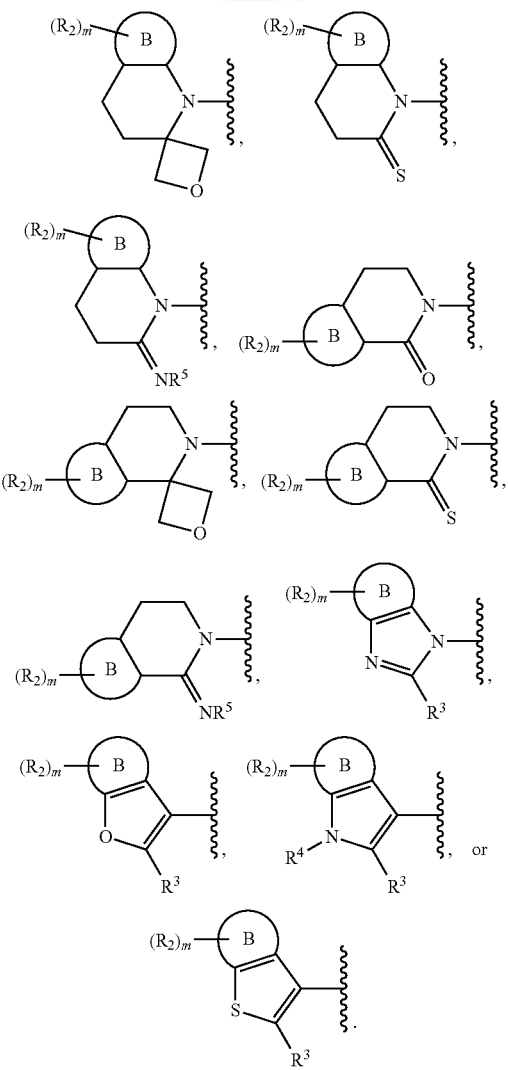
In some embodiments, Ring A is
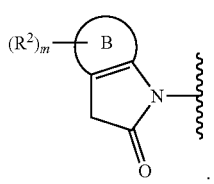
In some embodiments, Ring A is
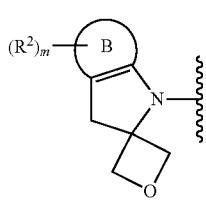
In some embodiments, Ring A is
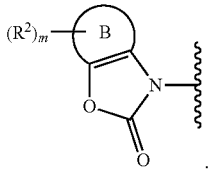
In some embodiments, Ring A is
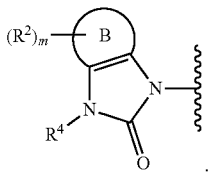
In some embodiments, Ring A is
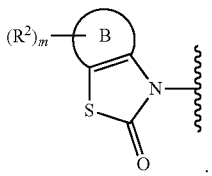
In some embodiments, Ring A is
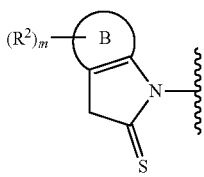
In some embodiments, Ring A is
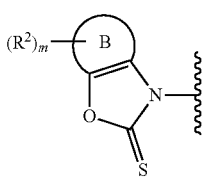
In some embodiments, Ring A is
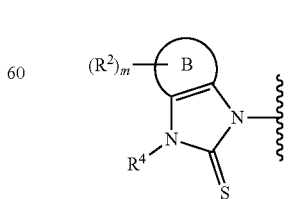

In some embodiments, Ring A is
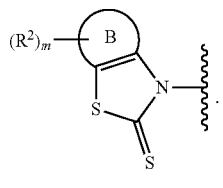
In some embodiments, Ring A is
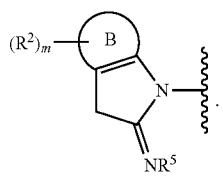
In some embodiments, Ring A is
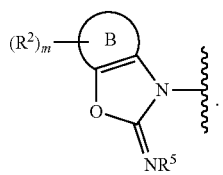
In some embodiments, Ring A is
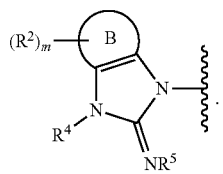
In some embodiments, Ring A is
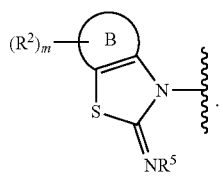
In some embodiments, Ring A is
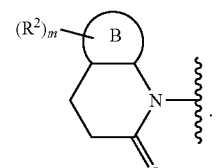
In some embodiments, Ring A is
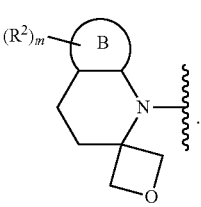
In some embodiments, Ring A is
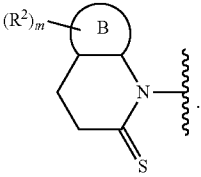
In some embodiments, Ring A is
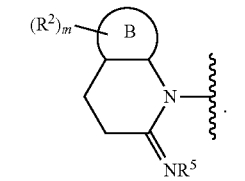
In some embodiments, Ring A is
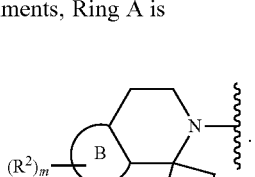
In some embodiments, Ring A is
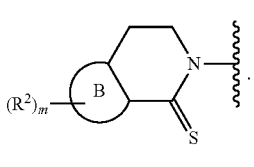

In some embodiments, Ring A is

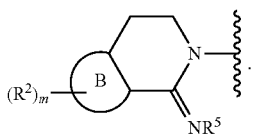

In some embodiments, Ring A is

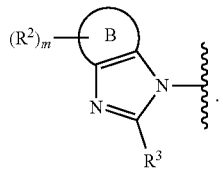

In some embodiments, Ring A is

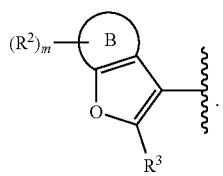

In some embodiments, Ring A is

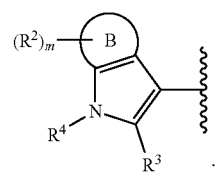

In some embodiments, Ring A is

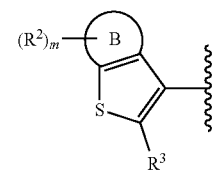

In some embodiments, Ring A is selected from those depicted in Table 1, below.

As defined above and described herein, Ring B is a fused ring selected from 6-membered aryl containing 0-3 nitrogen atoms, 5 to 7-membered partially saturated carbocyclyl, 5 to 7-membered partially saturated heterocyclyl with 1-3 heteroatoms independently selected from nitrogen, oxygen or sulfur, or 5-membered heteroaryl with 1-3 heteroatoms independently selected from boron, nitrogen, oxygen, silicon, and sulfur.

In some embodiments, Ring B is a 6-membered aryl containing 0-3 nitrogen atoms. In some embodiments, Ring B is a 5 to 7-membered partially saturated carbocyclyl. In some embodiments, Ring B is 5 to 7-membered partially saturated heterocyclyl with 1-3 heteroatoms independently selected from boron, nitrogen, oxygen, silicon, or sulfur. In some embodiments, Ring B is 5-membered heteroaryl with 1-3 heteroatoms independently selected from boron, nitrogen, oxygen, silicon, or sulfur.

In some embodiments, Ring B is

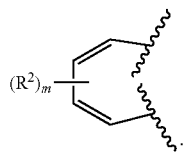

In some embodiments, Ring B is

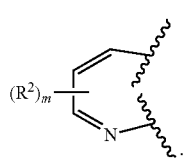

In some embodiments, Ring B is

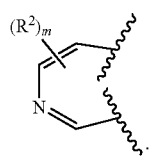

In some embodiments, Ring B is

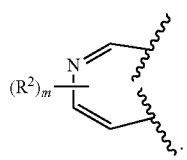

In some embodiments, Ring B is

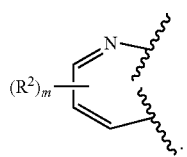

In some embodiments, each Ring B is

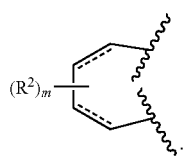

In some embodiments, each Ring B is

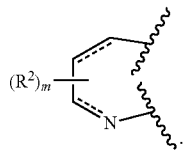

In some embodiments, each Ring B is

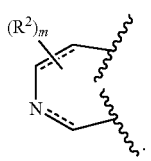

In some embodiments, each Ring B is

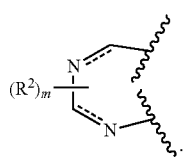

In some embodiments, Ring B is

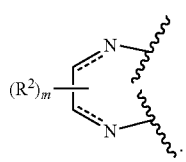

In some embodiments, Ring B is

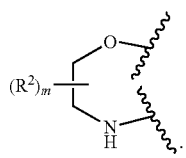

In some embodiments, Ring B is

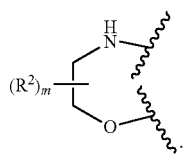

In some embodiments, Ring B is

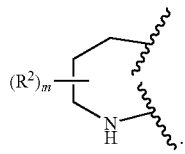

In some embodiments, Ring B is

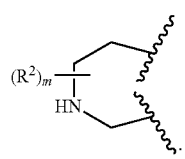

In some embodiments, Ring B is

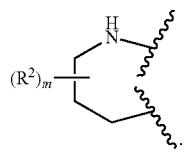

In some embodiments, Ring B is

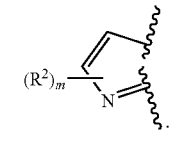

In some embodiments, Ring B is

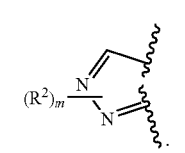

In some embodiments, Ring B is

In some embodiments, Ring B is
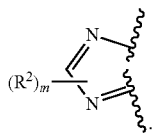
In some embodiments, Ring B is
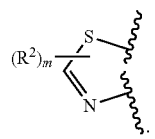
In some embodiments, Ring B is
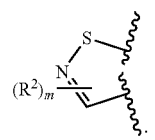
In some embodiments, Ring B is
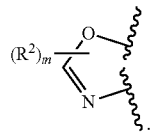
In some embodiments, Ring B is
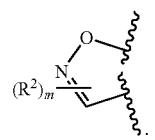
In some embodiments, Ring B is
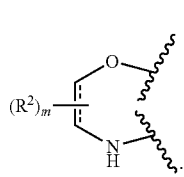
In some embodiments, Ring B is
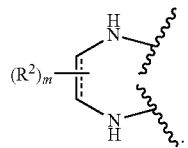
In some embodiments, Ring B is
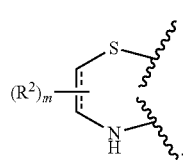
In some embodiments, Ring B is
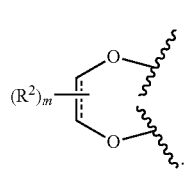
In some embodiments, Ring B is
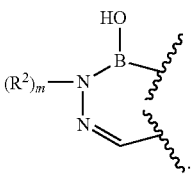
In some embodiments, Ring B is selected from
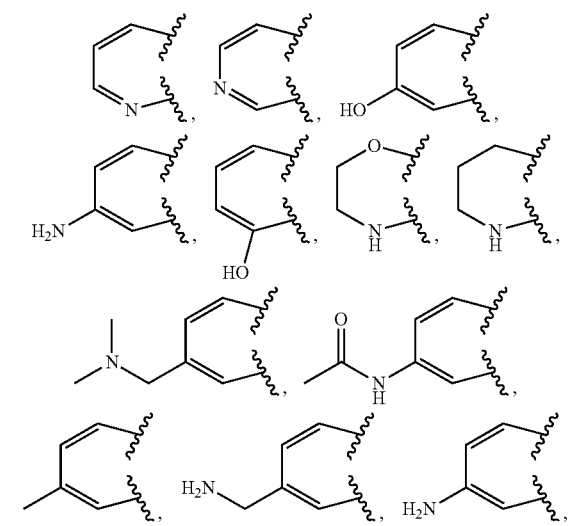

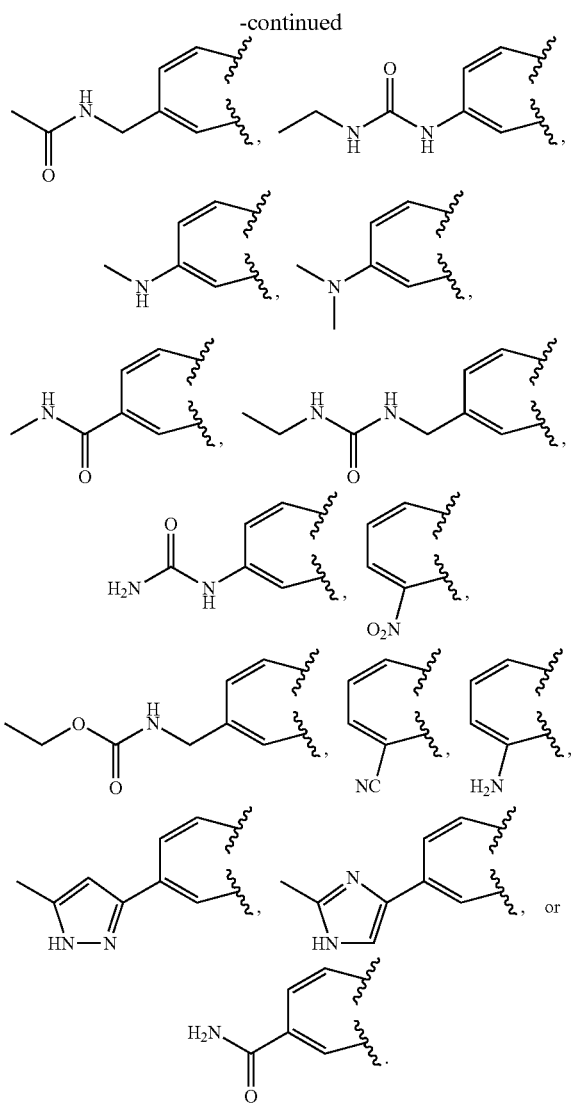

In some embodiments, Ring B is selected from those depicted in Table 1, below.

As defined above and described herein, ═══ is a single or double bond. ═══

In some embodiments, ═══ is a single bond. In some embodiments, ═══ is a double bond.

In some embodiments, ═══ is selected from those depicted in Table 1, below.

As defined above and described herein, $R^3$ is selected from hydrogen, deuterium, halogen, —CN, —NO$_2$, —OR, —NR$_2$, —SR, —S(O)$_2$R, —S(O)$_2$NR$_2$, —S(O)R, —C(O)R, —C(O)OR, —C(O)NR$_2$, —C(O)NR(OR), —OC(O)R, —OC(O)NR$_2$, —OP(O)(OR)$_2$, —OP(O)(NR$_2$)$_2$, —OP(O)(OR)NR$_2$, —N(R)C(O)R, —N(R)C(O)OR, —N(R)C(O)NR$_2$, —N(R)S(O)$_2$R, —N(R)S(O)$_2$NR$_2$, —N(R)P(O)(OR)$_2$, —N(R)P(O)(OR)NR$_2$, —P(O)(OR)$_2$, —P(O)(NR$_2$)OR, —P(O)(NR$_2$)$_2$, —Si(OH)$_2$R, —Si(OH)(R)$_2$, or —Si(R)$_3$.

In some embodiments, $R^3$ is hydrogen. In some embodiments, $R^3$ is deuterium. In some embodiments, $R^3$ is halogen. In some embodiments, $R^3$ is —CN. In some embodiments, $R^3$ is —NO$_2$. In some embodiments, $R^3$ is —OR. In some embodiments, $R^3$ is —NR$_2$. In some embodiments, $R^3$ is —SR. In some embodiments, $R^3$ is —S(O)$_2$R. In some embodiments, $R^3$ is —S(O)$_2$NR$_2$. In some embodiments, $R^3$ is —S(O)R. In some embodiments, $R^3$ is —C(O)R. In some embodiments, $R^3$ is —C(O)OR. In some embodiments, $R^3$ is —C(O)NR$_2$. In some embodiments, $R^3$ is —C(O)NR(OR). In some embodiments, $R^3$ is —OC(O)R. In some embodiments, $R^3$ is —OC(O)NR$_2$. In some embodiments, $R^3$ is —OP(O)(OR)$_2$. In some embodiments, $R^3$ is —OP(O)(NR$_2$)$_2$. In some embodiments, $R^3$ is —OP(O)(OR)NR$_2$. In some embodiments, $R^3$ is —N(R)C(O)R. In some embodiments, $R^3$ is —N(R)C(O)OR. In some embodiments, $R^3$ is —N(R)C(O)NR$_2$. In some embodiments, $R^3$ is —N(R)S(O)$_2$R. In some embodiments, $R^3$ is —N(R)S(O)$_2$NR$_2$. In some embodiments, $R^3$ is —N(R)P(O)(OR)$_2$. In some embodiments, $R^3$ is —N(R)P(O)(OR)NR$_2$. In some embodiments, $R^3$ is —P(O)(OR)$_2$. In some embodiments, $R^3$ is —P(O)(NR$_2$)OR. In some embodiments, $R^3$ is —P(O)(NR$_2$)$_2$. In some embodiments, $R^3$ is —Si(OH)$_2$R. In some embodiments, $R^3$ is —Si(OH)(R)$_2$. In some embodiments, $R^3$ is —Si(R)$_3$.

In some embodiments, $R^3$ is methyl. In some embodiments, $R^3$ is —OCH$_3$. In some embodiments, $R^3$ is chloro.

In some embodiments, $R^3$ is selected from those depicted in Table 1, below.

As defined above and described herein, each $R^4$ is independently hydrogen, deuterium, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —P(O)(OR)$_2$, —P(O)(NR$_2$)OR, or —P(O)(NR$_2$)$_2$.

In some embodiments, $R^4$ is hydrogen. In some embodiments, $R^4$ is —$R^6$. In some embodiments, $R^4$ is halogen. In some embodiments, $R^4$ is —CN. In some embodiments, $R^4$ is —NO$_2$. In some embodiments, $R^4$ is —OR. In some embodiments, $R^4$ is —SR. In some embodiments, $R^4$ is —NR$_2$. In some embodiments, $R^4$ is —S(O)$_2$R. In some embodiments, $R^4$ is —S(O)$_2$NR$_2$. In some embodiments, $R^4$ is —S(O)R. In some embodiments, $R^4$ is —C(O)R. In some embodiments, $R^4$ is —C(O)OR. In some embodiments, $R^4$ is —C(O)NR$_2$. In some embodiments, $R^4$ is —C(O)N(R)OR. In some embodiments, $R^4$ is —OC(O)R. In some embodiments, $R^4$ is —OC(O)NR$_2$. In some embodiments, $R^4$ is —N(R)C(O)OR. In some embodiments, $R^4$ is —N(R)C(O)R. In some embodiments, $R^4$ is —N(R)C(O)NR$_2$. In some embodiments, $R^4$ is —N(R)S(O)$_2$R. In some embodiments, $R^4$ is —P(O)(OR)$_2$. In some embodiments, $R^4$ is —P(O)(NR$_2$)OR. In some embodiments, $R^4$ is —P(O)(NR$_2$)$_2$.

In some embodiments, $R^4$ is independently an optionally substituted group selected from C$_{1-6}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur.

In some embodiments, $R^4$ is an optionally substituted C$_{1-6}$ aliphatic. In some embodiments, $R^4$ is an optionally substituted phenyl. In some embodiments, $R^4$ is an optionally substituted 4-7 membered saturated or partially unsaturated heterocyclic ring having 1-3 heteroatoms independently selected from boron, nitrogen, oxygen, silicon, and sulfur. In some embodiments, $R^4$ is an optionally substituted 5-6 membered heteroaryl ring having 1-4 heteroatoms independently selected from boron, nitrogen, oxygen, silicon, and sulfur.

In some embodiments, $R^4$ is methyl. In some embodiments, $R^4$ is ethyl. In some embodiments, $R^4$ is cyclopropyl.

In some embodiments, $R^4$ is selected from those depicted in Table 1, below.

As defined above and described herein, $R^5$ is hydrogen, deuterium, an optionally substituted $C_{1-4}$ aliphatic, or —CN.

In some embodiments, $R^5$ is hydrogen. In some embodiments, $R^5$ is deuterium. In some embodiments, $R^5$ is an optionally substituted $C_{1-4}$ aliphatic. In some embodiments, $R^5$ is —CN.

In some embodiments, $R^5$ is selected from those depicted in Table 1, below.

As defined above and described herein, each $R^6$ is independently an optionally substituted group selected from $C_{1-6}$ aliphatic, phenyl, a 4-7 membered saturated or partially unsaturated heterocyclic ring having 1-3 heteroatoms independently selected from boron, nitrogen, oxygen, silicon, and sulfur, and a 5-6 membered heteroaryl ring having 1-4 heteroatoms independently selected from boron, nitrogen, oxygen, silicon, and sulfur.

In some embodiments, $R^6$ is an optionally substituted $C_{1-6}$ aliphatic. In some embodiments, $R^6$ is an optionally substituted phenyl. In some embodiments, $R^6$ is an optionally substituted 4-7 membered saturated or partially unsaturated heterocyclic ring having 1-3 heteroatoms independently selected from boron, nitrogen, oxygen, silicon, and sulfur. In some embodiments, $R^6$ is an optionally substituted 5-6 membered heteroaryl ring having 1-4 heteroatoms independently selected from boron, nitrogen, oxygen, silicon, and sulfur.

In some embodiments, $R^6$ is selected from those depicted in Table 1, below.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

As defined above and described herein, each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is deuterium. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-2 heteroatoms independently selected from nitrogen, oxygen, and sulfur. In some embodiments, R is optionally substituted 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

In certain embodiments, the present invention provides a compound of formula I-i:

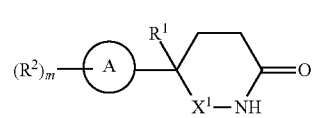

or a pharmaceutically acceptable salt thereof, wherein:

$X^1$ is a bivalent moiety selected from a covalent bond —CH$_2$—, —C(O)—, —C(S)—, or

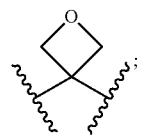 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

each $R^2$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

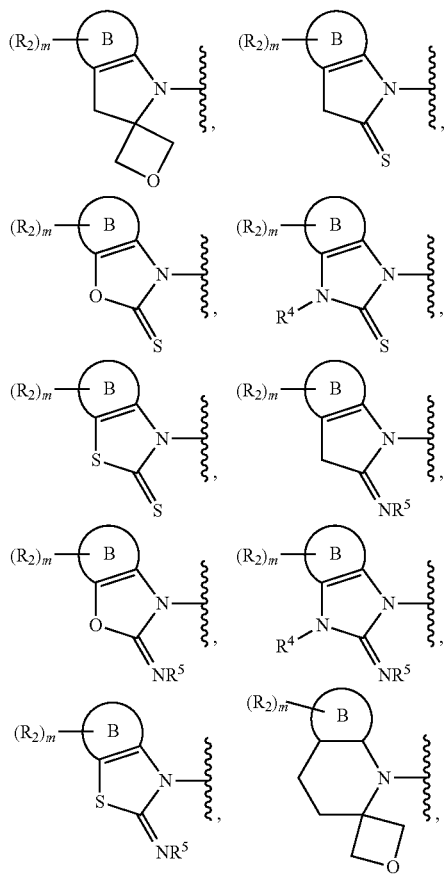

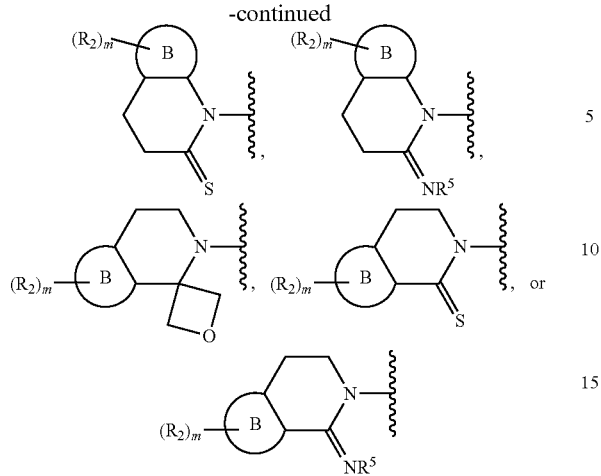

wherein
Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the present invention provides a compound of formula I-i wherein each variable is as described in embodiments provided herein, both singly and in combination.

In some embodiments, the present invention provides a compound of formula II, wherein $X^1$, $R^1$, $R^5$, and R are recited as for formula I as above and herein, and Ring A, Ring B, $R^2$, $R^3$, $R^4$, m, n, and p are recited as for formula II as below and herein.

As defined above and described herein, Ring A is a mono- or bicyclic ring selected from

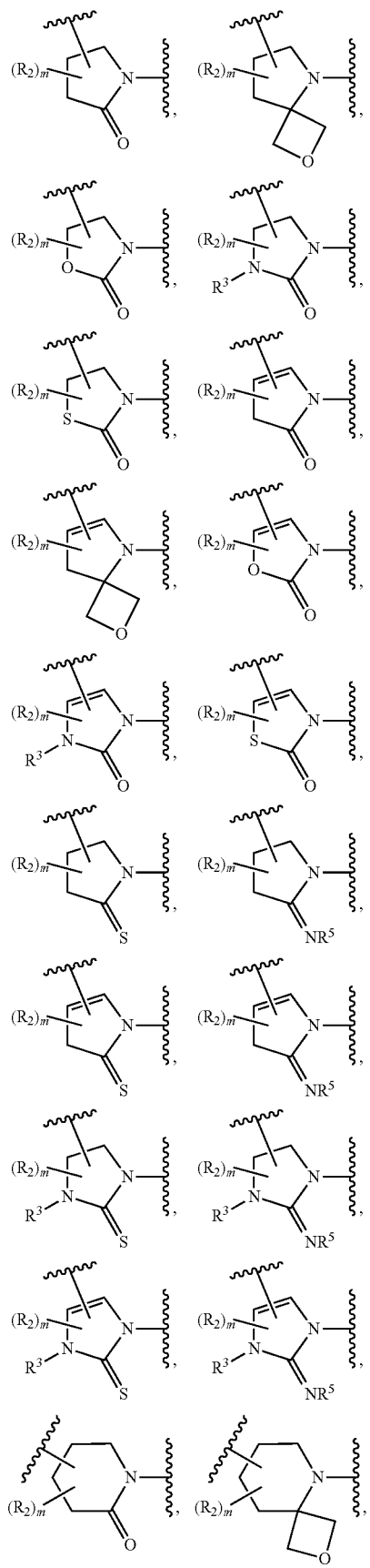

-continued
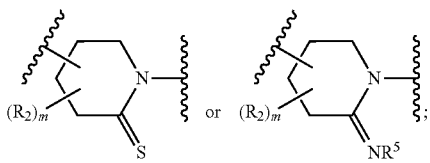 or
In some embodiments, Ring A is
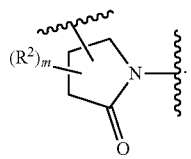
In some embodiments, Ring A is
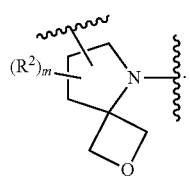
In some embodiments, Ring A is
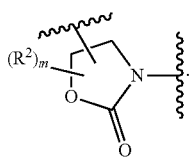
In some embodiments, Ring A is
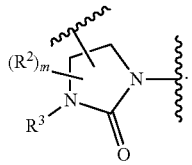
In some embodiments, Ring A is
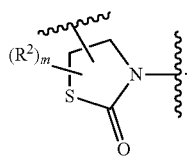
In some embodiments, Ring A is
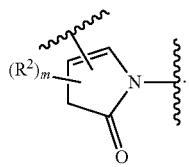
In some embodiments, Ring A is
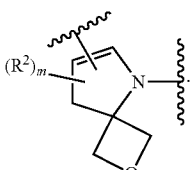
In some embodiments, Ring A is
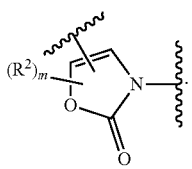
In some embodiments, Ring A is
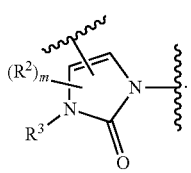
In some embodiments, Ring A is
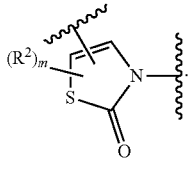
In some embodiments, Ring A is
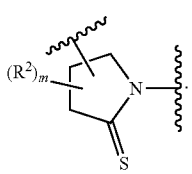

In some embodiments, Ring A is

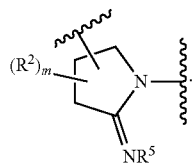

In some embodiments, Ring A is

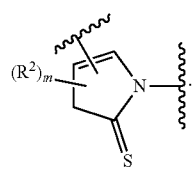

In some embodiments, Ring A is

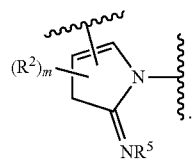

In some embodiments, Ring A is

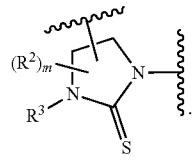

In some embodiments, Ring A is

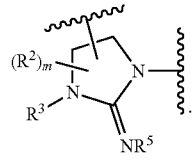

In some embodiments, Ring A is

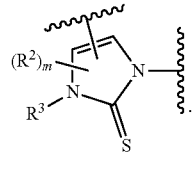

In some embodiments, Ring A is

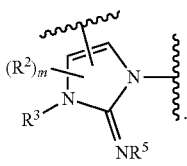

In some embodiments, Ring A is

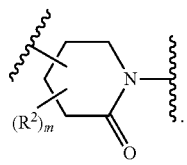

In some embodiments, Ring A is

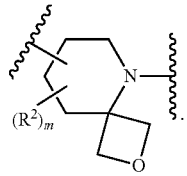

In some embodiments, Ring A is

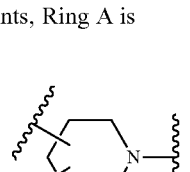

In some embodiments, Ring A is

In some embodiments, Ring A is selected from

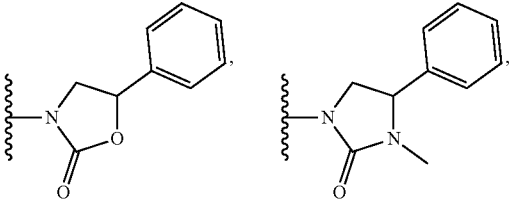

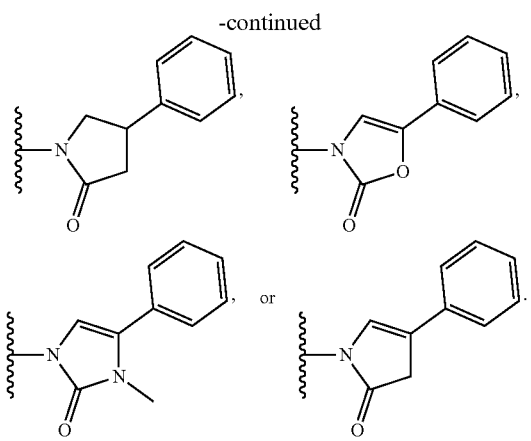

In some embodiments, Ring A is selected from those depicted in Table 1, below.

As defined above and described herein, each $R^2$ is independently hydrogen, —$R^4$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —$N(R)S(O)_2R$.

In some embodiments, $R^2$ is hydrogen. In some embodiments, $R^2$ is —$R^4$. In some embodiments, $R^2$ is halogen. In some embodiments, $R^2$ is —CN. In some embodiments, $R^2$ is —$NO_2$. In some embodiments, $R^2$ is —OR. In some embodiments, $R^2$ is —SR. In some embodiments, $R^2$ is —$NR_2$. In some embodiments, $R^2$ is —$S(O)_2R$. In some embodiments, $R^2$ is —$S(O)_2NR_2$. In some embodiments, $R^2$ is —S(O)R. In some embodiments, $R^2$ is —C(O)R. In some embodiments, $R^2$ is —C(O)OR. In some embodiments, $R^2$ is —$C(O)NR_2$. In some embodiments, $R^2$ is —C(O)N(R)OR. In some embodiments, $R^2$ is —OC(O)R. In some embodiments, $R^2$ is —$OC(O)NR_2$. In some embodiments, $R^2$ is —N(R)C(O)OR. In some embodiments, $R^2$ is —N(R)C(O)R. In some embodiments, $R^2$ is —N(R)C(O)$NR_2$. In some embodiments, $R^2$ is —$N(R)S(O)_2R$.

In some embodiments, $R^2$ is methyl.

In some embodiments, $R^2$ is selected from those depicted in Table 1, below.

As defined above and described herein, Ring B is selected from a 6-membered aryl containing 0-2 nitrogen atoms or a 5-membered heteroaryl with 1-3 heteroatoms independently selected from nitrogen, oxygen or sulfur.

In some embodiments, Ring B is a 6-membered aryl containing 0-2 nitrogen atoms. In some embodiments, Ring B is a 5-membered heteroaryl with 1-3 heteroatoms independently selected from nitrogen, oxygen or sulfur.

In some embodiments, Ring B is selected from those depicted in Table 1, below.

As defined above and described herein, each $R^3$ is independently hydrogen, —$R^4$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —N(R)C(O)$NR_2$, or —$N(R)S(O)_2R$.

In some embodiments, $R^3$ is hydrogen. In some embodiments, $R^3$ is —$R^4$. In some embodiments, $R^3$ is halogen. In some embodiments, $R^3$ is —CN. In some embodiments, $R^3$ is —$NO_2$. In some embodiments, $R^3$ is —OR. In some embodiments, $R^3$ is —SR. In some embodiments, $R^3$ is —$NR_2$. In some embodiments, $R^3$ is —$S(O)_2R$. In some embodiments, $R^3$ is —$S(O)_2NR_2$. In some embodiments, $R^3$ is —S(O)R. In some embodiments, $R^3$ is —C(O)R. In some embodiments, $R^3$ is —C(O)OR. In some embodiments, $R^3$ is —$C(O)NR_2$. In some embodiments, $R^3$ is —C(O)N(R)OR. In some embodiments, $R^3$ is —OC(O)R. In some embodiments, $R^3$ is —$OC(O)NR_2$. In some embodiments, $R^3$ is —N(R)C(O)OR. In some embodiments, $R^3$ is —N(R)C(O)R. In some embodiments, $R^3$ is —N(R)C(O)$NR_2$. In some embodiments, $R^3$ is —$N(R)S(O)_2R$.

In some embodiments, $R^3$ is selected from those depicted in Table 1, below.

As defined above and described herein, each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^4$ is an optionally substituted $C_{1-6}$ aliphatic. In some embodiments, $R^4$ is an optionally substituted phenyl. In some embodiments, $R^4$ is an optionally substituted 4-7 membered saturated or partially unsaturated heterocyclic ring having 1-2 heteroatoms independently selected from nitrogen, oxygen, and sulfur. In some embodiments, $R^4$ is an optionally substituted 5-6 membered heteroaryl ring having 1-4 heteroatoms independently selected from nitrogen, oxygen, and sulfur.

In some embodiments, $R^4$ is methyl.

In some embodiments, $R^4$ is selected from those depicted in Table 1, below.

As defined above and described herein, m is 0, 1, or 2.

In some embodiments, m is 0. In some embodiments, m is 1. In some embodiments, m is 2.

In some embodiments, m is selected from those depicted in Table 1, below.

As defined above and described herein, n is 0, 1, 2, 3, 4 or 5.

In some embodiments, n is 0. In some embodiments, n is 1. In some embodiments, n is 2. In some embodiments, n is 3. In some embodiments, n is 4. In some embodiments, n is 5.

In some embodiments, n is selected from those depicted in Table 1, below.

As defined above and described herein, p is 0 or 1, wherein when p is 0, the bond connecting Ring A and Ring B terminates in a hydrogen.

In some embodiments, p is 0, wherein the bond connecting Ring A and Ring B terminates in a hydrogen. In some embodiments, p is 1.

In some embodiments, p is selected from those depicted in Table 1, below.

As described above, in certain embodiments, the present invention provides a compound of formula II-i:

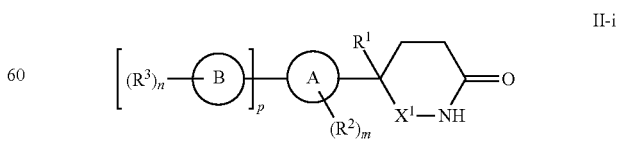

II-i or a pharmaceutically acceptable salt thereof, wherein:
$X^1$ is a bivalent moiety selected from a covalent bond, —$CH_2$—, —C(O)—, —C(S)—, or

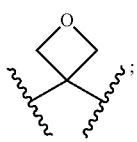 [SMILES: *C1(*)COC1]

R¹ is hydrogen, deuterium, halogen, —CN, —OR, —SR, —S(O)R, —S(O)₂R, —NR₂, or an optionally substituted C₁₋₄ aliphatic;

Ring A is selected from,

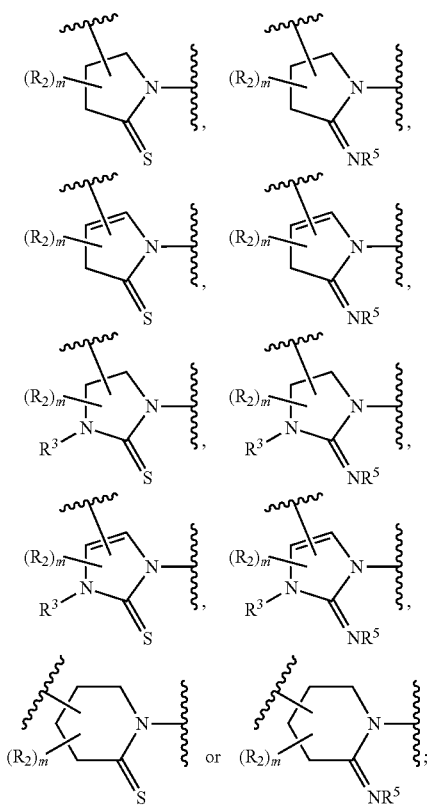

each $R^2$ is independently hydrogen, —$R^4$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each $R^3$ is independently hydrogen, —$R^4$, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

each $R^4$ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$R^5$ is hydrogen, C₁₋₄ aliphatic, or —CN;

m is 0, 1, or 2;

n is 0, 1, 2, 3, 4 or 5;

p is 0 or 1, wherein when p is 0, the bond connecting Ring A and Ring B terminates in a hydrogen; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the present invention provides a compound of formula II-i wherein each variable is as described in embodiments provided herein, both singly and in combination.

Exemplary compounds of the invention are set forth in Table 1, below.

TABLE 1

Exemplary Compounds

| Compound Number | Structure |
|---|---|
| I-1 | <img> |

TABLE 1-continued

Exemplary Compounds

| Compound Number | Structure |
|---|---|
| I-2 | 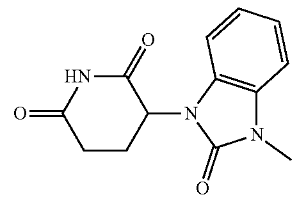 [SMILES: Cn1c(=O)n(C2CCC(=O)NC2=O)c2ccccc21] |
| I-3 | 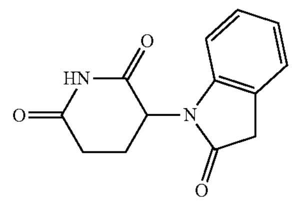 [SMILES: O=C1CCC(N2C(=O)Cc3ccccc32)C(=O)N1] |
| I-4 | 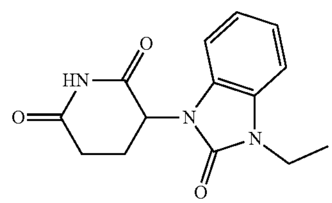 [SMILES: CCn1c(=O)n(C2CCC(=O)NC2=O)c2ccccc21] |
| I-5 | 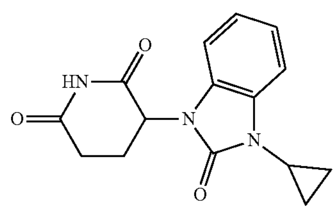 [SMILES: O=C1CCC(n2c(=O)n(C3CC3)c3ccccc32)C(=O)N1] |
| I-6 | 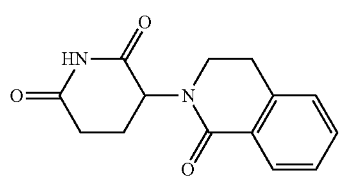 [SMILES: O=C1CCC(N2CCc3ccccc3C2=O)C(=O)N1] |
| I-7 | 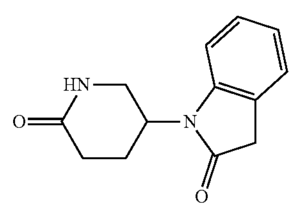 [SMILES: O=C1CCC(N2C(=O)Cc3ccccc32)CN1] |
| I-8 | 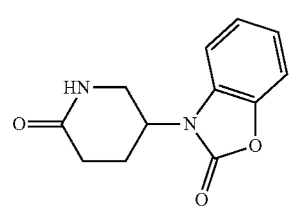 [SMILES: O=C1CCC(n2c(=O)oc3ccccc32)CN1] |

TABLE 1-continued

Exemplary Compounds

| Compound Number | Structure |
|---|---|
| I-9 | 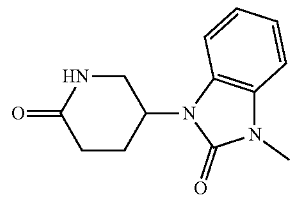 [SMILES: Cn1c(=O)n(C2CCC(=O)NC2)c2ccccc21] |
| I-10 | 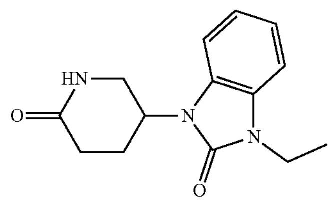 [SMILES: CCn1c(=O)n(C2CCC(=O)NC2)c2ccccc21] |
| I-11 | 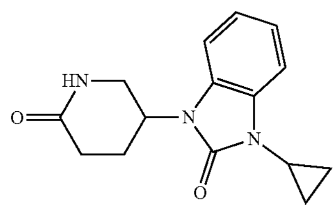 [SMILES: O=C1CCC(n2c(=O)n(C3CC3)c3ccccc32)CN1] |
| I-12 | 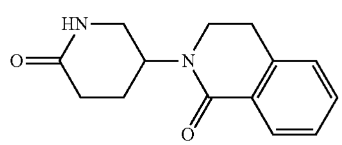 [SMILES: O=C1CCC(N2CCc3ccccc3C2=O)CN1] |
| I-13 | 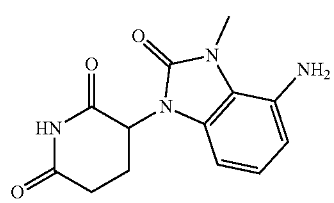 [SMILES: Cn1c(=O)n(C2CCC(=O)NC2=O)c2cccc(N)c21] |
| I-14 | 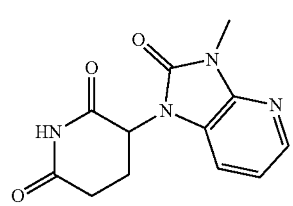 [SMILES: Cn1c(=O)n(C2CCC(=O)NC2=O)c2cccnc21] |
| I-15 | 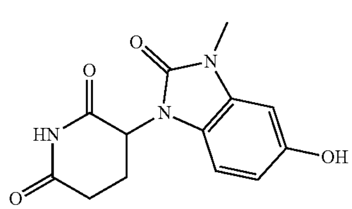 [SMILES: Cn1c(=O)n(C2CCC(=O)NC2=O)c2ccc(O)cc21] |

TABLE 1-continued

Exemplary Compounds

| Compound Number | Structure |
|---|---|
| I-16 | 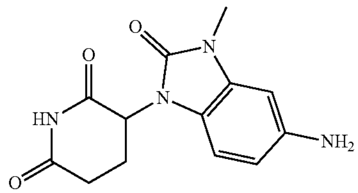 [SMILES: Cn1c(=O)n(C2CCC(=O)NC2=O)c2ccc(N)cc21] |
| I-17 | 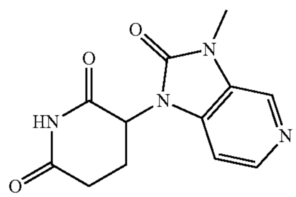 [SMILES: Cn1c(=O)n(C2CCC(=O)NC2=O)c2ccncc21] |
| I-18 | 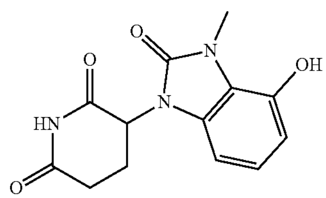 [SMILES: Cn1c(=O)n(C2CCC(=O)NC2=O)c2cccc(O)c21] |
| I-19 | 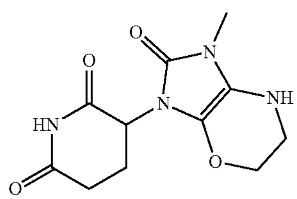 [SMILES: Cn1c2c(n(C3CCC(=O)NC3=O)c1=O)OCCN2] |
| I-20 | 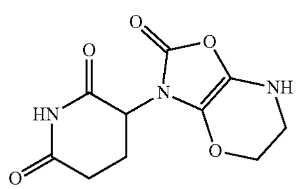 [SMILES: O=C1CCC(n2c3c(oc2=O)NCCO3)C(=O)N1] |
| I-21 | 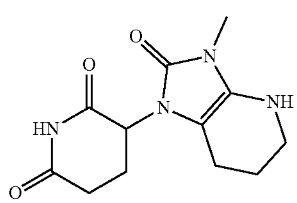 [SMILES: Cn1c2c(n(C3CCC(=O)NC3=O)c1=O)CCCN2] |
| I-22 | 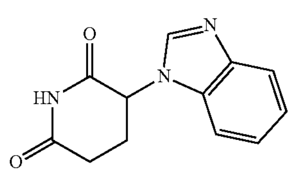 [SMILES: O=C1CCC(n2cnc3ccccc32)C(=O)N1] |
| I-23 | 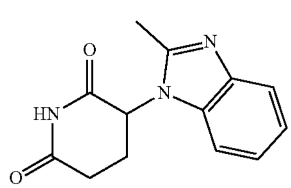 [SMILES: Cc1nc2ccccc2n1C1CCC(=O)NC1=O] |

TABLE 1-continued

Exemplary Compounds

| Compound Number | Structure |
| --- | --- |
| I-24 | 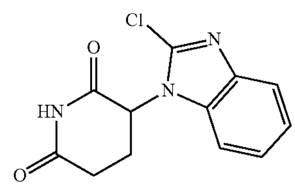 [SMILES: O=C1CCC(n2c(Cl)nc3ccccc32)C(=O)N1] |
| I-25 | 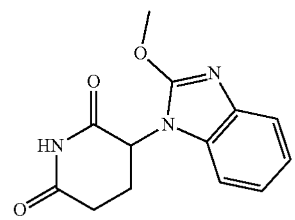 [SMILES: COc1nc2ccccc2n1C1CCC(=O)NC1=O] |
| I-26 | 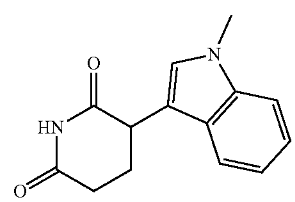 [SMILES: Cn1cc(C2CCC(=O)NC2=O)c2ccccc21] |
| I-27 | 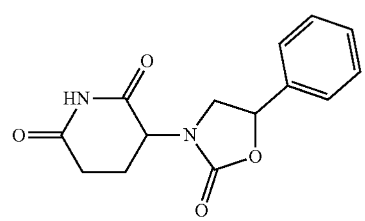 [SMILES: O=C1CCC(N2CC(c3ccccc3)OC2=O)C(=O)N1] |
| I-28 | 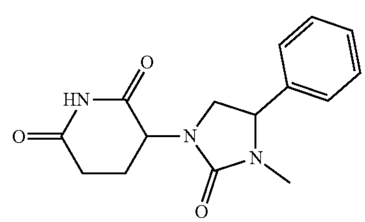 [SMILES: CN1C(=O)N(C2CCC(=O)NC2=O)CC1c1ccccc1] |
| I-29 | 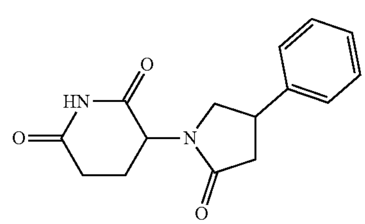 [SMILES: O=C1CCC(N2CC(c3ccccc3)CC2=O)C(=O)N1] |
| I-30 | 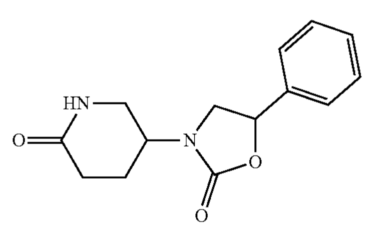 [SMILES: O=C1CCC(N2CC(c3ccccc3)OC2=O)CN1] |

TABLE 1-continued

Exemplary Compounds

| Compound Number | Structure |
|---|---|
| I-31 | 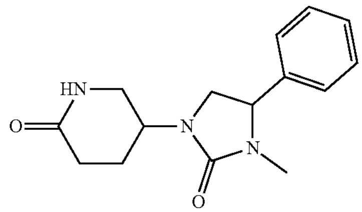 [SMILES: CN1C(=O)N(C2CCC(=O)NC2)CC1c1ccccc1] |
| I-32 | 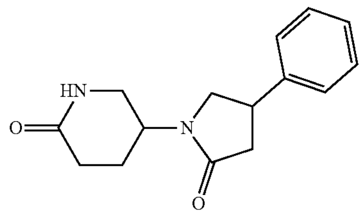 [SMILES: O=C1CCC(N2CC(c3ccccc3)CC2=O)CN1] |
| I-33 | 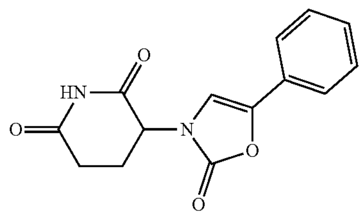 [SMILES: O=C1CCC(n2cc(-c3ccccc3)oc2=O)C(=O)N1] |
| I-34 | 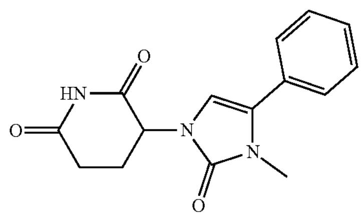 [SMILES: Cn1c(-c2ccccc2)cn(C2CCC(=O)NC2=O)c1=O] |
| I-35 | 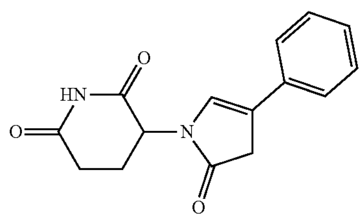 [SMILES: O=C1CCC(N2C=C(c3ccccc3)CC2=O)C(=O)N1] |
| I-36 | 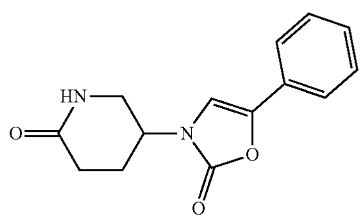 [SMILES: O=C1CCC(n2cc(-c3ccccc3)oc2=O)CN1] |
| I-37 | 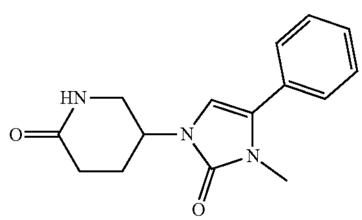 [SMILES: Cn1c(-c2ccccc2)cn(C2CCC(=O)NC2)c1=O] |

TABLE 1-continued
Exemplary Compounds
| Compound Number | Structure |
|---|---|
| I-38 | 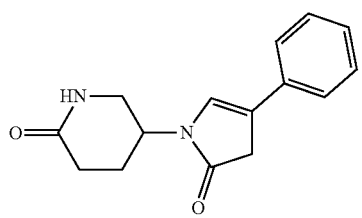 [SMILES: O=C1CCC(N2C=C(c3ccccc3)CC2=O)CN1] |
| I-39 | 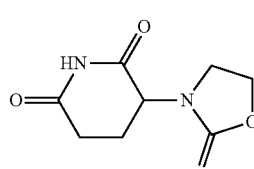 |
| I-40 | 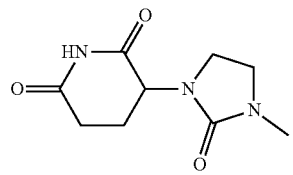 |
| I-41 | 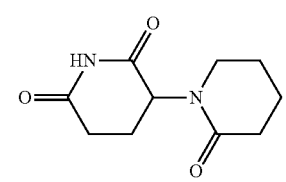 [SMILES: O=C1CCC(N2CCCCC2=O)C(=O)N1] |
| I-42 | 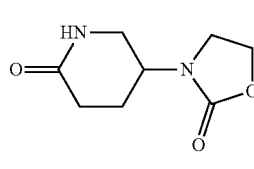 |
| I-43 | 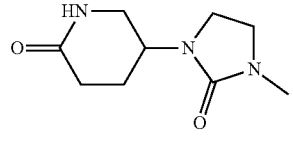 |
| I-44 | 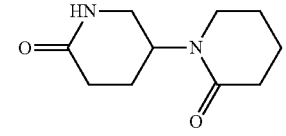 [SMILES: O=C1CCC(N2CCCCC2=O)CN1] |
| I-45 | 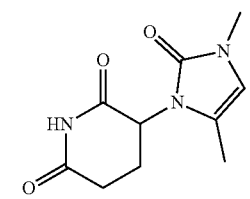 [SMILES: Cc1cn(C)c(=O)n1C1CCC(=O)NC1=O] |

TABLE 1-continued

Exemplary Compounds

| Compound Number | Structure |
| --- | --- |
| I-61 | 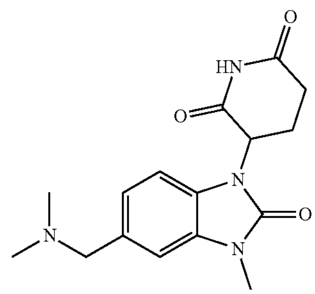 [SMILES: CN(C)Cc1ccc2c(c1)n(C)c(=O)n2C1CCC(=O)NC1=O] |
| I-62 | 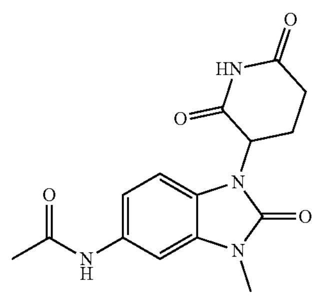 [SMILES: CC(=O)Nc1ccc2c(c1)n(C)c(=O)n2C1CCC(=O)NC1=O] |
| I-63 | 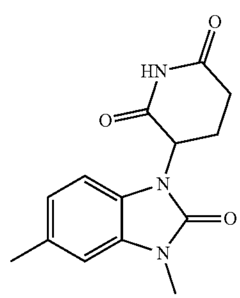 [SMILES: Cc1ccc2c(c1)n(C)c(=O)n2C1CCC(=O)NC1=O] |
| I-64 | 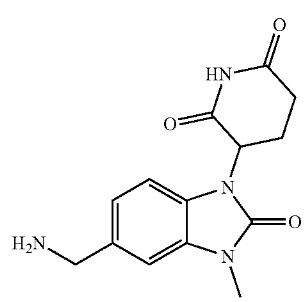 [SMILES: Cn1c(=O)n(C2CCC(=O)NC2=O)c2ccc(CN)cc21] |
| I-65 | 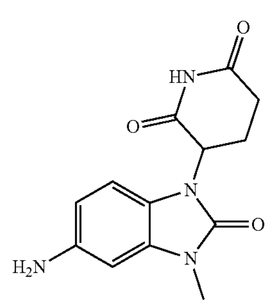 [SMILES: Cn1c(=O)n(C2CCC(=O)NC2=O)c2ccc(N)cc21] |

TABLE 1-continued
Exemplary Compounds
| Compound Number | Structure |
|---|---|
| I-66 | 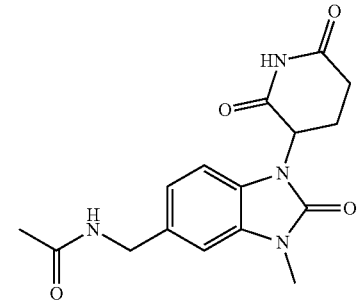 [SMILES: CC(=O)NCc1ccc2c(c1)n(C)c(=O)n2C1CCC(=O)NC1=O] |
| I-67 | 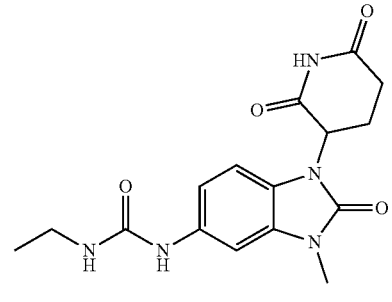 [SMILES: CCNC(=O)Nc1ccc2c(c1)n(C)c(=O)n2C1CCC(=O)NC1=O] |
| I-68 | 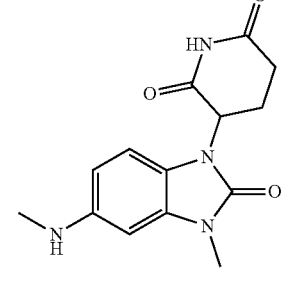 |
| I-69 | 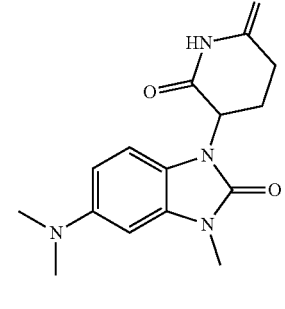 |
| I-70 | 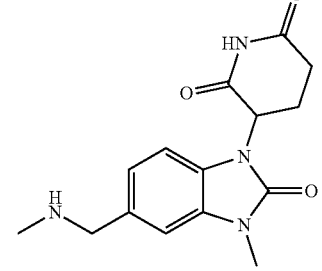 |

TABLE 1-continued

Exemplary Compounds

| Compound Number | Structure |
|---|---|
| I-71 | 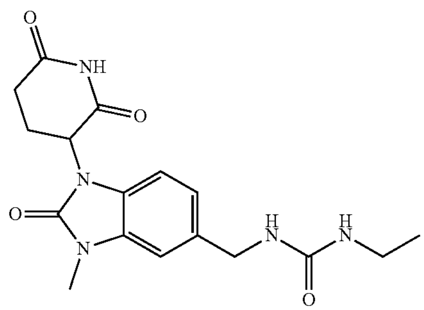 [SMILES: CCNC(=O)NCc1ccc2c(c1)n(C)c(=O)n2C1CCC(=O)NC1=O] |
| I-72 | 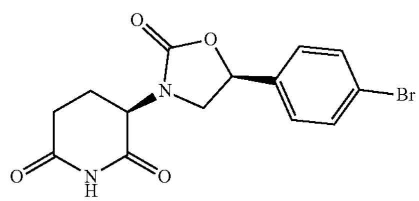 [SMILES: O=C1CC[C@@H](N2C[C@H](c3ccc(Br)cc3)OC2=O)C(=O)N1] |
| I-73 | 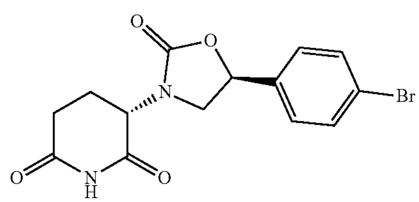 [SMILES: O=C1CC[C@H](N2C[C@H](c3ccc(Br)cc3)OC2=O)C(=O)N1] |
| I-74 | 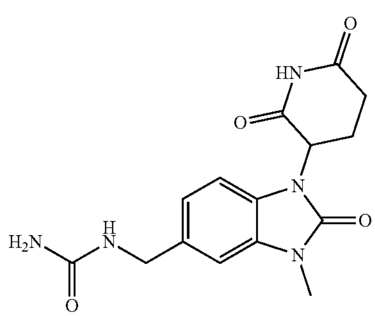 [SMILES: Cn1c(=O)n(C2CCC(=O)NC2=O)c2ccc(CNC(N)=O)cc21] |
| I-75 | 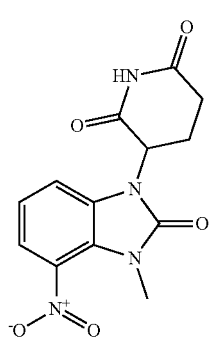 |

TABLE 1-continued

Exemplary Compounds

| Compound Number | Structure |
|---|---|
| I-76 | 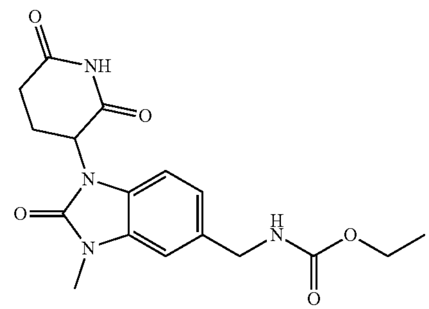 [SMILES: CCOC(=O)NCc1ccc2c(c1)n(C)c(=O)n2C1CCC(=O)NC1=O] |
| I-77 | 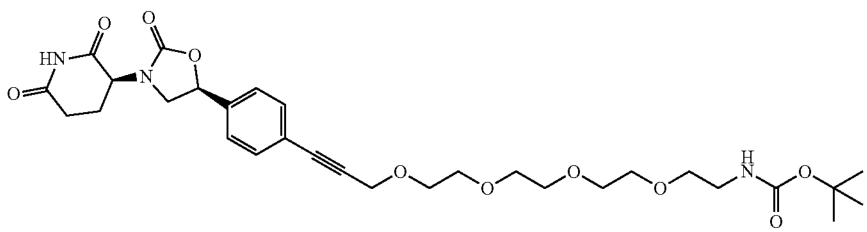 [SMILES: CC(C)(C)OC(=O)NCCOCCOCCOCCOCC#Cc1ccc([C@H]2CN([C@H]3CCC(=O)NC3=O)C(=O)O2)cc1] |
| I-78 | 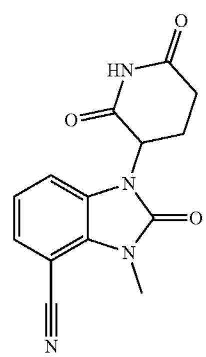 [SMILES: Cn1c(=O)n(C2CCC(=O)NC2=O)c2cccc(C#N)c21] |
| I-79 | 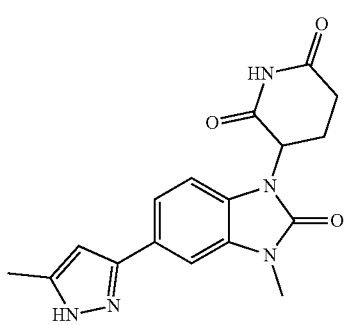 [SMILES: Cc1cc(-c2ccc3c(c2)n(C)c(=O)n3C2CCC(=O)NC2=O)n[nH]1] |
| I-80 | 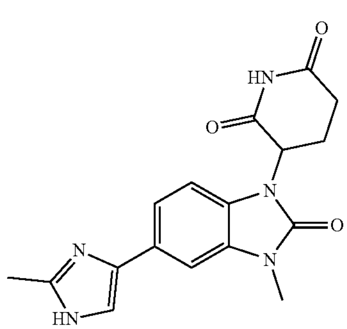 [SMILES: Cc1nc(-c2ccc3c(c2)n(C)c(=O)n3C2CCC(=O)NC2=O)c[nH]1] |

TABLE 1-continued
Exemplary Compounds
| Compound Number | Structure |
| --- | --- |
| I-81 | 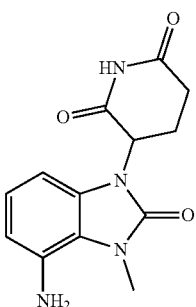 |
| I-82 | 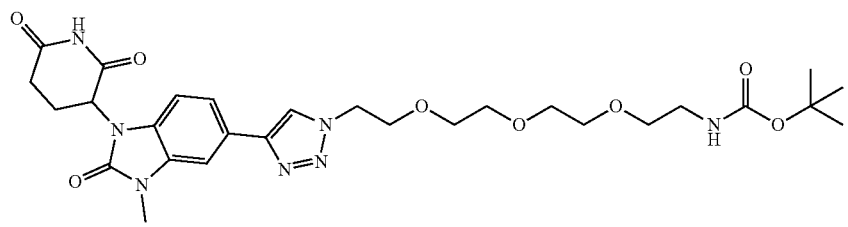 [SMILES: Cn1c(=O)n(C2CCC(=O)NC2=O)c2ccc(-c3cn(CCOCCOCCOCCNC(=O)OC(C)(C)C)nn3)cc21] |
| I-83 | 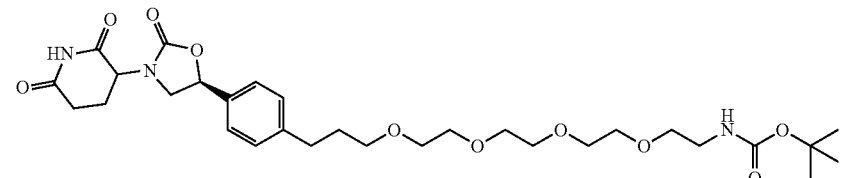 |
| I-84 | 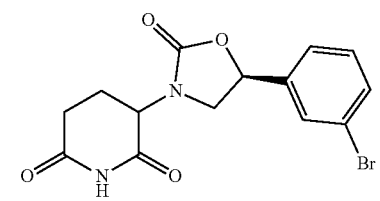 [SMILES: O=C1CCC(N2C[C@H](c3cccc(Br)c3)OC2=O)C(=O)N1] |
| I-85 | 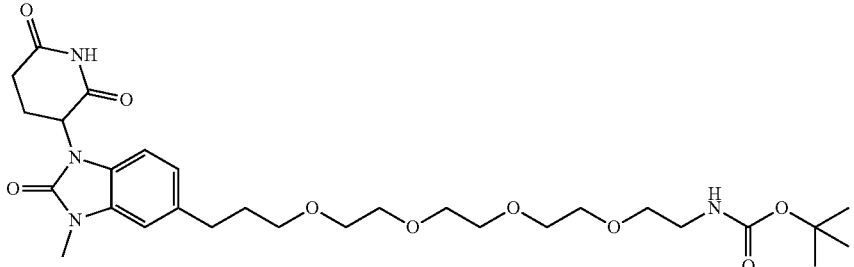 |
| I-86 | 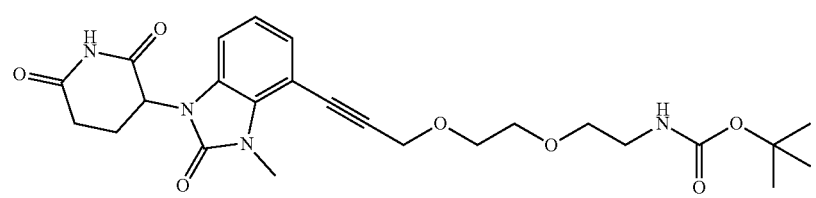 [SMILES: Cn1c(=O)n(C2CCC(=O)NC2=O)c2cccc(C#CCOCCOCCNC(=O)OC(C)(C)C)c21] |

TABLE 1-continued
Exemplary Compounds
| Compound Number | Structure |
|---|---|
| I-87 | 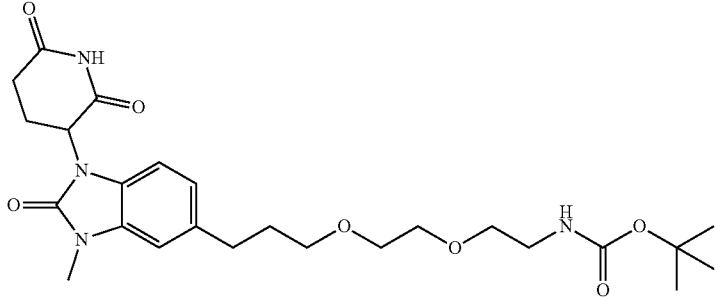 [SMILES: Cn1c(=O)n(C2CCC(=O)NC2=O)c2ccc(CCCOCCOCCNC(=O)OC(C)(C)C)cc21] |
| I-88 | 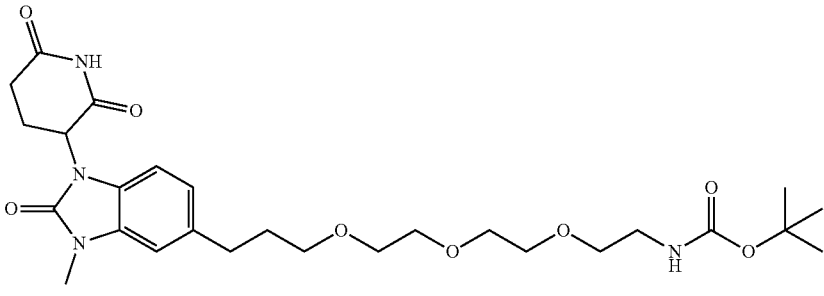 [SMILES: Cn1c(=O)n(C2CCC(=O)NC2=O)c2ccc(CCCOCCOCCOCCNC(=O)OC(C)(C)C)cc21] |
| I-89 | 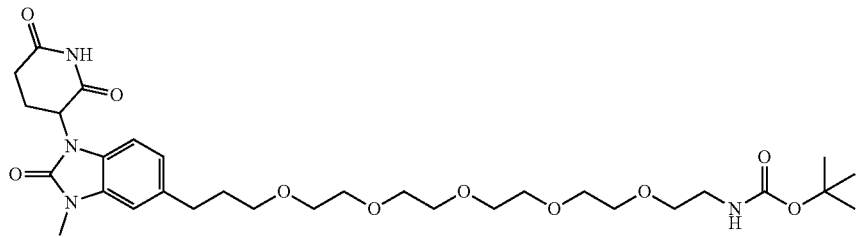 [SMILES: Cn1c(=O)n(C2CCC(=O)NC2=O)c2ccc(CCCOCCOCCOCCOCCOCCNC(=O)OC(C)(C)C)cc21] |
| I-90 | 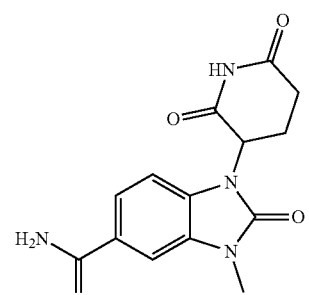 |

In some embodiments, the method employs a compound set forth in Table 1, above, or a pharmaceutically acceptable salt thereof.

In some embodiments, the present invention provides a compound of formula I, wherein the compound is not any of compounds depicted in Table A-1, below.

TABLE A-1

| Compound Number | Structure |
|---|---|
| I-46 | 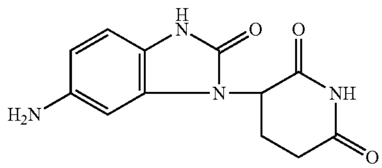 [SMILES: Nc1ccc2[nH]c(=O)n(C3CCC(=O)NC3=O)c2c1] |
| I-47 | 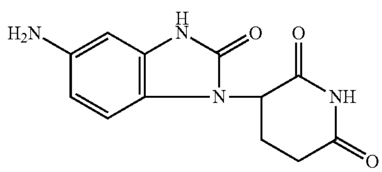 [SMILES: Nc1ccc2c(c1)[nH]c(=O)n2C1CCC(=O)NC1=O] |
| I-48 | 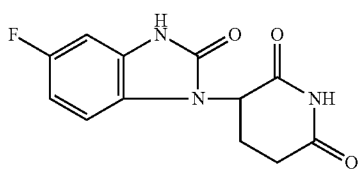 [SMILES: O=C1CCC(n2c(=O)[nH]c3cc(F)ccc32)C(=O)N1] |
| I-49 | 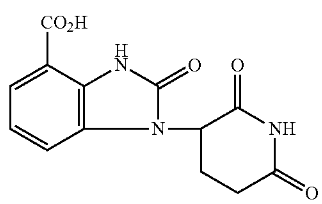 [SMILES: O=C1CCC(n2c(=O)[nH]c3c(C(=O)O)cccc32)C(=O)N1] |
| I-50 | 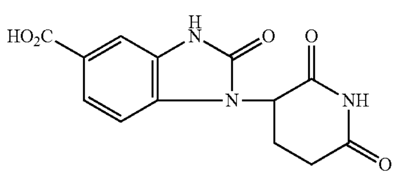 [SMILES: O=C1CCC(n2c(=O)[nH]c3cc(C(=O)O)ccc32)C(=O)N1] |
| I-51 | 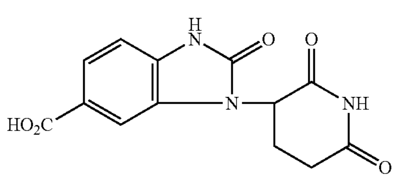 [SMILES: O=C1CCC(n2c(=O)[nH]c3ccc(C(=O)O)cc32)C(=O)N1] |
| I-52 | 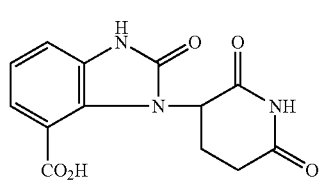 [SMILES: O=C1CCC(n2c(=O)[nH]c3cccc(C(=O)O)c32)C(=O)N1] |

TABLE A-1-continued

| Compound Number | Structure |
|---|---|
| I-53 | 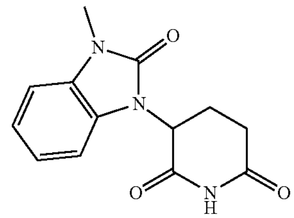 [SMILES: Cn1c(=O)n(C2CCC(=O)NC2=O)c2ccccc21] |
| I-54 | 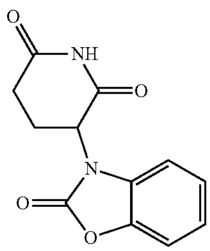 [SMILES: O=C1CCC(n2c(=O)oc3ccccc32)C(=O)N1] |
| I-55 | 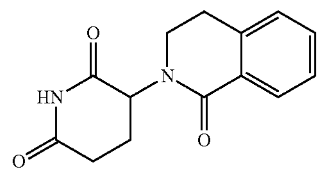 [SMILES: O=C1CCC(N2CCc3ccccc3C2=O)C(=O)N1] |

In some embodiments, the present invention provides a compound of formula II, wherein the compound is not any of compounds depicted in Table A-2, below.

TABLE A-2

| Compound Number | Structure |
|---|---|
| I-56 | 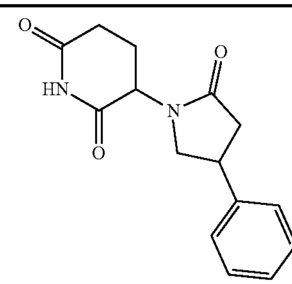 |
| I-57 | 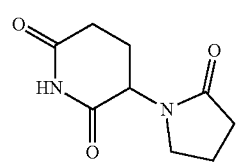 [SMILES: O=C1CCC(N2CCCC2=O)C(=O)N1] |
| I-58 | 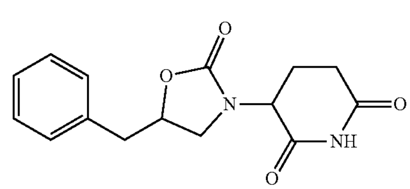 [SMILES: O=C1CCC(N2CC(Cc3ccccc3)OC2=O)C(=O)N1] |

TABLE A-2-continued

| Compound Number | Structure |
|---|---|
| I-59 | 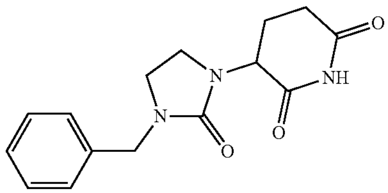 [SMILES: O=C1CCC(N2CCN(Cc3ccccc3)C2=O)C(=O)N1] |
| I-60 | 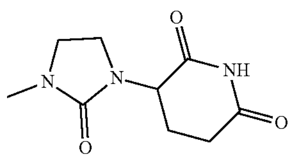 |

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably bind CRBN, or a mutant thereof, in a biological sample or in a patient. In certain embodiments, the amount of compound in compositions of this invention is such that is effective to measurably bind CRBN, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an active metabolite or residue thereof.

As used herein, the term "active metabolite or residue thereof" means that a metabolite or residue thereof is also a binder of CRBN, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the modulation of CRBN. In some embodiments the protein complex bound by the compounds and methods of the invention comprises CRBN.

Cereblon is a protein that in humans is encoded by the CRBN gene. CRBN orthologs are highly conserved from plants to humans, which underscores its physiological importance. Cereblon forms an E3 ubiquitin ligase complex with damaged DNA binding protein 1 (DDB1), Cullin-4A (CUL4A), and regulator of cullins 1 (ROC1). This complex ubiquitinates a number of other proteins. Through a mechanism which has not been completely elucidated, cereblon ubquitination of target proteins results in increased levels of fibroblast growth factor 8 (FGF8) and fibroblast growth factor 10 (FGF10). FGF8 in turn regulates a number of developmental processes, such as limb and auditory vesicle formation. The net result is that this ubiquitin ligase complex is important for limb outgrowth in embryos. In the absence of cereblon, DDB1 forms a complex with DDB2 that functions as a DNA damage-binding protein.

Accordingly, compounds that bind CRBN are beneficial, especially those with selectivity over other E3 ligases. Such compounds should deliver a pharmacological response that favorably treats one or more of the conditions described herein without the side-effects associated with the binding of other E3 ligases.

Even though CRBN ligands are known in the art, there is a continuing need to provide novel ligands having more effective or advantageous pharmaceutically relevant properties. For example, compounds with increased activity, selectivity over other E3 ligases, and ADMET (absorption, distribution, metabolism, excretion, and/or toxicity) properties. Thus, in some embodiments, the present invention provides binders of CRBN which show selectivity over other E3 ligases.

The activity of a compound utilized in this invention as an binder of CRBN, or a mutant thereof, may be assayed in vitro, in vivo or in a cell line. In vitro assays include assays that determine the subsequent functional consequences, or activity of activated CRBN, or a mutant thereof. Alternate in vitro assays quantitate the ability of the compound to bind to CRBN. Compound binding may be measured by radiolabeling the compound prior to binding, isolating the compound/CRBN complex and determining the amount of radiolabel bound. Alternatively, compound binding may be determined by running a competition experiment where new compounds are incubated with CRBN bound to known radioligands. Representative in vitro and in vivo assays useful in assaying a CRBN binder include those described and disclosed in, Boichenko et al. J. Med. Chem. (2016) 59, 770-774 and Iconomou and Saunders Biochemical Journal (2016) 473, 4083-4101, each of which is herein incorporated by reference in its entirety. Detailed conditions for assaying a compound utilized in this invention as a binder of CRBN, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are binders of CRBN and are therefore useful for treating one or more disorders associated with activity of CRBN or mutants thereof. Thus, in certain embodiments, the present invention provides a method for treating a CRBN-mediated disorder comprising the step of administering to a patient in need thereof a compound of the present invention, or pharmaceutically acceptable composition thereof.

As used herein, the term "CRBN-mediated" disorders, diseases, and/or conditions as used herein means any disease or other deleterious condition in which CRBN or a mutant thereof is known to play a role. Accordingly, another embodiment of the present invention relates to treating or lessening the severity of one or more diseases in which CRBN, or a mutant thereof, is known to play a role. Such CRBN-mediated disorders include but are not limited to proliferative disorders, neurological disorders and disorders associated with transplantation.

In some embodiments, the present invention provides a method for treating one or more disorders, wherein the disorders are selected from proliferative disorders, neurological disorders and disorders associated with transplantation, said method comprising administering to a patient in need thereof, a pharmaceutical composition comprising an effective amount of a compound of the present invention, or a pharmaceutically acceptable salt thereof.

In some embodiments, the disorder is a proliferative disorder. In some embodiments, the proliferative disorder is a hematological cancer. In some embodiments, the proliferative disorder is a leukemia. In some embodiments, the proliferative disorder is a leukemia selected from the group consisting of anemia, acute leukemia, acute lymphoblastic leukemia (ALL), chronic lymphocytic leukemia (CLL), acute myelogenous leukemia, acute myeloid leukemia (AML), myelodysplastic syndromes (MDS), adult acute basophilic leukemia, adult acute eosinophilic leukemia, adult acute megakaryoblastic leukemia, adult acute minimally differentiated myeloid leukemia, adult acute monoblastic leukemia, adult acute monocytic leukemia, adult acute myeloblastic leukemia with maturation, adult acute myeloblastic leukemia without maturation, adult acute myeloid leukemia with abnormalities, adult acute myelomonocytic leukemia, adult erythroleukemia, adult pure erythroid leukemia, secondary acute myeloid leukemia, untreated adult acute myeloid leukemia, adult acute myeloid leukemia in remission, adult acute promyelocytic leukemia with PML-RARA, alkylating agent-related acute myeloid leukemia, prolymphocytic leukemia, and chronic myelomonocytic leukemia.

In some embodiments, the proliferative disorder is a lymphoma. In some embodiments, the proliferative disorder is a lymphoma selected from the group consisting of adult grade III lymphomatoid granulomatosis, adult nasal type extranodal NK/T-cell lymphoma, anaplastic large cell lymphoma, angioimmunoblastic T-cell lymphoma, cutaneous B-Cell non-Hodgkin lymphoma, extranodal marginal zone lymphoma of mucosa-associated lymphoid tissue, hepatosplenic T-cell lymphoma, intraocular lymphoma, lymphomatous involvement of non-cutaneous extranodal site, mature T-cell and NK-cell non-Hodgkin lymphoma, nodal marginal zone lymphoma, post-transplant lymphoproliferative disorder, recurrent adult Burkitt lymphoma, recurrent adult diffuse large cell lymphoma, recurrent adult diffuse mixed cell lymphoma, recurrent adult diffuse small cleaved cell lymphoma, recurrent adult grade III lymphomatoid granulomatosis, recurrent adult immunoblastic lymphoma, recurrent adult lymphoblastic lymphoma, recurrent adult T-cell leukemia/lymphoma, recurrent cutaneous T-cell non-Hodgkin lymphoma, recurrent grade 1 follicular lymphoma, recurrent grade 2 follicular lymphoma, recurrent grade 3 follicular lymphoma, recurrent mantle cell lymphoma, recurrent marginal zone lymphoma, recurrent mycosis fungoides and Sezary syndrome, recurrent small lymphocytic lymphoma, refractory chronic lymphocytic leukemia, refractory hairy cell leukemia, Richter syndrome, small intestinal lymphoma, splenic marginal zone lymphoma, T-cell large granular lymphocyte leukemia, testicular lymphoma, Waldenstrom macroglobulinemia, adult T-cell leukemia-lymphoma, peripheral T-cell lymphoma, B-cell lymphoma, Hodgkin's disease, cutaneous T-cell lymphoma, diffuse large B-cell lymphoma, MALT lymphoma, mantle cell lymphoma, non-Hodgkins lymphoma, central nervous system lymphoma, refractory primary-cutaneous large B-cell lymphoma (Leg-type), relapsed or refractory chronic lymphocytic leukemia, refractory anemia, refractory anemia with excess blasts, refractory anemia with ringed sideroblasts, refractory cytopenia with multilineage dysplasia, and secondary myelodysplastic syndromes.

In some embodiments, the disorder is a neurological disorder. In some embodiments, the neurological disorder is Alzheimer's disease.

In some embodiments, the disorder is associated with transplantation. In some embodiments the disorder associated with transplantation is transplant rejection, or graft versus host disease.

In some embodiments, the proliferative disorder is a cancer or tumor. In some embodiments, the proliferative disorder is a cancer or tumor selected from the group consisting of head and neck cancer, liver cancer, hormone-refractory prostate cancer, kidney cancer, small intestine cancer, glioblastoma, non-small cell lung cancer, ovarian cancer, endometrial cancer, esophageal cancer, colon cancer, lung cancer, brain and central nervous system tumors, gastrointestinal carcinoid tumor, islet cell tumor, and childhood solid tumor.

In some embodiments, the proliferative disorder is a myeloma. In some embodiments, the proliferative disorder is a multiple myeloma.

In some embodiments, the proliferative disorder is a myeloma selected from the group consisting of refractory multiple myeloma, stage I multiple myeloma, stage II multiple myeloma, stage III multiple myeloma, smoldering plasma cell myeloma, and plasma cell myeloma.

In some embodiments, the proliferative disorder is selected from the group consisting of hepatocellular carcinoma, melanoma, malignant melanoma, thyroid neoplasms, urinary bladder neoplasms, amyotrophic lateral sclerosis (ALS), sickle cell anemia, ankylosing spondylitis, arachnoiditis, arterivenous malformation, and hereditary hemorrhagic telangiectasia.

In some embodiments, the disorder is selected from the group consisting of AIDS-related Kaposi sarcoma, amyloidosis, hematochezia, melena, autism, burning mouth syndrome associated with HIV infection, hepatocellular carcinoma, non-small-cell lung carcinoma, central nervous system neoplasms, medulloblastoma, chronic myeloproliferative disorders, secondary myelofibrosis, chronic pancreatitis, chronic prostatitis, complex regional pain syndrome (RSD), Type 1 complex regional pain syndrome, Crohn's disease, cutaneous lupus erythematosus (CLE), discoid lupus erythematosus, endometriosis, neoplastic syndrome, gastrointestinal hemorrhage, gastrointestinal vascular malformation, hepatitis C, high grade squamous intra-epithelial lesion (HSIL), HIV wasting syndrome, HIV-associated mycobacterium infections, HIV-associated tuberculosis, HIV-associated aphthous stomatitis, HIV-associated avium-intracellulare infection, idiopathic pulmonary fibrosis (IPF), Langerhans cell histiocytosis (LCH), histiocytosis, Erdheim-Chester disease, histiocytic light chain deposition disease, myelofibrosis, myeloproliferative neoplasms, neurofibromatosis type 1, recurrent central nervous system neoplasm, recurrent childhood brain stem glioma, recurrent childhood visual pathway glioma, refractory central nervous system neoplasm, nonmalignant monoclonal gammopathy of undetermined significance (MGUS), primary amyloidosis, primary myelofibrosis, primary sclerosing cholangitis, plaque-type psoriasis, pulmonary fibrosis, radiation injuries, radiculopathy, recurrent uterine corpus sarcoma, uterine carcinosarcoma, refractory epilepsy, sarcoidosis, systemic scleroderma, systemic sclerosis, Sjogren's Syndrome, xerostomia, soft tissue sarcoma, thalassemia, and uveitis.

In some embodiments, compounds of the present invention bind to CRBN, altering the specificity of the complex to induce the ubiquitination and degradation of Ikaros (IKZF1) and Aiolos (IKZF3), transcription factors essential for multiple myeloma growth.

In some embodiments, compounds of the present invention bind to CRBN, altering the specificity of the complex to induce the ubiquitination and degradation of a complex-associated protein selected from the group consisting of A1BG, A1CF, A2M, A2ML1, A3GALT2, A4GALT, A4GNT, AAAS, AACS, AADAC, AADACL2, AADACL3, AADACL4, AADAT, AAED1, AAGAB, AAK1, AAMDC, AAMP, AANAT, AAR2, AARD, AARS, AARS2, AARSD1, AASDH, AASDHPPT, AASS, AATF, AATK, AATK-AS1, ABAT, ABCA1, ABCA10, ABCA12, ABCA13, ABCA2, ABCA3, ABCA4, ABCA5, ABCA6, ABCA7, ABCA8, ABCA9, ABCB1, ABCB10, ABCB11, ABCB4, ABCB5, ABCB6, ABCB7, ABCB8, ABCB9, ABCC1, ABCC10, ABCC11, ABCC12, ABCC2, ABCC3, ABCC4, ABCC5, ABCC6, ABCC8, ABCC9, ABCD1, ABCD2, ABCD3, ABCD4, ABCE1, ABCF1, ABCF2, ABCF3, ABCG1, ABCG2, ABCG4, ABCG5, ABCG8, ABHD1, ABHD10, ABHD11, ABHD12, ABHD12B, ABHD13, ABHD14A, ABHD14A-ACY1, ABHD14B, ABHD15, ABHD16A, ABHD16B, ABHD17A, ABHD17B, ABHD17C, ABHD18, ABHD2, ABHD3, ABHD4, ABHD5, ABHD6, ABHD8, ABI1, ABI2, ABI3, ABI3BP, ABL, ABL2, ABLIM1, ABLIM2, ABLIM3, ABO, ABR, ABRA, ABRACL, ABRAXAS1, ABRAXAS2, ABT1, ABTB1, ABTB2, AC001226.2, AC002094.3, AC002115.2, AC002310.4, AC002310.5, AC002429.2, AC002985.1, AC002996.1, AC003002.1, AC003002.2, AC003002.3, AC003002.4, AC003005.1, AC003006.1, AC003688.1, AC004076.1, AC004080.3, AC004223.3, AC004233.2, AC004556.1, AC004691.2, AC004706.4, AC004754.1, AC004805.1, AC004832.3, AC004922.1, AC004997.1, AC005020.2, AC005041.1, AC005154.6, AC005258.1, AC005324.3, AC005324.4, AC005520.1, AC005551.1, AC005670.2, AC005697.1, AC005702.2, AC005726.2, AC005779.2, AC005832.4, AC005833.1, AC005833.3, AC005837.2, AC005841.2, AC005885.1, AC005943.1, AC006030.1, AC006254.1, AC006269.1, AC006449.4, AC006486.1, AC006538.2, AC006978.2, AC007040.2, AC007192.1, AC007240.1, AC007325.1, AC007325.2, AC007325.4, AC007326.4, AC007375.2, AC007383.6, AC007537.5, AC007731.5, AC007906.2, AC007998.2, AC008073.3, AC008162.2, AC008393.2, AC008403.1, AC008481.3, AC008537.1, AC008560.1, AC008575.1, AC008575.2, AC008687.1, AC008687.4, AC008687.8, AC008695.1, AC008735.6, AC008750.8, AC008758.1, AC008758.4, AC008758.5, AC008758.6, AC008763.2, AC008763.3, AC008764.1, AC008764.4, AC008770.2, AC008770.3, AC008878.1, AC008878.2, AC008878.3, AC008982.1, AC008982.3, AC009014.1, AC009086.2, AC009119.2, AC009122.1, AC009133.6, AC009163.2, AC009163.4, AC009286.3, AC009336.2, AC009477.2, AC009690.1, AC009690.3, AC009779.3, AC010132.3, AC010255.3, AC010319.2, AC010323.1, AC010325.1, AC010326.2, AC010327.1, AC010422.3, AC010422.5, AC010422.6, AC010463.1, AC010487.3, AC010522.1, AC010531.1, AC010542.3, AC010547.4, AC010547.5, AC010615.4, AC010616.1, AC010619.1, AC010646.1, AC010724.2, AC011005.1, AC011043.1, AC011043.2, AC011195.2, AC011295.1, AC011346.1, AC011448.1, AC011452.1, AC011455.3, AC011455.4, AC011462.1, AC011473.4, AC011479.1, AC011498.4, AC011499.1, AC011511.1, AC011511.4, AC011530.1, AC011604.2, AC011841.1, AC012184.2, AC012254.2, AC012309.1, AC012314.1, AC012314.10, AC012314.11, AC012314.12, AC012314.4, AC012314.5, AC012314.6, AC012314.8, AC012531.3, AC012651.1, AC013269.1, AC013271.1, AC013394.1, AC013470.2, AC015688.5, AC015802.6, AC015813.2, AC017081.3, AC017081.4, AC017081.5, AC017083.4, AC018512.1, AC018523.2, AC018554.3, AC018630.6, AC018709.1, AC018755.2, AC018793.1, AC018793.2, AC018793.3, AC018793.4, AC018793.5, AC019117.3, AC020636.2, AC020909.1, AC020914.1, AC020915.1, AC020915.2, AC020915.6, AC020922.1, AC020934.3, AC021072.1, AC022016.2, AC022167.5, AC022335.1, AC022384.1, AC022400.6, AC022826.2, AC023055.1, AC023491.2, AC023509.3, AC024592.3, AC024940.1, AC024940.6, AC025165.3, AC025263.2, AC025283.2, AC025287.4, AC025594.2, AC026369.8, AC026398.1, AC026461.4, AC026464.1, AC026464.3, AC026464.4, AC026786.1, AC026954.2, AC027796.3, AC034102.2, AC036214.3, AC037459.1, AC037482.2, AC037482.3, AC040162.1, AC040162.4, AC044810.8, AC046185.1, AC048338.1, AC051649.2, AC053481.5, AC055811.2, AC058822.1, AC064853.2, AC064853.3, AC064853.4, AC064853.5, AC064853.6, AC067968.1, AC068234.1, AC068533.4, AC068547.1, AC068580.4, AC068631.2, AC068775.1, AC068775.2, AC068790.8, AC068896.1, AC068946.1, AC068987.5, AC069257.3, AC069368.1, AC069503.2, AC069544.2, AC072022.1, AC073082.1, AC073111.3, AC073111.5, AC073264.3, AC073508.2, AC073610.2, AC073610.3, AC073612.1, AC073896.1, AC074143.1, AC078927.1, AC079325.2, AC079447.1, AC079594.2, AC083800.1, AC083902.2, AC084337.2, AC087289.3, AC087498.1, AC087632.1, AC090004.1, AC090227.1, AC090360.1, AC090527.2, AC090958.3, AC091167.3, AC091167.7, AC091167.8, AC091304.7, AC091491.1, AC091551.1, AC091959.3, AC091980.2, AC092017.3, AC092042.3, AC092073.1, AC092111.3, AC092143.1, AC092329.3, AC092442.1, AC092587.1, AC092647.5, AC092718.3, AC092718.8, AC092821.1, AC092824.3, AC092835.1, AC093155.3, AC093227.3, AC093423.3, AC093525.1, AC093525.2, AC093668.1, AC093762.1, AC093762.2, AC093762.3, AC093899.2, AC096582.3, AC096887.1, AC097372.1, AC097495.1, AC097637.1, AC097662.2, AC098484.3, AC098650.1, AC098850.4, AC099329.3, AC099489.1, AC099518.3, AC099811.2, AC099850.2, AC100868.1, AC104109.3, AC104151.1, AC104304.1, AC104452.1, AC104532.1, AC104534.3, AC104581.1, AC104581.3, AC104662.2, AC104836.1, AC105001.2, AC105052.1, AC106774.10, AC106774.5, AC106774.6, AC106774.7, AC106774.8, AC106774.9, AC106782.1, AC106886.5, AC107871.1, AC108488.2, AC108750.1, AC108941.2, AC109583.3, AC110275.1, AC112229.3, AC112484.1, AC113189.6, AC113189.9, AC113331.2, AC113554.2, AC114296.1, AC114490.2, AC115220.1, AC116366.3, AC116565.1, AC117457.1, AC118470.1, AC118553.2, AC119396.1, AC119674.2, AC120057.3, AC120114.5, AC124312.1, AC126755.2, AC127537.5, AC127537.6, AC127537.8, AC129492.3, AC131097.2, AC131160.1, AC133551.1, AC133555.3, AC134669.2, AC134772.2, AC135050.2, AC135068.1, AC135068.2, AC135068.3, AC135068.8, AC135178.2, AC135586.2, AC136352.3, AC136352.4, AC136428.1, AC136612.1, AC136616.1, AC136616.2, AC136616.3, AC137834.1, AC138517.2, AC138647.1, AC138696.1, AC138811.2, AC138894.1, AC138969.1, AC139530.2, AC139677.1, AC139677.2, AC140504.1, AC141272.1, AC142391.1, AC142525.4, AC145029.2, AC145212.1, AC145212.2, AC171558.1, AC171558.3, AC171558.5, AC171558.6, AC187653.1, AC207056.1, AC209232.1, AC209539.2, AC210544.1, AC213203.1, AC229888.1, AC229888.10, AC229888.2, AC229888.3, AC229888.4, AC229888.5, AC229888.6, AC229888.7, AC229888.8, AC229888.9, AC233282.1, AC233282.2, AC233723.1, AC233724.12, AC233724.16, AC233724.17, AC233724.18, AC233724.19, AC233724.20, AC233724.21, AC233724.6, AC233755.1, AC233755.2, AC233992.2, AC234301.1, AC234301.3, AC234635.1, AC234635.3, AC234635.4, AC234635.5, AC236040.1, AC239612.1, AC239618.1, AC239618.2, AC239618.3, AC239618.4, AC239618.5, AC239618.6, AC239618.7, AC239618.9, AC239799.1, AC240274.1, AC241401.1, AC241409.2, AC241410.1, AC241556.3, AC241556.4, AC241640.1, AC241640.2, AC241640.4, AC242528.1, AC242528.2, AC243547.3, AC243733.1, AC243734.1, AC243756.1, AC243790.1, AC243967.1, AC244196.1, AC244196.2, AC244196.3, AC244196.4, AC244196.5, AC244197.3, AC244216.4, AC244216.5, AC244226.1, AC244226.2, AC244472.1, AC244472.2, AC244472.3, AC244472.4, AC244472.5, AC244489.1, AC244489.2, AC244517.10, AC244517.6, AC245033.1, AC245034.2, AC245078.1, AC245088.2, AC245088.3, AC245369.1, AC245369.2, AC245369.3, AC245369.4, AC245369.6, AC245427.1, AC245427.3, AC245427.4, AC245427.5, AC245427.6, AC245427.7, AC245427.8, AC245427.9, AC245748.1, AC247036.3, AC247036.4, AC247036.5, AC247036.6, AC254560.1, AC254788.1, AC254788.2, AC254952.1, AC255093.3, AC255093.5, AC256236.1, AC256236.2, AC256236.3, AC256300.2, AC256309.2, AC270107.1, AC270107.10, AC270107.12, AC270107.2, AC270107.3, AC270107.4, AC270107.5, AC270107.7, AC270107.8, AC270107.9, AC270227.1, AC270306.4, AC275455.2, ACAA1, ACAA2, ACACA, ACACB, ACAD10, ACAD11, ACAD8, ACAD9, ACADL, ACADM, ACADS, ACADSB, ACADVL, ACAN, ACAP1, ACAP2, ACAP3, ACAT1, ACAT2, ACBD3, ACBD4, ACBD5, ACBD6, ACBD7, ACCS, ACCSL, ACD, ACE, ACE2, ACER1, ACER2, ACER3, ACHE, ACIN1, ACKR1, ACKR2, ACKR3, ACKR4, ACLY, ACMSD, ACO1, ACO2, ACOD1, ACOT1, ACOT11, ACOT12, ACOT13, ACOT2, ACOT4, ACOT6, ACOT7, ACOT8, ACOT9, ACOX1, ACOX2, ACOX3, ACOXL, ACP1, ACP2, ACP4, ACP5, ACP6, ACP7, ACPP, ACR, ACRBP, ACRV1, ACSBG1, ACSBG2, ACSF2, ACSF3, ACSL1, ACSL3, ACSL4, ACSL5, ACSL6, ACSM1, ACSM2A, ACSM2B, ACSM3, ACSM4, ACSM5, ACSM6, ACSS1, ACSS2, ACSS3, ACTA1, ACTA2, ACTB, ACTBL2, ACTC1, ACTG1, ACTG2, ACTL10, ACTL6A, ACTL6B, ACTL7A, ACTL7B, ACTL8, ACTL9, ACTN1, ACTN2, ACTN3, ACTN4, ACTR10, ACTRIA, ACTRIB, ACTR2, ACTR3, ACTR3B, ACTR3C, ACTR5, ACTR6, ACTR8, ACTRT1, ACTRT2, ACTRT3, ACVR1, ACVR1B, ACVR1C, ACVR2A, ACVR2B, ACVRL1, ACY1, ACY3, ACYP1, ACYP2, AD000671.1, AD000671.2, ADA, ADA2, ADAD1, ADAD2, ADAL, ADAM10, ADAM11, ADAM12, ADAM15, ADAM17, ADAM18, ADAM19, ADAM2, ADAM20, ADAM21, ADAM22, ADAM23, ADAM28, ADAM29, ADAM30, ADAM32, ADAM33, ADAM7, ADAM8, ADAM9, ADAMDEC1, ADAMTS1, ADAMTS10, ADAMTS12, ADAMTS13, ADAMTS14, ADAMTS15, ADAMTS16, ADAMTS17, ADAMTS18, ADAMTS19, ADAMTS2, ADAMTS20, ADAMTS3, ADAMTS4, ADAMTS5, ADAMTS6, ADAMTS7, ADAMTS8, ADAMTS9, ADAMTSL1, ADAMTSL2, ADAMTSL3, ADAMTSL4, ADAMTSL5, ADAP1, ADAP2, ADAR, ADARB1, ADARB2, ADAT1, ADAT2, ADAT3, ADCK1, ADCK2, ADCK5, ADCY1, ADCY10, ADCY2, ADCY3, ADCY4, ADCY5, ADCY6, ADCY7, ADCY8, ADCY9, ADCYAP1, ADCYAP1R[1], ADD1, ADD2, ADD3, ADGB, ADGRA1, ADGRA2, ADGRA3, ADGRB1, ADGRB2, ADGRB3, ADGRD1, ADGRD2, ADGRE1, ADGRE2, ADGRE3, ADGRE5, ADGRF1, ADGRF2, ADGRF3, ADGRF4, ADGRF5, ADGRG1, ADGRG2, ADGRG3, ADGRG4, ADGRG5, ADGRG6, ADGRG7, ADGRL1, ADGRL2, ADGRL3, ADGRL4, ADGRV1, ADH1A, ADH1B, ADH1C, ADH4, ADH5, ADH6, ADH7, ADHFE1, ADI1, ADIG, ADIPOQ, ADIPOR1, ADIPOR2, ADIRF, ADK, ADM, ADM2, ADM5, ADNP, ADNP2, ADO, ADORA1, ADORA2A, ADORA2B, ADORA3, ADPGK, ADPRH, ADPRHL1, ADPRHL2, ADPRM, ADRA1A, ADRA1B, ADRA1D, ADRA2A, ADRA2B, ADRA2C, ADRB1, ADRB2, ADRB3, ADRM1, ADSL, ADSS, ADSSL1, ADTRP, AEBP1, AEBP2, AEN, AES, AF130351.1, AF241726.2, AFAP1, AFAP1L1, AFAP1L2, AFDN, AFF1, AFF2, AFF3, AFF4, AFG1L, AFG3L2, AFM, AFMID, AFP, AFTPH, AGA, AGAP1, AGAP2, AGAP3, AGAP4, AGAP5, AGAP6, AGAP9, AGBL1, AGBL2, AGBL3, AGBL4, AGBL5, AGER, AGFG1, AGFG2, AGGF1, AGK, AGL, AGMAT, AGMO, AGO1, AGO2, AGO3, AGO4, AGPAT1, AGPAT2, AGPAT3, AGPAT4, AGPAT5, AGPS, AGR2, AGR3, AGRN, AGRP, AGT, AGTPBP1, AGTR1, AGTR2, AGTRAP, AGXT, AGXT2, AHCTF1, AHCY, AHCYL1, AHCYL2, AHDC1, AHI1, AHNAK, AHNAK2, AHR, AHRR, AHSA1, AHSA2, AHSG, AHSP, AICDA, AIDA, AIF1, AIF1L, AIFM1, AIFM2, AIFM3, AIG1, AIM2, AIMP1, AIMP2, AIP, AIPL1, AIRE, AJAP1, AJUBA, AK1, AK2, AK3, AK4, AK5, AK6, AK7, AK8, AK9, AKAIN1, AKAP1, AKAP10, AKAP11, AKAP12, AKAP13, AKAP14, AKAP17A, AKAP2, AKAP3, AKAP4, AKAP5, AKAP6, AKAP7, AKAP8, AKAP8L, AKAP9, AKIP1, AKIRIN1, AKIRIN2, AKNA, AKNAD1, AKR1A1, AKR1B1, AKR1B10, AKR1B15, AKR1C1, AKR1C2, AKR1C3, AKR1C4, AKR1D1, AKR1E2, AKR7A2, AKR7A3, AKR7L, AKT1, AKT1S1, AKT2, AKT3, AKTIP, AL020996.2, AL021154.3, AL021546.1, AL021997.3, AL022238.4, AL022318.4, AL024498.2, AL031708.1, AL032819.3, AL033529.1, AL035425.2, AL035460.1, AL049634.2, AL049650.1, AL049697.1, AL049779.1, AL049839.2, AL049844.1, AL049844.3, AL080251.1, AL096814.1, AL096870.1, AL109810.2, AL109811.4, AL109827.1, AL109936.3, AL109936.4, AL110118.2, AL110118.4, AL117258.1, AL117339.5, AL117348.2, AL121581.1, AL121594.3, AL121722.1, AL121753.1, AL121758.1, AL121845.2, AL121845.3, AL132671.2, AL132780.3, AL133352.1, AL133414.1, AL133414.2, AL136295.1, AL136295.3, AL136295.4, AL136295.5, AL136373.1, AL136531.2, AL138694.1, AL138752.2, AL138826.1, AL139011.2, AL139260.3, AL139300.1, AL139353.1, AL157392.5, AL159163.1, AL160275.1, AL160276.1, AL160396.2, AL161669.4, AL161911.1, AL162231.1, AL162231.3, AL163195.3, AL163636.2, AL353572.3, AL353588.1, AL354761.2, AL354822.1, AL355102.2, AL355315.1, AL355860.1, AL355916.3, AL355987.1, AL355987.3, AL356585.9, AL357673.1, AL358075.4, AL359736.1, AL359736.3, AL359922.1, AL360181.3, AL360181.5, AL365205.1, AL365214.3, AL365232.1, AL365273.2, AL391650.1, AL449266.1, AL451007.3, AL512428.1, AL512506.3, AL512785.2, AL513165.2, AL513523.10, AL513523.9, AL583836.1, AL589666.1, AL590132.1, AL590560.1, AL591806.3, AL592183.1, AL592490.1, AL593848.2, AL603832.3, AL645922.1, AL645941.2, AL662828.1, AL662852.6, AL662899.1, AL662899.2, AL662899.3, AL669918.1, AL672043.1, AL672142.1, AL691442.1, AL713999.1, AL772284.2, AL807752.6, AL807752.7, AL844853.2, AL845331.2, AL845464.1, AL928654.4, AL929554.1, AL929561.7, ALAD, ALAS1, ALAS2, ALB, ALCAM, ALDH16A1, ALDH18A1, ALDH1A1, ALDH1A2, ALDH1A3, ALDH1B1, ALDH1L1, ALDH1L2, ALDH2, ALDH3A1, ALDH3A2, ALDH3B1, ALDH3B2, ALDH4A1, ALDH5A1, ALDH6A1, ALDH7A1, ALDH8A1, ALDH9A1, ALDOA, ALDOB, ALDOC, ALG1, ALG10, ALG10B, ALG11, ALG12, ALG13, ALG14, ALG1L, ALG1L2, ALG2, ALG3, ALG5, ALG6, ALG8, ALG9, ALK, ALKAL1, ALKAL2, ALKBH1, ALKBH2, ALKBH3, ALKBH4, ALKBH5, ALKBH6, ALKBH7, ALKBH8, ALLC, ALMS1, ALOX12, ALOX12B, ALOX15, ALOX15B, ALOX5, ALOX5AP, ALOXE3, ALPI, ALPK1, ALPK2, ALPK3, ALPL, ALPP, ALPPL2, ALS2, ALS2CL, ALS2CR12, ALX1, ALX3, ALX4, ALYREF, AMACR, AMBN, AMBP, AMBRA1, AMD1, AMDHD1, AMDHD2, AMELX, AMELY, AMER1, AMER2, AMER3, AMFR, AMH, AMHR2, AMIGO1, AMIGO2, AMIGO3, AMMECR1, AMMECR1L, AMN, AMN1, AMOT, AMOTL1, AMOTL2, AMPD1, AMPD2, AMPD3, AMPH, AMT, AMTN, AMY1A, AMY1B, AMY1C, AMY2A, AMY2B, AMZ1, AMZ2, ANAPC1, ANAPC10, ANAPC11, ANAPC13, ANAPC15, ANAPC16, ANAPC2, ANAPC4, ANAPC5, ANAPC7, ANG, ANGEL1, ANGEL2, ANGPT1, ANGPT2, ANGPT4, ANGPTL1, ANGPTL2, ANGPTL3, ANGPTL4, ANGPTL5, ANGPTL6, ANGPTL7, ANGPTL8, ANHX, ANK1, ANK2, ANK3, ANKAR, ANKDD1A, ANKDD1B, ANKEF1, ANKFN1, ANKFY1, ANKH, ANKHD1, ANKHD1-EIF4EBP3, ANKIB1, ANKK1, ANKLE1, ANKLE2, ANKMY1, ANKMY2, ANKRA2, ANKRD1, ANKRD10, ANKRD11, ANKRD12, ANKRD13A, ANKRD13B, ANKRD13C, ANKRD13D, ANKRD16, ANKRD17, ANKRD18A, ANKRD18B, ANKRD2, ANKRD20A1, ANKRD20A2, ANKRD20A3, ANKRD20A4, ANKRD20A8P, ANKRD22, ANKRD23, ANKRD24, ANKRD26, ANKRD27, ANKRD28, ANKRD29, ANKRD30A, ANKRD30B, ANKRD30BL, ANKRD31, ANKRD33, ANKRD33B, ANKRD34A, ANKRD34B, ANKRD34C, ANKRD35, ANKRD36, ANKRD36B, ANKRD36C, ANKRD37, ANKRD39, ANKRD40, ANKRD42, ANKRD44, ANKRD45, ANKRD46, ANKRD49, ANKRD50, ANKRD52, ANKRD53, ANKRD54, ANKRD55, ANKRD6, ANKRD60, ANKRD61, ANKRD62, ANKRD63, ANKRD65, ANKRD66, ANKRD7, ANKRD9, ANKS1A, ANKS1B, ANKS3, ANKS4B, ANKS6, ANKUB1, ANKZF1, ANLN, ANO1, ANO10, ANO2, ANO3, ANO4, ANO5, ANO6, ANO7, ANO8, ANO9, ANOS1, ANP32A, ANP32B, ANP32D, ANP32E, ANPEP, ANTXR1, ANTXR2, ANTXRL, ANXA1, ANXA10, ANXA11, ANXA13, ANXA2, ANXA2R, ANXA3, ANXA4, ANXA5, ANXA6, ANXA7, ANXA8, ANXA8L1, ANXA9, AOAH, AOC1, AOC2, AOC3, AOX1, AP000275.2, AP000295.1, AP000311.1, AP000322.1, AP000349.1, AP000350.12, AP000350.4, AP000351.3, AP000351.7, AP000721.1, AP000781.2, AP001160.5, AP001273.2, AP001458.2, AP001781.3, AP001931.1, AP002360.1, AP002373.1, AP002495.1, AP002512.3, AP002512.4, AP002748.4, AP002990.1, AP003071.5, AP003108.2, AP003419.2, AP004243.1, AP006285.3, AP1AR, AP1B1, AP1G1, AP1G2, AP1M1, AP1M2, AP1S1, AP1S2, AP1S3, AP2A1, AP2A2, AP2B1, AP2M1, AP2S1, AP3B1, AP3B2, AP3D1, AP3M1, AP3M2, AP3S1, AP3S2, AP4B1, AP4E1, AP4M1, AP4S1, AP5B1, AP5M1, AP5S1, AP5Z1, APAF1, APBA1, APBA2, APBA3, APBB1, APBBIP, APBB2, APBB3, APC, APC2, APCDD1, APCDD1L, APCS, APEH, APELA, APEX1, APEX2, APH1A, APH1B, APIS, APIP, APLF, APLN, APLNR, APLP1, APLP2, APMAP, APOA1, APOA2, APOA4, APOA5, APOB, APOBEC1, APOBEC2, APOBEC3A, APOBEC3B, APOBEC3C, APOBEC3D, APOBEC3F, APOBEC3G, APOBEC3H, APOBEC4, APOBR, APOC1, APOC2, APOC3, APOC4, APOC4-APOC2, APOD, APOE, APOF, APOH, APOL1, APOL2, APOL3, APOL4, APOL, APOL6, APOLD1, APOM, APOO, APOOL, APOPT1, APP, APPBP2, APPL1, APPL2, APRT, APTX, AQP1, AQP10, AQP11, AQP12A, AQP12B, AQP2, AQP3, AQP4, AQP5, AQP6, AQP7, AQP8, AQP9, AQR, AR, ARAF, ARAP1, ARAP2, ARAP3, ARC, ARCN1, AREG, AREL1, ARF1, ARF3, ARF4, ARF5, ARF6, ARFGAP1, ARFGAP2, ARFGAP3, ARFGEF1, ARFGEF2, ARFGEF3, ARFIP1, ARFIP2, ARFRP1, ARG1, ARG2, ARGFX, ARGLU1, ARHGAP1, ARHGAP10, ARHGAP11A, ARHGAP11B, ARHGAP12, ARHGAP15, ARHGAP17, ARHGAP18, ARHGAP19, ARHGAP19-SLIT1, ARHGAP20, ARHGAP21, ARHGAP22, ARHGAP23, ARHGAP24, ARHGAP25, ARHGAP26, ARHGAP27, ARHGAP28, ARHGAP29, ARHGAP30, ARHGAP31, ARHGAP32, ARHGAP33, ARHGAP35, ARHGAP36, ARHGAP39, ARHGAP4, ARHGAP40, ARHGAP42, ARHGAP44, ARHGAP45, ARHGAP5, ARHGAP6, ARHGAP8, ARHGAP9, ARHGDIA, ARHGDIB, ARHGDIG, ARHGEF1, ARHGEF10, ARHGEF10L, ARHGEF11, ARHGEF12, ARHGEF15, ARHGEF16, ARHGEF17, ARHGEF18, ARHGEF19, ARHGEF2, ARHGEF25, ARHGEF26, ARHGEF28, ARHGEF3, ARHGEF33, ARHGEF35, ARHGEF37, ARHGEF38, ARHGEF39, ARHGEF4, ARHGEF40, ARHGEF5, ARHGEF6, ARHGEF7, ARHGEF9, ARID1A, ARID1B, ARID2, ARID3A, ARID3B, ARID3C, ARID4A, ARID4B, ARID5A, ARID5B, ARIH1, ARIH2, ARIH2OS, ARL1, ARL10, ARL11, ARL13A, ARL13B, ARL14, ARL14EP, ARL14EPL, ARL15, ARL16, ARL17A, ARL17B, ARL2, ARL2BP, ARL2-SNX15, ARL3, ARL4A, ARL4C, ARL4D, ARL5A, ARL5B, ARL5C, ARL6, ARL6IP1, ARL6IP4, ARL6IP5, ARL6IP6, ARL8A, ARL8B, ARL9, ARMC1, ARMC10, ARMC12, ARMC2, ARMC3, ARMC4, ARMC5, ARMC6, ARMC7, ARMC8, ARMC9, ARMCX1, ARMCX2, ARMCX3, ARMCX4, ARMCX5, ARMCX6, ARMS2, ARMT1, ARNT, ARNT2, ARNTL, ARNTL2, ARPC1A, ARPCIB, ARPC2, ARPC3, ARPC4, ARPC4-TTLL3, ARPC5, ARPC5L, ARPIN, ARPP19, ARPP21, ARR3, ARRB1, ARRB2, ARRDC1, ARRDC2, ARRDC3, ARRDC4, ARRDC5, ARSA, ARSB, ARSD, ARSE, ARSF, ARSG, ARSH, ARSI, ARSJ, ARSK, ART1, ART3, ART4, ART5, ARTN, ARV1, ARVCF, ARX, AS3MT, ASAH1, ASAH2, ASAH2B, ASAP1, ASAP2, ASAP3, ASB1, ASB10, ASB11, ASB12, ASB13, ASB14, ASB15, ASB16, ASB17, ASB18, ASB2, ASB3, ASB4, ASB5, ASB6, ASB7, ASB8, ASB9, ASCC1, ASCC2, ASCC3, ASCL1, ASCL2, ASCL3, ASCL4, ASCL5, ASF1A, ASF1B, ASGR1, ASGR2, ASH1L, ASH2L, ASIC1, ASIC2, ASIC3, ASIC4, ASIC5, ASIP, ASL, ASMT, ASMTL, ASNA1, ASNS, ASNSD1, ASPA, ASPDH, ASPG, ASPH, ASPHD1, ASPHD2, ASPM, ASPN, ASPRV1, ASP-SCR1, ASRGL1, ASS1, ASTE1, ASTL, ASTN1, ASTN2, ASXL1, ASXL2, ASXL3, ASZ1, ATAD1, ATAD2, ATAD2B, ATAD3A, ATAD3B, ATAD3C, ATAD5, ATAT1, ATCAY, ATE1, ATF1, ATF2, ATF3, ATF4, ATF5, ATF6, ATF6B, ATF7, ATF7IP, ATF7IP2, ATG10, ATG101, ATG12, ATG13, ATG14, ATG16L1, ATG16L2, ATG2A, ATG2B, ATG3, ATG4A, ATG4B, ATG4C, ATG4D, ATG5, ATG7, ATG9A, ATG9B, ATIC, ATL1, ATL2, ATL3, ATM, ATMIN, ATN1, ATOH1, ATOH7, ATOH8, ATOX1, ATP1OA, ATP10B, ATP1OD, ATP11A, ATP11B, ATP11C, ATP12A, ATPI3A1, ATPI3A2, ATPI3A3, ATPI3A4, ATPI3A5, ATP1A1, ATP1A2, ATP1A3, ATP1A4, ATP1B1, ATP1B2, ATP1B3, ATP1B4, ATP23, ATP2A1, ATP2A2, ATP2A3, ATP2B1, ATP2B2, ATP2B3, ATP2B4, ATP2C1, ATP2C2, ATP4A, ATP4B, ATP5A1, ATP5B, ATP5C1, ATP5D, ATP5E, ATP5EP2, ATP5F1, ATP5G1, ATP5G2, ATP5G3, ATP5H, ATP5I, ATP5J, ATP5J2, ATP5J2-PTCD1, ATP5L, ATP5L2, ATP50, ATP5S, ATP6AP1, ATP6AP1L, ATP6AP2, ATP6VOA1, ATP6VOA2, ATP6VOA4, ATP6VOB, ATP6VOC, ATP6VOD1, ATP6VOD2, ATP6VOE1, ATP6VOE2, ATP6V1A, ATP6V1B1, ATP6V1B2, ATP6V1C1, ATP6V1C2, ATP6V1D, ATP6V1E1, ATP6V1E2, ATP6V1F, ATP6V1G1, ATP6V1G2, ATP6V1G2-DDX39B, ATP6V1G3, ATP6V1H, ATP7A, ATP7B, ATP8A1, ATP8A2, ATP8B1, ATP8B2, ATP8B3, ATP8B4, ATP9A, ATP9B, ATPAF1, ATPAF2, ATPIF1, ATR, ATRAID, ATRIP, ATRN, ATRNL1, ATRX, ATXN1, ATXN10, ATXN1L, ATXN2, ATXN2L, ATXN3, ATXN3L, ATXN7, ATXN7L1, ATXN7L2, ATXN7L3, ATXN7L3B, AUH, AUNIP, AUP1, AURKA, AURKAIP, AURKB, AURKC, AUTS2, AVEN, AVIL, AVL9, AVP, AVPI1, AVPR1A, AVPR1B, AVPR2, AWAT1, AWAT2, AXDND1, AXIN1, AXIN2, AXL, AZGP1, AZI2, AZIN1, AZIN2, AZU1, B2M, B3GALNT1, B3GALNT2, B3GALT1, B3GALT2, B3GALT4, B3GALT5, B3GALT6, B3GAT1, B3GAT2, B3GAT3, B3GLCT, B3GNT2, B3GNT3, B3GNT4, B3GNT5, B3GNT6, B3GNT7, B3GNT8, B3GNT9, B3GNTL1, B4GALNT1, B4GALNT2, B4GALNT3, B4GALNT4, B4GALT1, B4GALT2, B4GALT3, B4GALT4, B4GALT5, B4GALT6, B4GALT7, B4GAT1, B9D1, B9D2, BAALC, BAAT, BABAM, BABAM2, BACE1, BACE2, BACH1, BACH2, BAD, BAG1, BAG2, BAG3, BAG4, BAG5, BAG6, BAGE3, BAHCC1, BAHD1, BAIAP2, BAIAP2L1, BAIAP2L2, BAIAP3, BAK1, BAMBI, BANF1, BANF2, BANK1, BANP, BAP1, BARD1, BARHL1, BARHL2, BARX1, BARX2, BASP1, BATF, BATF2, BATF3, BAX, BAZ1A, BAZ1B, BAZ2A, BAZ2B, BBC3, BBIP1, BBOF1, BBOX1, BBS1, BBS10, BBS12, BBS2, BBS4, BBS5, BBS7, BBS9, BBX, BCAM, BCAN, BCAP29, BCAP31, BCAR1, BCAR3, BCAS1, BCAS2, BCAS3, BCAS4, BCAT1, BCAT2, BCCIP, BCDIN3D, BCHE, BCKDHA, BCKDHB, BCKDK, BCL10, BCL11A, BCL11B, BCL2, BCL2A1, BCL2L1, BCL2L10, BCL2L11, BCL2L12, BCL2L13, BCL2L14, BCL2L15, BCL2L2, BCL2L2-PABPN1, BCL3, BCL6, BCL6B, BCL7A, BCL7B, BCL7C, BCL9, BCL9L, BCLAF1, BCLAF3, BCO1, BCO2, BCOR, BCORL1, BCR, BCS1L, BDH1, BDH2, BDKRB1, BDKRB2, BDNF, BDP1, BEAN1, BECN1, BECN2, BEGAIN, BEND2, BEND3, BEND4, BEND5, BEND6, BEND7, BEST1, BEST2, BEST3, BEST4, BET1, BET1L, BEX1, BEX2, BEX3, BEX4, BEX5, BFAR, BFSP1, BFSP2, BGLAP, BGN, BHLHA15, BHLHA9, BHLHB9, BHLHE22, BHLHE23, BHLHE40, BHLHE41, BHMG1, BHMT, BHMT2, BICC1, BICD1, BICD2, BICDL1, BICDL2, BICRA, BICRAL, BID, BIK, BIN1, BIN2, BIN3, BIRC2, BIRC3, BIRC5, BIRC6, BIRC7, BIRC8, BIVM, BIVM-ERCC5, BLACE, BLCAP, BLID, BLK, BLM, BLMH, BLNK, BLOC1S1, BLOC1S2, BLOC1S3, BLOC1S4, BLOC1S5, BLOC1S5-TXNDC5, BLOC1S6, BLVRA, BLVRB, BLZF1, BMF, BM1, BMP1, BMP10, BMP15, BMP2, BMP2K, BMP3, BMP4, BMP5, BMP6, BMP7, BMP8A, BMP8B, BMPER, BMPR1A, BMPR1B, BMPR2, BMS1, BMT2, BMX, BNC1, BNC2, BNIP1, BNIP2, BNIP3, BNIP3L, BNIPL, BOC, BOD1, BOD1L1, BOD1L2, BOK, BOLA1, BOLA2, BOLA2B, BOLA2-SMG1P6, BOLA3, BOLL, BOP1, BORA, BORCS5, BORCS6, BORCS7, BORCS7-ASMT, BORCS8, BORCS8-MEF2B, BPGM, BPHL, BPI, BPIFA1, BPIFA2, BPIFA3, BPIFB1, BPIFB2, BPIFB3, BPIFB4, BPIFB6, BPIFC, BPNT1, BPTF, BPY2, BPY2B, BPY2C, BRAF, BRAP, BRAT1, BRCA1, BRCA2, BRCC3, BRD1, BRD2, BRD3, BRD4, BRD7, BRD8, BRD9, BRDT, BRF1, BRF2, BRI3, BRI3BP, BRICD5, BRINP1, BRINP2, BRINP3, BRIP1, BRIX, BRK1, BRMS1, BRMS1L, BROX, BRPF1, BRPF3, BRS3, BRSK1, BRSK2, BRWD1, BRWD3, BSCL2, BSDC1, BSG, BSN, BSND, BSPH1, BSPRY, BST1, BST2, BSX, BTAF1, BTBD1, BTBD10, BTBD11, BTBD16, BTBD17, BTBD18, BTBD19, BTBD2, BTBD3, BTBD6, BTBD7, BTBD8, BTBD9, BTC, BTD, BTF3, BTF3L4, BTG1, BTG2, BTG3, BTG4, BTK, BTLA, BTN1A1, BTN2A1, BTN2A2, BTN3A1, BTN3A2, BTN3A3, BTNL2, BTNL3, BTNL8, BTNL9, BTRC, BUB1, BUB1B, BUB1B-PAK6, BUB3, BUD13, BUD23, BUD31, BVES, BX004987.1, BX072566.1, BX088645.1, BX248244.1, BX248413.4, BX248415.1, BX248516.1, BX276092.9, BYSL, BZW1, BZW2, C10orf10, C10orf105, C10orf107, C10orf113, C10orf120, C10orf126, C10orf128, C10orf142, C10orf35, C10orf53, C10orf55, C10orf62, C10orf67, C10orf71, C10orf76, C10orf82, C10orf88, C10orf90, C10orf95, C10orf99, C11orf1, C11orf16, C11orf21, C11orf24, C11orf40, C11orf42, C11orf45, C11orf49, C11orf52, C11orf53, C11orf54, C11orf57, C11orf58, C11orf63, C11orf65, C11orf68, C11orf70, C11orf71, C11orf74, C11orf80, C11orf84, C11orf86, C11orf87, C11orf88, C11orf91, C11orf94, C11orf95, C11orf96, C11orf97, C11orf98, C12orf10, C12orf29, C12orf4, C12orf40, C12orf42, C12orf43, C12orf45, C12orf49, C12orf50, C12orf54, C12orf56, C12orf57, C12orf60, C12orf65, C12orf66, C12orf71, C12orf73, C12orf74, C12orf75, C12orf76, C13orf42, C14orf105, C14orf119, C14orf132, C14orf159, C14orf166, C14orf177, C14orf178, C14orf180, C14orf2, C14orf28, C14orf37, C14orf39, C14orf79, C14orf80, C14orf93, C15orf38-AP3S2, C15orf39, C15orf40, C15orf41, C15orf48, C15orf52, C15orf53, C15orf59, C15orf61, C15orf62, C15orf65, C16orf45, C16orf46, C16orf52, C16orf54, C16orf58, C16orf59, C16orf62, C16orf70, C16orf71, C16orf72, C16orf74, C16orf78, C16orf82, C16orf86, C16orf87, C16orf89, C16orf90, C16orf91, C16orf92, C16orf95, C16orf96, C17orf100, C17orf105, C17orf107, C17orf113, C17orf47, C17orf49, C17orf50, C17orf51, C17orf53, C17orf58, C17orf62, C17orf64, C17orf67, C17orf74, C17orf75, C17orf77, C17orf78, C17orf80, C17orf97, C17orf98, C17orf99, C18orf21, C18orf25, C18orf32, C18orf54, C18orf63, C18orf8, C19orf12, C19orf18, C19orf24, C19orf25, C19orf33, C19orf35, C19orf38, C19orf44, C19orf47, C19orf48, C19orf53, C19orf54, C19orf57, C19orf60, C19orf66, C19orf67, C19orf68, C19orf70, C19orf71, C19orf73, C19orf81, C19orf84, C1D, C1GALT1, C1GALT1C1, C1GALT1C1L, C1orf100, C1orf105, C1orf109, C1orf112, C1orf115, C1orf116, C1orf122, C1orf123, C1orf127, C1orf131, C1orf141, C1orf146, C1orf158, C1orf159, C1orf162, C1orf167, C1orf174, C1orf185, C1orf186, C1orf189, C1orf194, C1orf198, C1orf21, C1orf210, C1orf216, C1orf226, C1orf228, C1orf232, C1orf27, C1orf35, C1orf43, C1orf50, C1orf52, C1orf53, C1orf54, C1orf56, C1orf61, C1orf64, C1orf68, C1orf74, C1orf87, C1orf94, C1QA, C1QB, C1QBP, C1QC, C1QL1, C1QL2, C1QL3, C1QL4, C1QTNF1, C1QTNF12, C1QTNF2, C1QTNF3, C1QTNF3-AMACR, C1QTNF4, C1QTNF5, C1QTNF6, C1QTNF7, C1QTNF8, C1QTNF9, C1QTNF9B, C1R, C1RL, C1S, C2, C20orf141, C20orf144, C20orf173, C20orf194, C20orf96, C20orf202, C20orf204, C20orf24, C20orf27, C20orf85, C20orf96, C21orf140, C21orf2, C21orf33, C21orf58, C21orf59, C21orf62, C21orf91, C22orf15, C22orf23, C22orf31, C22orf39, C22orf42, C22orf46, C2CD2, C2CD2L, C2CD3, C2CD4A, C2CD4B, C2CD4C, C2CD4D, C2CD5, C2CD6, C2orf15, C2orf16, C2orf40, C2orf42, C2orf49, C2orf50, C2orf54, C2orf66, C2orf68, C2orf69, C2orf70, C2orf71, C2orf72, C2orf73, C2orf74, C2orf76, C2orf78, C2orf80, C2orf81, C2orf82, C2orf83, C2orf88, C2orf91, C3, C3AR1, C3orf14, C3orf18, C3orf20, C3orf22, C3orf30, C3orf33, C3orf35, C3orf36, C3orf38, C3orf49, C3orf52, C3orf56, C3orf58, C3orf62, C3orf67, C3orf70, C3orf80, C3orf84, C3orf85, C4A, C4B, C4B_2, C4BPA, C4BPB, C4orf17, C4orf19, C4orf22, C4orf26, C4orf3, C4orf32, C4orf33, C4orf36, C4orf45, C4orf46, C4orf47, C4orf48, C4orf50, C4orf51, C5, C5AR1, C5AR2, C5orf15, C5orf22, C5orf24, C5orf30, C5orf34, C5orf38, C5orf42, C5orf46, C5orf47, C5orf49, C5orf51, C5orf52, C5orf56, C5orf58, C5orf60, C5orf63, C5orf67, C6, C6orf10, C6orf106, C6orf118, C6orf120, C6orf132, C6orf136, C6orf141, C6orf15, C6orf163, C6orf201, C6orf203, C6orf222, C6orf223, C6orf226, C6orf229, C6orf47, C6orf48, C6orf52, C6orf58, C6orf62, C6orf89, C7, C7orf25, C7orf26, C7orf31, C7orf33, C7orf34, C7orf43, C7orf49, C7orf50, C7orf55-LUC7L2, C7orf57, C7orf61, C7orf72, C7orf73, C7orf77, C8A, C8B, C8G, C8orf22, C8orf33, C8orf34, C8orf37, C8orf4, C8orf44, C8orf44-SGK3, C8orf46, C8orf48, C8orf58, C8orf59, C8orf74, C8orf76, C8orf82, C8orf86, C8orf88, C8orf89, C9, C9orf116, C9orf129, C9orf131, C9orf135, C9orf152, C9orf153, C9orf16, C9orf172, C9orf24, C9orf3, C9orf40, C9orf43, C9orf47, C9orf50, C9orf57, C9orf64, C9orf66, C9orf72, C9orf78, C9orf84, C9orf85, C9orf92, CA1, CA10, CA11, CA12, CA13, CA14, CA2, CA3, CA4, CA5A, CA5B, CA6, CA7, CA8, CA9, CAAP1, CAB39, CAB39L, CABIN1, CABLES1, CABLES2, CABP1, CABP2, CABP4, CABP5, CABP7, CABS1, CABYR, CACFD1, CACHD1, CACNA1A, CACNA1B, CACNA1C, CACNA1D, CACNA1E, CACNA1F, CACNA1G, CACNA1H, CACNA1I, CACNA1S, CACNA2D1, CACNA2D2, CACNA2D3, CACNA2D4, CACNB1, CACNB2, CACNB3, CACNB4, CACNG1, CACNG2, CACNG3, CACNG4, CACNG5, CACNG6, CACNG7, CACNG8, CACTIN, CACUL1, CACYBP, CAD, CADM1, CADM2, CADM3, CADM4, CADPS, CADPS2, CAGE1, CALB1, CALB2, CALCA, CALCB, CALCOCO1, CALCOCO2, CALCR, CALCRL, CALD1, CALHM1, CALHM2, CALHM3, CALM1, CALM2, CALM3, CALML3, CALML4, CALML5, CALML6, CALN1, CALR, CALR3, CALU, CALY, CAMK1, CAMK1D, CAMK1G, CAMK2A, CAMK2B, CAMK2D, CAMK2G, CAMK2N1, CAMK2N2, CAMK4, CAMKK1, CAMKK2, CAMKMT, CAMKV, CAMLG, CAMP, CAMSAP1, CAMSAP2, CAMSAP3, CAMTA1, CAMTA2, CAND1, CAND2, CANT1, CANX, CAP1, CAP2, CAPG, CAPN1, CAPN10, CAPN11, CAPN12, CAPN13, CAPN14, CAPN15, CAPN2, CAPN3, CAPN5, CAPN6, CAPN7, CAPN8, CAPN9, CAPNS1, CAPNS2, CAPRIN1, CAPRIN2, CAPS, CAPS2, CAPSL, CAPZA1, CAPZA2, CAPZA3, CAPZB, CARD10, CARD11, CARD14, CARD16, CARD17, CARD18, CARD19, CARD6, CARD8, CARD9, CARF, CARHSP1, CARM1, CARMIL1, CARMIL2, CARMIL3, CARNMT1, CARNS1, CARS, CARS2, CARTPT, CASC1, CASC10, CASC3, CASC4, CASD1, CASK, CASKIN1, CASKIN2, CASP1, CASP10, CASP12, CASP14, CASP2, CASP3, CASP4, CASP5, CASP6, CASP7, CASP8, CASP8AP2, CASP9, CASQ1, CASQ2, CASR, CASS4, CAST, CASTOR1, CASTOR2, CASZ1, CAT, CATIP, CATSPER1, CATSPER2, CATSPER3, CATSPER4, CATSPERB, CATSPERD, CATSPERE, CATSPERG, CATSPERZ, CAV1, CAV2, CAV3, CAVIN1, CAVIN2, CAVIN3, CAVIN4, CBARP, CBFA2T2, CBFA2T3, CBFB, CBL, CBLB, CBLC, CBLL1, CBLN1, CBLN2, CBLN3, CBLN4, CBR1, CBR3, CBR4, CBS, CBSL, CBWD1, CBWD2, CBWD3, CBWD5, CBWD6, CBX1, CBX2, CBX3, CBX4, CBX5, CBX6, CBX7, CBX8, CBY1, CBY3, CC2D1A, CC2D1B, CC2D2A, CC2D2B, CCAR1, CCAR2, CCBE1, CCDC102A, CCDC102B, CCDC103, CCDC105, CCDC106, CCDC107, CCDC110, CCDC112, CCDC113, CCDC114, CCDC115, CCDC116, CCDC117, CCDC12, CCDC120, CCDC121, CCDC122, CCDC124, CCDC125, CCDC126, CCDC127, CCDC129, CCDC13, CCDC130, CCDC134, CCDC136, CCDC137, CCDC138, CCDC14, CCDC140, CCDC141, CCDC142, CCDC144A, CCDC144NL, CCDC146, CCDC148, CCDC149, CCDC15, CCDC150, CCDC151, CCDC152, CCDC153, CCDC154, CCDC155, CCDC157, CCDC158, CCDC159, CCDC160, CCDC163, CCDC166, CCDC167, CCDC168, CCDC169, CCDC169-SOHLH2, CCDC17, CCDC170, CCDC171, CCDC172, CCDC173, CCDC174, CCDC175, CCDC177, CCDC178, CCDC179, CCDC18, CCDC180, CCDC181, CCDC182, CCDC183, CCDC184, CCDC185, CCDC186, CCDC187, CCDC188, CCDC189, CCDC190, CCDC191, CCDC192, CCDC194, CCDC195, CCDC196, CCDC197, CCDC22, CCDC24, CCDC25, CCDC27, CCDC28A, CCDC28B, CCDC3, CCDC30, CCDC32, CCDC33, CCDC34, CCDC36, CCDC38, CCDC39, CCDC40, CCDC42, CCDC43, CCDC47, CCDC50, CCDC51, CCDC54, CCDC57, CCDC58, CCDC59, CCDC6, CCDC60, CCDC61, CCDC62, CCDC63, CCDC65, CCDC66, CCDC68, CCDC69, CCDC7, CCDC70, CCDC71, CCDC71L, CCDC73, CCDC74A, CCDC74B, CCDC77, CCDC78, CCDC8, CCDC80, CCDC81, CCDC82, CCDC83, CCDC84, CCDC85A, CCDC85B, CCDC85C, CCDC86, CCDC87, CCDC88A, CCDC88B, CCDC88C, CCDC89, CCDC9, CCDC90B, CCDC91, CCDC92, CCDC93, CCDC94, CCDC96, CCDC97, CCER1, CCER2, CCHCR1, CCIN, CCK, CCKAR, CCKBR, CCL1, CCL11, CCL13, CCL14, CCL15, CCL15-CCL14, CCL16, CCL17, CCL18, CCL19, CCL2, CCL20, CCL21, CCL22, CCL23, CCL24, CCL25, CCL26, CCL27, CCL28, CCL3, CCL3L1, CCL3L3, CCL4, CCL4L2, CCL5, CCL7, CCL8, CCM2, CCM2L, CCNA1, CCNA2, CCNB1, CCNB1IP1, CCNB2, CCNB3, CCNC, CCND1, CCND2, CCND3, CCNDBP1, CCNE1, CCNE2, CCNF, CCNG1, CCNG2, CCNH, CCNI, CCNI2, CCNJ, CCNJL, CCNK, CCNL1, CCNL2, CCNO, CCNT1, CCNT2, CCNY, CCNYL1, CCP110, CCPG1, CCR1, CCR10, CCR2, CCR3, CCR4, CCR5, CCR6, CCR7, CCR8, CCR9, CCRL2, CCS, CCSAP, CCSER1, CCSER2, CCT2, CCT3, CCT4, CCT5, CCT6A, CCT6B, CCT7, CCT8, CCT8L2, CCZ1, CCZ1B, CD101, CD109, CD14, CD151, CD160, CD163, CD163L1, CD164, CD164L2, CD177, CD180, CD19, CD1A, CD1B, CD1C, CD1D, CD1E, CD2, CD200, CD200R1, CD200R1L, CD207, CD209, CD22, CD226, CD24, CD244, CD247, CD248, CD27, CD274, CD276, CD28, CD2AP, CD2BP2, CD300A, CD300C, CD300E, CD300LB, CD300LD, CD300LF, CD300LG, CD302, CD320, CD33, CD34, CD36, CD37, CD38, CD3D, CD3E, CD3EAP, CD3G, CD4, CD40, CD40LG, CD44, CD46, CD47, CD48, CD5, CD52, CD53, CD55, CD58, CD59, CD5L, CD6, CD63, CD68, CD69, CD7, CD70, CD72, CD74, CD79A, CD79B, CD80, CD81, CD82, CD83, CD84, CD86, CD8A, CD8B, CD9, CD93, CD96, CD99, CD99L2, CDA, CDADC1, CDAN1, CDC123, CDC14A, CDC14B, CDC16, CDC20, CDC20B, CDC23, CDC25A, CDC25B, CDC25C, CDC26, CDC27, CDC34, CDC37, CDC37L1, CDC40, CDC42, CDC42BPA, CDC42BPB, CDC42BPG, CDC42EP1, CDC42EP2, CDC42EP3, CDC42EP4, CDC42EP5, CDC42SE1, CDC42SE2, CDC45, CDC5L, CDC6, CDC7, CDC73, CDCA2, CDCA3, CDCA4, CDCA5, CDCA7, CDCA7L, CDCA8, CDCP1, CDCP2, CDH1, CDH10, CDH11, CDH12, CDH13, CDH15, CDH16, CDH17, CDH18, CDH19, CDH2, CDH20, CDH22, CDH23, CDH24, CDH26, CDH3, CDH4, CDH5, CDH6, CDH7, CDH8, CDH9, CDHR1, CDHR2, CDHR3, CDHR4, CDHR5, CDIP1, CDIPT, CDK1, CDK10, CDK11A, CDK11B, CDK12, CDK13, CDK14, CDK15, CDK16, CDK17, CDK18, CDK19, CDK2, CDK20, CDK2AP1, CDK2AP2, CDK3, CDK4, CDK5, CDK5R1, CDK5R2, CDK5RAP1, CDK5RAP2, CDK5RAP3, CDK6, CDK7, CDK8, CDK9, CDKAL1, CDKL1, CDKL2, CDKL3, CDKL4, CDKL5, CDKN1A, CDKN1B, CDKN1C, CDKN2A, CDKN2AIP, CDKN2AIPNL, CDKN2B, CDKN2C, CDKN2D, CDKN3, CDNF, CDO1, CDON, CDPF1, CDR1, CDR2, CDR2L, CDRT1, CDRT15, CDRT15L2, CDRT4, CDS1, CDS2, CDSN, CDT1, CDV3, CDX1, CDX2, CDX4, CDY1, CDY1B, CDY2A, CDY2B, CDYL, CDYL2, CEACAM1, CEACAM16, CEACAM19, CEACAM20, CEACAM21, CEACAM3, CEACAM4, CEACAM5, CEACAM6, CEACAM7, CEACAM8, CEBPA, CEBPB, CEBPD, CEBPE, CEBPG, CEBPZ, CEBPZOS, CECR2, CEL, CELA1, CELA2A, CELA2B, CELA3A, CELA3B, CELF1, CELF2, CELF3, CELF4, CELF5, CELF6, CELSR1, CELSR2, CELSR3, CEMIP, CEMP1, CEND1, CENPA, CENPB, CENPBD1, CENPC, CENPE, CENPF, CENPH, CENPI, CENPJ, CENPK, CENPL, CENPM, CENPN, CENPO, CENPP, CENPQ, CENPS, CENPS-CORT, CENPT, CENPU, CENPV, CENPVL1, CENPVL2, CENPVL3, CENPW, CENPX, CEP104, CEP112, CEP120, CEP126, CEP128, CEP131, CEP135, CEP152, CEP162, CEP164, CEP170, CEP170B, CEP19, CEP192, CEP250, CEP290, CEP295, CEP295NL, CEP350, CEP41, CEP44, CEP55, CEP57, CEP57L1, CEP63, CEP68, CEP70, CEP72, CEP76, CEP78, CEP83, CEP85, CEP85L, CEP89, CEP95, CEP97, CEPT1, CER1, CERCAM, CERK, CERKL, CERS1, CERS2, CERS3, CERS4, CERS5, CERS6, CES1, CES2, CES3, CES4A, CESSA, CETN1, CETN2, CETN3, CETP, CFAP100, CFAP126, CFAP157, CFAP161, CFAP20, CFAP206, CFAP221, CFAP36, CFAP43, CFAP44, CFAP45, CFAP46, CFAP47, CFAP52, CFAP53, CFAP54, CFAP57, CFAP58, CFAP61, CFAP65, CFAP69, CFAP70, CFAP73, CFAP74, CFAP77, CFAP97, CFAP99, CFB, CFC1, CFC1B, CFD, CFDP1, CFH, CFHR1, CFHR2, CFHR3, CFHR4, CFHR5, CFI, CFL1, CFL2, CFLAR, CFP, CFTR, CGA, CGB1, CGB2, CGB3, CGB5, CGB7, CGB8, CGGBP1, CGN, CGNL1, CGREF1, CGRRF1, CH25H, CHAC1, CHAC2, CHAD, CHADL, CHAF1A, CHAF1B, CHAMP1, CHAT, CHCHD1, CHCHD10, CHCHD2, CHCHD3, CHCHD4, CHCHD5, CHCHD6, CHCHD7, CHD1, CHD1L, CHD2, CHD3, CHD4, CHD5, CHD6, CHD7, CHD8, CHD9, CHDH, CHEK1, CHEK2, CHERP, CHFR, CHGA, CHGB, CHI3L1, CHI3L2, CHIA, CHIC1, CHIC2, CHID1, CHIT1, CHKA, CHKB, CHKB-CPT1B, CHL1, CHM, CHML, CHMP1A, CHMP1B, CHMP2A, CHMP2B, CHMP3, CHMP4A, CHMP4B, CHMP4C, CHMP5, CHMP6, CHMP7, CHN1, CHN2, CHODL, CHORDC1, CHP1, CHP2, CHPF, CHPF2, CHPT1, CHRAC1, CHRD, CHRDL1, CHRDL2, CHRFAM7A, CHRM1, CHRM2, CHRM3, CHRM4, CHRM5, CHRNA1, CHRNA10, CHRNA2, CHRNA3, CHRNA4, CHRNA5, CHRNA6, CHRNA7, CHRNA9, CHRNB1, CHRNB2, CHRNB3, CHRNB4, CHRND, CHRNE, CHRNG, CHST1, CHST10, CHST11, CHST12, CHST13, CHST14, CHST15, CHST2, CHST3, CHST4, CHST5, CHST6, CHST7, CHST8, CHST9, CHSY1, CHSY3, CHTF18, CHTF8, CHTOP, CHUK, CHURC1, CHURC1-FNTB, CIAO1, CIAPIN1, CIART, CIB1, CIB2, CIB3, CIB4, CIC, CIDEA, CIDEB, CIDEC, CIITA, CILP, CILP2, CINP, CIPC, CIR1, CIRBP, CISD1, CISD2, CISD3, CISH, CIT, CITED1, CITED2, CITED4, CIZ1, CKAP2, CKAP2L, CKAP4, CKAP5, CKB, CKLF, CKLF-CMTM1, CKM, CKMT1A, CKMT1B, CKMT2, CKS1B, CKS2, CLASP1, CLASP2, CLASRP, CLC, CLCA1, CLCA2, CLCA4, CLCC1, CLCF1, CLCN1, CLCN2, CLCN3, CLCN4, CLCN5, CLCN6, CLCN7, CLCNKA, CLCNKB, CLDN1, CLDN10, CLDN11, CLDN12, CLDN14, CLDN15, CLDN16, CLDN17, CLDN18, CLDN19, CLDN2, CLDN20, CLDN22, CLDN23, CLDN24, CLDN25, CLDN3, CLDN34, CLDN4, CLDN5, CLDN6, CLDN7, CLDN8, CLDN9, CLDND1, CLDND2, CLEC10A, CLEC11A, CLEC12A, CLEC12B, CLEC14A, CLEC16A, CLEC17A, CLEC18A, CLEC18B, CLEC18C, CLEC19A, CLEC1A, CLECIB, CLEC20A, CLEC2A, CLEC2B, CLEC2D, CLEC2L, CLEC3A, CLEC3B, CLEC4A, CLEC4C, CLEC4D, CLEC4E, CLEC4F, CLEC4G, CLEC4M, CLEC5A, CLEC6A, CLEC7A, CLEC9A, CLECL1, CLGN, CLHC1, CLIC1, CLIC2, CLIC3, CLIC4, CLIC5, CLIC6, CLINT1, CLIP1, CLIP2, CLIP3, CLIP4, CLK1, CLK2, CLK3, CLK4, CLLU1, CLLU1OS, CLMN, CLMP, CLN3, CLN5, CLN6, CLN8, CLNK, CLNS1A, CLOCK, CLP1, CLPB, CLPP, CLPS, CLPSL1, CLPSL2, CLPTM1, CLPTM1L, CLPX, CLRN1, CLRN2, CLRN3, CLSPN, CLSTN1, CLSTN2, CLSTN3, CLTA, CLTB, CLTC, CLTCL1, CLU, CLUAP1, CLUH, CLUL1, CLVS1, CLVS2, CLYBL, CMA1, CMAS, CMBL, CMC1, CMC2, CMC4, CMIP, CMKLR1, CMPK1, CMPK2, CMSS1, CMTM1, CMTM2, CMTM3, CMTM4, CMTM5, CMTM6, CMTM7, CMTM8, CMTR1, CMTR2, CMYA5, CNBD1, CNBD2, CNBP, CNDP1, CNDP2, CNEP1R1, CNFN, CNGA1, CNGA2, CNGA3, CNGA4, CNGB1, CNGB3, CNIH1, CNIH2, CNIH3, CNIH4, CNKSR1, CNKSR2, CNKSR3, CNMD, CNN1, CNN2, CNN3, CNNM1, CNNM2, CNNM3, CNNM4, CNOT1, CNOT10, CNOT11, CNOT2, CNOT3, CNOT4, CNOT6, CNOT6L, CNOT7, CNOT8, CNOT9, CNP, CNPPD1, CNPY, CNPY2, CNPY3, CNPY4, CNR1, CNR2, CNRIP1, CNST, CNTD1, CNTD2, CNTF, CNTFR, CNTLN, CNTN1, CNTN2, CNTN3, CNTN4, CNTN5, CNTN6, CNTNAP1, CNTNAP2, CNTNAP3, CNTNAP3B, CNTNAP4, CNTNAP5, CNTRL, CNTROB, COA1, COA3, COA4, COA5, COA6, COA7, COASY, COBL, COBLL1, COCH, COG1, COG2, COG3, COG4, COG5, COG6, COG7, COG8, COIL, COL10A1, COL11A1, COL11A2, COL12A1, COL13A1, COL14A1, COL15A1, COL16A1, COL17A1, COL18A1, COL19A1, COL1A1, COL1A2, COL20A1, COL21A1, COL22A1, COL23A1, COL24A1, COL25A1, COL26A1, COL27A1, COL28A1, COL2A1, COL3A1, COL4A1, COL4A2, COL4A3, COL4A3BP, COL4A4, COL4A5, COL4A6, COL5A1, COL5A2, COL5A3, COL6A1, COL6A2, COL6A3, COL6A5, COL6A6, COL7A1, COL8A1, COL8A2, COL9A1, COL9A2, COL9A3, COLCA2, COLEC10, COLEC11, COLEC12, COLGALT1, COLGALT2, COLQ, COMMD1, COMMD10, COMMD2, COMMD3, COMMD3-BMI1, COMMD4, COMMD5, COMMD6, COMMD7, COMMD8, COMMD9, COMP, COMT, COMTD1, COPA, COPB1, COPB2, COPE, COPG1, COPG2, COPRS, COPS2, COPS3, COPS4, COPS5, COPS6, COPS7A, COPS7B, COPS8, COPS9, COPZ1, COPZ2, COQ10A, COQ10B, COQ2, COQ3, COQ4, COQ5, COQ6, COQ7, COQ8A, COQ8B, COQ9, CORIN, CORO1A, COROIB, COROIC, CORO2A, CORO2B, CORO6, CORO7, CORO7-PAM16, CORT, COTL1, COX10, COX11, COX14, COX15, COX16, COX17, COX18, COX19, COX20, COX4I1, COX4I2, COX5A, COX5B, COX6A1, COX6A2, COX6B1, COX6B2, COX6C, COX7A1, COX7A2, COX7A2L, COX7B, COX7B2, COX7C, COX8A, COX8C, CP, CPA1, CPA2, CPA3, CPA4, CPA5, CPA6, CPAMD8, CPB1, CPB2, CPD, CPE, CPEB1, CPEB2, CPEB3, CPEB4, CPED1, CPLX1, CPLX2, CPLX3, CPLX4, CPM, CPN1, CPN2, CPNE1, CPNE2, CPNE3, CPNE4, CPNE5, CPNE6, CPNE7, CPNE8, CPNE9, CPO, CPOX, CPPED1, CPQ, CPS1, CPSF1, CPSF2, CPSF3, CPSF4, CPSF4L, CPSF6, CPSF7, CPT1A, CPT1B, CPT1C, CPT2, CPTP, CPVL, CPXCR1, CPXM1, CPXM2, CPZ, CR1, CR1L, CR2, CR354443.1, CR354443.2, CR388407.3, CR547123.3, CR753842.1, CR753845.2, CR759815.2, CR788250.1, CR847794.2, CR854858.1, CR933783.3, CR936239.1, CRABP1, CRABP2, CRACR2A, CRACR2B, CRADD, CRAMP1, CRAT, CRB1, CRB2, CRB3, CRBN, CRCP, CRCT1, CREB1, CREB3, CREB3L1, CREB3L2, CREB3L3, CREB3L4, CREB5, CREBBP, CREBL2, CREBRF, CREBZF, CREG1, CREG2, CRELDI, CRELD2, CREM, CRH, CRHBP, CRHR1, CRHR2, CRIM1, CRIP1, CRIP2, CRIP3, CRIPT, CRISP1, CRISP2, CRISP3, CRISPLD1, CRISPLD2, CRK, CRKL, CRLF1, CRLF2, CRLF3, CRLS1, CRMP1, CRNKL1, CRNN, CROCC, CROCC2, CROT, CRP, CRTAC1, CRTAM, CRTAP, CRTC1, CRTC2, CRTC3, CRX, CRY1, CRY2, CRYAA, CRYAB, CRYBA1, CRYBA2, CRYBA4, CRYBBI, CRYBB2, CRYBB3, CRYBG1, CRYBG2, CRYBG3, CRYGA, CRYGB, CRYGC, CRYGD, CRYGN, CRYGS, CRYL1, CRYM, CRYZ, CRYZL1, CS, CSAD, CSAG1, CSAG2, CSAG3, CSDC2, CSDE1, CSE1L, CSF1, CSF1R, CSF2, CSF2RA, CSF2RB, CSF3, CSF3R, CSGALNACT1, CSGALNACT2, CSH1, CSH2, CSHL1, CSK, CSMD1, CSMD2, CSMD3, CSN1S1, CSN2, CSN3, CSNK1A1, CSNK1A1L, CSNK1D, CSNK1E, CSNK1G1, CSNK1G2, CSNK1G3, CSNK2A1, CSNK2A2, CSNK2A3, CSNK2B, CSPG4, CSPG5, CSPP1, CSRNP1, CSRNP2, CSRNP3, CSRP1, CSRP2, CSRP3, CST1, CST11, CST2, CST3, CST4, CST5, CST6, CST7, CST8, CST9, CST9L, CSTA, CSTB, CSTF1, CSTF2, CSTF2T, CSTF3, CSTL1, CT45A1, CT45A10, CT45A2, CT45A3, CT45A5, CT45A6, CT45A7, CT45A8, CT45A9, CT476828.1, CT476828.10, CT476828.11, CT476828.12, CT476828.13, CT476828.14, CT476828.15, CT476828.16, CT476828.17, CT476828.18, CT476828.19, CT476828.2, CT476828.20, CT476828.21, CT476828.22, CT476828.3, CT476828.4, CT476828.5, CT476828.6, CT476828.7, CT476828.8, CT476828.9, CT47A1, CT47A10, CT47A11, CT47A12, CT47A2, CT47A3, CT47A4, CT47A5, CT47A6, CT47A7, CT47A8, CT47A9, CT47B1, CT55, CT62, CT83, CTAG1A, CTAG1B, CTAG2, CTAGE1, CTAGE15, CTAGE4, CTAGE5, CTAGE6, CTAGE8, CTAGE9, CTBP1, CTBP2, CTBS, CTC1, CTCF, CTCFL, CTDNEP1, CTDP1, CTDSP1, CTDSP2, CTDSPL, CTDSPL2, CTF1, CTGF, CTH, CTHRC1, CTIF, CTLA4, CTNNA1, CTNNA2, CTNNA3, CTNNAL1, CTNNB1, CTNNBIP1, CTNNBL1, CTNND1, CTNND2, CTNS, CTPS1, CTPS2, CTR9, CTRB1, CTRB2, CTRC, CTRL, CTSA, CTSB, CTSC, CTSD, CTSE, CTSF, CTSG, CTSH, CTSK, CTSL, CTSO, CTSS, CTSV, CTSW, CTSZ, CTTN, CTTNBP2, CTTNBP2NL, CTU1, CTU2, CTXN1, CTXN2, CTXN3, CTXND1, CU464060.1, CU633846.1, CU633980.1, CU633980.2, CU639417.1, CU639417.2, CUBN, CUEDC1, CUEDC2, CUL1, CUL2, CUL3, CUL4A, CUL4B, CUL5, CUL7, CUL9, CUTA, CUTC, CUX1, CUX2, CUZD1, CWC15, CWC22, CWC25, CWC27, CWF19L1, CWF19L2, CWH43, CX3CL1, CX3CR1, CXADR, CXCL1, CXCL10, CXCL11, CXCL12, CXCL13, CXCL14, CXCL16, CXCL17, CXCL2, CXCL3, CXCL5, CXCL6, CXCL8, CXCL9, CXCR1, CXCR2, CXCR3, CXCR4, CXCR5, CXCR6, CXorf21, CXorf36, CXorf38, CXorf40A, CXorf40B, CXorf49, CXorf49B, CXorf51A, CXorf51B, CXorf56, CXorf57, CXorf58, CXorf65, CXorf66, CXorf67, CXXC1, CXXC4, CXXC5, CYB561, CYB561A3, CYB561D1, CYB561D2, CYB5A, CYB5B, CYB5D1, CYB5D2, CYB5R$^1$, CYB5R$^2$, CYB5R$^3$, CYB5R$^4$, CYB5RL, CYBA, CYBB, CYBRD1, CYC1, CYCS, CYFIP1, CYFIP2, CYGB, CYHR1, CYLC1, CYLC2, CYLD, CYP11A1, CYP11B1, CYP11B2, CYP17A1, CYP19A1, CYP1A1, CYP1A2, CYP1B1, CYP20A1, CYP21A2, CYP24A1, CYP26A1, CYP26B1, CYP26C1, CYP27A1, CYP27B1, CYP27C1, CYP2A13, CYP2A6, CYP2A7, CYP2B6, CYP2C18, CYP2C19, CYP2C8, CYP2C9, CYP2D6, CYP2D7, CYP2E1, CYP2F1, CYP2J2, CYP2R1, CYP2S1, CYP2U1, CYP2W1, CYP39A1, CYP3A4, CYP3A43, CYP3A5, CYP3A7, CYP3A7-CYP3A51P, CYP46A1, CYP4A11, CYP4A22, CYP4B1, CYP4F11, CYP4F12, CYP4F2, CYP4F22, CYP4F3, CYP4F8, CYP4V2, CYP4X1, CYP4Z1, CYP51A1, CYP7A1, CYP7B1, CYP8B1, CYR61, CYS1, CYSLTR1, CYSLTR2, CYSRT1, CYSTM1, CYTH1, CYTH2, CYTH3, CYTH4, CYTIP, CYTL1, CYYR1, D2HGDH, DAAM1, DAAM2, DAB1, DAB2, DAB2IP, DACH1, DACH2, DACT1, DACT2, DACT3, DAD1, DAG1, DAGLA, DAGLB, DALRD3, DAND5, DAO, DAOA, DAP, DAP3, DAPK1, DAPK2, DAPK3, DAPL1, DAPP1, DARS, DARS2, DAW1, DAXX, DAZ1, DAZ2, DAZ3, DAZ4, DAZAP1, DAZAP2, DAZL, DBF4, DBF4B, DBH, DBI, DBN1, DBNDD1, DBNDD2, DBNL, DBP, DBR1, DBT, DBX1, DBX2, DCAF1, DCAF10, DCAF11, DCAF12, DCAF12L1, DCAF12L2, DCAF13, DCAF15, DCAF16, DCAF17, DCAF4, DCAF4L1, DCAF4L2, DCAF5, DCAF6, DCAF7, DCAF8, DCAF8L1, DCAF8L2, DCAKD, DCANP1, DCBLD1, DCBLD2, DCC, DCD, DCDC1, DCDCl$_2$, DCDCl$_2$B, DCDCl$_2$C, DCHS1, DCHS2, DCK, DCLK1, DCLK2, DCLK3, DCLRE1A, DCLRE1B, DCLREIC, DCN, DCP1A, DCP1B, DCP2, DCPS, DCST1, DCST2, DCSTAMP, DCT, DCTD, DCTN1, DCTN2, DCTN3, DCTN4, DCTN5, DCTN6, DCTPP1, DCUN1D1, DCUN1D2, DCUN1D3, DCUN1D4, DCUN1D5, DCX, DCXR, DDA1, DDAH1, DDAH2, DDB1, DDB2, DDC, DDHD1, DDHD2, DDI1, DDI2, DDIAS, DDIT3, DDIT4, DDIT4L, DDN, DDO, DDOST, DDR1, DDR2, DDRGK1, DDT, DDTL, DDX1, DDX10, DDX11, DDX17, DDX18, DDX19A, DDX19B, DDX20, DDX21, DDX23, DDX24, DDX25, DDX27, DDX28, DDX31, DDX39A, DDX39B, DDX3X, DDX3Y, DDX4, DDX41, DDX42, DDX43, DDX46, DDX47, DDX49, DDX5, DDX50, DDX51, DDX52, DDX53, DDX54, DDX55, DDX56, DDX58, DDX59, DDX6, DDX60, DDX60L, DEAF1, DEC, DECR1, DECR2, DEDD, DEDD2, DEF6, DEF8, DEFA1, DEFA1B, DEFA3, DEFA4, DEFA5, DEFA6, DEFB1, DEFB103A, DEFB103B, DEFB104A, DEFB104B, DEFB105A, DEFB105B, DEFB106A, DEFB106B, DEFB107A, DEFB107B, DEFB108B, DEFB110, DEFB112, DEFB113, DEFB114, DEFB115, DEFB116, DEFB118, DEFB119, DEFB121, DEFB123, DEFB124, DEFB125, DEFB126, DEFB127, DEFB128, DEFB129, DEFB130A, DEFB130B, DEFB131A, DEFB131B, DEFB132, DEFB133, DEFB134, DEFB135, DEFB136, DEFB4A, DEFB4B, DEGS1, DEGS2, DEK, DENND1A, DENND1B, DENND1C, DENND2A, DENND2C, DENND2D, DENND3, DENND4A, DENND4B, DENND4C, DENND5A, DENND5B, DENND6A, DENND6B, DENR, DEPDC1, DEPDC1B, DEPDC4, DEPDC5, DEPDC7, DEPTOR, DERA, DERL1, DERL2, DERL3, DES, DESI1, DESI2, DET1, DEUP1, DEXI, DFFA, DFFB, DFNA5, DFNB59, DGAT1, DGAT2, DGAT2L6, DGCR2, DGCR6, DGCR6L, DGCR8, DGKA, DGKB, DGKD, DGKE, DGKG, DGKH, DGKI, DGKK, DGKQ, DGKZ, DGUOK, DHCR24, DHCR7, DHDDS, DHDH, DHFR, DHFR2, DHH, DHODH, DHPS, DHRS1, DHRS11, DHRS12, DHRS13, DHRS2, DHRS3, DHRS4, DHRS4L2, DHRS7, DHRS7B, DHRS7C, DHRS9, DHRSX, DHTKD1, DHX15, DHX16, DHX29, DHX30, DHX32, DHX33, DHX34, DHX35, DHX36, DHX37, DHX38, DHX40, DHX57, DHX58, DHX8, DHX9, DIABLO, DIAPH1, DIAPH2, DIAPH3, DICER1, DIDO1, DIEXF, DIMT1, DIO1, DIO2, DIO3, DIP2A, DIP2B, DIP2C, DIRAS1, DIRAS2, DIRAS3, DIRC1, DIRC2, DIRC3, DIS3, DIS3L, DIS3L2, DISC1, DISP1, DISP2, DISP3, DIXDC1, DKC1, DKK1, DKK2, DKK3, DKK4, DKKL1, DLAT, DLC1, DLD, DLEC1, DLEU7, DLG1, DLG2, DLG3, DLG4, DLG5, DLGAP1, DLGAP2, DLGAP3, DLGAP4, DLGAP5, DLK1, DLK2, DLL1, DLL3, DLL4, DLST, DLX1, DLX2, DLX3, DLX4, DLX5, DLX6, DMAC1, DMAC2, DMAP1, DMBT1, DMBX1, DMC1, DMD, DMGDH, DMKN, DMP1, DMPK, DMRT1, DMRT2, DMRT3, DMRTA1, DMRTA2, DMRTB1, DMRTC1, DMRTC1B, DMRTC2, DMTF1, DMTN, DMWD, DMXL1, DMXL2, DNA2, DNAAF1, DNAAF2, DNAAF3, DNAAF4, DNAAF5, DNAH1, DNAH10, DNAH100S, DNAH11, DNAH12, DNAH14, DNAH17, DNAH2, DNAH3, DNAH5, DNAH6, DNAH7, DNAH8, DNAH9, DNAI1, DNAI2, DNAJA1, DNAJA2, DNAJA3, DNAJA4, DNAJB1, DNAJB11, DNAJB12, DNAJB13, DNAJB14, DNAJB2, DNAJB4, DNAJB5, DNAJB6, DNAJB7, DNAJB8, DNAJB9, DNAJC1, DNAJC10, DNAJC11, DNAJC12, DNAJC13, DNAJC14, DNAJC15, DNAJC16, DNAJC17, DNAJC18, DNAJC19, DNAJC2, DNAJC21, DNAJC22, DNAJC24, DNAJC25, DNAJC25-GNG10, DNAJC27, DNAJC28, DNAJC3, DNAJC30, DNAJC4, DNAJC5, DNAJC5B, DNAJC5G, DNAJC6, DNAJC7, DNAJC8, DNAJC9, DNAL1, DNAL4, DNALI1, DNASE1, DNASE1L1, DNASE1L2, DNASE1L3, DNASE2, DNASE2B, DND1, DNER, DNHD1, DNLZ, DNM1, DNM1L, DNM2, DNM3, DNMBP, DNMT1, DNMT3A, DNMT3B, DNMT3L, DNPEP, DNPH1, DNTT, DNTTIP1, DNTTIP2, DOC2A, DOC2B, DOCK1, DOCK10, DOCK11, DOCK2, DOCK3, DOCK4, DOCK5, DOCK6, DOCK7, DOCK8, DOCK9, DOHH, DOK1, DOK2, DOK3, DOK4, DOK5, DOK6, DOK7, DOLK, DOLPP1, DONSON, DOPEY1, DOPEY2, DOT1L, DPAGT1, DPCD, DPCR1, DPEP1, DPEP2, DPEP3, DPF1, DPF2, DPF3, DPH1, DPH2, DPH3, DPH5, DPH6, DPH7, DPM1, DPM2, DPM3, DPP10, DPP3, DPP4, DPP6, DPP7, DPP8, DPP9, DPPA2, DPPA3, DPPA4, DPPA5, DPRX, DPT, DPY19L1, DPY19L2, DPY19L3, DPY19L4, DPY30, DPYD, DPYS, DPYSL2, DPYSL3, DPYSL4, DPYSL5, DQX1, DR1, DRAM1, DRAM2, DRAP1, DRAXIN, DRC1, DRC3, DRC7, DRD1, DRD2, DRD3, DRD4, DRD5, DRG1, DRG2, DRGX, DRICH1, DROSHA, DRP2, DSC1, DSC2, DSC3, DSCAM, DSCAML1, DSCC1, DSCR3, DSCR4, DSCR8, DSE, DSEL, DSG1, DSG2, DSG3, DSG4, DSN1, DSP, DSPP, DST, DSTN, DSTYK, DTD1, DTD2, DTHD1, DTL, DTNA, DTNB, DTNBP1, DTWD1, DTWD2, DTX1, DTX2, DTX3, DTX3L, DTX4, DTYMK, DUOX1, DUOX2, DUOXA1, DUOXA2, DUPD1, DUS1L, DUS2, DUS3L, DUS4L, DUSP1, DUSP10, DUSP11, DUSP12, DUSP13, DUSP14, DUSP15, DUSP16, DUSP18, DUSP19, DUSP2, DUSP21, DUSP22, DUSP23, DUSP26, DUSP27, DUSP28, DUSP3, DUSP4, DUSP5, DUSP6, DUSP7, DUSP8, DUSP9, DUT, DUX4, DUXA, DUXB, DVL1, DVL2, DVL3, DWORF, DXO, DYDC1, DYDC2, DYM, DYNAP, DYNC1H1, DYNC1I1, DYNC1I2, DYNC1LI1, DYNC1LI2, DYNC2H1, DYNC2LI1, DYNLL1, DYNLL2, DYNLRB1, DYNLRB2, DYNLT1, DYNLT3, DYRK1A, DYRK1B, DYRK2, DYRK3, DYRK4, DYSF, DYTN, DZANK1, DZIP1, DZIP1L, DZIP3, E2F1, E2F2, E2F3, E2F4, E2F5, E2F6, E2F7, E2F8, E4F1, EAF1, EAF2, EAPP, EARS2, EBAG9, EBF1, EBF2, EBF3, EBF4, EBI3, EBLN1, EBLN2, EBNA1BP2, EBP, EBPL, ECD, ECE1, ECE2, ECEL1, ECH1, ECHDC1, ECHDC2, ECHDC3, ECHS1, ECI1, ECI2, ECM1, ECM2, ECSCR, ECSIT, ECT2, ECT2L, EDA, EDA2R, EDAR, EDARADD, EDC3, EDC4, EDDM13, EDDM3A, EDDM3B, EDEM1, EDEM2, EDEM3, EDF1, EDIL3, EDN1, EDN2, EDN3, EDNRA, EDNRB, EDRF1, EEA1, EED, EEF1A1, EEF1A2, EEF1AKMT1, EEF1AKMT2, EEF1AKMT3, EEF1B2, EEF1D, EEF1E1, EEF1E1-BLOC1S5, EEF1G, EEF2, EEF2K, EEF2KMT, EEFSEC, EEPD1, EFCAB1, EFCAB10, EFCAB11, EFCAB12, EFCAB13, EFCAB14, EFCAB2, EFCAB3, EFCAB5, EFCAB6, EFCAB7, EFCAB8, EFCAB9, EFCC1, EFEMP1, EFEMP2, EFHB, EFHC1, EFHC2, EFHD1, EFHD2, EFL1, EFNA1, EFNA2, EFNA3, EFNA4, EFNA5, EFNB1, EFNB2, EFNB3, EFR3A, EFR3B, EFS, EFTUD2, EGF, EGFL6, EGFL7, EGFL8, EGFLAM, EGFR, EGLN1, EGLN2, EGLN3, EGR1, EGR2, EGR3, EGR4, EHBP1, EHBP1L1, EHD1, EHD2, EHD3, EHD4, EHF, EHHADH, EHMT1, EHMT2, EI24, EID1, EID2, EID2B, EID3, EIF1, EIF1AD, EIF1AX, EIF1AY, EIF1B, EIF2A, EIF2AK1, EIF2AK2, EIF2AK3, EIF2AK4, EIF2B1, EIF2B2, EIF2B3, EIF2B4, EIF2B5, EIF2D, EIF2S1, EIF2S2, EIF2S3, EIF3A, EIF3B, EIF3C, EIF3CL, EIF3D, EIF3E, EIF3F, EIF3G, EIF3H, EIF3I, EIF3J, EIF3K, EIF3L, EIF3M, EIF4A1, EIF4A2, EIF4A3, EIF4B, EIF4E, EIF4EIB, EIF4E2, EIF4E3, EIF4EBP1, EIF4EBP2, EIF4EBP3, EIF4ENIF1, EIF4G1, EIF4G2, EIF4G3, EIF4H, EIF5, EIF5A, EIF5A2, EIF5AL1, EIF5B, EIF6, EIPR1, ELAC1, ELAC2, ELANE, ELAVL1, ELAVL2, ELAVL3, ELAVL4, ELF1, ELF2, ELF3, ELF4, ELF5, ELFN1, ELFN2, ELK1, ELK3, ELK4, ELL, ELL2, ELL3, ELMO1, ELMO2, ELMO3, ELMOD, ELMOD2, ELMOD3, ELMSAN1, ELN, ELOA, ELOA2, ELOA3, ELOA3B, ELOA3C, ELOA3D, ELOB, ELOC, ELOF1, ELOVL1, ELOVL2, ELOVL3, ELOVL4, ELOVL5, ELOVL6, ELOVL7, ELP1, ELP2, ELP3, ELP4, ELP5, ELP6, ELSPBP1, EMB, EMC1, EMC10, EMC2, EMC3, EMC4, EMC6, EMC7, EMC8, EMC9, EMCN, EMD, EME1, EME2, EMG1, EMID1, EMILIN1, EMILN2, EMILIN3, EML1, EML2, EML3, EML4, EML5, EML6, EMP1, EMP2, EMP3, EMSY, EMX1, EMX2, EN1, EN2, ENAH, ENAM, ENC1, ENDOD1, ENDOG, ENDOU, ENDOV, ENG, ENGASE, ENHO, ENKD1, ENKUR, ENO1, ENO2, ENO3, ENO4, ENOPH1, ENOSF1, ENOX1, ENOX2, ENPEP, ENPP1, ENPP2, ENPP3, ENPP4, ENPP5, ENPP6, ENPP7, ENSA, ENTHD1, ENTPD1, ENTPD2, ENTPD3, ENTPD4, ENTPD5, ENTPD6, ENTPD7, ENTPD8, ENY2, EOGT, EOMES, EP300, EP400, EPAS1, EPB41, EPB41L1, EPB41L2, EPB41L3, EPB41L4A, EPB41L4B, EPB41L5, EPB42, EPC1, EPC2, EPCAM, EPDR1, EPG5, EPGN, EPHA1, EPHA10, EPHA2, EPHA3, EPHA4, EPHA5, EPHA6, EPHA7, EPHA8, EPHB1, EPHB2, EPHB3, EPHB4, EPHB6, EPHX1, EPHX2, EPHX3, EPHX4, EPM2A, EPM2AIP1, EPN1, EPN2, EPN3, EPO, EPOP, EPOR, EPPIN, EPPIN-WFDC6, EPPK1, EPRS, EPS15, EPS15L1, EPS8, EPS8L1, EPS8L2, EPS8L3, EPSTI1, EPX, EPYC, EQTN, ERAL1, ERAP1, ERAP2, ERAS, ERBB2, ERBB3, ERBB4, ERBIN, ERC1, ERC2, ERCC1, ERCC2, ERCC3, ERCC4, ERCC5, ERCC6, ERCC6L, ERCC6L2, ERCC8, EREG, ERF, ERFE, ERG, ERG28, ERGIC1, ERGIC2, ERGIC3, ERH, ERI1, ERI2, ERI3, ERICH, ERICH2, ERICH3, ERICH4, ERICH5, ERICH6, ERICH6B, ERLEC1, ERLIN1, ERLIN2, ERMAP, ERMARD, ERMN, ERMP1, ERN1, ERN2, ERO1A, ERO1B, ERP27, ERP29, ERP44, ERRFI1, ERV3-1, ERVFRD-1, ERVMER34-1, ERVV-1, ERVV-2, ERVW-1, ESAM, ESCO1, ESCO2, ESD, ESF1, ESM1, ESPL1, ESPN, ESPNL, ESR1, ESR2, ESRP1, ESRP2, ESRRA, ESRRB, ESRRG, ESS2, ESX1, ESYT1, ESYT2, ESYT3, ETAA1, ETDA, ETDB, ETDC, ETF1, ETFA, ETFB, ETFBKMT, ETFDH, ETFRF1, ETHE1, ETNK1, ETNK2, ETNPPL, ETS1, ETS2, ETV1, ETV2, ETV3, ETV3L, ETV4, ETV5, ETV6, ETV7, EVA1A, EVA1B, EVA1C, EVC, EVC2, EVI2A, EVI2B, EVI5, EVI5L, EVL, EVPL, EVPLL, EVX1, EVX2, EWSR1, EXD1, EXD2, EXD3, EXO1, EXO5, EXOC1, EXOCIL, EXOC2, EXOC3, EXOC3L1, EXOC3L2, EXOC3L4, EXOC4, EXOC5, EXOC6, EXOC6B, EXOC7, EXOC8, EXOG, EXOSCI, EXOSC10, EXOSC2, EXOSC3, EXOSC4, EXOSC5, EXOSC6, EXOSC7, EXOSC8, EXOSC9, EXPH5, EXT1, EXT2, EXTL1, EXTL2, EXTL3, EYA, EYA2, EYA3, EYA4, EYS, EZH1, EZH2, EZR, F10, F11, F1R, F12, F13A1, F13B, F2, F2R, F2RL1, F2RL2, F2RL3, F3, F5, F7, F8, F8A1, F8A2, F8A3, F9, FA2H, FAAH, FAAH2, FAAP100, FAAP20, FAAP24, FABP1, FABP12, FABP2, FABP3, FABP4, FABP5, FABP6, FABP7, FABP9, FADD, FADS1, FADS2, FADS3, FADS6, FAF1, FAF2, FAH, FAHD1, FAHD2A, FAHD2B, FAIM, FAIM2, FAM102A, FAM102B, FAM103A1, FAM104A, FAM104B, FAM105A, FAM106A, FAM107A, FAM107B, FAM109A, FAM109B, FAM110A, FAM110B, FAM110C, FAM110D, FAM111A, FAM111B, FAM114A1, FAM114A2, FAM117A, FAM117B, FAM118A, FAM118B, FAM120A, FAM120AOS, FAM120B, FAM120C, FAM122A, FAM122B, FAM122C, FAM124A, FAM124B, FAM126A, FAM126B, FAM129A, FAM129B, FAM129C, FAM131A, FAM131B, FAM131C, FAM133A, FAM133B, FAM135A, FAM135B, FAM136A, FAM13A, FAM13B, FAM13C, FAM149A, FAM149B1, FAM151A, FAM151B, FAM153A, FAM153B, FAM153C, FAM155A, FAM155B, FAM156A, FAM156B, FAM159A, FAM159B, FAM160A1, FAM160A2, FAM160B1, FAM160B2, FAM161A, FAM161B, FAM162A, FAM162B, FAM163A, FAM163B, FAM166A, FAM166B, FAM167A, FAM167B, FAM168A, FAM168B, FAM169A, FAM169B, FAM170A, FAM170B, FAM171A1, FAM171A2, FAM171B, FAM172A, FAM173A, FAM173B, FAM174A, FAM174B, FAM177A1, FAM177B, FAM178B, FAM180A, FAM180B, FAM181A, FAM181B, FAM182B, FAM183A, FAM184A, FAM184B, FAM185A, FAM186A, FAM186B, FAM187A, FAM187B, FAM189A1, FAM189A2, FAM189B, FAM192A, FAM193A, FAM193B, FAM196A, FAM196B, FAM198A, FAM198B, FAM199X, FAM19A1, FAM19A2, FAM19A3, FAM19A4, FAM19A5, FAM200A, FAM200B, FAM204A, FAM205A, FAM205C, FAM206A, FAM207A, FAM208A, FAM208B, FAM209A, FAM209B, FAM20A, FAM20B, FAM20C, FAM210A, FAM210B, FAM212A, FAM212B, FAM213A, FAM213B, FAM214A, FAM214B, FAM216A, FAM216B, FAM217A, FAM217B, FAM218A, FAM219A, FAM219B, FAM220A, FAM221A, FAM221B, FAM222A, FAM222B, FAM227A, FAM227B, FAM228A, FAM228B, FAM229A, FAM229B, FAM230A, FAM231A, FAM231B, FAM231C, FAM231D, FAM234A, FAM234B, FAM236A, FAM236B, FAM236C, FAM236D, FAM237A, FAM237B, FAM240A, FAM240B, FAM24A, FAM24B, FAM25A, FAM25C, FAM25G, FAM26D, FAM26E, FAM26F, FAM32A, FAM35A, FAM3A, FAM3B, FAM3C, FAM3D, FAM43A, FAM43B, FAM45A, FAM46A, FAM46B, FAM46C, FAM46D, FAM47A, FAM47B, FAM47C, FAM47E, FAM47E-STBD1, FAM49A, FAM49B, FAM50A, FAM50B, FAM53A, FAM53B, FAM53C, FAM57A, FAM57B, FAM58A, FAM60A, FAM69A, FAM69B, FAM69C, FAM71A, FAM71B, FAM71C, FAM71D, FAM71E1, FAM71E2, FAM71F1, FAM71F2, FAM72A, FAM72B, FAM72C, FAM72D, FAM76A, FAM76B, FAM78A, FAM78B, FAM81A, FAM81B, FAM83A, FAM83B, FAM83C, FAM83D, FAM83E, FAM83F, FAM83G, FAM83H, FAM84A, FAM84B, FAM86B1, FAM86B2, FAM86C1, FAM89A, FAM89B, FAM8A1, FAM90A1, FAM90A26, FAM91A1, FAM92A, FAM92B, FAM95C, FAM96A, FAM96B, FAM98A, FAM98B, FAM98C, FAM9A, FAM9B, FAM9C, FAN1, FANCA, FANCB, FANCC, FANCD2, FANCD2OS, FANCE, FANCF, FANCG, FANCI, FANCL, FANCM, FANK1, FAP, FAR1, FAR2, FARP1, FARP2, FARS2, FARSA, FARSB, FAS, FASLG, FASN, FASTK, FASTKD1, FASTKD2, FASTKD3, FASTKD5, FAT1, FAT2, FAT3, FAT4, FATE1, FAU, FAXC, FAXDC2, FBF1, FBL, FBLIM1, FBLL1, FBLN1, FBLN2, FBLN5, FBLN7, FBN1, FBN2, FBN3, FBP1, FBP2, FBRS, FBRSL1, FBXL12, FBXL13, FBXL14, FBXL15, FBXL16, FBXL17, FBXL18, FBXL19, FBXL2, FBXL20, FBXL22, FBXL3, FBXL4, FBXL5, FBXL6, FBXL7, FBXL8, FBXO10, FBXO11, FBXO15, FBXO16, FBXO17, FBXO18, FBXO2, FBXO21, FBXO22, FBXO24, FBXO25, FBXO27, FBXO28, FBXO3, FBXO30, FBXO31, FBXO32, FBXO33, FBXO34, FBXO36, FBXO38, FBXO39, FBXO4, FBXO40, FBXO41, FBXO42, FBXO43, FBXO44, FBXO45, FBXO46, FBXO47, FBXO48, FBXO5, FBXO6, FBXO7, FBXO8, FBXO9, FBXW10, FBXW11, FBXW12, FBXW2, FBXW4, FBXW5, FBXW7, FBXW8, FBXW9, FCAMR, FCAR, FCER1A, FCER1G, FCER2, FCF1, FCGBP, FCGR1A, FCGR1B, FCGR2A, FCGR2B, FCGR2C, FCGR3A, FCGR3B, FCGRT, FCHO1, FCHO2, FCHSD1, FCHSD2, FCMR, FCN1, FCN2, FCN3, FCRL1, FCRL2, FCRL3, FCRL4, FCRL5, FCRL6, FCRLA, FCRLB, FDCSP, FDFT1, FDPS, FDX1, FDX2, FDXACB1, FDXR, FECH, FEM1A, FEM1B, FEM1C, FEN1, FER, FER1L5, FER1L6, FERD3L, FERMT1, FERMT2, FERMT3, FES, FETUB, FEV, FEZ1, FEZ2, FEZF1, FEZF2, FFAR1, FFAR2, FFAR3, FFAR4, FGA, FGB, FGD1, FGD2, FGD3, FGD4, FGD5, FGD6, FGF1, FGF10, FGF11, FGF12, FGF13, FGF14, FGF16, FGF17, FGF18, FGF19, FGF2, FGF20, FGF21, FGF22, FGF23, FGF3, FGF4, FGF5, FGF6, FGF7, FGF8, FGF9, FGFBP1, FGFBP2, FGFBP3, FGFR1, FGFR1OP, FGFR1OP2, FGFR2, FGFR3, FGFR4, FGFRL1, FGG, FGGY, FGL1, FGL2, FGR, FH, FHAD1, FHDC1, FHIT, FHL1, FHL2, FHL3, FHL5, FHOD1, FHOD3, FIBCD1, FIBIN, FIBP, FICD, FIG4, FIGLA, FIGN, FIGNL1, FIGNL2, FILIP1, FILIPL, FIP1L1, FIS1, FITM1, FITM2, FIZ1, FJX1, FKBP10, FKBP11, FKBP14, FKBP15, FKBP1A, FKBP1B, FKBP 1C, FKBP2, FKBP3, FKBP4, FKBP5, FKBP6, FKBP7, FKBP8, FKBP9, FKBPL, FKRP, FKTN, FLAD1, FLCN, FLG, FLG2, FLI1, FLII, FLNA, FLNB, FLNC, FLOT1, FLOT2, FLRT1, FLRT2, FLRT3, FLT1, FLT3, FLT3LG, FLT4, FLVCR1, FLVCR2, FLYWCH1, FLYWCH2, FMC1, FMN1, FMN2, FMNL1, FMNL2, FMNL3, FMO1, FMO2, FMO3, FMO4, FMO5, FMOD, FMR1, FMR1NB, FN1, FN3K, FN3KRP, FNBP1, FNBP1L, FNBP4, FNDC1, FNDC10, FNDC11, FNDC3A, FNDC3B, FNDC4, FNDC5, FNDC7, FNDC8, FNDC9, FNIP1, FNIP2, FNTA, FNTB, F0681492.1, F0681542.1, FOCAD, FOLH1, FOLR1, FOLR2, FOLR3, FOPNL, FOS, FOSB, FOSL1, FOSL2, FOXA1, FOXA2, FOXA3, FOXB1, FOXB2, FOXC1, FOXC2, FOXD1, FOXD2, FOXD3, FOXD4, FOXD4L1, FOXD4L3, FOXD4L4, FOXD4L5, FOXD4L6, FOXE1, FOXE3, FOXF1, FOXF2, FOXG1, FOXH1, FOXI1, FOXI2, FOXI3, FOXJ1, FOXJ2, FOXJ3, FOXK1, FOXK2, FOXL1, FOXL2, FOXL2NB, FOXM1, FOXN1, FOXN2, FOXN3, FOXN4, FOXO1, FOXO3, FOXO4, FOXO6, FOXP1, FOXP2, FOXP3, FOXP4, FOXQ1, FOXR1, FOXR2, FOXRED1, FOXRED2, FOXS1, FP236240.1, FP565260.1, FP565260.2, FP565260.3, FP565260.4, FP565260.6, FP565260.7, FP565324.1, FP565324.2, FPGS, FPGT, FPGT-TNNI3K, FPR1, FPR2, FPR3, FRA1OAC1, FRAS1, FRAT1, FRAT2, FREM1, FREM2, FREM3, FRG1, FRG2, FRG2B, FRG2C, FRK, FRMD1, FRMD3, FRMD4A, FRMD4B, FRMD5, FRMD6, FRMD7, FRMD8, FRMPD1, FRMPD2, FRMPD3, FRMPD4, FRRS1, FRRS1L, FRS2, FRS3, FRY, FRYL, FRZB, FSBP, FSCB, FSCN1, FSCN2, FSCN3, FSD1, FSD1L, FSD2, FSHB, FSHR, FSIP1, FSIP2, FST, FSTL1, FSTL3, FSTL4, FSTL5, FTCD, FTCDNL1, FTH1, FTHL17, FTL, FTMT, FTO, FTSJ1, FTSJ3, FUBP1, FUBP3, FUCA1, FUCA2, FUK, FUNDC1, FUNDC2, FUOM, FURIN, FUS, FUT1, FUT10, FUT11, FUT2, FUT3, FUT4, FUT5, FUT6, FUT7, FUT8, FUT9, FUZ, FXN, FXR1, FXR2, FXYD1, FXYD2, FXYD3, FXYD4, FXYD5, FXYD6, FXYD6-FXYD2, FXYD7, FYB1, FYB2, FYCO1, FYN, FYTTD1, FZD1, FZD10, FZD2, FZD3, FZD4, FZD5, FZD6, FZD7, FZD8, FZD9, FZR1, GOS2, G2E3, G3BP1, G3BP2, G6PC, G6PC2, G6PC3, G6PD, GAA, GAB1, GAB2, GAB3, GAB4, GABARAP, GABARAPL1, GABARAPL2, GABBR1, GABBR2, GABPA, GABPB1, GABPB2, GABRA1, GABRA2, GABRA3, GABRA4, GABRA5, GABRA6, GABRB1, GABRB2, GABRB3, GABRD, GABRE, GABRG1, GABRG2, GABRG3, GABRP, GABRQ, GABRR1, GABRR2, GABRR3, GAD1, GAD2, GADD45A, GADD45B, GADD45G, GADD45GIP1, GADL1, GAGE1, GAGE10, GAGE12B, GAGE12C, GAGE12D, GAGE12E, GAGE12F, GAGE12G, GAGE12H, GAGE12J, GAGE13, GAGE2A, GAGE2E, GAK, GAL, GAL3ST1, GAL3ST2, GAL3ST3, GAL3ST4, GALC, GALE, GALK1, GALK2, GALM, GALNS, GALNT1, GALNT10, GALNT11, GALNT12, GALNT13, GALNT14, GALNT15, GALNT16, GALNT17, GALNT18, GALNT2, GALNT3, GALNT4, GALNT5, GALNT6, GALNT7, GALNT8, GALNT9, GALNTL5, GALNTL6, GALP, GALR1, GALR2, GALR3, GALT, GAMT, GAN, GANAB, GANC, GAP43, GAPDH, GAPDHS, GAPT, GAPVD1, GAR1, GAREMI, GAREM2, GARNL3, GARS, GART, GAS1, GAS2, GAS2L1, GAS2L2, GAS2L3, GAS6, GAS7, GAS8, GAST, GATA1, GATA2, GATA3, GATA4, GATA5, GATA6, GATADI, GATAD2A, GATAD2B, GATB, GATC, GATD1, GA™, GATS, GBA, GBA2, GBA3, GBE1, GBF1, GBGT1, GBP1, GBP2, GBP3, GBP4, GBP5, GBP6, GBP7, GBX1, GBX2, GC, GCA, GCAT, GCC1, GCC2, GCDH, GCFC2, GCG, GCGR, GCH1, GCHFR, GCK, GCKR, GCLC, GCLM, GCM1, GCM2, GCN1, GCNA, GCNT1, GCNT2, GCNT3, GCNT4, GCNT7, GCOM1, GCSAM, GCSAML, GCSH, GDA, GDAP1, GDAP1L1, GDAP2, GDE1, GDF1, GDF10, GDF11, GDF15, GDF2, GDF3, GDF5, GDF5OS, GDF6, GDF7, GDF9, GDI1, GDI2, GDNF, GDPD1, GDPD2, GDPD3, GDPD4, GDPD5, GDPGP1, GEM, GEMIN2, GEMIN4, GEMIN5, GEMIN6, GEMIN7, GEMIN8, GEN1, GET4, GFAP, GFER, GFI, GFI1B, GFM1, GFM2, GFOD1, GFOD2, GFPT1, GFPT2, GFRA1, GFRA2, GFRA3, GFRA4, GFRAL, GFY, GGA1, GGA2, GGA3, GGACT, GGCT, GGCX, GGH, GGN, GGNBP2, GGPS1, GGT1, GGT2, GGT5, GGT6, GGT7, GGTLC1, GGTLC2, GGTLC3, GH1, GH2, GHDC, GHI™, GHR, GHRH, GHRHR, GHRL, GHSR, GID4, GID8, GIF, GIGYF1, GIGYF2, GIMAP1, GIMAP1-GIMAP5, GIMAP2, GIMAP4, GIMAP5, GIMAP6, GIMAP7, GIMAP8, GIMD1, GIN1, GINM1, GINS1, GINS2, GINS3, GINS4, GIP, GIPC1, GIPC2, GIPC3, GIPR, GIT1, GIT2, GJA1, GJA10, GJA3, GJA4, GJA5, GJA8, GJA9, GJB1, GJB2, GJB3, GJB4, GJB5, GJB6, GJB7, GJC1, GJC2, GJC3, GJD2, GJD3, GJD4, GJE1, GK, GK2, GK3P, GK5, GKAP1, GKN1, GKN2, GLA, GLB1, GLB1L, GLB1L2, GLB1L3, GLCCI1, GLCE, GLDC, GLDN, GLE1, GLG1, GLI1, GLI2, GLI3, GLI4, GLIPR1, GLIPR1L1, GLIPR1L2, GLIPR2, GLIS1, GLIS2, GLIS3, GLMN, GLMP, GLO1, GLOD4, GLOD5, GLP1R, GLP2R, GLRA1, GLRA2, GLRA3, GLRA4, GLRB, GLRX, GLRX2, GLRX3, GLRX5, GLS, GLS2, GLT1D1, GLT6D1, GLT8D1, GLT8D2, GLTP, GLTPD2, GLUD1, GLUD2, GLUL, GLYAT, GLYATL1, GLYATL1P3, GLYATL2, GLYATL3, GLYCTK, GLYR1, GM2A, GMCL1, GMDS, GMEB1, GMEB2, GMFB, GMFG, GMIP, GML, GMNC, GMNN, GMPPA, GMPPB, GMPR, GMPR2, GMPS, GNA11, GNA12, GNA13, GNA14, GNA15, GNAI1, GNAI2, GNAI3, GNAL, GNAO1, GNAQ, GNAS, GNAT1, GNAT2, GNAT3, GNAZ, GNB1, GNB1L, GNB2, GNB3, GNB4, GNB5, GNE, GNG10, GNG11, GNG12, GNG13, GNG14, GNG2, GNG3, GNG4, GNG5, GNG7, GNG8, GNGT1, GNGT2, GNL1, GNL2, GNL3, GNL3L, GNLY, GNMT, GNPAT, GNPDA1, GNPDA2, GNPNAT1, GNPTAB, GNPTG, GNRH1, GNRH2, GNRHR, GNS, GOLGA1, GOLGA2, GOLGA3, GOLGA4, GOLGA5, GOLGA6A, GOLGA6B, GOLGA6C, GOLGA6D, GOLGA6L1, GOLGA6L10, GOLGA6L2, GOLGA6L22, GOLGA6L4, GOLGA6L6, GOLGA6L7P, GOLGA6L9, GOLGA7, GOLGA7B, GOLGA8A, GOLGA8B, GOLGA8F, GOLGA8G, GOLGA8H, GOLGA8J, GOLGA8K, GOLGA8M, GOLGA8N, GOLGA80, GOLGA8Q, GOLGA8R, GOLGA8S, GOLGA8T, GOLGB1, GOLIM4, GOLM1, GOLPH3, GOLPH3L, GOLTIA, GOLTIB, GON4L, GON7, GOPC, GORAB, GORASP1, GORASP2, GOSR1, GOSR2, GOT1, GOT1L1, GOT2, GP1BA, GP1BB, GP2, GP5, GP6, GP9, GPA33, GPAA1, GPALPP1, GPAM, GPANK1, GPAT2, GPAT3, GPAT4, GPATCH1, GPATCH11, GPATCH2, GPATCH2L, GPATCH3, GPATCH4, GPATCH8, GPBAR1, GPBP1, GPBP1L1, GPC1, GPC2, GPC3, GPC4, GPC5, GPC6, GPCPD1, GPD1, GPD1L, GPD2, GPER1, GPHA2, GPHB5, GPHN, GPI, GPIBP1, GPKOW, GPLD1, GPM6A, GPM6B, GPN1, GPN2, GPN3, GPNMB, GPR1, GPR101, GPR107, GPR108, GPR119, GPR12, GPR132, GPR135, GPR137, GPR137B, GPR137C, GPR139, GPR141, GPR142, GPR143, GPR146, GPR148, GPR149, GPR15, GPR150, GPR151, GPR152, GPR153, GPR155, GPR156, GPR157, GPR158, GPR160, GPR161, GPR162, GPR17, GPR171, GPR173, GPR174, GPR176, GPR179, GPR18, GPR180, GPR182, GPR183, GPR19, GPR20, GPR21, GPR22, GPR25, GPR26, GPR27, GPR3, GPR31, GPR32, GPR33, GPR34, GPR35, GPR37, GPR37L1, GPR39, GPR4, GPR42, GPR45, GPR50, GPR52, GPR55, GPR6, GPR61, GPR62, GPR63, GPR65, GPR68, GPR75, GPR75-ASB3, GPR78, GPR82, GPR83, GPR84, GPR85, GPR87, GPR88, GPR89A, GPR89B, GPRASP1, GPRASP2, GPRC5A, GPRC5B, GPRC5C, GPRC5D, GPRC6A, GPRIN1, GPRIN2, GPRIN3, GPS1, GPS2, GPSM1, GPSM2, GPSM3, GPT, GPT2, GPX1, GPX2, GPX3, GPX4, GPX5, GPX6, GPX7, GPX8, GRAMD1A, GRAMD1B, GRAMD1C, GRAMD2A, GRAMD2B, GRAMD4, GRAP, GRAP2, GRAPL, GRASP, GRB10, GRB14, GRB2, GRB7, GREB1, GREBIL, GREM1, GREM2, GRHL1, GRHL2, GRHL3, GRHPR, GRIA1, GRIA2, GRIA3, GRIA4, GRID1, GRID2, GRID2IP, GRIFIN, GRIK1, GRIK2, GRIK3, GRIK4, GRIK5, GRIN1, GRIN2A, GRIN2B, GRIN2C, GRIN2D, GRIN3A, GRIN3B, GRINA, GRIP1, GRIP2, GRIPAP1, GRK1, GRK2, GRK3, GRK4, GRK5, GRK6, GRK7, GRM1, GRM2, GRM3, GRM4, GRM5, GRM6, GRM7, GRM8, GRN, GRP, GRPEL1, GRPEL2, GRPR, GRSF1, GRTP1, GRWD1, GRXCR1, GRXCR2, GSAP, GSC, GSC2, GSDMA, GSDMB, GSDMC, GSDMD, GSE1, GSG1, GSG1L, GSG1L2, GSK3A, GSK3B, GSKIP, GSN, GSPT1, GSPT2, GSR, GSS, GSTA1, GSTA2, GSTA3, GSTA4, GSTA5, GSTCD, GSTK1, GSTM1, GSTM2, GSTM3, GSTM4, GSTM5, GSTO1, GSTO2, GSTP1, GSTT1, GSTT2, GSTT2B, GSTTP1, GSTZ1, GSX1, GSX2, GTDC1, GTF2A1, GTF2A1L, GTF2A2, GTF2B, GTF2E1, GTF2E2, GTF2F1, GTF2F2, GTF2H1, GTF2H2, GTF2H2C, GTF2H2C_2, GTF2H3, GTF2H4, GTF2H5, GTF2I, GTF2IRD1, GTF2IRD2, GTF2IRD2B, GTF3A, GTF3C1, GTF3C2, GTF3C3, GTF3C4, GTF3C5, GTF3C6, GTPBP1, GTPBP10, GTPBP2, GTPBP3, GTPBP4, GTPBP6, GTPBP8, GTSE1, GTSF1, GTSF1L, GU182339.1, GU182339.3, GU182343.1, GU182343.2, GU182345.1, GU182345.2, GU182347.1, GU182351.2, GU182352.2, GU182353.1, GU182355.1, GU182355.2, GU182355.3, GU182357.1, GU182357.3, GU182359.1, GU182359.2, GUCA1A, GUCA1B, GUCA1C, GUCA2A, GUCA2B, GUCD1, GUCY1A2, GUCY1A3, GUCY1B3, GUCY2C, GUCY2D, GUCY2F, GUF1, GUK1, GULP1, GUSB, GVQW2, GXYLT1, GXYLT2, GYG1, GYG2, GYPA, GYPB, GYPC, GYPE, GYS1, GYS2, GZF1, GZMA, GZMB, GZMH, GZMK, GZMM, H1F0, H1FNT, H1FOO, H1FX, H2AFB1, H2AFB2, H2AFB3, H2AFJ, H2AFV, H2AFX, H2AFY, H2AFY2, H2AFZ, H2BFM, H2BFS, H2BFWT, H3F3A, H3F3B, H3F3C, H6PD, HAAO, HABP2, HABP4, HACD1, HACD2, HACD3, HACD4, HACE1, HACL1, HADH, HADHA, HADHB, HAGH, HAGHL, HAL, HAMP, HAND1, HAND2, HAO1, HA2, HAP1, HAPLN1, HAPLN2, HAPLN3, HAPLN4, HARBII, HARS, HARS2, HAS1, HAS2, HAS3, HASPIN, HAT1, HAUS1, HAUS2, HAUS3, HAUS4, HAUS5, HAUS6, HAUS7, HAUS8, HAVCR1, HAVCR2, HAX1, HBA1, HBA2, HBB, HBD, HBE1, HBEGF, HBG1, HBG2, HBM, HBP1, HBQ, HBS1L, HBZ, HCAR1, HCAR2, HCAR3, HCCS, HCFC1, HCFC1R1, HCFC2, HCK, HCLS1, HCN1, HCN2, HCN3, HCN4, HCRT, HCRTR1, HCRTR2, HCST, HDAC1, HDAC10, HDAC11, HDAC2, HDAC3, HDAC4, HDAC5, HDAC6, HDAC7, HDAC8, HDAC9, HDC, HDDC2, HDDC3, HDGF, HDGFL1, HDGFL2, HDGFL3, HDHD2, HDHD3, HDHD5, HDLBP, HDX, HEATR, HEATR3, HEATR4, HEATR5A, HEATR5B, HEATR6, HEATR9, HEBP1, HEBP2, HECA, HECTD1, HECTD2, HECTD3, HECTD4, HECW1, HECW2, HEG1, HELB, HELLS, HELQ, HELT, HELZ, HELZ2, HEMGN, HEMK1, HENMT1, HEPACAM, HEPACAM2, HEPH, HEPHL1, HEPN1, HERC1, HERC2, HERC3, HERC4, HERC5, HERC6, HERPUDI, HERPUD2, HES1, HES2, HES3, HES4, HES5, HES6, HES7, HESX1, HEXA, HEXB, HEXDC, HEXIM1, HEXIM2, HEY1, HEY2, HEYL, HFE, HFE2, HFM1, HGD, HGF, HGFAC, HGH1, HGNC:18790, HGNC:24955, HGS, HGSNAT, HHAT, HHATL, HHEX, HHIP, HHIPL, HHIPL2, HHLA1, HHLA2, HHLA3, HIBADH, HIBCH, HIC1, HIC2, HID1, HIF1A, HIF1AN, HIF3A, HIGD1A, HIGD1B, HIGD1C, HIGD2A, HIGD2B, HIKESHI, HILPDA, HINFP, HINT1, HINT2, HINT3, HIP1, HIP1R, HIPK1, HIPK2, HIPK3, HIPK4, HIRA, HIRIP3, HISTHA, HIST1H1B, HIST1H1C, HIST1H1D, HIST1H1E, HIST1H1T, HIST1H2AA, HIST1H2AB, HIST1H2AC, HIST1H2AD, HIST1H2AE, HIST1H2AG, HIST1H2AH, HIST1H2AI, HIST1H2AJ, HIST1H2AK, HIST1H2AL, HIST1H2AM, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2BO, HIST1H3A, HIST1H3B, HIST1H3C, HIST1H3D, HIST1H3E, HIST1H3F, HIST1H3G, HIST1H3H, HIST1H3I, HIST1H3J, HIST1H4A, HIST1H4B, HIST1H4C, HIST1H4D, HIST1H4E, HIST1H4F, HIST1H4G, HIST1H4H, HIST1H4I, HIST1H4J, HIST1H4K, HIST1H4L, HIST2H2AA3, HIST2H2AA4, HIST2H2AB, HIST2H2AC, HIST2H2BE, HIST2H2BF, HIST2H3A, HIST2H3C, HIST2H3D, HIST2H3PS2, HIST2H4A, HIST2H4B, HIST3H2A, HIST3H2BB, HIST3H3, HIST4H4, HIVEP1, HIVEP2, HIVEP3, HJURP, HK1, HK2, HK3, HKDC1, HKR1, HLA-A, HLA-B, HLA-C, HLA-DMA, HLA-DMB, HLA-DOA, HLA-DOB, HLA-DPA1, HLA-DPB1, HLA-DQA1, HLA-DQA2, HLA-DQB1, HLA-DQB2, HLA-DRA, HLA-DRB1, HLA-DRB3, HLA-DRB4, HLA-DRB5, HLA-E, HLA-F, HLA-G, HLCS, HLF, HLTF, HLX, HM13, HM190170.1, HMBOX1, HMBS, HMCES, HMCN1, HMCN2, HMG20A, HMG20B, HMGA1, HMGA2, HMGB1, HMGB2, HMGB3, HMGB4, HMGCL, HMGCLL1, HMGCR, HMGCS1, HMGCS2, HMGN1, HMGN2, HMGN3, HMGN4, HMGN5, HMGXB3, HMGXB4, HMHB1, HMMR, HMOX1, HMOX2, HMSD, HMX1, HMX2, HMX3, HNF1A, HNF1B, HNF4A, HNF4G, HNMT, HNRNPA0, HNRNPA1, HNRNPA1L2, HNRNPA2B1, HNRNPA3, HNRNPAB, HNRNPC, HNRNPCL1, HNRNPCL2, HNRNPCL3, HNRNPCL4, HNRNPD, HNRNPDL, HNRNPF, HNRNPH1, HNRNPH2, HNRNPH3, HNRNPK, HNRNPL, HNRNPLL, HNRNPM, HNRNPR, HNRNPU, HNRNPUL1, HNRNPUL2, HNRNPUL2-BSCL2, HOGA1, *HOMER1*, HOMER2, HOMER3, HOMEZ, HOOK1, HOOK2, HOOK3, HOPX, HORMAD1, HORMAD2, HOXA1, HOXA10, HOXA11, HOXA13, HOXA2, HOXA3, HOXA4, HOXA5, HOXA6, HOXA7, HOXA9, HOXB1, HOXB13, HOXB2, HOXB3, HOXB4, HOXB5, HOXB6, HOXB7, HOXB8, HOXB9, HOXC10, HOXC11, HOXC12, HOXC13, HOXC4, HOXC5, HOXC6, HOXC8, HOXC9, HOXD1, HOXD10, HOXD11, HOXD12, HOXD13, HOXD3, HOXD4, HOXD8, HOXD9, HP, HP1BP3, HPCA, HPCAL1, HPCAL4, HPD, HPDL, HPF1, HPGD, HPGDS, HPN, HPR, HPRT1, HPS1, HPS3, HPS4, HPS5, HPS6, HPSE, HPSE2, HPX, HR, HRAS, HRASLS, HRASLS2, HRASLS5, HRC, HRCT1, HRG, HRH1, HRH2, HRH3, HRH4, HRK, HRNR, HS1BP3, HS2ST1, HS3ST1, HS3ST2, HS3ST3A1, HS3ST3B1, HS3ST4, HS3ST5, HS3ST6, HS6ST1, HS6ST2, HS6ST3, HSBP1, HSBP1L1, HSCB, HSD11B1, HSD11B1L, HSD11B2, HSD17B1, HSD17B10, HSD17B11, HSD17B12, HSD17B13, HSD17B14, HSD17B2, HSD17B3, HSD17B4, HSD17B6, HSD17B7, HSD17B8, HSD3B1, HSD3B2, HSD3B7, HSDL1, HSDL2, HSF1, HSF2, HSF2BP, HSF4, HSF5, HSFX1, HSFX2, HSFX3, HSFX4, HSFY1, HSFY2, HSH2D, HSP90AA1, HSP90AB1, HSP90B1, HSPA12A, HSPA12B, HSPA13, HSPA14, HSPA1A, HSPA1B, HSPA1L, HSPA2, HSPA4, HSPA4L, HSPA5, HSPA6, HSPA8, HSPA9, HSPB1, HSPB11, HSPB2, HSPB2-C11orf52, HSPB3, HSPB6, HSPB7, HSPB8, HSPB9, HSPBAP1, HSPBP1, HSPD1, HSPE1, HSPE1-MOB4, HSPG2, HSPH1, HTATIP2, HTATSF1, HTD2, HTN1, HTN3, HTR1A, HTR1B, HTR1D, HTR1E, HTR1F, HTR2A, HTR2B, HTR2C, HTR3A, HTR3B, HTR3C, HTR3D, HTR3E, HTR4, HTR5A, HTR6, HTR7, HTRA1, HTRA2, HTRA3, HTRA4, HTT, HUNK, HUS1, HUS1B, HUWE1, HVCN1, HYAL1, HYAL2, HYAL3, HYAL4, HYDIN, HYI, HYKK, HYLS1, HYOU1, HYPK, HYPM, IAH1, IAPP, IARS, IARS2, IBA57, IBSP, IBTK, ICA1, ICA1L, ICAM1, ICAM2, ICAM3, ICAM4, ICAM5, ICE1, ICE2, ICK, ICMT, ICOS, ICOSLG, ID1, ID2, ID3, ID4, IDE, IDH1, IDH2, IDH3A, IDH3B, IDH3G, IDI1, IDI2, IDNK, IDO1, IDO2, IDS, IDUA, IER2, IER3, IER3IP1, IER5, IER5L, IFFO1, IFFO2, IFI16, IFI27, IFI27L1, IFI27L2, IFI30, IFI35, IFI44, IFI44L, IFI6, IFIH1, IFIT1, IFIT1B, IFIT2, IFIT3, IFIT5, IFITM1, IFITM10, IFITM2, IFITM3, IFITM5, IFNA1, IFNA10, IFNA13, IFNA14, IFNA16, IFNA17, IFNA2, IFNA21, IFNA4, IFNA5, IFNA6, IFNA7, IFNA8, IFNAR1, IFNAR2, IFNB1, IFNE, IFNG, IFNGR1, IFNGR2, IFNK, IFNL1, IFNL2, IFNL3, IFNL4, IFNLR1, IFNW1, IFRD1, IFRD2, IFT122, IFT140, IFT172, IFT20, IFT22, IFT27, IFT43, IFT46, IFT52, IFT57, IFT74, IFT80, IFT81, IFT88, IGBP1, IGDCC3, IGDCC4, IGF1, IGF1R, IGF2, IGF2BP1, IGF2BP2, IGF2BP3, IGF2R, IGFALS, IGFBP1, IGFBP2, IGFBP3, IGFBP4, IGFBP5, IGFBP6, IGFBP7, IGFBPL1, IGFL1, IGFL2, IGFL3, IGFL4, IGFLR1, IGFN1, IGHA1, IGHA2, IGHD, IGHD1-1, IGHD1-14, IGHD1-20, IGHD1-26, IGHD1-7, IGHD1OR15-1A, IGHD1OR15-1B, IGHD2-15, IGHD2-2, IGHD2-21, IGHD2-8, IGHD2OR15-2A, IGHD2OR15-2B, IGHD3-10, IGHD3-16, IGHD3-22, IGHD3-3, IGHD3-9, IGHD3OR15-3A, IGHD3OR15-3B, IGHD4-11, IGHD4-17, IGHD4-23, IGHD4-4, IGHD4OR15-4A, IGHD4OR15-4B, IGHD5-12, IGHD5-18, IGHD5-24, IGHD5-5, IGHD5OR15-5A, IGHD5OR15-5B, IGHD6-13, IGHD6-19, IGHD6-25, IGHD6-6, IGHD7-27, IGHE, IGHG1, IGHG2, IGHG3, IGHG4, IGHJ1, IGHJ2, IGHJ3, IGHJ4, IGHJ5, IGHJ6, IGHM, IGHMBP2, IGHV1-18, IGHV1-2, IGHV1-24, IGHV1-3, IGHV1-45, IGHV1-46, IGHV1-58, IGHV1-69, IGHV1OR15-1, IGHV1OR15-9, IGHV1OR21-1, IGHV2-26, IGHV2-5, IGHV2-70, IGHV2OR16-5, IGHV3-11, IGHV3-13, IGHV3-15, IGHV3-16, IGHV3-20, IGHV3-21, IGHV3-23, IGHV3-30, IGHV3-33, IGHV3-35, IGHV3-38, IGHV3-43, IGHV3-48, IGHV3-49, IGHV3-53, IGHV3-64, IGHV3-66, IGHV3-7, IGHV3-72, IGHV3-73, IGHV3-74, IGHV30R15-7, IGHV30R16-10, IGHV30R16-12, IGHV30R16-13, IGHV30R16-8, IGHV30R16-9, IGHV4-28, IGHV4-31, IGHV4-34, IGHV4-39, IGHV4-4, IGHV4-59, IGHV4-61, IGHV4OR15-8, IGHV5-51, IGHV6-1, IGHV7-81, IGIP, IGKC, IGKJ1, IGKJ2, IGKJ3, IGKJ4, IGKJ5, IGKV1-12, IGKV1-16, IGKV1-17, IGKV1-27, IGKV1-33, IGKV1-37, IGKV1-39, IGKV1-5, IGKV1-6, IGKV1-8, IGKV1-9, IGKV1D-12, IGKV1D-13, IGKV1D-16, IGKV1D-17, IGKV1D-33, IGKV1D-37, IGKV1D-39, IGKV1D-42, IGKV1D-43, IGKV1D-8, IGKV1OR2-108, IGKV2-24, IGKV2-28, IGKV2-30, IGKV2-40, IGKV2D-24, IGKV2D-26, IGKV2D-28, IGKV2D-29, IGKV2D-30, IGKV2D-40, IGKV3-11, IGKV3-15, IGKV3-20, IGKV3-7, IGKV3D-11, IGKV3D-15, IGKV3D-20, IGKV3D-7, IGKV3OR2-268, IGKV4-1, IGKV5-2, IGKV6-21, IGKV6D-21, IGKV6D-41, IGLC1, IGLC2, IGLC3, IGLC7, IGLJ1, IGLJ2, IGLJ3, IGLJ4, IGLJ5, IGLJ6, IGLJ7, IGLL1, IGLL5, IGLONS, IGLV10-54, IGLV11-55, IGLV1-36, IGLV1-40, IGLV1-44, IGLV1-47, IGLV1-50, IGLV1-51, IGLV2-11, IGLV2-14, IGLV2-18, IGLV2-23, IGLV2-33, IGLV2-8, IGLV3-1, IGLV3-10, IGLV3-12, IGLV3-16, IGLV3-19, IGLV3-21, IGLV3-22, IGLV3-25, IGLV3-27, IGLV3-32, IGLV3-9, IGLV4-3, IGLV4-60, IGLV4-69, IGLV5-37, IGLV5-45, IGLV5-48, IGLV5-52, IGLV6-57, IGLV7-43, IGLV7-46, IGLV8-61, IGLV9-49, IGSF1, IGSF10, IGSF11, IGSF21, IGSF22, IGSF23, IGSF3, IGSF5, IGSF6, IGSF8, IGSF9, IGSF9B, IHH, IK, IKBIP, IKBKB, IKBKE, IKBKG, IKZF1, IKZF2, IKZF3, IKZF4, IKZF5, IL10, IL10RA, IL10RB, IL11, IL11RA, IL12A, IL12B, IL12RB1, IL12RB2, IL13, IL13RA1, IL13RA2, IL15, IL15RA, IL16, IL17A, IL17B, IL17C, IL17D, IL17F, IL17RA, IL17RB, IL17RC, IL17RD, IL17RE, IL17REL, IL18, IL18BP, IL18R1, IL18RAP, IL19, IL1A, IL1B, IL1F10, IL1R1, IL1R2, IL1RAP, ILIRAPL, IL1RAPL2, IL1RL1, IL1RL2, IL1RN, IL2, IL20, IL20RA, IL20RB, IL21, IL21R, IL22, IL22RA1, IL22RA2, IL23A, IL23R, IL24, IL25, IL26, IL27, IL27RA, IL2RA, IL2RB, IL2RG, IL3, IL31, IL31RA, IL32, IL33, IL34, IL36A, IL36B, IL36G, IL36RN, IL37, IL3RA, IL4, IL4I1, IL4R, IL5, IL5RA, IL6, IL6R, IL6ST, IL7, IL7R, IL9, IL9R, ILDR1, ILDR2, ILF2, ILF3, ILK, ILKAP, ILVBL, IMMP1L, IMMP2L, IMMT, IMP3, IMP4, IMPA1, IMPA2, IMPACT, IMPAD1, IMPDH1, IMPDH2, IMPG1, IMPG2, INA, INAFM1, INAFM2, INAVA, INCA1, INCENP, INF2, ING1, ING2, ING3, ING4, ING, INHA, INHBA, INHBB, INHBC, INHBE, INIP, INMT, INMT-MINDY4, INO80, INO80B, INO80B-WBP1, INO80C, INO80D, INO80E, INPP1, INPP4A, INPP4B, INPP5A, INPP5B, INPP5D, INPP5E, INPP5F, INPP5J, INPP5K, INPPL1, INS, INSC, INSIGI, INSIG2, INS-IGF2, INSL3, INSL4, INSL5, INSL6, INSM1, INSM2, INSR, INSRR, INTS1, INTS10, INTS11, INTS12, INTS13, INTS14, INTS2, INTS3, INTS4, INTS5, INTS6, INTS6L, INTS7, INTS8, INTS9, INTU, INVS, IP6K1, IP6K2, IP6K3, IPCEF1, IPMK, IPO11, IPO13, IPO4, IP05, IPO7, IPO8, IPO9, IPP, IPPK, IQANK, IQCA1, IQCA1L, IQCB1, IQCC, IQCD, IQCE, IQCF1, IQCF2, IQCF3, IQCF5, IQCF6, IQCG, IQCH, IQCJ, IQCJ-SCHIP1, IQCK, IQCM, IQGAP1, IQGAP2, IQGAP3, IQSEC1, IQSEC2, IQSEC3, IQUB, RAK1, IRAKIBP1, IRAK2, RAK3, IRAK4, IREB2, IRF1, IRF2, IRF2BP1, IRF2BP2, IRF2BPL, IRF3, IRF4, IRF5, IRF6, IRF7, IRF8, IRF9, IRGC, IRGM, IRGQ, IRS1, IRS2, IRS4, IRX1, IRX2, IRX3, IRX4, IRX5, IRX6, ISCA1, ISCA2, ISCU, ISG15, ISG20, ISG20L2, ISL1, ISL2, ISLR, ISLR2, ISM1, ISM2, ISOC1, ISOC2, ISPD, IST1, ISX, ISY1, ISY1-RAB43, ISYNA1, ITCH, ITFG1, ITFG2, ITGA1, ITGA10, ITGA11, ITGA2, ITGA2B, ITGA3, ITGA4, ITGA5, ITGA6, ITGA7, ITGA8, ITGA9, ITGAD, ITGAE, ITGAL, ITGAM, ITGAV, ITGAX, ITGB1, ITGB1BP1, ITGB1BP2, ITGB2, ITGB3, ITGB3BP, ITGB4, ITGB5, ITGB6, ITGB7, ITGB8, ITGBL1, ITIH1, ITIH2, ITIH3, ITIH4, ITIH5, ITIH6, ITK, ITLN1, ITLN2, ITM2A, ITM2B, ITM2C, ITPA, ITPK1, ITPKA, ITPKB, ITPKC, ITPR1, ITPR2, ITPR3, ITPRIP, ITPRIPL1, ITPRIPL2, ITSN1, ITSN2, IVD, IVL, IVNS1ABP, IWS1, IYD, IZUMO1, IZUMO1R, IZUMO2, IZUMO3, IZUMO4, JADE1, JADE2, JADE3, JAG1, JAG2, JAGN1, JAK1, JAK2, JAK3, JAKMIP1, JAKMIP2, JAKMIP3, JAM2, JAM3, JAML, JARID2, JAZF1, JCAD, JCHAIN, JDP2, JKAMP, JMJD1C, JMJD4, JMJD6, JMJD7, JMJD7-PLA2G4B, JMJD8, JMY, JOSD1, JOSD2, JPH1, JPH2, JPH3, JPH4, JPT1, JPT2, JRK, JRKL, JSRP1, JTB, JUN, JUNB, JUND, JUP, KAAG1, KALRN, KANK1, KANK2, KANK3, KANK4, KANSL1, KANSL1L, KANSL2, KANSL3, KANTR, KARS, KAT14, KAT2A, KAT2B, KAT5, KAT6A, KAT6B, KAT7, KAT8, KATNA1, KATNAL1, KATNAL2, KATNB1, KATNBL1, KAZALD1, KAZN, KBTBD11, KBTBD11-OT1, KBTBD12, KBTBD13, KBTBD2, KBTBD3, KBTBD4, KBTBD6, KBTBD7, KBTBD8, KCMF1, KCNA1, KCNA10, KCNA2, KCNA3, KCNA4, KCNA5, KCNA7, KCNAB1, KCNAB2, KCNAB3, KCNB1, KCNB2, KCNC1, KCNC2, KCNC3, KCNC4, KCND1, KCND2, KCND3, KCNE1, KCNE1B, KCNE2, KCNE3, KCNE4, KCNE5, KCNF1, KCNG1, KCNG2, KCNG3, KCNG4, KCNH1, KCNH2, KCNH3, KCNH4, KCNH5, KCNH6, KCNH7, KCNH8, KCNIP1, KCNIP2, KCNIP3, KCNIP4, KCNJ1, KCNJ10, KCNJ11, KCNJ12, KCNJ13, KCNJ14, KCNJ15, KCNJ16, KCNJ18, KCNJ2, KCNJ3, KCNJ4, KCNJ5, KCNJ6, KCNJ8, KCNJ9, KCNK1, KCNK10, KCNK12, KCNK13, KCNK15, KCNK16, KCNK17, KCNK18, KCNK2, KCNK3, KCNK4, KCNK5, KCNK6, KCNK7, KCNK9, KCNMA1, KCNMB1, KCNMB2, KCNMB3, KCNMB4, KCNN1, KCNN2, KCNN3, KCNN4, KCNQ1, KCNQ2, KCNQ3, KCNQ4, KCNQ5, KCNRG, KCNS1, KCNS2, KCNS3, KCNT1, KCNT2, KCNU1, KCNV1, KCNV2, KCP, KCTD1, KCTD10, KCTD11, KCTD12, KCTD13, KCTD14, KCTD15, KCTD16, KCTD17, KCTD18, KCTD19, KCTD2, KCTD20, KCTD21, KCTD3, KCTD4, KCTD5, KCTD6, KCTD7, KCTD8, KCTD9, KDELC1, KDELC2, KDELR1, KDELR2, KDELR3, KDF1, KDM1A, KDM1B, KDM2A, KDM2B, KDM3A, KDM3B, KDM4A, KDM4B, KDM4C, KDM4D, KDM4E, KDM4F, KDM5A, KDM5B, KDM5C, KDM5D, KDM6A, KDM6B, KDM7A, KDM8, KDR, KDSR, KEAP1, KEL, KERA, KF459570.1, KHDC1, KHDC1L, KHDC3L, KHDRBS1, KHDRBS2, KHDRBS3, KHK, KHNYN, KHSRP, KIAA0040, KIAA0100, KIAA0141, KIAA0232, KIAA0319, KIAA0319L, KIAA0355, KIAA0368, KIAA0391, KIAA0408, KIAA0513, KIAA0556, KIAA0586, KIAA0753, KIAA0825, KIAA0895, KIAA0895L, KIAA0907, KIAA0930, KIAA1024, KIAA1024L, KIAA1107, KIAA1109, KIAA1143, KIAA1147, KIAA1161, KIAA1191, KIAA1210, KIAA1211, KIAA1211L, KIAA1217, KIAA1257, KIAA1324, KIAA1324L, KIAA1328, KIAA1456, KIAA1468, KIAA1522, KIAA1524, KIAA1549, KIAA1549L, KIAA1551, KIAA1586, KIAA1614, KIAA1644, KIAA1671, KIAA1683, KIAA1755, KIAA1841, KIAA1958, KIAA2012, KIAA2013, KIAA2026, KIDINS220, KIF11, KIF12, KIF13A, KIF13B, KIF14, KIF15, KIF16B, KIF17, KIF18A, KIF18B, KIF19, KIF1A, KIF1B, KIF1BP, KIF1C, KIF20A, KIF20B, KIF21A, KIF21B, KIF22, KIF23, KIF24, KIF25, KIF26A, KIF26B, KIF27, KIF2A, KIF2B, KIF2C, KIF3A, KIF3B, KIF3C, KIF4A, KIF4B, KIF5A, KIF5B, KIF5C, KIF6, KIF7, KIF9, KIFAP3, KIFC1, KIFC2, KIFC3, KIN, KIR2DL1, KIR2DL2, KIR2DL3, KIR2DL4, KIR2DL5A, KIR2DL5B, KIR2DP1, KIR2DS1, KIR2DS2, KIR2DS3, KIR2DS4, KIR2DS5, KIR3DL1, KIR3DL2, KIR3DL3, KIR3DP1, KIR3DS1, KIR3DX1, KIRREL1, KIRREL2, KIRREL3, KISS1, KISS1R, KIT, KITLG, KIZ, KL, KLB, KLC1, KLC2, KLC3, KLC4, KLF1, KLF10, KLF11, KLF12, KLF13, KLF14, KLF15, KLF16, KLF17, KLF18, KLF2, KLF3, KLF4, KLF5, KLF6, KLF7, KLF8, KLF9, KLHDC1, KLHDC10, KLHDC2, KLHDC3, KLHDC4, KLHDC7A, KLHDC7B, KLHDC8A, KLHDC8B, KLHDC9, KLHL1, KLHL10, KLHL11, KLHL12, KLHL13, KLHL14, KLHL15, KLHL17, KLHL18, KLHL2, KLHL20, KLHL21, KLHL22, KLHL23, KLHL24, KLHL25, KLHL26, KLHL28, KLHL29, KLHL3, KLHL30, KLHL31, KLHL32, KLHL33, KLHL34, KLHL35, KLHL36, KLHL38, KLHL4, KLHL40, KLHL41, KLHL42, KLHL5, KLHL6, KLHL7, KLHL8, KLHL9, KLK1, KLK10, KLK11, KLK12, KLK13, KLK14, KLK15, KLK2, KLK3, KLK4, KLK5, KLK6, KLK7, KLK8, KLK9, KLKB1, KLLN, KLRB1, KLRC1, KLRC2, KLRC3, KLRC4, KLRC4-KLRK1, KLRD1, KLRF1, KLRF2, KLRG1, KLRG2, KLRK1, KMO, KMT2A, KMT2B, KMT2C, KMT2D, KMT2E, KMT5A, KMT5B, KMT5C, KNCN, KNDC1, KNG1, KNL1, KNOP1, KNSTRN, KNTC1, KP420437.1, KP420437.2, KP420437.3, KP420439.1, KP420440.1, KP420440.2, KP420440.3, KP420440.4, KP420440.5, KP420440.6, KP420440.7, KP420440.8, KP420440.9, KP420441.1, KP420441.2, KP420441.3, KP420441.4, KP420441.5, KP420442.2, KP420442.3, KP420443.1, KP420444.1, KP420444.2, KP420444.3, KP420444.4, KP420444.5, KP420444.6, KP420444.7, KP420446.1, KP420446.2, KPNA1, KPNA2, KPNA3, KPNA4, KPNA5, KPNA6, KPNA7, KPNB1, KPRP, KPTN, KRAS, KRBA1, KRBA2, KRBOX1, KRBOX4, KRCC1, KREMEN1, KREMEN2, KRI1, KRIT1, KRR1, KRT1, KRT10, KRT12, KRT13, KRT14, KRT15, KRT16, KRT17, KRT18, KRT19, KRT2, KRT20, KRT222, KRT23, KRT24, KRT25, KRT26, KRT27, KRT28, KRT3, KRT31, KRT32, KRT33A, KRT33B, KRT34, KRT35, KRT36, KRT37, KRT38, KRT39, KRT4, KRT40, KRT5, KRT6A, KRT6B, KRT6C, KRT7, KRT71, KRT72, KRT73, KRT74, KRT75, KRT76, KRT77, KRT78, KRT79, KRT8, KRT80, KRT81, KRT82, KRT83, KRT84, KRT85, KRT86, KRT9, KRTAP10-1, KRTAP1O-10, KRTAP10-11, KRTAP10-12, KRTAP10-2, KRTAP10-3, KRTAP10-4, KRTAP10-5, KRTAP10-6, KRTAP10-7, KRTAP10-8, KRTAP10-9, KRTAP1-1, KRTAP11-1, KRTAP12-1, KRTAP12-2, KRTAP12-3, KRTAP12-4, KRTAP1-3, KRTAPI3-1, KRTAPI3-2, KRTAPI3-3, KRTAPI3-4, KRTAP1-4, KRTAP1-5, KRTAP15-1, KRTAP16-1, KRTAP17-1, KRTAP19-1, KRTAP19-2, KRTAP19-3, KRTAP19-4, KRTAP19-5, KRTAP19-6, KRTAP19-7, KRTAP19-8, KRTAP20-1, KRTAP20-2, KRTAP20-3, KRTAP20-4, KRTAP2-1, KRTAP21-1, KRTAP21-2, KRTAP21-3, KRTAP2-2, KRTAP22-1, KRTAP22-2, KRTAP2-3, KRTAP23-1, KRTAP2-4, KRTAP24-1, KRTAP25-1, KRTAP26-1, KRTAP27-1, KRTAP29-1, KRTAP3-1, KRTAP3-2, KRTAP3-3, KRTAP4-1, KRTAP4-11, KRTAP4-12, KRTAP4-16, KRTAP4-2, KRTAP4-3, KRTAP4-4, KRTAP4-5, KRTAP4-6, KRTAP4-7, KRTAP4-8, KRTAP4-9, KRTAP5-1, KRTAP5-10, KRTAP5-11, KRTAP5-2, KRTAP5-3, KRTAP5-4, KRTAP5-5, KRTAP5-6, KRTAP5-7, KRTAP5-8, KRTAP5-9, KRTAP6-1, KRTAP6-2, KRTAP6-3, KRTAP7-1, KRTAP8-1, KRTAP9-1, KRTAP9-2, KRTAP9-3, KRTAP9-4, KRTAP9-6, KRTAP9-7, KRTAP9-8, KRTAP9-9, KRTCAP2, KRTCAP3, KRTDAP, KSR1, KSR2, KTI12, KTN1, KU645196.1, KU645196.2, KU645196.3, KU645196.4, KU645196.5, KU645196.6, KU645196.7, KU645196.8, KU645196.9, KU645197.1, KU645197.2, KU645197.3, KU645197.4, KU645197.5, KU645198.1, KXD1, KY, KYAT1, KYAT3, KYNU, L1CAM, L1TD1, L2HGDH, L34079.1, L3HYPDH, L3MBTL1, L3MBTL2, L3MBTL3, L3MBTL4, LACC1, LACRT, LACTB, LACTB2, LACTBL1, LAD1, LAG3, LAGE3, LAIR1, LAIR2, LALBA, LAMA1, LAMA2, LAMA3, LAMA4, LAMA5, LAMB1, LAMB2, LAMB3, LAMB4, LAMC1, LAMC2, LAMC3, LAMP1, LAMP2, LAMP3, LAMP5, LAMTOR1, LAMTOR2, LAMTOR3, LAMTOR4, LAMTOR5, LANCL1, LANCL2, LANCL3, LAP3, LAPTM4A, LAPTM4B, LAPTM5, LARGE1, LARGE2, LARP1, LARP1B, LARP4, LARP4B, LARP6, LARP7, LARS, LARS2, LAS1L, LASP1, LAT, LAT2, LATS1, LATS2, LAX1, LAYN, LBH, LBHD1, LBP, LBR, LBX1, LBX2, LCA5, LCA5L, LCAT, LCE1A, LCE1B, LCE1C, LCE1D, LCE1E, LCE1F, LCE2A, LCE2B, LCE2C, LCE2D, LCE3A, LCE3B, LCE3C, LCE3D, LCE3E, LCE4A, LCE5A, LCE6A, LCK, LCLAT1, LCMT1, LCMT2, LCN1, LCN10, LCN12, LCN15, LCN2, LCN6, LCN8, LCN9, LCNL1, LCOR, LCORL, LCP1, LCP2, LCT, LCTL, LDAH, LDB1, LDB2, LDB3, LDHA, LDHAL6A, LDHAL6B, LDHB, LDHC, LDHD, LDLR, LDLRAD1, LDLRAD2, LDLRAD3, LDLRAD4, LDLRAP1, LDOC1, LEAP2, LECT2, LEF1, LEFTY1, LEFTY2, LEKR1, LELP1, LEMD1, LEMD2, LEMD3, LENEP, LENG1, LENG8, LENG9, LEO1, LEP, LEPR, LEPROT, LEPROTL1, LETM1, LETM2, LETMD1, LEUTX, LEXM, LFNG, LGALS1, LGALS12, LGALS13, LGALS14, LGALS16, LGALS2, LGALS3, LGALS3BP, LGALS4, LGALS7, LGALS7B, LGALS8, LGALS9, LGALS9B, LGALS9C, LGALSL, LGI1, LGI2, LGI3, LGI4, LGMN, LGR4, LGR5, LGR6, LGSN, LHB, LHCGR, LHFPL1, LHFPL2, LHFPL3, LHFPL4, LHFPL5, LHFPL6, LHPP, LHX1, LHX2, LHX3, LHX4, LHX5, LHX6, LHX8, LHX9, LIAS, LIF, LIFR, LIG1, LIG3, LIG4, LILRA, LILRA2, LILRA3, LILRA4, LILRA5, LILRA6, LILRB1, LILRB2, LILRB3, LILRB4, LILRB5, LIM2, LMA1, LIMCH1, LIMD1, LIMD2, LIME1, LIMK1, LIMK2, LIMS1, LIMS2, LIMS3, LIMS4, LIN28A, LIN28B, LIN37, LIN52, LIN54, LIN7A, LIN7B, LIN7C, LIN9, LINC00094, LINC00116, LINC00282, LINC00672, LINC00675, LINC00694, LINC00854, LINC00890, LINC00959, LINC01125, LINC01556, LINC02210-CRHR1, LINGO1, LING2, LING3, LINGO4, LINS1, LIPA, LIPC, LIPE, LIPF, LIPG, LIPH, LIP1, LIPJ, LIPK, LIPM, LIPN, LIPT1, LIPT2, LITAF, LIX1, LIX1L, LKAAEAR1, LLGL1, LLGL2, LLPH, LMAN1, LMAN1L, LMAN2, LMAN2L, LMBR1, LMBR1L, LMBRD1, LMBRD2, LMCD1, LMF1, LMF2, LMLN, LMNA, LMNB1, LMNB2, LMNTD1, LMNTD2, LMO1, LMO2, LMO3, LMO4, LMO7, LMO7DN, LMOD1, LMOD2, LMOD3, LMTK2, LMTK3, LMX1A, LMX1B, LNP1, LNPEP, LNPK, LNX1, LNX2, LO000005.1, LONP1, LONP2, LONRF1, LONRF2, LONRF3, LOR, LOX, LOXHD1, LOXL1, LOXL2, LOXL3, LOXL4, LPA, LPAR1, LPAR2, LPAR3, LPAR4, LPAR5, LPAR6, LPCAT1, LPCAT2, LPCAT3, LPCAT4, LPGAT1, LPIN1, LPIN2, LPIN3, LPL, LPO, LPP, LPXN, LRAT, LRBA, LRCH1, LRCH2, LRCH3, LRCH4, LRCOL1, LRFN1, LRFN2, LRFN3, LRFN4, LRFN5, LRG1, LRGUK, LRIF1, LRIG1, LRIG2, LRIG3, LRIT1, LRIT2, LRIT3, LRMDA, LRMP, LRP1, LRP10, LRP11, LRP12, LRP1B, LRP2, LRP2BP, LRP3, LRP4, LRP5, LRP5L, LRP6, LRP8, LRPAP1, LRPPRC, LRR1, LRRC1, LRRC10, LRRC10B, LRRC14, LRRC14B, LRRC15, LRRC17, LRRC18, LRRC19, LRRC2, LRRC20, LRRC23, LRRC24, LRRC25, LRRC26, LRRC27, LRRC28, LRRC29, LRRC3, LRRC30, LRRC31, LRRC32, LRRC34, LRRC36, LRRC37A, LRRC37A2, LRRC37A3, LRRC37B, LRRC38, LRRC39, LRRC3B, LRRC3C, LRRC4, LRRC40, LRRC41, LRRC42, LRRC43, LRRC45, LRRC46, LRRC47, LRRC49, LRRC4B, LRRC4C, LRRC52, LRRC53, LRRC55, LRRC56, LRRC57, LRRC58, LRRC59, LRRC6, LRRC61, LRRC63, LRRC66, LRRC69, LRRC7, LRRC70, LRRC71, LRRC72, LRRC73, LRRC74A, LRRC74B, LRRC75A, LRRC75B, LRRC8A, LRRC8B, LRRC8C, LRRC8D, LRRC8E, LRRC9, LRRCC1, LRRD1, LRRFIP1, LRRFIP2, LRRIQ1, LRRIQ3, LRRIQ4, LRRK1, LRRK2, LRRN1, LRRN2, LRRN3, LRRN4, LRRN4CL, LRRTM1, LRRTM2, LRRTM3, LRRTM4, LRSAM1, LRTM1, LRTM2, LRTOMT, LRWD1, LSAMP, LSG1, LSM1, LSM10, LSM11, LSM12, LSM14A, LSM14B, LSM2, LSM3, LSM4, LSM5, LSM6, LSM7, LSM8, LSMEM1, LSMEM2, LSP1, LSR, LSS, LST1, LTA, LTA4H, LTB, LTB4R, LTB4R2, LTBP1, LTBP2, LTBP3, LTBP4, LTBR, LTC4S, LTF, LTK, LTN1, LTV1, LUC7L, LUC7L2, LUC7L3, LUM, LURAP1, LURAP1L, LUZP1, LUZP2, LUZP4, LUZP6, LVRN, LXN, LY6D, LY6E, LY6G5B, LY6G5C, LY6G6C, LY6G6D, LY6G6E, LY6G6F, LY6H, LY6K, LY6L, LY75, LY75-CD302, LY86, LY9, LY96, LYAR, LYG1, LYG2, LYL1, LYN, LYNX1, LYPD1, LYPD2, LYPD3, LYPD4, LYPD5, LYPD6, LYPD6B, LYPD8, LYPLA1, LYPLA2, LYPLAL1, LYRM1, LYRM2, LYRM4, LYRM7, LYRM9, LYSMD1, LYSMD2, LYSMD3, LYSMD4, LYST, LYVE1, LYZ, LYZL1, LYZL2, LYZL4, LYZL6, LZIC, LZTFL1, LZTR1, LZTS1, LZTS2, LZTS3, M1AP, M6PR, MAATS1, MAB21L1, MAB21L2, MAB21L3, MACC1, MACF, MACROD1, MACROD2, MAD1L1, MAD2L1, MAD2L1BP, MAD2L2, MADCAM1, MADD, MAEA, MAEL, MAF, MAF1, MAFA, MAFB, MAFF, MAFG, MAFK, MAG, MAGEA1, MAGEA10, MAGEA11, MAGEA12, MAGEA2, MAGEA2B, MAGEA3, MAGEA4, MAGEA6, MAGEA8, MAGEA9, MAGEA9B, MAGEB1, MAGEB10, MAGEB16, MAGEB17, MAGEB18, MAGEB2, MAGEB3, MAGEB4, MAGEB5, MAGEB6, MAGEB6P1, MAGEC1, MAGEC2, MAGEC3, MAGED1, MAGED2, MAGED4, MAGED4B, MAGEE1, MAGEE2, MAGEFI, MAGEHI, MAGEL2, MAGI1, MAGI2, MAGI3, MAGIX, MAGOH, MAGOHB, MAGT1, MAIP1, MAJIN, MAK, MAK16, MAL, MAL2, MALL, MALRD1, MALSU1, MALT1, MAMDC2, MAMDC4, MAML1, MAML2, MAML3, MAMLD1, MAMSTR, MAN1A1, MAN1A2, MAN1B1, MAN1C$_1$, MAN2A1, MAN2A2, MAN2B1, MAN2B2, MAN2C1, MANBA, MANBAL, MANEA, MANEAL, MANF, MANSCI, MANSC4, MAOA, MAOB, MAP10, MAP1A, MAP1B, MAP1LC3A, MAP1LC3B, MAP1LC3B2, MAP1LC3C, MAP1S, MAP2, MAP2K1, MAP2K2, MAP2K3, MAP2K4, MAP2K5, MAP2K6, MAP2K7, MAP3K1, MAP3K10, MAP3K11, MAP3K12, MAP3K13, MAP3K14, MAP3K15, MAP3K19, MAP3K2, MAP3K20, MAP3K21, MAP3K3, MAP3K4, MAP3K5, MAP3K6, MAP3K7, MAP3K7CL, MAP3K8, MAP3K9, MAP4, MAP4K1, MAP4K2, MAP4K3, MAP4K4, MAP4K5, MAP6, MAP6D1, MAP7, MAP7D1, MAP7D2, MAP7D3, MAP9, MAPK1, MAPK10, MAPK11, MAPK12, MAPK13, MAPK14, MAPK15, MAPK1IP1L, MAPK3, MAPK4, MAPK6, MAPK7, MAPK8, MAPK8IP1, MAPK8IP2, MAPK8IP3, MAPK9, MAPKAP1, MAPKAPK2, MAPKAPK3, MAPKAPK5, MAPKBP1, MAPRE1, MAPRE2, MAPRE3, MAPT, MARC1, MARC2, MARCHI, MARCH10, MARCH11, MARCH2, MARCH3, MARCH4, MARCH5, MARCH6, MARCH7, MARCH8, MARCH9, MARCKS, MARCKSL1, MARCO, MARF1, MARK1, MARK2, MARK3, MARK4, MARS, MARS2, MARVELD1, MARVELD2, MARVELD3, MAS1, MAS1L, MASP1, MASP2, MAST1, MAST2, MAST3, MAST4, MASTL, MAT1A, MAT2A, MAT2B, MATK, MATN1, MATN2, MATN3, MATN4, MATR3, MAU2, MAVS, MAX, MAZ, MB, MB21D1, MB21D2, MBD1, MBD2, MBD3, MBD3L1, MBD3L2, MBD3L2B, MBD3L3, MBD3L4, MBD3L5, MBD4, MBD5, MBD6, MBIP, MBL2, MBLAC1, MBLAC2, MBNL1, MBNL2, MBNL3, MBOAT1, MBOAT2, MBOAT4, MBOAT7, MBP, MBTD1, MBTPS1, MBTPS2, MC1R, MC2R, MC3R, MC4R, MC5R, MCAM, MCAT, MCC, MCCC1, MCCC2, MCCD1, MCEE, MCEMP1, MCF2, MCF2L, MCF2L2, MCFD2, MCHR1, MCHR2, MCIDAS, MCL1, MCM10, MCM2, MCM3, MCM3AP, MCM4, MCM5, MCM6, MCM7, MCM8, MCM9, MCMBP, MCMDC2, MCOLN1, MCOLN2, MCOLN3, MCPH1, MCRIP1, MCRIP2, MCRS1, MCTP1, MCTP2, MCTS1, MCU, MCUB, MCUR1, MDC1, MDFI, MDFIC, MDFIC2, MDGA1, MDGA2, MDH1, MDH1B, MDH2, MDK, MDM1, MDM2, MDM4, MDN1, MDP1, MDS2, ME1, ME2, ME3, MEA1, MEAF6, MECOM, MECP2, MECR, MED1, MED10, MED11, MED12, MED12L, MED13, MED13L, MED14, MED14OS, MED15, MED16, MED17, MED18, MED19, MED20, MED21, MED22, MED23, MED24, MED25, MED26, MED27, MED28, MED29, MED30, MED31, MED4, MED6, MED7, MED8, MED9, MEDAG, MEF2A, MEF2B, MEF2C, MEF2D, MEFV, MEGF10, MEGF11, MEGF6, MEGF8, MEGF9, MEI, MEI4, MEIG1, MEIKIN, MEIOB, MEIOC, MEIS1, MEIS2, MEIS3, MELK, MELTF, MEMO1, MEN1, MEOX1, MEOX2, MEP1A, MEP1B, MEPCE, MEPE, MERTK, MESD, MESP1, MESP2, MEST, MET, METAP1, METAPID, METAP2, METRN, METRNL, METTL1, METTL11B, METTL12, METTL13, METTL14, METTL15, METTL16, METTL17, METTL18, METTL21A, METTL21C, METTL22, METTL23, METTL24, METTL25, METTL26, METTL27, METTL2A, METTL2B, METTL3, METTL4, METTL5, METTL6, METTL7A, METTL7B, METTL8, METTL9, MEX3A, MEX3B, MEX3C, MEX3D, MFAP1, MFAP2, MFAP3, MFAP3L, MFAP4, MFAP5, MFF, MFGE8, MFHAS1, MIFN1, MFN2, MFNG, MFRP, MFSD1, MFSD10, MFSD11, MFSD12, MFSD13A, MFSD14A, MFSD14B, MFSD14C, MFSD2A, MFSD2B, MFSD3, MFSD4A, MFSD4B, MFSD5, MFSD6, MFSD6L, MFSD7, MFSD8, MFSD9, MGA, MGAM, MGAM2, MGARP, MGAT1, MGAT2, MGAT3, MGAT4A, MGAT4B, MGAT4C, MGAT4D, MGAT5, MGAT5B, MGEA5, MGLL, MGME1, MGMT, MGP, MGRN1, MGST1, MGST2, MGST3, MIA, MIA3, MIA-RAB4B, MIB1, MIB2, MICA, MICAL1, MICAL2, MICAL3, MICALCL, MICALL1, MICALL2, MICB, MICU1, MICU2, MICU3, MID1, MID1IP1, MID2, MIDN, MIEF1, MIEF2, MIEN1, MIER1, MIER2, MIER3, MIF, MIF4GD, MIGA1, MIGA2, MIIP, MILR1, MINDY1, MINDY2, MINDY3, MINDY4, MINDY4B, MINK1, MINOSI, MINOS1-NBL1, MINPP1, MIOS, MIOX, MIP, MIPEP, MIPOL1, MIS12, MIS18A, MIS18BP1, MISP, MISP3, MITD1, MITF, MIXL1, MKI67, MKKS, MKL1, MKL2, MKLN1, MKNK1, MKNK2, MKRN1, MKRN2, MKRN2OS, MKRN3, MKS1, MKX, MLANA, MLC1, MLEC, MLF1, MLF2, MLH1, MLH3, MLIP, MLKL, MLLT1, MLLT10, MLLT11, MLLT3, MLLT6, MLN, MLNR, MLPH, MLST8, MLX, MLXIP, MLXIPL, MLYCD, MMAA, MMAB, MMACHC, MMADHC, MMD, MMD2, MME, MMEL1, MMGT1, MMP1, MMP10, MMP11, MMP12, MMPI3, MMP14, MMP15, MMP16, MMP17, MMP19, MMP2, MMP20, MMP21, MMP23B, MMP24, MMP24-AS1, MMP25, MMP26, MMP27, MMP28, MMP3, MMP7, MMP8, MMP9, MMRN1, MMRN2, MMS19, MMS22L, MN1, MNAT 1, MND1, MNDA, MNS1, MNT, MNX1, MOAP1, MOB1A, MOB1B, MOB2, MOB3A, MOB3B, MOB3C, MOB4, MOBP, MOCOS, MOCS1, MOCS2, MOCS3, MOG, MOGATI, MOGAT2, MOGAT3, MOGS, MOK, MON1A, MON1B, MON2, MORC1, MORC2, MORC3, MORC4, MORF4L1, MORF4L2, MORN1, MORN2, MORN3, MORN4, MORN5, MOS, MOSPD1, MOSPD2, MOSPD3, MOV10, MOV10L1, MOXD1, MPC1, MPC1L, MPC2, MPDU1, MPDZ, MPEG1, MPG, MPHOSPH10, MPHOSPH6, MPHOSPH8, MPHOSPH9, MPI, MPIG6B, MPL, MPLKIP, MPND, MPO, MPP1, MPP2, MPP3, MPP4, MPP5, MPP6, MPP7, MPPE1, MPPED1, MPPED2, MPRIP, MPST, MPV17, MPV17L, MPV17L2, MPZ, MPZL1, MPZL2, MPZL3, MR1, MRAP, MRAP2, MRAS, MRC1, MRC2, MRE11, MREG, MRFAP1, MRFAP1L1, MRGBP, MRGPRD, MRGPRE, MRGPRF, MRGPRG, MRGPRX1, MRGPRX2, MRGPRX3, MRGPRX4, MRI1, MRLN, MRM1, MRM2, MRM3, MRNIP, MRO, MROH1, MROH2A, MROH2B, MROH5, MROH6, MROH7, MROH7-TTC4, MROH8, MROH9, MRPL1, MRPL10, MRPL11, MRPL12, MRPL13, MRPL14, MRPL15, MRPL16, MRPL17, MRPL18, MRPL19, MRPL2, MRPL20, MRPL21, MRPL22, MRPL23, MRPL24, MRPL27, MRPL28, MRPL3, MRPL30, MRPL32, MRPL33, MRPL34, MRPL35, MRPL36, MRPL37, MRPL38, MRPL39, MRPL4, MRPL40, MRPL41, MRPL42, MRPL43, MRPL44, MRPL45, MRPL46, MRPL47, MRPL48, MRPL49, MRPL50, MRPL51, MRPL52, MRPL53, MRPL54, MRPL55, MRPL57, MRPL58, MRPL9, MRPS10, MRPS11, MRPS12, MRPS14, MRPS15, MRPS16, MRPS17, MRPS18A, MRPS18B, MRPS18C, MRPS2, MRPS21, MRPS22, MRPS23, MRPS24, MRPS25, MRPS26, MRPS27, MRPS28, MRPS30, MRPS31, MRPS33, MRPS34, MRPS35, MRPS36, MRPS5, MRPS6, MRPS7, MRPS9, MRRF, MRS2, MRTO4, MRVI1, MS4A1, MS4A10, MS4A12, MS4A13, MS4A14, MS4A15, MS4A2, MS4A3, MS4A4A, MS4A4E, MS4A5, MS4A6A, MS4A6E, MS4A7, MS4A8, MSANTD1, MSANTD2, MSANTD3, MSANTD3-TMEFF1, MSANTD4, MSC, MSGN1, MSH2, MSH3, MSH4, MSH5, MSH5-SAPCD1, MSH6, MSI1, MSI2, MSL1, MSL2, MSL3, MSLN, MSLNL, MSMB, MSMO1, MSMP, MSN, MSR1, MSRA, MSRB1, MSRB2, MSRB3, MSS51, MST1, MST1R, MSTN, MSTO1, MSX1, MSX2, MT1A, MT1B, MT1E, MT1F, MT1G, MT1H, MT1IL1, MT1M, MT1X, MT2A, MT3, MT4, MTA1, MTA2, MTA3, MTAP, MT-ATP6, MT-ATP8, MTBP, MTCH1, MTCH2, MTCL1, MT-CO1, MT-C02, MT-C03, MTCP1, MT-CYB, MTDH, MTERF1, MTERF2, MTERF3, MTERF4, MTF1, MTF2, MTFMT, MTFP1, MTFR1, MTFR1L, MTFR2, MTG1, MTG2, MTHFD1, MTHFD1L, MTHFD2, MTHFD2L, MTHFR, MTHFS, MTHFSD, MTIF2, MTIF3, MTM1, MTMR1, MTMR10, MTMR11, MTMR12, MTMR14, MTMR2, MTMR3, MTMR4, MTMR6, MTMR7, MTMR8, MTMR9, MT-ND1, MT-ND2, MT-ND3, MT-ND4, MT-ND4L, MT-ND5, MT-ND6, MTNR1A, MTNR1B, MTO1, MTOR, MTPAP, MTPN, MTR, MTRF1, MTRF1L, MTRNR2L1, MTRNR2L10, MTRNR2L11, MTRNR2L12, MTRNR2L13, MTRNR2L3, MTRNR2L4, MTRNR2L5, MTRNR2L6, MTRNR2L7, MTRNR2L8, MTRR, MTSS1, MTSS1L, MTTP, MTURN, MTUS1, MTUS2, MTX1, MTX2, MTX3, MUC1, MUC12, MUC13, MUC15, MUC16, MUC17, MUC2, MUC20, MUC21, MUC22, MUC3A, MUC4, MUC5AC, MUC5B, MUC6, MUC7, MUCL1, MUL1, MUM1, MUM1L1, MUS81, MUSK, MUSTN1, MUT, MUTYH, MVB12A, MVB12B, MVD, MVK, MVP, MX1, MX2, MXD1, MXD3, MXD4, MXI1, MXRA5, MXRA7, MXRA8, MYADM, MYADML2, MYB, MYBBP1A, MYBL1, MYBL2, MYBPC1, MYBPC2, MYBPC3, MYBPH, MYBPHL, MYC, MYCBP, MYCBP2, MYCBPAP, MYCL, MYCN, MYCT1, MYD88, MYDGF, MYEF2, MYEOV, MYF5, MYF6, MYH1, MYH10, MYH11, MYH13, MYH14, MYH15, MYH2, MYH3, MYH4, MYH6, MYH7, MYH7B, MYH8, MYH9, MYL1, MYL10, MYL12A, MYL12B, MYL2, MYL3, MYL4, MYL5, MYL6, MYL6B, MYL7, MYL9, MYLIP, MYLK, MYLK2, MYLK3, MYLK4, MYLPF, MYMK, MYMX, MYNN, MYO10, MYO15A, MYO15B, MYO16, MYO18A, MYO18B, MYO19, MYO1A, MYO1B, MYO1C, MYO1D, MYO1E, MYO1F, MYO1G, MYO1H, MYO3A, MYO3B, MYO5A, MYO5B, MYO5C, MYO6, MYO7A, MYO7B, MYO9A, MYO9B, MYOC, MYOCD, MYOCOS, MYOD1, MYOF, MYOG, MYOM1, MYOM2, MYOM3, MYOT, MYOZ1, MYOZ2, MYOZ3, MYPN, MYPOP, MYRF, MYRFL, MYRIP, MYSM1, MYT1, MYT1L, MYZAP, MZB1, MZF1, MZT1, MZT2A, MZT2B, N4BP1, N4BP2, N4BP2L1, N4BP2L2, N4BP3, N6AMT1, NAA10, NAA11, NAA15, NAA16, NAA20, NAA25, NAA30, NAA35, NAA38, NAA40, NAA50, NAA60, NAAA, NAALAD2, NAALADL1, NAALADL2, NAB1, NAB2, NABP1, NABP2, NACA, NACA2, NACAD, NACC1, NACC2, NADK, NADK2, NADSYN1, NAE1, NAF1, NAGA, NAGK, NAGLU, NAGPA, NAGS, NAIF1, NAIP, NALCN, NAMPT, NANOG, NANOGNB, NANOGP8, NANOS, NANOS2, NANOS3, NANP, NANS, NAP1L1, NAP1L2, NAP1L3, NAP1L4, NAP1L5, NAPA, NAPB, NAPEPLD, NAPG, NAPRT, NAPSA, NARF, NARFL, NARS, NARS2, NASP, NAT 1, NAT 10, NAT14, NAT 16, NAT2, NAT6, NAT8, NAT8B, NAT8L, NAT9, NATD1, NAV1, NAV2, NAV3, NAXD, NAXE, NBAS, NBDY, NBEA, NBEAL1, NBEAL2, NBL1, NBN, NBPF1, NBPF10, NBPF11, NBPF12, NBPF14, NBPF15, NBPF19, NBPF20, NBPF26, NBPF3, NBPF4, NBPF6, NBPF9, NBR1, NCALD, NCAM1, NCAM2, NCAN, NCAPD2, NCAPD3, NCAPG, NCAPG2, NCAPH, NCAPH2, NCBP1, NCBP2, NCBP2-AS2, NCBP2L, NCBP3, NCCRP1, NCDN, NCEH1, NCF1, NCF2, NCF4, NCK1, NCK2, NCKAP1, NCKAP1L, NCKAP5, NCKAP5L, NCKIPSD, NCL, NCLN, NCMAP, NCOA1, NCOA2, NCOA3, NCOA4, NCOA5, NCOA6, NCOA7, NCOR1, NCOR2, NCR1, NCR2, NCR3, NCR3LG1, NCS1, NCSTN, NDC1, NDC80, NDE1, NDEL1, NDFIP1, NDFIP2, NDN, NDNF, NDOR1, NDP, NDRG1, NDRG2, NDRG3, NDRG4, NDST1, NDST2, NDST3, NDST4, NDUFA1, NDUFA10, NDUFA11, NDUFA12, NDUFA13, NDUFA2, NDUFA3, NDUFA4, NDUFA4L2, NDUFA5, NDUFA6, NDUFA7, NDUFA8, NDUFA9, NDUFAB1, NDUFAF1, NDUFAF2, NDUFAF3, NDUFAF4, NDUFAF5, NDUFAF6, NDUFAF7, NDUFAF8, NDUFB1, NDUFB10, NDUFB11, NDUFB2, NDUFB3, NDUFB4, NDUFB5, NDUFB6, NDUFB7, NDUFB8, NDUFB9, NDUFC1, NDUFC2, NDUFC2-KCTD14, NDUFS1, NDUFS2, NDUFS3, NDUFS4, NDUFS5, NDUFS6, NDUFS7, NDUFS8, NDUFV1, NDUFV2, NDUFV3, NEB, NEBL, NECAB1, NECAB2, NECAB3, NECAP1, NECAP2, NECTIN1, NECTIN2, NECTIN3, NECTIN4, NEDD1, NEDD4, NEDD4L, NEDD8, NEDD8-MDP1, NEDD9, NEFH, NEFL, NEFM, NEGR1, NEIL1, NEIL2, NEIL3, NEK1, NEK10, NEK11, NEK2, NEK3, NEK4, NEK5, NEK6, NEK7, NEK8, NEK9, NELFA, NELFB, NELFCD, NELFE, NELL1, NELL2, NEMF, NEMP1, NEMP2, NENF, NEO1, NEPRO, NES, NET1, NETO1, NETO2, NEU1, NEU2, NEU3, NEU4, NEURL1, NEURLB, NEURL2, NEURL3, NEURL4, NEUROD1, NEUROD2, NEUROD4, NEUROD6, NEUROG1, NEUROG2, NEUROG3, NEXMIF, NEXN, NF1, NF2, NFAM1, NFASC, NFAT5, NFATC1, NFATC2, NFATC2IP, NFATC3, NFATC4, NFE2, NFE2L1, NFE2L2, NFE2L3, NFE4, NFIA, NFIB, NFIC, NFIL3, NFIX, NFKB1, NFKB2, NFKBIA, NFKBIB, NFKBID, NFKBIE, NFKBIL1, NFKBIZ, NFRKB, NFS1, NFU1, NFX1, NFXL1, NFYA, NFYB, NFYC, NGB, NGDN, NGEF, NGF, NGFR, NGLY1, NGRN, NHEJ1, NHLH1, NHLH2, NHLRC1, NHLRC2, NHLRC3, NHLRC4, NHP2, NHS, NHSL1, NHSL2, NICN1, NID1, NID2, NIF3L1, NIFK, NIM1K, NIN, NINJ1, NINJ2, NINL, NIP7, NIPA1, NIPA2, NIPAL1, NIPAL2, NIPAL3, NIPAL4, NIPBL, NIPSNAP1, NIPSNAP2, NIPSNAP3A, NIPSNAP3B, NISCH, NIT1, NIT2, NKAIN1, NKAIN2, NKAIN3, NKAIN4, NKAP, NKAPL, NKD1, NKD2, NKG7, NKIRAS1, NKIRAS2, NKPD1, NKRF, NKTR, NKX1-1, NKX1-2, NKX2-1, NKX2-2, NKX2-3, NKX2-4, NKX2-5, NKX2-6, NKX2-8, NKX3-1, NKX3-2, NKX6-1, NKX6-2, NKX6-3, NLE1, NLGN1, NLGN2, NLGN3, NLGN4X, NLGN4Y, NLK, NLN, NLRC3, NLRC4, NLRC5, NLRP1, NLRP10, NLRP11, NLRP12, NLRPI3, NLRP14, NLRP2, NLRP2B, NLRP3, NLRP4, NLRP5, NLRP6, NLRP7, NLRP8, NLRP9, NLRX1, NMB, NMBR, NMD3, NME1, NME1-NME2, NME2, NME3, NME4, NME5, NME6, NME7, NME8, NME9, NMI, NMNAT1, NMNAT2, NMNAT3, NMRAL1, NMRK1, NMRK2, NMS, NMT1, NMT2, NMU, NMUR1, NMUR2, NNAT, NNMT, NNT, NOA1, NOB1, NOBOX, NOC2L, NOC3L, NOC4L, NOCT, NOD1, NOD2, NODAL, NOG, NOL10, NOL11, NOL12, NOL3, NOL4, NOL4L, NOL6, NOL7, NOL8, NOL9, NOLC1, NOM1, NOMO1, NOMO2, NOMO3, NONO, NOP10, NOP14, NOP16, NOP2, NOP53, NOP56, NOP58, NOP9, NOS1, NOS1AP, NOS2, NOS3, NOSIP, NOSTRIN, NOTCH, NOTCH2, NOTCH2NL, NOTCH3, NOTCH4, NOTO, NOTUM, NOV, NOVA1, NOVA2, NOX1, NOX3, NOX4, NOX5, NOXA1, NOXO1, NOXRED1, NPAP1, NPAS1, NPAS2, NPAS3, NPAS4, NPAT, NPB, NPBWR1, NPBWR2, NPC1, NPC1L1, NPC2, NPDC1, NPEPL1, NPEPPS, NPFF, NPFFR1, NPFFR2, NPHP1, NPHP3, NPHP3-ACAD11, NPHP4, NPHS1, NPHS2, NPIPA1, NPIPA2, NPIPA3, NPIPA5, NPIPA7, NPIPA8, NPIPB11, NPIPB12, NPIPB13, NPIPB15, NPIPB2, NPIPB3, NPIPB4, NPIPB5, NPIPB6, NPIPB7, NPIPB8, NPIPB9, NPL, NPLOC4, NPM1, NPM2, NPM3, NPNT, NPPA, NPPB, NPPC, NPR1, NPR2, NPR3, NPRL2, NPRL3, NPS, NPSR1, NPTN, NPTX1, NPTX2, NPTXR, NPVF, NPW, NPY, NPY1R, NPY2R, NPY4R, NPY4R2, NPY5R, NQO1, NQO2, NROB1, NROB2, NR1D1, NR1D2, NR1H2, NR1H3, NR1H4, NR1I2, NR1I3, NR2C1, NR2C2, NR2C2AP, NR2E1, NR2E3, NR2F1, NR2F2, NR2F6, NR3C1, NR3C2, NR4A1, NR4A2, NR4A3, NR5A1, NR5A2, NR6A1, NRAP, NRARP, NRAS, NRBF2, NRBP1, NRBP2, NRCAM, NRDC, NRDE2, NREP, NRF1, NRG1, NRG2, NRG3, NRG4, NRGN, NRIP1, NRIP2, NRIP3, NRK, NRL, NRM, NRN1, NRN1L, NRP1, NRP2, NRROS, NRSN1, NRSN2, NRTN, NRXN1, NRXN2, NRXN3, NSA2, NSD1, NSD2, NSD3, NSDHL, NSF, NSFL1C, NSL1, NSMAF, NSMCE1, NSMCE2, NSMCE3, NSMCE4A, NSMF, NSRP1, NSUN2, NSUN3, NSUN4, NSUN5, NSUN6, NSUN7, NT5C, NT5C1A, NT5C1B, NT5C1B-RDH14, NT5C2, NT5C3A, NT5C3B, NT5DC1, NT5DC2, NT5DC3, NT5DC4, NT5E, NT5M, NTAN1, NTF3, NTF4, NTHL1, NTM, NTMT1, NTN1, NTN3, NTN4, NTN5, NTNG1, NTNG2, NTPCR, NTRK1, NTRK2, NTRK3, NTS, NTSR1, NTSR2, NUAK1, NUAK2, NUB1, NUBP1, NUBP2, NUBPL, NUCB1, NUCB2, NUCKS1, NUDC, NUDCD1, NUDCD2, NUDCD3, NUDT1, NUDT10, NUDT 11, NUDT 12, NUDT13, NUDT 14, NUDT 15, NUDT 16, NUDT16L1, NUDT 17, NUDT18, NUDT19, NUDT2, NUDT21, NUDT22, NUDT3, NUDT4, NUDT4P1, NUDT5, NUDT6, NUDT7, NUDT8, NUDT9, NUF2, NUFIP1, NUFIP2, NUGGC, NUMA1, NUMB, NUMBL, NUP107, NUP133, NUP153, NUP155, NUP160, NUP188, NUP205, NUP210, NUP210L, NUP214, NUP35, NUP37, NUP43, NUP50, NUP54, NUP58, NUP62, NUP62CL, NUP85, NUP88, NUP93, NUP98, NUPL2, NUPR1, NUPR2, NUS1, NUSAP1, NUTF2, NUTM1, NUTM2A, NUTM2B, NUTM2D, NUTM2E, NUTM2F, NUTM2G, NVL, NWD1, NWD2, NXF1, NXF2, NXF2B, NXF3, NXF5, NXN, NXNL1, NXNL2, NXPE1, NXPE2, NXPE3, NXPE4, NXPH1, NXPH2, NXPH3, NXPH4, NXT1, NXT2, NYAP1, NYAP2, NYNRIN, NYX, OAF, OARD1, OAS1, OAS2, OAS3, OASL, OAT, OAZ1, OAZ2, OAZ3, OBP2A, OBP2B, OBSCN, OBSCN-AS1, OBSL1, OC90, OCA2, OCEL1, OCIAD1, OCIAD2, OCLM, OCLN, OCM, OCM2, OCRL, OCSTAMP, ODAM, ODC1, ODF1, ODF2, ODF2L, ODF3, ODF3B, ODF3L1, ODF3L2, ODF4, OFCC1, OFD1, OGDH, OGDHL, OGFOD1, OGFOD2, OGFOD3, OGFR, OGFRL1, OGG1, OGN, OGT, OIP5, OIT3, OLA1, OLAH, OLFM1, OLFM2, OLFM3, OLFM4, OLFML1, OLFML2A, OLFML2B, OLFML3, OLIG1, OLIG2, OLIG3, OLR1, OMA1, OMD, OMG, OMP, ONECUT1, ONECUT2, ONECUT3, OOEP, OOSP2, OPA1, OPA3, OPALIN, OPCML, OPHN1, OPLAH, OPN1LW, OPN1MW, OPN1MW2, OPN1MW3, OPNISW, OPN3, OPN4, OPN5, OPRD1, OPRK1, OPRL1, OPRM1, OPRPN, OPTC, OPTN, OR10A2, OR10A3, OR10A4, OR10A5, OR10A6, OR10A7, OR10AC1, OR10AD1, OR10AG1, OR10C1, OR10D3, OR10G2, OR10G3, OR10G4, OR10G6, OR10G7, OR10G8, OR10G9, OR10H1, OR10H2, OR10H3, OR10H4, OR10H5, OR10J1, OR10J3, OR10J4, OR10J5, OR10K1, OR10K2, OR10P1, OR10Q1, OR10R2, OR10S1, OR10T2, OR10V1, OR10W1, OR10X1, OR10Z1, OR11A1, OR11G2, OR11H1, OR11H12, OR11H2, OR11H4, OR11H6, OR11H7, OR11L1, OR12D1, OR12D2, OR12D3, OR13A1, OR13C2, OR13C3, OR13C4, OR13C5, OR13C7, OR13C8, OR13C9, OR13D1, OR13F1, OR13G1, OR13H1, OR13J1, OR14A16, OR14A2, OR14C36, OR14I1, OR14J1, OR14K1, OR1A1, OR1A2, OR1B1, OR1C1, OR1D2, OR1D5, OR1E1, OR1E2, OR1F1, OR1G1, OR1I1, OR1J1, OR1J2, OR1J4, OR1K1, OR1L1, OR1L3, OR1L4, OR1L6, OR1L8, OR1M1, OR1N1, OR1N2, OR1P1, OR1Q1, OR1S1, OR1S2, OR2A1, OR2A12, OR2A14, OR2A2, OR2A25, OR2A4, OR2A42, OR2A5, OR2A7, OR2AE1, OR2AG1, OR2AG2, OR2AJ1, OR2AK2, OR2AP1, OR2AT4, OR2B11, OR2B2, OR2B3, OR2B6, OR2C1, OR2C3, OR2D2, OR2D3, OR2F1, OR2F2, OR2G2, OR2G3, OR2G6, OR2H1, OR2H2, OR2J1, OR2J2, OR2J3, OR2K2, OR2L13, OR2L2, OR2L3, OR2L5, OR2L8, OR2M2, OR2M3, OR2M4, OR2M5, OR2M7, OR2S2, OR2T1, OR2T10, OR2T11, OR2T12, OR2T2, OR2T27, OR2T29, OR2T3, OR2T33, OR2T34, OR2T35, OR2T4, OR2T5, OR2T6, OR2T7, OR2T8, OR2V1, OR2V2, OR2W1, OR2W3, OR2Y1, OR2Z1, OR3A1, OR3A2, OR3A3, OR4A15, OR4A16, OR4A47, OR4A5, OR4A8, OR4B1, OR4C11, OR4C12, OR4C13, OR4C15, OR4C16, OR4C3, OR4C45, OR4C46, OR4C5, OR4C6, OR4D1, OR4D10, OR4D11, OR4D2, OR4D5, OR4D6, OR4D9, OR4E1, OR4E2, OR4F15, OR4F16, OR4F17, OR4F21, OR4F29, OR4F3, OR4F4, OR4F5, OR4F6, OR4K1, OR4K13, OR4K14, OR4K15, OR4K17, OR4K2, OR4K3, OR4K5, OR4L1, OR4M1, OR4M2, OR4N2, OR4N4, OR4N5, OR4P4, OR4Q2, OR4Q3, OR4S1, OR4S2, OR4X1, OR4X2, OR51A2, OR51A4, OR51A7, OR51B2, OR51B4, OR51B5, OR51B6, OR51D1, OR51E1, OR51E2, OR51F1, OR51F2, OR51G1, OR51G2, OR51H1, OR51I1, OR51I2, OR51J1, OR51L1, OR51M1, OR51Q1, OR51S1, OR51T1, OR51V1, OR52A1, OR52A5, OR52B2, OR52B4, OR52B6, OR52D1, OR52E2, OR52E4, OR52E5, OR52E6, OR52E8, OR52H1, OR52I1, OR52I2, OR52J3, OR52K1, OR52K2, OR52L1, OR52M1, OR52N1, OR52N2, OR52N4, OR52N5, OR52R1, OR52W1, OR52Z1, OR56A1, OR56A3, OR56A4, OR56A5, OR56B1, OR56B4, OR5A1, OR5A2, OR5AC1, OR5AC2, OR5AK2, OR5AN, OR5AP2, ORAR, ORSAS1, OR5AU1, OR5B12, OR5B17, OR5B2, OR5B21, OR5B3, OR5C1, OR5D13, OR5D14, OR5D16, OR5D18, OR5F1, OR5G3, OR5H1, OR5H14, OR5H15, OR5H2, OR5H6, OR5H8, OR5I1, OR5J2, OR5K1, OR5K2, OR5K3, OR5K4, OR5L1, OR5L2, OR5M1, OR5M10, OR5M11, OR5M3, OR5M8, OR5M9, OR5P2, OR5P3, OR5R1, OR5T1, OR5T2, OR5T3, OR5V1, OR5W2, OR6A2, OR6B1, OR6B2, OR6B3, OR6C1, OR6C2, OR6C3, OR6C4, OR6C6, OR6C65, OR6C68, OR6C70, OR6C74, OR6C75, OR6C76, OR6F1, OR6J1, OR6K2, OR6K3, OR6K6, OR6M1, OR6N1, OR6N2, OR6P1, OR6Q1, OR6S1, OR6T1, OR6V1, OR6X1, OR6Y1, OR7A10, OR7A17, OR7A5, OR7C1, OR7C2, OR7D2, OR7D4, OR7E24, OR7G1, OR7G2, OR7G3, OR8A1, OR8B12, OR8B2, OR8B3, OR8B4, OR8B8, OR8D1, OR8D2, OR8D4, OR8G1, OR8G5, OR8H1, OR8H2, OR8H3, OR8I2, OR8J1, OR8J2, OR8J3, OR8K1, OR8K3, OR8K5, OR8S1, OR8U1, OR8U8, OR9A2, OR9A4, OR9G1, OR9G4, OR9G9, OR9H1P, OR9I1, OR9K2, OR9Q1, OR9Q2, ORAI1, ORAI2, ORAI3, ORAOV1, ORC1, ORC2, ORC3, ORC4, ORC5, ORC6, ORM1, ORM2, ORMDL1, ORMDL2, ORMDL3, OS9, OSBP, OSBP2, OSBPL10, OSBPL11, OSBPL1A, OSBPL2, OSBPL3, OSBPL5, OSBPL6, OSBPL7, OSBPL8, OSBPL9, OSCAR, OSCP1, OSER1, OSGEP, OSGEPL1, OSGIN1, OSGIN2, OSM, OSMR, OSR1, OSR2, OST4, OSTC, OSTF1, OSTM1, OSTN, OTC, OTOA, OTOF, OTOG, OTOGL, OTOL1, OTOP1, OTOP2, OTOP3, OTOR, OTOS, OTP, OTUB1, OTUB2, OTUD1, OTUD3, OTUD4, OTUD5, OTUD6A, OTUD6B, OTUD7A, OTUD7B, OTULIN, OTX1, OTX2, OVCA2, OVCH1, OVCH2, OVGP1, OVOL1, OVOL2, OVOL3, OXA1L, OXCT1, OXCT2, OXER1, OXGR1, OXLD1, OXNAD1, OXR1, OXSM, OXSR1, OXT, OXTR, P2RX1, P2RX2, P2RX3, P2RX4, P2RX5, P2RX5-TAX1BP3, P2RX6, P2RX7, P2RY1, P2RY10, P2RY11, P2RY12, P2RY13, P2RY14, P2RY2, P2RY4, P2RY6, P2RY8, P3H1, P3H2, P3H3, P3H4, P4HA1, P4HA2, P4HA3, P4HB, P4HTM, PA2G4, PAAF1, PABPC1, PABPC1L, PABPC1L2A, PABPC1L2B, PABPC3, PABPC4, PABPC4L, PABPC5, PABPN1, PABPN1L, PACRG, PACRGL, PACS1, PACS2, PACSIN1, PACSIN2, PACSIN3, PADI1, PADI2, PADI3, PADI4, PADI6, PAEP, PAF1, PAFAHIBI, PAFAH1B2, PAFAH1B3, PAFAH2, PAG1, PAGE1, PAGE2, PAGE2B, PAGE3, PAGE4, PAGE5, PAGR1, PAH, PAICS, PAIP1, PAIP2, PAIP2B, PAK1, PAK1IP1, PAK2, PAK3, PAK4, PAK5, PAK6, PALB2, PALD1, PALLD, PALM, PALM2, PALM2-AKAP2, PALM3, PALMD, PAM, PAM16, PAMR1, PAN2, PAN3, PANK1, PANK2, PANK3, PANK4, PANO1, PANX1, PANX2, PANX3, PAOX, PAPD4, PAPD5, PAPD7, PAPLN, PAPOLA, PAPOLB, PAPOLG, PAPPA, PAPPA2, PAPSS1, PAPSS2, PAQR3, PAQR4, PAQR5, PAQR6, PAQR7, PAQR8, PAQR9, PARD3, PARD3B, PARD6A, PARD6B, PARD6G, PARG, PARK7, PARL, PARM1, PARN, PARP1, PARP10, PARP11, PARP12, PARP14, PARP15, PARP16, PARP2, PARP3, PARP4, PARP6, PARP8, PARP9, PARPBP, PARS2, *PARVA*, PARVB, PARVG, PASD1, PASK, PATE1, PATE2, PATE3, PATE4, PATJ, PATL1, PATL2, PATZ1, PAWR, PAX1, PAX2, PAX3, PAX4, PAX5, PAX6, PAX7, PAX8, PAX9, PAXBP1, PAXIP1, PAXX, PBDC1, PBK, PBLD, PBOV1, PBRM1, PBX1, PBX2, PBX3, PBX4, PBXIP1, PC, PCBD1, PCBD2, PCBP1, PCBP2, PCBP3, PCBP4, PCCA, PCCB, PCDH1, PCDH10, PCDH11X, PCDH11Y, PCDH12, PCDH15, PCDH17, PCDH18, PCDH19, PCDH20, PCDH7, PCDH8, PCDH9, PCDHA1, PCDHA10, PCDHA11, PCDHA12, PCDHA13, PCDHA2, PCDHA3, PCDHA4, PCDHA5, PCDHA6, PCDHA7, PCDHA8, PCDHA9, PCDHAC1, PCDHAC2, PCDHB1, PCDHB10, PCDHB11, PCDHB12, PCDHB13, PCDHB14, PCDHB15, PCDHB16, PCDHB2, PCDHB3, PCDHB4, PCDHB5, PCDHB6, PCDHB7, PCDHB8, PCDHB9, PCDHGA1, PCDHGA10, PCDHGA11, PCDHGA12, PCDHGA2, PCDHGA3, PCDHGA4, PCDHGA5, PCDHGA6, PCDHGA7, PCDHGA8, PCDHGA9, PCDHGB1, PCDHGB2, PCDHGB3, PCDHGB4, PCDHGB5, PCDHGB6, PCDHGB7, PCDHGC3, PCDHGC4, PCDHGC5, PCED1A, PCED1B, PCF11, PCGF1, PCGF2, PCGF3, PCGF5, PCGF6, PCID2, PCIF1, PCK1, PCK2, PCLAF, PCLO, PCM1, PCMT1, PCMTD1, PCMTD2, PCNA, PCNP, PCNT, PCNX1, PCNX2, PCNX3, PCNX4, PCOLCE, PCOLCE2, PCOTH, PCP2, PCP4, PCP4L1, PCSK1, PCSKIN, PCSK2, PCSK4, PCSK5, PCSK6, PCSK7, PCSK9, PCTP, PCYOX1, PCYOX1L, PCYT1A, PCYTIB, PCYT2, PDAP1, PDC, PDCD1, PDCD10, PDCD11, PDCD1LG2, PDCD2, PDCD2L, PDCD4, PDCD5, PDCD6, PDCD6P, PDCD7, PDCL, PDCL2, PDCL3, PDE1OA, PDE11A, PDE12, PDE1A, PDE1B, PDE1C, PDE2A, PDE3A, PDE3B, PDE4A, PDE4B, PDE4C, PDE4D, PDE4DIP, PDE5A, PDE6A, PDE6B, PDE6C, PDE6D, PDE6G, PDE6H, PDE7A, PDE7B, PDE8A, PDE8B, PDE9A, PDF, PDGFA, PDGFB, PDGFC, PDGFD, PDGFRA, PDGFRB, PDGFRL, PDHA1, PDHA2, PDHB, PDHX, PDIA2, PDIA3, PDIA4, PDIA5, PDIA6, PDIK1L, PDILT, PDK1, PDK2, PDK3, PDK4, PDLIM1, PDLIM2, PDLIM3, PDLIM4, PDLIM5, PDLIM7, PDP1, PDP2, PDPK1, PDPN, PDPR, PDRG1, PDS5A, PDS5B, PDSS1, PDSS2, PDX1, PDXDC1, PDXK, PDXP, PDYN, PDZD11, PDZD2, PDZD3, PDZD4, PDZD7, PDZD8, PDZD9, PDZK1, PDZK1IP1, PDZRN3, PDZRN4, PEA15, PEAK1, PEAR1, PEBP1, PEBP4, PECAM1, PECR, PEF, PEG10, PEG3, *PELI*1, *PELI*2, *PELI*3, PELO, PELP1, PEMT, PENK, PEPD, PER1, PER2, PER3, PERM1, PERP, PES1, PET100, PET117, PEX1, PEX10, PEX11A, PEX11B, PEX11G, PEX12, PEX13, PEX14, PEX16, PEX19, PEX2, PEX26, PEX3, PEX5, PEX5L, PEX6, PEX7, PF4, PF4V1, PFAS, PFDN1, PFDN2, PFDN4, PFDN5, PFDN6, PFKFB1, PFKFB2, PFKFB3, PFKFB4, PFKL, PFKM, PFKP, PFN1, PFN2, PFN3, PFN4, PGA3, PGA4, PGA5, PGAM1, PGAM2, PGAM4, PGAM5, PGAP1, PGAP2, PGAP3, PGBD1, PGBD2, PGBD4, PGBD5, PGC, PGD, PGF, PGGHG, PGGTIB, PGK1, PGK2, PGLS, PGLYRP1, PGLYRP2, PGLYRP3, PGLYRP4, PGM1, PGM2, PGM2L1, PGM3, PGM5, PGP, PGPEP1, PGPEP1L, PGR, PGRMC1, PGRMC2, PGS1, PHACTR1, PHACTR2, PHACTR3, PHACTR4, PHAX, PHB, PHB2, PHC1, PHC2, PHC3, PHEX, PHF1, PHF10, PHF11, PHF12, PHF13, PHF14, PHF19, PHF2, PHF20, PHF20L1, PHF21A, PHF21B, PHF23, PHF24, PHF3, PHF5A, PHF6, PHF7, PHF8, PHGDH, PHGR1, PHIP, PHKA1, PHKA2, PHKB, PHKG1, PHKG2, PHLDA, PHLDA2, PHLDA3, PHLDB1, PHLDB2, PHLDB3, PHLPP1, PHLPP2, PHOSPHO1, PHOSPHO2, PHOX2A, PHOX2B, PHPT1, PHRF1, PHTF1, PHTF2, PHYH, PHYHD1, PHYHIP, PHYHIPL, PHYKPL, PI15, PI16, PI3, PI4K2A, PI4K2B, PI4KA, PI4KB, PIANP, PIAS1, PIAS2, PIAS3, PIAS4, PIBF1, PICALM, PICK1, PID1, PIDD1, PIEZO1, PIEZO2, PIF1, PIFO, PIGA, PIGB, PIGBOS1, PIGC, PIGF, PIGG, PIGH, PIGK, PIGL, PIGM, PIGN, PIGO, PIGP, PIGQ, PIGR, PIGS, PIGT, PIGU, PIGV, PIGW, PIGX, PIGY, PIGZ, PIH1D1, PIH1D2, PIH1D3, PIK3AP1, PIK3C2A, PIK3C2B, PIK3C2G, PIK3C3, PIK3CA, PIK3CB, PIK3CD, PIK3CG, PIK3IP1, PIK3R1, PIK3R2, PIK3R3, PIK3R4, PIK3R5, PIK3R6, PIKFYVE, PILRA, PILRB, PIM1, PIM2, PIM3, PIMREG, PIN1, PIN4, PINK1, PINLYP, PINX1, PIP, PIP4K2A, PIP4K2B, PIP4K2C, PIP5K1A, PIP5K1B, PIP5K1C, PIP5KL1, PIPOX, PIR, PIRT, PISD, PITHD1, PITPNA, PITPNB, PITPNC1, PITPNM1, PITPNM2, PITPNM3, PITRM1, PITX1, PITX2, PITX3, PIWIL1, PIWIL2, PIWIL3, PIWIL4, PJA1, PJA2, PKD1, PKD1L1, PKD1L2, PKD1L3, PKD2, PKD2L1, PKD2L2, PKDCC, PKDREJ, PKHD1, PKHD1L1, PKIA, PKIB, PKIG, PKLR, PKM, PKMYT1, PKN1, PKN2, PKN3, PKNOX1, PKNOX2, PKP1, PKP2, PKP3, PKP4, PLA1A, PLA2G10, PLA2G12A, PLA2G12B, PLA2G15, PLA2G16, PLA2G1B, PLA2G2A, PLA2G2C, PLA2G2D, PLA2G2E, PLA2G2F, PLA2G3, PLA2G4A, PLA2G4B, PLA2G4C, PLA2G4D, PLA2G4E, PLA2G4F, PLA2G5, PLA2G6, PLA2G7, PLA2R1, PLAA, PLAC1, PLAC4, PLAC8, PLAC8L1, PLAC9, PLAG1, PLAGL1, PLAGL2, PLAT, PLAU, PLAUR, PLB1, PLBD1, PLBD2, PLCB1, PLCB2, PLCB3, PLCB4, PLCD1, PLCD3, PLCD4, PLCE1, PLCG1, PLCG2, PLCH1, PLCH2, PLCL1, PLCL2, PLCXD1, PLCXD2, PLCXD3, PLCZ1, PLD1, PLD2, PLD3, PLD4, PLD5, PLD6, PLEC, PLEK, PLEK2, PLEKHA1, PLEKHA2, PLEKHA3, PLEKHA4, PLEKHA5, PLEKHA6, PLEKHA7, PLEKHA8, PLEKHB1, PLEKHB2, PLEKHD1, PLEKHF1, PLEKHF2, PLEKHG1, PLEKHG2, PLEKHG3, PLEKHG4, PLEKHG4B, PLEKHG5, PLEKHG6, PLEKHG7, PLEKHHI, PLEKHH2, PLEKHH3, PLEKHJ1, PLEKHMI, PLEKHM2, PLEKHM3, PLEKHN1, PLEKHO1, PLEKHO2, PLEKHS1, PLET1, PLG, PLGLB1, PLGLB2, PLGRKT, PLIN1, PLIN2, PLIN3, PLIN4, PLIN5, PLK1, PLK2, PLK3, PLK4, PLK5, PLLP, PLN, PLOD1, PLOD2, PLOD3, PLP1, PLP2, PLPBP, PLPP1, PLPP2, PLPP3, PLPP4, PLPP5, PLPP6, PLPP7, PLPPR1, PLPPR2, PLPPR3, PLPPR4, PLPPR5, PLRG1, PLS1, PLS3, PLSCR1, PLSCR2, PLSCR3, PLSCR4, PLSCR5, PLTP, PLVAP, PLXDC1, PLXDC2, PLXNA1, PLXNA2, PLXNA3, PLXNA4, PLXNB1, PLXNB2, PLXNB3, PLXNC1, PLXND1, PM20D1, PM20D2, PMAIP1, PMCH, PMEL, PMEPA1, PMF1, PMF1-BGLAP, PMFBP1, PML, PMM1, PMM2, PMP2, PMP22, PMPCA, PMPCB, PMS1, PMS2, PMVK, PNCK, PNISR, PNKD, PNKP, PNLDC1, PNLIP, PNLIPRP1, PNLIPRP2, PNLIPRP3, PNMA1, PNMA2, PNMA3, PNMA5, PNMA6A, PNMA6E, PNMA6F, PNMA8A, PNMA8B, PNMA8C, PNMT, PNN, PNO1, PNOC, PNP, PNPLA1, PNPLA2, PNPLA3, PNPLA4, PNPLA5, PNPLA6, PNPLA7, PNPLA8, PNPO, PNPT1, PNRC1, PNRC2, POC1A, POC1B, POC1B-GALNT4, POC5, PODN, PODNL1, PODXL, PODXL2, POF1B, POFUT1, POFUT2, POGK, POGLUT1, POGZ, POLA1, POLA2, POLB, POLD1, POLD2, POLD3, POLD4, POLDIP2, POLDIP3, POLE, POLE2, POLE3, POLE4, POLG, POLG2, POLH, POLI, POLK, POLL, POLM, POLN, POLQ, POLR1A, POLR1B, POLR1C, POLR1D, POLR1E, POLR2A, POLR2B, POLR2C, POLR2D, POLR2E, POLR2F, POLR2G, POLR2H, POLR2I, POLR2J, POLR2J2, POLR2J3, POLR2K, POLR2L, POLR2M, POLR3A, POLR3B, POLR3C, POLR3D, POLR3E, POLR3F, POLR3G, POLR3GL, POLR3H, POLR3K, POLRMT, POM121, POM121C, POM121L12, POM121L2, POMC, POMGNT1, POMGNT2, POMK, POMP, POMT1, POMT2, POMZP3, PON1, PON2, PON3, POP1, POP4, POP5, POP7, POPDC2, POPDC3, POR, PORCN, POSTN, POT1, POTEA, POTEB, POTEB2, POTEB3, POTEC, POTED, POTEE, POTEF, POTEG, POTEH, POTEI, POTEJ, POTEM, POU1F1, POU2AF1, POU2F1, POU2F2, POU2F3, POU3F1, POU3F2, POU3F3, POU3F4, POU4F1, POU4F2, POU4F3, POU5F1, POU5F1B, POU5F2, POU6F1, POU6F2, PP2D1, PPA1, PPA2, PPAN, PPAN-P2RY11, PPARA, PPARD, PPARG, PPARGC1A, PPARGC1B, PPAT, PPBP, PPCDC, PPCS, PPDPF, PPEF1, PPEF2, PPFIA1, PPFIA2, PPFIA3, PPFIA4, PPFIBP1, PPFIBP2, PPHLN1, PPIA, PPIAL4A, PPIAL4C, PPIAL4D, PPIAL4E, PPIAL4F, PPIAL4G, PPIB, PPIC, PPID, PPIE, PPIF, PPIG, PPIH, PPIL1, PPIL2, PPIL3, PPIL4, PPIL6, PPIP5K1, PPIP5K2, PPL, PPM1A, PPM1B, PPM1D, PPM1E, PPM1F, PPM1G, PPM1H, PPM1J, PPM1K, PPM1L, PPM1M, PPM1N, PPME1, PPOX, PPP1CA, PPP1CB, PPP1CC, PPP1R10, PPP1R11, PPP1R12A, PPP1R12B, PPP1R12C, PPP1R13B, PPP1R13L, PPP1R14A, PPP1R14B, PPP1R14C, PPP1R14D, PPP1R15A, PPP1R15B, PPP1R16A, PPP1R16B, PPP1R17, PPP1R18, PPP1R1A, PPP1R1B, PPP1R1C, PPP1R2, PPP1R21, PPP1R26, PPP1R27, PPP1R2P3, PPP1R2P9, PPP1R32, PPP1R35, PPP1R36, PPP1R37, PPP1R3A, PPP1R3B, PPP1R3C, PPP1R3D, PPP1R3E, PPP1R3F, PPP1R3G, PPP1R42, PPP1R7, PPP1R8, PPP1R9A, PPP1R9B, PPP2CA, PPP2CB, PPP2R1A, PPP2R1B, PPP2R2A, PPP2R2B, PPP2R2C, PPP2R2D, PPP2R3A, PPP2R3B, PPP2R3C, PPP2R5A, PPP2R5B, PPP2R5C, PPP2R5D, PPP2R5E, PPP3CA, PPP3CB, PPP3CC, PPP3R1, PPP3R2, PPP4C, PPP4R1, PPP4R2, PPP4R3A, PPP4R3B, PPP4R3CP, PPP4R4, PPP5C, PPP5D1, PPP6C, PPP6R1, PPP6R2, PPP6R3, PPRC1, PPT1, PPT2, PPT2-EGFL8, PPTC7, PPWD1, PPY, PQBP1, PQLC1, PQLC2, PQLC2L, PQLC3, PRAC1, PRAC2, PRADC1, PRAF2, PRAG1, PRAM1, PRAME, PRAMEF1, PRAMEF10, PRAMEF11, PRAMEF12, PRAMEF13, PRAMEF14, PRAMEF15, PRAMEF17, PRAMEF18, PRAMEF19, PRAMEF2, PRAMEF20, PRAMEF25, PRAMEF26, PRAMEF27, PRAMEF33, PRAMEF4, PRAMEF5, PRAMEF6, PRAMEF7, PRAMEF8, PRAMEF9, PRAP1, PRB1, PRB2, PRB3, PRB4, PRC1, PRCC, PRCD, PRCP, PRDM1, PRDM10, PRDM11, PRDM12, PRDM13, PRDM14, PRDM15, PRDM16, PRDM2, PRDM4, PRDM5, PRDM6, PRDM7, PRDM8, PRDM9, PRDX1, PRDX2, PRDX3, PRDX4, PRDX5, PRDX6, PREB, PRELID1, PRELID2, PRELID3A, PRELID3B, PRELP, PREP, PREPL, PREX1, PREX2, PRF1, PRG2, PRG3, PRG4, PRH1, PRH2, PRICKLE1, PRICKLE2, PRICKLE3, PRICKLE4, PRIM1, PRIM2, PRIMA1, PRIMPOL, PRKAA1, PRKAA2, PRKAB1, PRKAB2, PRKACA, PRKACB, PRKACG, PRKAG1, PRKAG2, PRKAG3, PRKAR1A, PRKAR1B, PRKAR2A, PRKAR2B, PRKCA, PRKCB, PRKCD, PRKCE, PRKCG, PRKCH, PRKCI, PRKCQ, PRKCSH, PRKCZ, PRKD1, PRKD2, PRKD3, PRKDC, PRKG1, PRKG2, PRKN, PRKRA, PRKRIP1, PRKX, PRL, PRLH, PRLHR, PRLR, PRM1, PRM2, PRM3, PRMT1, PRMT2, PRMT3, PRMT5, PRMT6, PRMT7, PRMT8, PRMT9, PRND, PRNP, PRNT, PROB1, PROC, PROCA1, PROCR, PRODH, PRODH2, PROK1, PROK2, PROKR1, PROKR2, PROM1, PROM2, PROP1, PRORY, PROS1, PROSER1, PROSER2, PROSER3, PROX1, PROX2, PROZ, PRPF18, PRPF19, PRPF3, PRPF31, PRPF38A, PRPF38B, PRPF39, PRPF4, PRPF40A, PRPF40B, PRPF4B, PRPF6, PRPF8, PRPH, PRPH2, PRPS1, PRPS1L1, PRPS2, PRPSAP1, PRPSAP2, PRR11, PRR12, PRR13, PRR14, PRR14L, PRR15, PRR15L, PRR16, PRR18, PRR19, PRR20A, PRR20B, PRR20C, PRR20D, PRR20E, PRR21, PRR22, PRR23A, PRR23B, PRR23C, PRR23D1, PRR23D2, PRR25, PRR26, PRR27, PRR29, PRR3, PRR30, PRR32, PRR34, PRR35, PRR36, PRR4, PRR5, PRR5-ARHGAP8, PRR5L, PRR7, PRR9, PRRC1, PRRC2A, PRRC2B, PRRC2C, PRRG1, PRRG2, PRRG3, PRRG4, PRRT1, PRRT2, PRRT3, PRRT4, PRRX1, PRRX2, PRSS1, PRSS12, PRSS16, PRSS2, PRSS21, PRSS22, PRSS23, PRSS27, PRSS3, PRSS33, PRSS35, PRSS36, PRSS37, PRSS38, PRSS41, PRSS42, PRSS45, PRSS46, PRSS48, PRSS50, PRSS51, PRSS53, PRSS54, PRSS55, PRSS56, PRSS57, PRSS58, PRSS8, PRTFDC1, PRTG, PRTN3, PRUNE1, PRUNE2, PRX, PRY, PRY2, PSAP, PSAPL1, PSAT1, PSCA, PSD, PSD2, PSD3, PSD4, PSEN1, PSEN2, PSENEN, PSG1, PSG11, PSG2, PSG3, PSG4, PSG5, PSG6, PSG7, PSG8, PSG9, PSIP1, PSKH1, PSKH2, PSMA1, PSMA2, PSMA3, PSMA4, PSMA5, PSMA6, PSMA7, PSMA8, PSMB1, PSMB10, PSMB11, PSMB2, PSMB3, PSMB4, PSMB5, PSMB6, PSMB7, PSMB8, PSMB9, PSMC1, PSMC2, PSMC3, PSMC3IP, PSMC4, PSMC5, PSMC6, PSMD1, PSMD10, PSMD11, PSMD12, PSMD13, PSMD14, PSMD2, PSMD3, PSMD4, PSMD5, PSMD6, PSMD7, PSMD8, PSMD9, PSME1, PSME2, PSME3, PSME4, PSMF1, PSMG1, PSMG2, PSMG3, PSMG4, PSORSIC1, PSORS1C2, PSPC1, PSPH, PSPN, PSRC1, PSTK, PSTPIP1, PSTPIP2, PTAFR, PTAR1, PTBP1, PTBP2, PTBP3, PTCD1, PTCD2, PTCD3, PTCH1, PTCH2, PTCHD1, PTCHD3, PTCHD4, PTCRA, PTDSS1, PTDSS2, PTEN, PTER, PTF1A, PTGDR, PTGDR2, PTGDS, PTGER1, PTGER2, PTGER3, PTGER4, PTGES, PTGES2, PTGES3, PTGES3L, PTGES3L-AARSD1, PTGFR, PTGFRN, PTGIR, PTGIS, PTGR1, PTGR2, PTGS1, PTGS2, PTH, PTH1R, PTH2, PTH2R, PTHLH, PTK2, PTK2B, PTK6, PTK7, PTMA, PTMS, PTN, PTOV1, PTP4A1, PTP4A2, PTP4A3, PTPA, PTPDC1, PTPMT1, PTPN1, PTPN11, PTPN12, PTPN13, PTPN14, PTPN18, PTPN2, PTPN20, PTPN21, PTPN22, PTPN23, PTPN3, PTPN4, PTPN5, PTPN6, PTPN7, PTPN9, PTPRA, PTPRB, PTPRC, PTPRCAP, PTPRD, PTPRE, PTPRF, PTPRG, PTPRH, PTPRJ, PTPRK, PTPRM, PTPRN, PTPRN2, PTPRO, PTPRQ, PTPRR, PTPRS, PTPRT, PTPRU, PTPRZ1, PTRH1, PTRH2, PTRHD1, PTS, PTTG1, PTTG1IP, PTTG2, PTX3, PTX4, PUDP, PUF60, PUM1, PUM2, PUM3, *PURA*, PURB, PURG, PUS1, PUS10, PUS3, PUS7, PUS7L, PUSL1, PVALB, PVR, PVRIG, PWP1, PWP2, PWWP2A, PWWP2B, PXDC1, PXDN, PXDNL, PXK, PXMP2, PXMP4, PXN, PXT1, PXYLP1, PYCARD, PYCR1, PYCR2, PYCR3, PYDC1, PYDC2, PYGB, PYGL, PYGM, PYGO1, PYGO2, PYHIN1, PYM1, PYROXD1, PYROXD2, PYURF, PYY, PZP, QARS, QDPR, QKI, QPCT, QPCTL, QPRT, QRFP, QRFPR, QRICH1, QRICH2, QRSL1, QSER1, QSOX1, QSOX2, QTRT1, QTRT2, R3HCC1, R3HCC1L, R3HDM1, R3HDM2, R3HDM4, R3HDML, RAB10, RAB11A, RAB11B, RAB11FIP1, RAB11FIP2, RAB11FIP3, RAB11FIP4, RAB11FIP5, RAB12, RAB13, RAB14, RAB15, RAB17, RAB18, RAB19, RAB1A, RAB1B, RAB20, RAB21, RAB22A, RAB23, RAB24, RAB25, RAB26, RAB27A, RAB27B, RAB28, RAB29, RAB2A, RAB2B, RAB30, RAB31, RAB32, RAB33A, RAB33B, RAB34, RAB35, RAB36, RAB37, RAB38, RAB39A, RAB39B, RAB3A, RAB3B, RAB3C, RAB3D, RAB3GAP1, RAB3GAP2, RAB3IL1, RAB3IP, RAB40A, RAB40AL, RAB40B, RAB40C, RAB41, RAB42, RAB43, RAB44, RAB4A, RAB4B, RAB4B-EGLN2, RAB5A, RAB5B, RAB5C, RAB6A, RAB6B, RAB6C, RAB7A, RAB7B, RAB8A, RAB8B, RAB9A, RAB9B, RABAC1, RABEP1, RABEP2, RABEPK, RABGAP1, RABGAP1L, RABGEF1, RABGGTA, RABGGTB, RABIF, RABL2A, RABL2B, RABL3, RABL6, RAC1, RAC2, RAC3, RACGAP1, RACK1, RAD1, RAD17, RAD18, RAD21, RAD21L1, RAD23A, RAD23B, RAD50, RAD51, RAD51AP1, RAD51AP2, RAD51B, RAD51C, RAD51D, RAD52, RAD54B, RAD54L, RAD54L2, RAD9A, RAD9B, RADIL, RAE1, RAET1E, RAET1G, RAET1L, RAF1, RAG1, RAG2, RAI1, RAI14, RAI2, RALA, RALB, RALBP1, RALGAPA1, RALGAPA2, RALGAPB, RAL-GDS, RALGPS1, RALGPS2, RALY, RALYL, RAMP1, RAMP2, RAMP3, RAN, RANBP1, RANBP10, RANBP17, RANBP2, RANBP3, RANBP3L, RANBP6, RANBP9, RANGAP1, RANGRF, RAP1A, RAP1B, RAP1GAP, RAP1GAP2, RAP1GDS1, RAP2A, RAP2B, RAP2C, RAPGEF1, RAPGEF2, RAPGEF3, RAPGEF4, RAPGEF5, RAPGEF6, RAPGEFL1, RAPH1, RAPSN, RARA, RARB, RARG, RARRES1, RARRES2, RARRES3, RARS, RARS2, RASA1, RASA2, RASA3, RASA4, RASA4B, RASAL1, RASAL2, RASAL3, RASD1, RASD2, RASEF, RASGEFA, RASGEF1B, RASGEF1C, RASGRF1, RAS-GRF2, RASGRP1, RASGRP2, RASGRP3, RASGRP4, RASIP1, RASL10A, RASL10B, RASL1A, RASL11B, RASL12, RASSF1, RASSF10, RASSF2, RASSF3, RASSF4, RASSF5, RASSF6, RASSF7, RASSF8, RASSF9, RAVER1, RAVER2, RAX, RAX2, RB1, RB1CC1, RBAK, RBAK-RBAKDN, RBBP4, RBBP5, RBBP6, RBBP7, RBBP8, RBBP8NL, RBBP9, RBCK1, RBFA, RBFOX1, RBFOX2, RBFOX3, RBKS, RBL1, RBL2, RBM10, RBM11, RBM12, RBM12B, RBM14, RBM14-RBM4, RBM15, RBM15B, RBM17, RBM18, RBM19, RBM20, RBM22, RBM23, RBM24, RBM25, RBM26, RBM27, RBM28, RBM3, RBM33, RBM34, RBM38, RBM39, RBM4, RBM41, RBM42, RBM43, RBM44, RBM45, RBM46, RBM47, RBM48, RBM4B, RBM5, RBM6, RBM7, RBM8A, RBMS1, RBMS2, RBMS3, RBMX, RBMX2, RBMXL1, RBMXL2, RBMXL3, RBMY1A1, RBMY1B, RBMY1D, RBMYE, RBMY1F, RBMY1J, RBP1, RBP2, RBP3, RBP4, RBP5, RBP7, RBPJ, RBPJL, RBPMS, RBPMS2, RBSN, RBX1, RC3H1, RC3H2, RCAN1, RCAN2, RCAN3, RCBTB1, RCBTB2, RCC1, RCC1L, RCC2, RCCD1, RCE1, RCHY1, RCL1, RCN1, RCN2, RCN3, RCOR1, RCOR2, RCOR3, RCSD1, RCVRN, RD3, RD3L, RDH10, RDH11, RDH12, RDH13, RDH14, RDH16, RDH5, RDH8, RDM1, RDX, REC114, REC8, RECK, RECQL, RECQL4, RECQL5, REEP1, REEP2, REEP3, REEP4, REEP5, REEP6, REG1A, REG1B, REG3A, REG3G, REG4, REL, RELA, RELB, RELL1, RELL2, RELN, RELT, REM1, REM2, REN, RENBP, REP15, REPIN1, REPS1, REPS2, RER1, RERE, RERG, RERGL, RESP18, REST, RET, RETN, RETNLB, RETREG1, RETREG2, RETREG3, RETSAT, REV1, REV3L, REXO1, REXO2, REXO4, REXO, RFC1, RFC2, RFC3, RFC4, RFC5, RFESD, RFFL, RFK, RFLNA, RFLNB, RFNG, RFPL1, RFPL2, RFPL3, RFPL3S, RFPL4A, RFPL4AL1, RFPL4B, RFT1, RFTN1, RFTN2, RFWD2, RFWD3, RFX1, RFX2, RFX3, RFX4, RFX5, RFX6, RFX7, RFX8, RFXANK, RFXAP, RGCC, RGL1, RGL2, RGL3, RGL4, RGMA, RGMB, RGN, RGP1, RGPD1, RGPD2, RGPD3, RGPD4, RGPD5, RGPD6, RGPD8, RGR, RGS1, RGS10, RGS11, RGS12, RGS13, RGS14, RGS16, RGS17, RGS18, RGS19, RGS2, RGS20, RGS21, RGS22, RGS3, RGS4, RGS5, RGS6, RGS7, RGS7BP, RGS8, RGS9, RGS9BP, RGSL1, RHAG, RHBDD1, RHBDD2, RHBDD3, RHBDF1, RHBDF2, RHBDL1, RHBDL2, RHBDL3, RHBG, RHCE, RHCG, RHD, RHEB, RHEBL1, RHNO1, RHO, RHOA, RHOB, RHOBTB1, RHOBTB2, RHOBTB3, RHOC, RHOD, RHOF, RHOG, RHOH, RHOJ, RHOQ, RHOT1, RHOT2, RHOU, RHOV, RHOXF1, RHOXF2, RHOXF2B, RHPN1, RHPN2, RIBC1, RIBC2, RIC1, RIC3, RIC8A, RIC8B, RICTOR, RIDA, RIF1, RIIAD1, RILP, RILPL1, RILPL2, RIMBP2, RIMBP3, RIMBP3B, RIMBP3C, RIMKLA, RIMKLB, RIMS1, RIMS2, RIMS3, RIMS4, RIN1, RIN2, RIN3, RING1, RINL, RINT1, RIOK1, RIOK2, RIOK3, RIOX1, RIOX2, RIPK1, RIPK2, RIPK3, RIPK4, RIPOR1, RIPOR2, RIPOR3, RIPPLY1, RIPPLY2, RIPPLY3, RIT1, RIT2, RITA1, RLBP1, RLF, RLIM, RLN1, RLN2, RLN3, RMDN1, RMDN2, RMDN3, RMI1, RMI2, RMND1, RMND5A, RMND5B, RNASE1, RNASE10, RNASE11, RNASE12, RNASE13, RNASE2, RNASE3, RNASE4, RNASE6, RNASE7, RNASE8, RNASE9, RNASEH1, RNASEH2A, RNASEH2B, RNASEH2C, RNASEK, RNASEK-C17orf49, RNASEL, RNASET2, RND1, RND2, RND3, RNF10, RNF103, RNF103-CHMP3, RNF11, RNF111, RNF112, RNF113A, RNF113B, RNF114, RNF115, RNF121, RNF122, RNF123, RNF125, RNF126, RNF128, RNF13, RNF130, RNF133, RNF135, RNF138, RNF139, RNF14, RNF141, RNF144A, RNF144B, RNF145, RNF146, RNF148, RNF149, RNF150, RNF151, RNF152, RNF157, RNF165, RNF166, RNF167, RNF168, RNF169, RNF17, RNF170, RNF175, RNF180, RNF181, RNF182, RNF183, RNF185, RNF186, RNF187, RNF19A, RNF19B, RNF2, RNF20, RNF207, RNF208, RNF212, RNF212B, RNF213, RNF214, RNF215, RNF216, RNF217, RNF219, RNF220, RNF222, RNF223, RNF224, RNF225, RNF24, RNF25, RNF26, RNF31, RNF32, RNF34, RNF38, RNF39, RNF4, RNF40, RNF41, RNF43, RNF44, RNF5, RNF6, RNF7, RNF8, RNFT1, RNFT2, RNGTT, RNH1, RNLS, RNMT, RNPC3, RNPEP, RNPEPL1, RNPS1, ROBO1, ROBO2, ROBO3, ROBO4, ROCK1, ROCK2, ROGDI, ROM1, ROMO1, ROPN1, ROPN1B, ROPN1L, ROR1, ROR2, RORA, RORB, RORC, ROS1, RP1, RP1L1, RP2, RP9, RPA1, RPA2, RPA3, RPA4, RPAIN, RPAP1, RPAP2, RPAP3, RPE, RPE65, RPEL1, RPF1, RPF2, RPGR, RPGRIP1, RPGRIP1L, RPH3A, RPH3AL, RPIA, RPL10, RPL10A, RPL10L, RPL11, RPL12, RPL13, RPL13A, RPL14, RPL15, RPL17, RPL17-C18orf32, RPL18, RPL18A, RPL19, RPL21, RPL22, RPL22L1, RPL23, RPL23A, RPL24, RPL26, RPL26L1, RPL27, RPL27A, RPL28, RPL29, RPL3, RPL30, RPL31, RPL32, RPL34, RPL35, RPL35A, RPL36, RPL36A, RPL36A-HNRNPH2, RPL36AL, RPL37, RPL37A, RPL38, RPL39, RPL39L, RPL3L, RPL4, RPL41, RPL5, RPL6, RPL7, RPL7A, RPL7L1, RPL8, RPL9, RPLPO, RPLP1, RPLP2, RPN1, RPN2, RPP14, RPP21, RPP25, RPP25L, RPP30, RPP38, RPP40, RPRD1A, RPRD1B, RPRD2, RPRM, RPRML, RPS10, RPS10-NUDT3, RPS11, RPS12, RPS13, RPS14, RPS15, RPS15A, RPS16, RPS17, RPS18, RPS19, RPS19BP1, RPS2, RPS20, RPS21, RPS23, RPS24, RPS25, RPS26, RPS27, RPS27A, RPS27L, RPS28, RPS29, RPS3, RPS3A, RPS4X, RPS4Y, RPS4Y2, RPS5, RPS6, RPS6KA1, RPS6KA2, RPS6KA3, RPS6KA4, RPS6KA5, RPS6KA6, RPS6KB1, RPS6KB2, RPS6KC1, RPS6KL1, RPS7, RPS8, RPS9, RPSA, RPTN, RPTOR, RPUSD1, RPUSD2, RPUSD3, RPUSD4, RRAD, RRAGA, RRAGB, RRAGC, RRAGD, RRAS, RRAS2, RRBP1, RREB1, RRH, RRM1, RRM2, RRM2B, RRN3, RRNAD1, RRP1, RRP12, RRP15, RRP1B, RRP36, RRP7A, RRP8, RRP9, RRS1, RS1, RSAD1, RSAD2, RSBN1, RSBN1L, RSC1A1, RSF1, RSG1, RSL1D1, RSL24D1, RSPH1, RSPH10B, RSPH10B2, RSPH14, RSPH3, RSPH4A, RSPH6A, RSPH9, RSPO1, RSPO2, RSPO3, RSPO4, RSPRY1, RSRC1, RSRC2, RSRP1, RSU1, RTBDN, RTCA, RTCB, RTEL1, RTEL1-TNFRSF6B, RTF1, RTFDC1, RTKN, RTKN2, RTL1, RTL10, RTL3, RTL4, RTL5, RTL6, RTL8A, RTL8B, RTL8C, RTL9, RTN1, RTN2, RTN3, RTN4, RTN4IP1, RTN4R, RTN4RL1, RTN4RL2, RTP1, RTP2, RTP3, RTP4, RTP5, RTTN, RUBCN, RUBCNL, RUFY1, RUFY2, RUFY3, RUFY4, RUNDC1, RUNDC3A, RUNDC3B, RUNX1, RUNX1T1, RUNX2, RUNX3, RUSC1, RUSC2, RUVBL1, RUVBL2, RWDD1, RWDD2A, RWDD2B, RWDD3, RWDD4, RXFP1, RXFP2, RXFP3, RXFP4, RXRA, RXRB, RXRG, RYBP, RYK, RYR1, RYR2, RYR3, S100A1, S100A10, S100A11, S100A12, S100A13, S100A14, S100A16, S100A2, S100A3, S100A4, S100A5, S100A6, S100A7, S100A7A, S100A7L2, S100A8, S100A9, S100B, S100G, S100P, S100PBP, S100Z, S1PR1, S1PR2, S1PR3, S1PR4, S1PR5, SAA1, SAA2, SAA2-SAA4, SAA4, SAAL1, SAC3D1, SACM1L, SACS, SAE1, SAFB, SAFB2, SAG, SAGE1, SALL1, SALL2, SALL3, SALL4, SAMD1, SAMD10, SAMD11, SAMD12, SAMD13, SAMD14, SAMD15, SAMD3, SAMD4A, SAMD4B, SAMD5, SAMD7, SAMD8, SAMD9, SAMD9L, SAMIHD1, SAMM50, SAMSN1, SAP130, SAP18, SAP25, SAP30, SAP30BP, SAP30L, SAPCD1, SAPCD2, SAR1A, SAR1B, SARAF, SARDH, SARM1, SARNP, SARS, SARS2, SART1, SART3, SASH1, SASH3, SASS6, SAT1, SAT2, SATB1, SATB2, SATL1, SAV1, SAXO1, SAXO2, SAYSD1, SBDS, SBF1, SBF2, SBK1, SBK2, SBK3, SBNO1, SBNO2, SBSN, SBSPON, SC5D, SCAF1, SCAF11, SCAF4, SCAF8, SCA1, SCAMP1, SCAMP2, SCAMP3, SCAMP4, SCAMP5, SCANDI, SCAP, SCAPER, SCARA3, SCARA5, SCARBI, SCARB2, SCARF1, SCARF2, SCART1, SCCPDH, SCD, SCD5, SCEL, SCFD1, SCFD2, SCG2, SCG3, SCG5, SCGB1A1, SCGB1C1, SCGB1C2, SCGB1D1, SCGB1D2, SCGB1D4, SCGB2A1, SCGB2A2, SCGB2B2, SCGB3A1, SCGB3A2, SCGN, SCHIP1, SCIMP, SCIN, SCLT1, SCLY, SCMH1, SCML1, SCML2, SCML4, SCN10A, SCN11A, SCN1A, SCN1B, SCN2A, SCN2B, SCN3A, SCN3B, SCN4A, SCN4B, SCN5A, SCN7A, SCN8A, SCN9A, SCNM1, SCNN1A, SCNN1B, SCNN1D, SCNN1G, SCO1, SC02, SCOC, SCP2, SCP2D1, SCPEP1, SCRG1, SCRIB, SCRN1, SCRN2, SCRN3, SCRT1, SCRT2, SCT, SCTR, SCUBE1, SCUBE2, SCUBE3, SCX, SCYL1, SCYL2, SCYL3, SDAD1, SDC1, SDC2, SDC3, SDC4, SDCBP, SDCBP2, SDCCAG3, SDCCAG8, SDE2, SDF2, SDF2L1, SDF4, SDHA, SDHAF1, SDHAF2, SDHAF3, SDHAF4, SDHB, SDHC, SDHD, SDK1, SDK2, SDR16C5, SDR39U1, SDR42E1, SDR42E2, SDR9C7, SDS, SDSL, SEBOX, SEC11A, SEC11C, SEC13, SEC14L1, SEC14L2, SEC14L3, SEC14L4, SEC14L5, SEC14L6, SEC16A, SEC16B, SEC22A, SEC22B, SEC22C, SEC23A, SEC23B, SEC23IP, SEC24A, SEC24B, SEC24C, SEC24D, SEC31A, SEC31B, SEC61A1, SEC61A2, SEC61B, SEC61G, SEC62, SEC63, SECISBP2, SECISBP2L, SECTM1, SEH1L, SEL1L, SEL1L2, SEL1L3, SELE, SELENBP1, SELENOF, SELENOH, SELENOI, SELENOK, SELENOM, SELENON, SELENOO, SELENOP, SELENOS, SELENOT, SELENOV, SELENOW, SELL, SELP, SELPLG, SEM1, SEMA3A, SEMA3B, SEMA3C, SEMA3D, SEMA3E, SEMA3F, SEMA3G, SEMA4A, SEMA4B, SEMA4C, SEMA4D, SEMA4F, SEMA4G, SEMA5A, SEMA5B, SEMA6A, SEMA6B, SEMA6C, SEMA6D, SEMA7A, SEMG1, SEMG2, SENP1, SENP2, SENP3, SENP3-EIF4A1, SENP5, SENP6, SENP7, SENP8, SEPHS1, SEPHS2, SEPSECS, SEPT1, SEPT10, SEPT11, SEPT12, SEPT14, SEPT2, SEPT3, SEPT4, SEPT5, SEPT6, SEPT7, SEPT8, SEPT9, SERAC1, SERBP1, SERF1A, SERF1B, SERF2, SERGEF, SERHL2, SERINC1, SERINC2, SERINC3, SERINC4, SERINC5, SERP1, SERP2, SERPINA1, SERPINA10, SERPINA11, SERPINA12, SERPINA2, SERPINA3, SERPINA4, SERPINA5, SERPINA6, SERPINA7, SERPINA9, SERPINB1, SERPINB10, SERPINB11, SERPINB12, SERPINB13, SERPINB2, SERPINB3, SERPINB4, SERPINB5, SERPINB6, SERPINB7, SERPINB8, SERPINB9, SERPINC1, SERPIND1, SERPINE1, SERPINE2, SERPINE3, SERPINF1, SERPINF2, SERPING1, SERPINH1, SERPINI1, SERPINI2, SERTAD1, SERTAD2, SERTAD3, SERTAD4, SERTM1, SESN1, SESN2, SESN3, SESTD1, SET, SETBP1, SETD1A, SETD1B, SETD2, SETD3, SETD4, SETD5, SETD6, SETD7, SETD9, SETDB1, SETDB2, SETMAR, SETSIP, SETX, SEZ6, SEZ6L, SEZ6L2, SF1, SF3A1, SF3A2, SF3A3, SF3B1, SF3B2, SF3B3, SF3B4, SF3B5, SF3B6, SFI1, SFMBT1, SFMBT2, SFN, SFPQ, SFR1, SFRP1, SFRP2, SFRP4, SFRP5, SFSWAP, SFT2D1, SFT2D2, SFT2D3, SFTA2, SFTA3, SFTPA1, SFTPA2, SFTPB, SFTPC, SFTPD, SFXN1, SFXN2, SFXN3, SFXN4, SFXN5, SGCA, SGCB, SGCD, SGCE, SGCG, SGCZ, SGF29, SGIP1, SGK1, SGK2, SGK3, SGK494, SGMS1, SGMS2, SGO1, SGO2, SGPL1, SGPP1, SGPP2, SGSH, SGSM1, SGSM2, SGSM3, SGTA, SGTB, SH2B1, SH2B2, SH2B3, SH2D1A, SH2D1B, SH2D2A, SH2D3A, SH2D3C, SH2D4A, SH2D4B, SH2D5, SH2D6, SH2D7, SH3BGR, SH3BGRL, SH3BGRL2, SH3BGRL3, SH3BP1, SH3BP2, SH3BP4, SH3BP5, SH3BP5L, SH3D19, SH3D21, SH3GL1, SH3GL2, SH3GL3, SH3GLB1, SH3GLB2, SH3KBP1, SH3PXD2A, SH3PXD2B, SH3RF1, SH3RF2, SH3RF3, SH3TC1, SH3TC2, SH3YL1, SHANK, SHANK2, SHANK3, SHARPIN, SHB, SHBG, SHC1, SHC2, SHC3, SHC4, SHCBP1, SHCBP1L, SHD, SHE, SHF, SHH, SHISA2, SHISA3, SHISA4, SHISA5, SHISA6, SHISA7, SHISA8, SHISA9, SHKBP1, SHMT1, SHMT2, SHOC2, SHOX, SHOX2, SHPK, SHPRH, SHQ1, SHROOMI, SHROOM2, SHROOM3, SHROOM4, SHTN1, SI, SIAE, SIAH1, SIAH2, SIAH3, SIDT1, SIDT2, SIGIRR, SIGLEC, SIGLEC10, SIGLEC1I, SIGLECl2, SIGLEC14, SIGLEC15, SIGLEC5, SIGLEC6, SIGLEC7, SIGLEC8, SIGLEC9, SIGLECL1, SIGMAR1, SIK1, SIK2, SIK3, SIKE1, SIL1, SIM1, SIv2, SMC1, SIN3A, SIN3B, SIPA1, SIPA1L1, SIPA1L2, SIPA1L3, SIRPA, SIRPB1, SIRPB2, SIRPD, SIRPG, SIRT1, SIRT2, SIRT3, SIRT4, SIRT5, SIRT6, SIRT7, SIT1, SIVA1, SIX1, SIX2, SIX3, SIX4, SIX5, SIX6, SKAI, SKA2, SKA3, SKAP1, SKAP2, SKI, SKIDA1, SKIL, SKIV2L, SKIV2L2, SKOR1, SKOR2, SKP1, SKP2, SLA, SLA2, SLAIN1, SLAIN2, SLAMF1, SLAMF6, SLAMF7, SLAMF8, SLAMF9, SLBP, SLC10A1, SLC10A2, SLC10A3, SLC10A4, SLC10A5, SLC10A6, SLC10A7, SLC11A1, SLC11A2, SLC12A1, SLC12A2, SLC12A3, SLC12A4, SLC12A5, SLC12A6, SLC12A7, SLC12A8, SLC12A9, SLC13A1, SLC13A2, SLC13A3, SLC13A4, SLC13A5, SLC14A1, SLC14A2, SLC15A1, SLC15A2, SLC15A3, SLC15A4, SLC15A5, SLC16A1, SLC16A10, SLC16A11, SLC16A12, SLC16A13, SLC16A14, SLC16A2, SLC16A3, SLC16A4, SLC16A5, SLC16A6, SLC16A7, SLC16A8, SLC16A9, SLC17A1, SLC17A2, SLC17A3, SLC17A4, SLC17A5, SLC17A6, SLC17A7, SLC17A8, SLC17A9, SLC18A1, SLC18A2, SLC18A3, SLC18B1, SLC19A1, SLC19A2, SLC19A3, SLC1A1, SLC1A2, SLC1A3, SLC1A4, SLC1A5, SLC1A6, SLC1A7, SLC20A1, SLC20A2, SLC22A1, SLC22A10, SLC22A11, SLC22A12, SLC22A13, SLC22A14, SLC22A15, SLC22A16, SLC22A17, SLC22A18, SLC22A18AS, SLC22A2, SLC22A23, SLC22A24, SLC22A25, SLC22A3, SLC22A31, SLC22A4, SLC22A5, SLC22A6, SLC22A7, SLC22A8, SLC22A9, SLC23A1, SLC23A2, SLC23A3, SLC24A1, SLC24A2, SLC24A3, SLC24A4, SLC24A5, SLC25A1, SLC25A10, SLC25A11, SLC25A12, SLC25A13, SLC25A14, SLC25A15, SLC25A16, SLC25A17, SLC25A18, SLC25A19, SLC25A2, SLC25A20, SLC25A21, SLC25A22, SLC25A23, SLC25A24, SLC25A25, SLC25A26, SLC25A27, SLC25A28, SLC25A29, SLC25A3, SLC25A30, SLC25A31, SLC25A32, SLC25A33, SLC25A34, SLC25A35, SLC25A36, SLC25A37, SLC25A38, SLC25A39, SLC25A4, SLC25A40, SLC25A41, SLC25A42, SLC25A43, SLC25A44, SLC25A45, SLC25A46, SLC25A47, SLC25A48, SLC25A5, SLC25A51, SLC25A52, SLC25A53, SLC25A6, SLC26A1, SLC26A10, SLC26A11, SLC26A2, SLC26A3, SLC26A4, SLC26A5, SLC26A6, SLC26A7, SLC26A8, SLC26A9, SLC27A1, SLC27A2, SLC27A3, SLC27A4, SLC27A5, SLC27A6, SLC28A1, SLC28A2, SLC28A3, SLC29A1, SLC29A2, SLC29A3, SLC29A4, SLC2A1, SLC2A10, SLC2A11, SLC2A12, SLC2A13, SLC2A14, SLC2A2, SLC2A3, SLC2A4, SLC2A4RG, SLC2A5, SLC2A6, SLC2A7, SLC2A8, SLC2A9, SLC30A1, SLC30A10, SLC30A2, SLC30A3, SLC30A4, SLC30A5, SLC30A6, SLC30A7, SLC30A8, SLC30A9, SLC31A1, SLC31A2, SLC32A1, SLC33A1, SLC34A1, SLC34A2, SLC34A3, SLC35A1, SLC35A2, SLC35A3, SLC35A4, SLC35A5, SLC35B1, SLC35B2, SLC35B3, SLC35B4, SLC35C1, SLC35C2, SLC35D1, SLC35D2, SLC35D3, SLC35E1, SLC35E2, SLC35E2B, SLC35E3, SLC35E4, SLC35F1, SLC35F2, SLC35F3, SLC35F4, SLC35F5, SLC35F6, SLC35G1, SLC35G2, SLC35G3, SLC35G4, SLC35G5, SLC35G6, SLC36A1, SLC36A2, SLC36A3, SLC36A4, SLC37A1, SLC37A2, SLC37A3, SLC37A4, SLC38A1, SLC38A10, SLC38A11, SLC38A2, SLC38A3, SLC38A4, SLC38A5, SLC38A6, SLC38A7, SLC38A8, SLC38A9, SLC39A1, SLC39A10, SLC39A11, SLC39A12, SLC39A13, SLC39A14, SLC39A2, SLC39A3, SLC39A4, SLC39A5, SLC39A6, SLC39A7, SLC39A8, SLC39A9, SLC3A1, SLC3A2, SLC40A1, SLC41A1, SLC41A2, SLC41A3, SLC43A1, SLC43A2, SLC43A3, SLC44A1, SLC44A2, SLC44A3, SLC44A4, SLC44A5, SLC45A1, SLC45A2, SLC45A3, SLC45A4, SLC46A1, SLC46A2, SLC46A3, SLC47A1, SLC47A2, SLC48A1, SLC4A1, SLC4A10, SLC4A11, SLC4A1AP, SLC4A2, SLC4A3, SLC4A4, SLC4A5, SLC4A7, SLC4A8, SLC4A9, SLC50A1, SLC51A, SLC51B, SLC52A1, SLC52A2, SLC52A3, SLC5A1, SLC5A10, SLC5A11, SLC5A12, SLC5A2, SLC5A3, SLC5A4, SLC5A5, SLC5A6, SLC5A7, SLC5A8, SLC5A9, SLC6A1, SLC6A11, SLC6A12, SLC6A13, SLC6A14, SLC6A15, SLC6A16, SLC6A17, SLC6A18, SLC6A19, SLC6A2, SLC6A20, SLC6A3, SLC6A4, SLC6A5, SLC6A6, SLC6A7, SLC6A8, SLC6A9, SLC7A1, SLC7A10, SLC7A11, SLC7A13, SLC7A14, SLC7A2, SLC7A3, SLC7A4, SLC7A5, SLC7A6, SLC7A6OS, SLC7A7, SLC7A8, SLC7A9, SLC8A1, SLC8A2, SLC8A3, SLC8B1, SLC9A1, SLC9A2, SLC9A3, SLC9A3R1, SLC9A3R2, SLC9A4, SLC9A5, SLC9A6, SLC9A7, SLC9A8, SLC9A9, SLC9B1, SLC9B2, SLC9C1, SLC9C2, SLCO1A2, SLCO1B1, SLCO1B3, SLCO1B7, SLCO1C1, SLCO2A1, SLCO2B1, SLCO3A1, SLCO4A1, SLCO4C1, SLCO5A1, SLC6A1, SLF1, SLF2, SLFN11, SLFN12, SLFN12L, SLFN13, SLFN14, SLFN5, SLFNL1, SLIRP, SLIT1, SLIT2, SLIT3, SLITRK1, SLITRK2, SLITRK3, SLITRK4, SLITRK5, SLITRK6, SLK, SLMAP, SLN, SLPI, SLTM, SLU7, SLURP1, SLURP2, SLX1A, SLX1B, SLX4, SLX4IP, SMAD1, SMAD2, SMAD3, SMAD4, SMAD5, SMAD6, SMAD7, SMAD9, SMAGP, SMAP1, SMAP2, SMARCA1, SMARCA2, SMARCA4, SMARCA5, SMARCAD1, SMARCAL1, SMARCB1, SMARCC1, SMARCC2, SMARCD1, SMARCD2, SMARCD3, SMARCE1, SMC1A, SMC1B, SMC2, SMC3, SMC4, SMC5, SMC6, SMCHD1, SMCO1, SMCO2, SMCO3, SMCO4, SMCP, SMCR8, SMDT1, SMG1, SMG5, SMG6, SMG7, SMG8, SMG9, SMIM1, SMIM10, SMIM10L1, SMIM10L2A, SMIM10L2B, SMIM11A, SMIM11B, SMIM12, SMIM13, SMIM14, SMIM15, SMIM17, SMIM18, SMIM19, SMI2, SMIM20, SMIM21, SMIM22, SMIM23, SMIM24, SMIM26, SM1M27, SMIM28, SMIM29, SMIM3, SMIM30, SMIM31, SMIM4, SMIM5, SMIM6, SMIM7, SMIM8, SMIM9, SMKR1, SMLR1, SMN1, SMN2, SMNDC1, SMO, SMOC1, SMOC2, SMOX, SMPD1, SMPD2, SMPD3, SMPD4, SMPDL3A, SMPDL3B, SMPX, SMR3A, SMR3B, SMS, SMTN, SMTNL1, SMTNL2, SMU1, SMUG1, SMURF1, SMURF2, SMYD1, SMYD2, SMYD3, SMYD4, SMYD5, SNAI1, SNAI2, SNAI3, SNAP23, SNAP25, SNAP29, SNAP47, SNAP91, SNAPC1, SNAPC2, SNAPC3, SNAPC4, SNAPC5, SNAPIN, SNCA, SNCAIP, SNCB, SNCG, SND1, SNED1, SNF8, SNHG28, SNIP1, SNN, SNPH, SNRK, SNRNP200, SNRNP25, SNRNP27, SNRNP35, SNRNP40, SNRNP48, SNRNP70, SNRPA, SNRPA1, SNRPB, SNRPB2, SNRPC, SNRPD1, SNRPD2, SNRPD3, SNRPE, SNRPF, SNRPG, SNRPN, SNTA1, SNTB1, SNTB2, SNTG1, SNTG2, SNTN, SNU13, SNUPN, SNURF, SNW1, SNX1, SNX10, SNX11, SNX12, SNX13, SNX14, SNX15, SNX16, SNX17, SNX18, SNX19, SNX2, SNX20, SNX21, SNX22, SNX24, SNX25, SNX27, SNX29, SNX3, SNX30, SNX31, SNX32, SNX33, SNX4, SNX5, SNX6, SNX7, SNX8, SNX9, SOAT1, SOAT2, SOBP, SOCS1, SOCS2, SOCS3, SOCS4, SOCS5, SOCS6, SOCS7, SOD1, SOD2, SOD3, SOGA1, SOGA3, SOHLH1, SOHLH2, SON, SORBS1, SORBS2, SORBS3, SORCS1, SORCS2, SORCS3, SORD, SORL1, SORT1, SOS1, SOS2, SOST, SOSTDC1, SOWAHA, SOWAHB, SOWAHC, SOWAHD, SOX1, SOX10, SOX11, SOX12, SOX13, SOX14, SOX15, SOX17, SOX18, SOX2, SOX21, SOX3, SOX30, SOX4, SOX5, SOX6, SOX7, SOX8, SOX9, SP1, SP100, SP110, SP140, SP140L, SP2, SP3, SP4, SP5, SP6, SP7, SP8, SP9, SPA17, SPAAR, SPACA1, SPACA3, SPACA4, SPACA5, SPACA5B, SPACA6, SPACA7, SPACA9, SPAG1, SPAG1A, SPAG1IB, SPAG16, SPAG17, SPAG4, SPAG5, SPAG6, SPAG7, SPAG8, SPAG9, SPAM1, SPANXA1, SPANXA2, SPANXB1, SPANXC, SPANXD, SPANXN1, SPANXN2, SPANXN3, SPANXN4, SPANXN5, SPARC, SPARCL1, SPART, SPAST, SPATA1, SPATA12, SPATA13, SPATA16, SPATA17, SPATA18, SPATA19, SPATA2, SPATA20, SPATA21, SPATA22, SPATA24, SPATA25, SPATA2L, SPATA3, SPATA31A1, SPATA31A3, SPATA31A5, SPATA31A6, SPATA31A7, SPATA3ID1, SPATA31D3, SPATA31D4, SPATA31E1, SPATA32, SPATA33, SPATA4, SPATA45, SPATA46, SPATA5, SPATA5L1, SPATA6, SPATA6L, SPATA7, SPATA8, SPATA9, SPATC1, SPATC1L, SPATS1, SPATS2, SPATS2L, SPC24, SPC25, SPCS1, SPCS2, SPCS3, SPDEF, SPDL1, SPDYA, SPDYC, SPDYE1, SPDYE16, SPDYE2, SPDYE2B, SPDYE3, SPDYE4, SPDYE5, SPDYE6, SPECC1, SPECC1L, SPECC1L-ADORA2A, SPEF1, SPEF2, SPEG, SPEM1, SPEN, SPERT, SPESP1, SPG11, SPG21, SPG7, SPHAR, SPHK1, SPHK2, SPHKAP, SPI1, SPIB, SPIC, SPICE1, SPIDR, SPIN1, SPIN2A, SPIN2B, SPIN3, SPIN4, SPINKI, SPINKI13, SPINK4, SPINK2, SPINK4, SPINK5, SPINK6, SPINK7, SPINK8, SPINK9, SPINTI, SPINT2, SPINT3, SPINT4, SPIRE1, SPIRE2, SPN, SPNS1, SPNS2, SPNS3, SPO11, SPOCD1, SPOCKI, SPOCK2, SPOCK3, SPON1, SPON2, SPOP, SPOPL, SPOUTI, SPP1, SPP2, SPPL2A, SPPL2B, SPPL2C, SPPL3, SPR, SPREDI, SPRED2, SPRED3, SPRN, SPRRA, SPRRB, SPRR2A, SPRR2B, SPRR2D, SPRR2E, SPRR2F, SPRR2G, SPRR3, SPRR4, SPRR5, SPRTN, SPRY1, SPRY2, SPRY3, SPRY4, SPRYD3, SPRYD4, SPRYD7, SPSB1, SPSB2, SPSB3, SPSB4, SPTA1, SPTAN1, SPTB, SPTBN1, SPTBN2, SPTBN4, SPTBN5, SPTLC1, SPTLC2, SPTLC3, SPTSSA, SPTSSB, SPTY2D1, SPTY2D1-AS1, SPX, SPZ1, SQLE, SQOR, SQSTM1, SRA1, SRBD1, SRC, SRCAP, SRCIN1, SRD5A1, SRD5A2, SRD5A3, SREBF1, SREBF2, SREK1, SREK1IP1, SRF, SRFBP1, SRGAP1, SRGAP2, SRGAP2B, SRGAP2C, SRGAP3, SRGN, SRI, SRL, SRM, SRMS, SRP14, SRP19, SRP54, SRP68, SRP72, SRP9, SRPK1, SRPK2, SRPK3, SRPRA, SRPRB, SRPX, SRPX2, SRR, SRRD, SRRM1, SRRM2, SRRM3, SRRM4, SRRM5, SRRT, SRSF1, SRSF10, SRSF11, SRSF12, SRSF2, SRSF3, SRSF4, SRSF5, SRSF6, SRSF7, SRSF8, SRSF9, SRXN1, SRY, SS18, SS18L1, SS18L2, SSB, SSBP1, SSBP2, SSBP3, SSBP4, SSC4D, SSC5D, SSFA2, SSH1, SSH2, SSH3, SSMEM1, SSNA1, SSPN, SSPO, SSR1, SSR2, SSR3, SSR4, SSRP1, SSSCA1, SST, SSTR1, SSTR2, SSTR3, SSTR4, SSTR5, SSU72, SSU72P8, SSUH2, SSX1, SSX2, SSX2B, SSX2IP, SSX3, SSX4, SSX4B, SSX5, SSX7, ST13, ST14, ST18, ST20, ST20-MTHFS, ST3GAL1, ST3GAL2, ST3GAL3, ST3GAL4, ST3GAL5, ST3GAL6, ST5, ST6GAL1, ST6GAL2, ST6GALNAC1, ST6GALNAC2, ST6GALNAC3, ST6GALNAC4, ST6GALNAC5, ST6GALNAC6, ST7, ST7L, ST8SIA1, ST8SIA2, ST8SIA3, ST8SIA4, ST8SIA5, ST8SIA6, STAB1, STAB2, STAC, STAC2, STAC3, STAG1, STAG2, STAG3, STAM, STAM2, STAMBP, STAMBPL1, STAP1, STAP2, STAR, STARD10, STARD13, STARD3, STARD3NL, STARD4, STARD5, STARD6, STARD7, STARD8, STARD9, STAT1, STAT2, STAT3, STAT4, STAT5A, STAT5B, STAT6, STATH, STAU1, STAU2, STBD1, STC1, STC2, STEAP1, STEAPIB, STEAP2, STEAP3, STEAP4, STH, STIL, STIM1, STIM2, STIP1, STK10, STK11, STK11IP, STK16, STK17A, STK17B, STK19, STK24, STK25, STK26, STK3, STK31, STK32A, STK32B, STK32C, STK33, STK35, STK36, STK38, STK38L, STK39, STK4, STK40, STKLD1, STMN1, STMN2, STMN3, STMN4, STMND1, STN1, STOM, STOML1, STOML2, STOML3, STON1, STON1-GTF2A1L, STON2, STOX1, STOX2, STPG1, STPG2, STPG3, STPG4, STRA6, STRA8, STRADA, STRADB, STRAP, STRBP, STRC, STRIP1, STRIP2, STRN, STRN3, STRN4, STS, STT3A, STT3B, STUB1, STUM, STX10, STX11, STX12, STX16, STX16-NPEPL1, STX17, STX18, STX19, STX1A, STX1B, STX2, STX3, STX4, STX5, STX6, STX7, STX8, STXBP1, STXBP2, STXBP3, STXBP4, STXBP5, STXBP5L, STXBP6, STYK1, STYX, STYXL1, SUB1, SUCLA2, SUCLG1, SUCLG2, SUCNR1, SUCO, SUDS3, SUFU, SUGCT, SUGP1, SUGP2, SUGT1, SULF1, SULF2, SULTIA1, SULT1A2, SULT1A3, SULT1A4, SULTIBI, SULT1C2, SULT1C3, SULT1C4, SULTIE1, SULT2A1, SULT2B1, SULT4A1, SULT6B1, SUMF1, SUMF2, SUMO1, SUMO2, SUMO3, SUMO4, SUN1, SUN2, SUN3, SUN5, SUOX, SUPT6H, SUPT20H, SUPT3H, SUPT4H1, SUPT5H, SUPT6H, SUPT7L, SUPV3L1, SURF1, SURF2, SURF4, SURF6, SUSD1, SUSD2, SUSD3, SUSD4, SUSD5, SUSD6, SUV39H1, SUV39H2, SUZ12, SV2A, SV2B, SV2C, SVBP, SVEP1, SVIL, SVIP, SVOP, SVOPL, SWAP70, SWI5, SWSAP1, SWT1, SYAP1, SYBU, SYCE1, SYCE1L, SYCE2, SYCE3, SYCN, SYCP1, SYCP2, SYCP2L, SYCP3, SYDE1, SYDE2, SYF2, SYK, SYMPK, SYN1, SYN2, SYN3, SYNC, SYNCRIP, SYNDIGI, SYNDIGIL, SYNE1, SYNE2, SYNE3, SYNE4, SYNGAP1, SYNGR1, SYNGR2, SYNGR3, SYNGR4, SYNJ1, SYNJ2, SYNJ2BP, SYNJ2BP-COX16, SYNM, SYNPO, SYNPO2, SYNPO2L, SYNPR, SYNRG, SYP, SYPL1, SYPL2, SYS1, SYS1-DBNDD2, SYT1, SYT10, SYT11, SYT12, SYT13, SYT14, SYT15, SYT16, SYT17, SYT2, SYT3, SYT4, SYT5, SYT6, SYT7, SYT8, SYT9, SYTL1, SYTL2, SYTL3, SYTL4, SYTL5, SYVN1, SZRD1, SZT2, T, TAAR1, TAAR2, TAAR5, TAAR6, TAAR8, TAAR9, TAB1, TAB2, TAB3, TAC1, TAC3, TAC4, TACC1, TACC2, TACC3, TACO1, TACR1, TACR2, TACR3, TACSTD2, TADA1, TADA2A, TADA2B, TADA3, TAF1, TAF10, TAF11, TAF12, TAF13, TAF15, TAFIA, TAF1B, TAF1C, TAF1D, TAF1L, TAF2, TAF3, TAF4, TAF4B, TAF5, TAF5L, TAF6, TAF6L, TAF7, TAF7L, TAF8, TAF9, TAF9B, TAGAP, TAGLN, TAGLN2, TAGLN3, TAL1, TAL2, TALDO1, TAMM41, TANC1, TANC2, TANGO2, TANGO6, TANK, TAOK1, TAOK2, TAOK3, TAP1, TAP2, TAPBP, TAPBPL, TAPT1, TARBP1, TARBP2, TARDBP, TARM1, TARS, TARS2, TARSL2, TAS1R1, TAS1R2, TAS1R3, TAS2R1, TAS2R10, TAS2R13, TAS2R14, TAS2R16, TAS2R19, TAS2R20, TAS2R3, TAS2R30, TAS2R31, TAS2R38, TAS2R39, TAS2R4, TAS2R40, TAS2R41, TAS2R42, TAS2R43, TAS2R46, TAS2R5, TAS2R50, TAS2R60, TAS2R7, TAS2R8, TAS2R9, TASP1, TAT, TATDN1, TATDN2, TATDN3, TAX1BP1, TAX1BP3, TAZ, TBATA, TBC1D1, TBC1D10A, TBC1D10B, TBC1D10C, TBC1D12, TBC1D13, TBC1D14, TBC1D15, TBC1D16, TBC1D17, TBC1D19, TBC1D2, TBC1D20, TBC1D21, TBC1D22A, TBC1D22B, TBC1D23, TBC1D24, TBC1D25, TBC1D26, TBC1D28, TBC1D29, TBC1D2B, TBC1D3, TBC1D30, TBC1D31, TBC1D32, TBC1D3B, TBC1D3C, TBC1D3D, TBC1D3E, TBC1D3F, TBC1D3G, TBC1D3H, TBC1D3I, TBC1D3K, TBC1D3L, TBC1D4, TBC1D5, TBC1D7, TBC1D8, TBC1D8B, TBC1D9, TBC1D9B, TBCA, TBCB, TBCC, TBCCD1, TBCD, TBCE, TBCEL, TBCK, TBK1, TBKBP1, TBL1X, TBL1XR1, TBL1Y, TBL2, TBL3, TBP, TBPL1, TBPL2, TBR1, TBRG1, TBRG4, TBX1, TBX10, TBX15, TBX18, TBX19, TBX2, TBX20, TBX21, TBX22, TBX3, TBX4, TBX5, TBX6, TBXA2R, TBXAS1, TC2N, TCAF1, TCAF2, TCAIM, TCAP, TCEA1, TCEA2, TCEA3, TCEAL1, TCEAL2, TCEAL3, TCEAL4, TCEAL5, TCEAL6, TCEAL7, TCEAL8, TCEAL9, TCEANC, TCEANC2, TCERG1, TCERG1L, TCF12, TCF15, TCF19, TCF20, TCF21, TCF23, TCF24, TCF25, TCF3, TCF4, TCF7, TCF7L1, TCF7L2, TCFL5, TCHH, TCHHL1, TCHP, TCIRG1, TCL1A, TCL1B, TCN1, TCN2, TCOF1, TCP1, TCP10, TCP10L, TCP10L2, TCP11, TCP11L1, TCP11L2, TCP11X$^2$, TCTA, TCTE1, TCTE3, TCTEX1D1, TCTEX1D2, TCTEX1D4, TCTN1, TCTN2, TCTN3, TDG, TDGF1, TDO2, TDP1, TDP2, TDRD1, TDRD10, TDRD12, TDRD15, TDRD3, TDRD5, TDRD6, TDRD7, TDRD9, TDRKH, TDRP, TEAD1, TEAD2, TEAD3, TEAD4, TEC, TECPR1, TECPR2, TECR, TECRL, TECTA, TECTB, TEDDM1, TEF, TEFM, TEK, TEKT1, TEKT2, TEKT3, TEKT4, TEKT5, TELO2, TEN1, TEN1-CDK3, TENM1, TENM2, TENM3, TENM4, TEP1, TEPP, TEPSIN, TERB1, TERB2, TERF1, TERF2, TERF2IP, TERT, TES, TESC, TESK1, TESK2, TESMIN, TESPA1, TET1, TET2, TET3, TEX10, TEX101, TEX11, TEX12, TEX13A, TEX13B, TEX13C, TEX13D, TEX14, TEX15, TEX19, TEX2, TEX22, TEX26, TEX261, TEX264, TEX28, TEX29, TEX30, TEX33, TEX35, TEX36, TEX37, TEX38, TEX43, TEX44, TEX45, TEX46, TEX47, TEX48, TEX49, TEX50, TEX51, TEX9, TF, TFAM, TFAP2A, TFAP2B, TFAP2C, TFAP2D, TFAP2E, TFAP4, TFB1M, TFB2M, TFCP2, TFCP2L1, TFDP1, TFDP2, TFDP3, TFE3, TFEB, TFEC, TFF1, TFF2, TFF3, TFG, TFIP11, TFP1, TFPI2, TFPT, TFR2, TFRC, TG, TGDS, TGFA, TGFB1, TGFB1I1, TGFB2, TGFB3, TGFBI, TGFBR1, TGFBR2, TGFBR3, TGFBR3L, TGFBRAP1, TGIF1, TGIF2, TGIF2-C20orf24, TGIF2LX, TGIF2LY, TGM1, TGM2, TGM3, TGM4, TGM5, TGM6, TGM7, TGOLN2, TGS1, TH, THADA, THAP1, THAP10, THAP11, THAP12, THAP2, THAP3, THAP4, THAP5, THAP6, THAP7, THAP8, THAP9, THBD, THBS1, THBS2, THBS3, THBS4, THEG, THEGL, THEM4, THEM5, THEM6, THEMIS, THEMIS2, THG1L, THNSL1, THNSL2, THOC1, THOC2, THOC3, THOC5, THOC6, THOC7, THOP1, THPO, THRA, THRAP3, THRB, THRSP, THSD1, THSD4, THSD7A, THSD7B, THTPA, THUMPD1, THUMPD2, THUMPD3, THY1, THYN1, TIA1, TIAF1, TIAL1, TIAM1, TIAM2, TICAM1, TICAM2, TICRR, TIE1, TIFA, TIFAB, TIGAR, TIGD1, TIGD2, TIGD3, TIGD4, TIGD5, TIGD6, TIGD7, TIGIT, TIMD4, TIMELESS, TIMM10, TIMM10B, TIMM13, TIMM17A, TIMM17B, TIMM21, TIMM22, TIMM23, TIMM23B, TIMM29, TIMM44, TIMM50, TIMM8A, TIMM8B, TIMM9, TIMMDC1, TIMP1, TIMP2, TIMP3, TIMP4, TINAG, TINAGL1, TINCR, TINF2, TIPARP, TIPIN, TIPRL, TRAP, TISP43, TJAP1, TJP1, TJP2, TJP3, TK1, TK2, TKFC, TKT, TKTL1, TKTL2, TLCD1, TLCD2, TLDC1, TLDC2, TLE1, TLE2, TLE3, TLE4, TLE6, TLK1, TLK2, TLL1, TLL2, TLN1, TLN2, TLNRD1, TLR1, TLR10, TLR2, TLR3, TLR4, TLR5, TLR6, TLR7, TLR8, TLR9, TLX1, TLX2, TLX3, TM2D1, TM2D2, TM2D3, TM4SF1, TM4SF18, TM4SF19, TM4SF19-TCTEX1D2, TM4SF20, TM4SF4, TM4SF5, TM6SF1, TM6SF2, TM7SF2, TM7SF3, TM9SF1, TM9SF2, TM9SF3, TM9SF4, TMA16, TMA7, TMBIM1, TMBIM4, TMBIM6, TMC1, TMC2, TMC3, TMC4, TMC5, TMC6, TMC7, TMC8, TMCC1, TMCC2, TMCC3, TMCO1, TMCO2, TMCO3, TMCO4, TMCO5A, TMCO6, TMED1, TMED10, TMED2, TMED3, TMED4, TMED5, TMED6, TMED7, TMED7-TICAM2, TMED8, TMED9, TMEFF1, TMEFF2, TMEM100, TMEM101, TMEM102, TMEM104, TMEM105, TMEM106A, TMEM106B, TMEM106C, TMEM107, TMEM108, TMEM109, TMEM11, TMEM110, TMEM110-MUSTN1, TMEM114, TMEM115, TMEM116, TMEM117, TMEM119, TMEM120A, TMEM120B, TMEM121, TMEM121B, TMEM123, TMEM125, TMEM126A, TMEM126B, TMEM127, TMEM128, TMEM129, TMEM130, TMEM131, TMEM131L, TMEM132A, TMEM132B, TMEM132C, TMEM132D, TMEM132E, TMEM133, TMEM134, TMEM135, TMEM136, TMEM138, TMEM139, TMEM140, TMEM141, TMEM143, TMEM144, TMEM145, TMEM147, TMEM14A, TMEM14B, TMEM14C, TMEM150A, TMEM150B, TMEM150C, TMEM151A, TMEM151B, TMEM154, TMEM155, TMEM156, TMEM158, TMEM159, TMEM160, TMEM161A, TMEM161B, TMEM163, TMEM164, TMEM165, TMEM167A, TMEM167B, TMEM168, TMEM169, TMEM17, TMEM170A, TMEM170B, TMEM171, TMEM173, TMEM174, TMEM175, TMEM176A, TMEM176B, TMEM177, TMEM178A, TMEM178B, TMEM179, TMEM179B, TMEM18, TMEM181, TMEM182, TMEM183A, TMEM184A, TMEM184B, TMEM184C, TMEM185A, TMEM185B, TMEM186, TMEM187, TMEM189, TMEM189-UBE2V1, TMEM19, TMEM190, TMEM191B, TMEM191C, TMEM192, TMEM196, TMEM198, TMEM199, TMEM2, TMEM200A, TMEM200B, TMEM200C, TMEM201, TMEM202, TMEM203, TMEM204, TMEM205, TMEM206, TMEM207, TMEM208, TMEM209, TMEM210, TMEM211, TMEM212, TMEM213, TMEM214, TMEM215, TMEM216, TMEM217, TMEM218, TMEM219, TMEM220, TMEM221, TMEM222, TMEM223, TMEM225, TMEM225B, TMEM229A, TMEM229B, TMEM230, TMEM231, TMEM232, TMEM233, TMEM234, TMEM235, TMEM236, TMEM237, TMEM238, TMEM239, TMEM240, TMEM241, TMEM242, TMEM243, TMEM244, TMEM245, TMEM246, TMEM247, TMEM248, TMEM249, TMEM25, TMEM250, TMEM251, TMEM252, TMEM253, TMEM254, TMEM255A, TMEM255B, TMEM256, TMEM256-PLSCR3, TMEM257, TMEM258, TMEM259, TMEM26, TMEM260, TMEM262, TMEM263, TMEM265, TMEM266, TMEM267, TMEM268, TMEM269, TMEM27, TMEM270, TMEM30A, TMEM30B, TMEM31, TMEM33, TMEM35A, TMEM35B, TMEM37, TMEM38A, TMEM38B, TMEM39A, TMEM39B, TMEM40, TMEM41A, TMEM41B, TMEM42, TMEM43, TMEM44, TMEM45A, TMEM45B, TMEM47, TMEM5, TMEM50A, TMEM50B, TMEM51, TMEM52, TMEM52B, TMEM53, TMEM54, TMEM55A, TMEM55B, TMEM56, TMEM56-RWDD3, TMEM57, TMEM59, TMEM59L, TMEM60, TMEM61, TMEM62, TMEM63A, TMEM63B, TMEM63C, TMEM64, TMEM65, TMEM67, TMEM68, TMEM69, TMEM70, TMEM71, TMEM72, TMEM74, TMEM74B, TMEM78, TMEM79, TMEM80, TMEM81, TMEM82, TMEM86A, TMEM86B, TMEM87A, TMEM87B, TMEM88, TMEM88B, TMEM89, TMEM8A, TMEM8B, TMEM9, TMEM91, TMEM92, TMEM94, TMEM95, TMEM97, TMEM98, TMEM99, TMEM9B, TMF1, TMIE, TMIGD1, TMIGD2, TMIGD3, TMLHE, TMOD1, TMOD2, TMOD3, TMOD4, TMPO, TMPPE, TMPRSS11A, TMPRSS11B, TMPRSS11D, TMPRSS11E, TMPRSS11F, TMPRSS12, TMPRSS13, TMPRSS15, TMPRSS2, TMPRSS3, TMPRSS4, TMPRSS4-AS1, TMPRSS5, TMPRSS6, TMPRSS7, TMPRSS9, TMSB10, TMSB15A, TMSB15B, TMSB4X, TMSB4Y, TMTC1, TMTC2, TMTC3, TMTC4, TMUB1, TMUB2, TMX1, TMX2, TMX2-CTNND1, TMX3, TMX4, TNC, TNF, TNFAIP1, TNFAIP2, TNFAIP3, TNFAIP6, TNFAIP8, TNFAIP8L1, TNFAIP8L2, TNFAIP8L3, TNFRSF10A, TNFRSF10B, TNFRSF10C, TNFRSF10D, TNFRSF11A, TNFRSF11B, TNFRSF12A, TNFRSF13B, TNFRSF13C, TNFRSF14, TNFRSF17, TNFRSF18, TNFRSF19, TNFRSF1A, TNFRSF1B, TNFRSF21, TNFRSF25, TNFRSF4, TNFRSF6B, TNFRSF8, TNFRSF9, TNFSF10, TNFSF11, TNFSF12, TNFSF12-TNFSF13, TNFSF13, TNFSF13B, TNFSF14, TNFSF15, TNFSF18, TNFSF4, TNFSF8, TNFSF9, TNIK, TNIP1, TNIP2, TNIP3, TNK1, TNK2, TNKS, TNKS1BP1, TNKS2, TNMD, TNN, TNNC1, TNNC2, TNNI1, TNNI2, TNNI3, TNNI3K, TNNT1, TNNT2, TNNT3, TNP1, TNP2, TNPO1, TNPO2, TNPO3, TNR, TNRC18, TNRC6A, TNRC6B, TNRC6C, TNS1, TNS2, TNS3, TNS4, TNXB, TOB1, TOB2, TOE1, TOGARAMI, TOGARAM2, TOLLIP, TOM1, TOM1L1, TOM1L2, TOMM20, TOMM20L, TOMM22, TOMM34, TOMM40, TOMM40L, TOMM5, TOMM6, TOMM7, TOMM70, TONSL, TOP1, TOP1MT, TOP2A, TOP2B, TOP3A, TOP3B, TOPAZ1, TOPBP1, TOPORS, TOR1A, TOR1AIP1, TOR1AIP2, TOR1B, TOR2A, TOR3A, TOR4A, TOX, TOX2, TOX3, TOX4, TP53, TP53AIP1, TP53BP1, TP53BP2, TP53I1, TP53I13, TP53I3, TP53INP1, TP53INP2, TP53RK, TP53TG3, TP53TG3B, TP53TG3C, TP53TG3D, TP53TG3E, TP53TG3F, TP53TG5, TP63, TP73, TPBG, TPBGL, TPCN1, TPCN2, TPD52, TPD52L1, TPD52L2, TPD52L3, TPGS1, TPGS2, TPH1, TPH2, TPI1, TPK1, TPM1, TPM2, TPM3, TPM4, TPMT, TPO, TPP1, TPP2, TPPP, TPPP2, TPPP3, TPR, TPRA1, TPRG1, TPRG1L, TPRKB, TPRN, TPRX1, TPSAB1, TPSB2, TPSD1, TPSG1, TPST1, TPST2, TPT1, TPTE, TPTE2, TPX2, TRA2A, TRA2B, TRABD, TRABD2A, TRABD2B, TRAC, TRADD, TRAF1, TRAF2, TRAF3, TRAF3IP1, TRAF3IP2, TRAF3IP3, TRAF4, TRAF5, TRAF6, TRAF7, TRAFD1, TRAIP, TRAJ1, TRAJ10, TRAJ11, TRAJ12, TRAJ13, TRAJ14, TRAJ16, TRAJ17, TRAJ18, TRAJ19, TRAJ2, TRAJ20, TRAJ21, TRAJ22, TRAJ23, TRAJ24, TRAJ25, TRAJ26, TRAJ27, TRAJ28, TRAJ29, TRAJ3, TRAJ3, TRAJ31, TRAJ32, TRAJ33, TRAJ34, TRAJ35, TRAJ36, TRAJ37, TRAJ38, TRAJ39, TRAJ4, TRAJ40, TRAJ41, TRAJ42, TRAJ43, TRAJ44, TRAJ45, TRAJ46, TRAJ47, TRAJ48, TRAJ49, TRAJ5, TRAJ50, TRAJ52, TRAJ53, TRAJ54, TRAJ56, TRAJ57, TRAJ58, TRAJ59, TRAJ6, TRAJ61, TRAJ7, TRAJ9, TRAK1, TRAK2, TRAM1, TRAM11, TRAM2, TRANK1, TRAP1, TRAPPC1, TRAPPC10, TRAPPC11, TRAPPC12, TRAPPC13, TRAPPC2, TRAPPC2L, TRAPPC3, TRAPPC3L, TRAPPC4, TRAPPC5, TRAPPC6A, TRAPPC6B, TRAPPC8, TRAPPC9, TRAT1, TRAV10, TRAV1-1, TRAV1-2, TRAV12-1, TRAV12-2, TRAV12-3, TRAV13-1, TRAV13-2, TRAV14DV4, TRAV16, TRAV17, TRAV18, TRAV19, TRAV2, TRAV20, TRAV21, TRAV22, TRAV23DV6, TRAV24, TRAV25, TRAV26-1, TRAV26-2, TRAV27, TRAV29DV5, TRAV3, TRAV30, TRAV34, TRAV36DV7, TRAV38-1, TRAV38-2DV8, TRAV39, TRAV4, TRAV40, TRAV41, TRAV5, TRAV6, TRAV7, TRAV8-1, TRAV8-2, TRAV8-3, TRAV8-4, TRAV8-6, TRAV8-7, TRAV9-1, TRAV9-2, TRBC2, TRBJ2-1, TRBJ2-2, TRBJ2-2P, TRBJ2-3, TRBJ2-4, TRBJ2-5, TRBJ2-6, TRBJ2-7, TRBV10-1, TRBV10-2, TRBV10-3, TRBV11-1, TRBV19, TRBV2, TRBV20-1, TRBV20OR9-2, TRBV21OR9-2, TRBV23-1, TRBV23OR9-2, TRBV24-1, TRBV25-1, TRBV27, TRBV28, TRBV29-1, TRBV30, TRBV3-1, TRBV4-1, TRBV4-2, TRBV5-1, TRBV5-3, TRBV5-4, TRBV5-5, TRBV5-6, TRBV5-7, TRBV6-1, TRBV6-4, TRBV6-5, TRBV6-6, TRBV6-7, TRBV6-8, TRBV7-1, TRBV7-3, TRBV7-4, TRBV7-6, TRBV7-7, TRBV7-9, TRBV9, TRDC, TRDD1, TRDD2, TRDD3, TRDJ1, TRDJ2, TRDJ3, TRDJ4, TRDMT1, TRDN, TRDV1, TRDV2, TRDV3, TREH, TREM1, TREM2, TREML1, TREML2, TREML4, TRERF1, TREX1, TREX2, TRGC1, TRGC2, TRGJ1, TRGJ2, TRGJP, TRGJP1, TRGJP2, TRGV1, TRGV10, TRGV11, TRGV2, TRGV3, TRGV4, TRGV5, TRGV8, TRGV9, TRH, TRHDE, TRHR, TRIAP1, TRIB1, TRIB2, TRIB3, TRIL, TRIM10, TRIM1, TRIM13, TRIM14, TRIM15, TRIM16, TRIM16L, TRM17, TRIM2, TRIM21, TRIM22, TRIM23, TRIM24, TRIM25, TRIM26, TRIM27, TRIM28, TRIM29, TRIM3, TRIM31, TRIM32, TRIM33, TRIM34, TRIM35, TRIM36, TRIM37, TRIM38, TRIM39, TRIM39-RPP21, TRIM4, TRIM40, TRIM41, TRIM42, TRIM43, TRIM43B, TRIM44, TRIM45, TRIM46, TRIM47, TRIM48, TRIM49, TRIM49B, TRIM49C, TRIM49D1, TRIM49D2, TRIM5, TRIM50, TRIM51, TRIM52, TRIM54, TRIM55, TRIM56, TRIM58, TRIM59, TRM6, TRIM60, TRIM61, TRIM62, TRIM63, TRIM64, TRIM64B, TRIM64C, TRIM65, TRIM66, TRIM67, TRIM68, TRIM69, TRIM6-TRIM34, TRIM7, TRIM71, TRIM72, TRIM73, TRIM74, TRIM75P, TRIM77, TRIM8, TRIM9, TRML1, TRIML2, TRIO, TRIOBP, TRIP10, TRIP11, TRIP12, TRIPI3, TRIP4, TRIP6, TRIQK, TRIR, TRIT1, TRMO, TRMT1, TRMT10A, TRMT10B, TRMT10C, TRMT11, TRMT112, TRMT12, TRMT13, TRMT1L, TRMT2A, TRMT2B, TRMT44, TRMT5, TRMT6, TRMT61A, TRMT61B, TRMU, TRNAU1AP, TRNP1, TRNT1, TRO, TROAP, TROVE2, TRPA1, TRPC1, TRPC3, TRPC4, TRPC4AP, TRPC5, TRPC50S, TRPC6, TRPC7, TRPM1, TRPM2, TRPM3, TRPM4, TRPM5, TRPM6, TRPM7, TRPM8, TRPS1, TRPT1, TRPV1, TRPV2, TRPV3, TRPV4, TRPV5, TRPV6, TRRAP, TRUB1, TRUB2, TSACC, TSC1, TSC2, TSC22D1, TSC22D2, TSC22D3, TSC22D4, TSEN15, TSEN2, TSEN34, TSEN54, TSFM, TSG101, TSGA10, TSGA10IP, TSGA13, TSHB, TSHR, TSHZ1, TSHZ2, TSHZ3, TSKS, TSKU, TSLP, TSN, TSNARE1, TSNAX, TSNAX-DISC1, TSNAXIP1, TSPAN1, TSPAN10, TSPAN11, TSPAN12, TSPAN13, TSPAN14, TSPAN15, TSPAN16, TSPAN17, TSPAN18, TSPAN19, TSPAN2, TSPAN3, TSPAN31, TSPAN32, TSPAN33, TSPAN4, TSPAN5, TSPAN6, TSPAN7, TSPAN8, TSPAN9, TSPEAR, TSPO, TSPO2, TSPOAP1, TSPY1, TSPY10, TSPY2, TSPY3, TSPY4, TSPY8, TSPYL1, TSPYL2, TSPYL4, TSPYL5, TSPYL6, TSR1, TSR2, TSR3, TSSC4, TSSK1B, TSSK2, TSSK3, TSSK4, TSSK6, TST, TSTA3, TSTD1, TSTD2, TSTD3, TTBK1, TTBK2, TTC1, TTC12, TTC13, TTC14, TTC16, TTC17, TTC19, TTC21A, TTC21B, TTC22, TTC23, TTC23L, TTC24, TTC25, TTC26, TTC27, TTC28, TTC29, TTC3, TTC30A, TTC30B, TTC31, TTC32, TTC33, TTC34, TTC36, TTC37, TTC38, TTC39A, TTC39B, TTC39C, TTC4, TTC5, TTC6, TTC7A, TTC7B, TTC8, TTC9, TTC9B, TTC9C, TTF1, TTF2, TTI1, TTI2, TTK, TTL, TTLL1, TTLL10, TTLL11, TTLL12, TTLL13P, TTLL2, TTLL3, TTLL4, TTLL5, TTLL6, TTLL7, TTLL8, TTLL9, TTN, TTPA, TTPAL, TTR, TTYH1, TTYH2, TTYH3, TUB, TUBA1A, TUBA1B, TUBA1C, TUBA3C, TUBA3D, TUBA3E, TUBA4A, TUBA4B, TUBA8, TUBAL3, TUBB, TUBB1, TUBB2A, TUBB2B, TUBB3, TUBB4A, TUBB4B, TUBB6, TUBB8, TUBD1, TUBE1, TUBG1, TUBG2, TUBGCP2, TUBGCP3, TUBGCP4, TUBGCP5, TUBGCP6, TUFM, TUFT1, TULP1, TULP2, TULP3, TULP4, TUNAR, TUSC1, TUSC2, TUSC3, TUSC5, TUT1, TVP23A, TVP23B, TVP23C, TVP23C-CDRT4, TWF1, TWF2, TWIST1, TWIST2, TWISTNB, TWNK, TWSG1, TXK, TXLNA, TXLNB, TXLNG, TXN, TXN2, TXNDC11, TXNDC12, TXNDC15, TXNDC16, TXNDC17, TXNDC2, TXNDC5, TXNDC8, TXNDC9, TXNIP, TXNL1, TXNL4A, TXNL4B, TXNRD1, TXNRD2, TXNRD3, TXNRD3NB, TYK2, TYMP, TYMS, TYR, TYRO3, TYROBP, TYRP1, TYSND1, TYW1, TYW1B, TYW3, TYW5, U2AF1, U2AF1L4, U2AF1L5, U2AF2, U2SURP, UACA, UAP1, UAP1L1, UBA1, UBA2, UBA3, UBA5, UBA52, UBA6, UBA7, UBAC1, UBAC2, UBALD1, UBALD2, UBAP1, UBAP1L, UBAP2, UBAP2L, UBASH3A, UBASH3B, UBB, UBC, UBD, UBE2A, UBE2B, UBE2C, UBE2D1, UBE2D2, UBE2D3, UBE2D4, UBE2E1, UBE2E2, UBE2E3, UBE2F, UBE2F-SCLY, UBE2G1, UBE2G2, UBE2H, UBE2I, UBE2J1, UBE2J2, UBE2K, UBE2L3, UBE2L5P, UBE2L6, UBE2M, UBE2N, UBE2NL, UBE2O, UBE2Q1, UBE2Q2, UBE2Q2L, UBE2QL1, UBE2R2, UBE2S, UBE2T, UBE2U, UBE2V1, UBE2V2, UBE2W, UBE2Z, UBE3A, UBE3B, UBE3C, UBE3D, UBE4A, UBE4B, UBFD1, UBIAD1, UBL3, UBL4A, UBL4B, UBL5, UBL7, UBLCP1, UBN1, UBN2, UBOX5, UBP1, UBQLN1, UBQLN2, UBQLN3, UBQLN4, UBQLNL, UBR1, UBR2, UBR3, UBR4, UBR5, UBR7, UBTD1, UBTD2, UBTF, UBTFL1, UBXN1, UBXN10, UBXN11, UBXN2A, UBXN2B, UBXN4, UBXN6, UBXN7, UBXN8, UCHL1, UCHL3, UCHL5, UCK1, UCK2, UCKL1, UCMA, UCN, UCN2, UCN3, UCP1, UCP2, UCP3, UEVLD, UFC1, UFD1, UFL1, UFM1, UFSP1, UFSP2, UGCG, UGDH, UGGT1, UGGT2, UGP2, UGT1A1, UGT1A10, UGT1A3, UGT1A4, UGT1A5, UGT1A6, UGT1A7, UGT1A8, UGT1A9, UGT2A1, UGT2A2, UGT2A3, UGT2B10, UGT2B11, UGT2B15, UGT2B17, UGT2B28, UGT2B4, UGT2B7, UGT3A1, UGT3A2, UGT8, UHMK1, UHRF1, UHRF1BP1, UHRF1BP1L, UHRF2, UIMC1, ULBP1, ULBP2, ULBP3, ULK1, ULK2, ULK3, ULK4, UMAD1, UMOD, UMODL1, UMPS, UNC119, UNC119B, UNC13A, UNC13B, UNC13C, UNC13D, UNC45A, UNC45B, UNC50, UNC5A, UNC5B, UNC5C, UNC5CL, UNC5D, UNC79, UNC80, UNC93A, UNC93B1, UNCX, UNG, UNK, UNKL, UPB1, UPF1, UPF2, UPF3A, UPF3B, UPK1A, UPK1B, UPK2, UPK3A, UPK3B, UPK3BL1, UPP1, UPP2, UPRT, UQCC1, UQCC2, UQCC3, UQCR10, UQCR11, UQCRB, UQCRC1, UQCRC2, UQCRF S1, UQCRH, UQCRHL, UQCRQ, URAD, URB1, URB2, URGCP, URGCP-MRPS24, URI1, URM1, UROC1, UROD, UROS, USB1, USE1, USF1, USF2, USF3, USH1C, USH1G, USH2A, USHBP1, USMG5, USO1, USP1, USP10, USP11, USP12, USP13, USP14, USP15, USP16, USP17L1, USP17L10, USP17L11, USP17L12, USP17L13, USP17L15, USP17L17, USP17L18, USP17L19, USP17L2, USP17L20, USP17L21, USP17L22, USP17L23, USP17L24, USP17L25, USP17L26, USP17L27, USP17L28, USP17L29, USP17L3, USP17L30, USP17L4, USP17L5, USP17L7, USP17L8, USP18, USP19, USP2, USP20, USP21, USP22, USP24, USP25, USP26, USP27X, USP28, USP29, USP3, USP30, USP31, USP32, USP33, USP34, USP35, USP36, USP37, USP38, USP39, USP4, USP40, USP41, USP42, USP43, USP44, USP45, USP46, USP47, USP48, USP49, USP5, USP50, USP51, USP53, USP54, USP6, USP6NL, USP7, USP8, USP9X, USP9Y, USPL1, UST, UTF1, UTP11, UTP14A, UTP14C, UTP15, UTP18, UTP20, UTP23, UTP3, UTP4, UTP6, UTRN, UTS2, UTS2B, UTS2R, UTY, UVRAG, UVSSA, UXS1, UXT, VAC14, VAMP1, VAMP2, VAMP3, VAMP4, VAMP5, VAMP7, VAMP8, VANGL, VANGL2, VAPA, VAPB, VARS, VARS2, VASH1, VASH2, VASN, VASP, VAT1, VAT1L, VAV1, VAV2, VAV3, VAX1, VAX2, VBP1, VCAM1, VCAN, VCL, VCP, VCPIP1, VCPKMT, VCX, VCX2, VCX3A, VCX3B, VCY, VCY1B, VDAC1, VDAC2, VDAC3, VDR, VEGFA, VEGFB, VEGFC, VEGFD, VENTX, VEPH1, VEZF1, VEZT, VGF, VGLL1, VGLL2, VGLL3, VGLL4, VHL, VHLL, VIL1, VILL, VIM, VIP, VIPAS39, VIPR1, VIPR2, VIRMA, VIT, VKORC1, VKORC1L1, VLDLR, VMA21, VMAC, VMO1, VMP1, VN1R1, VN1R2, VN1R4, VN1R5, VNN1, VNN2, VNN3, VOPP1, VPREB1, VPREB3, VPS11, VPS13A, VPS13B, VPS13C, VPS13D, VPS16, VPS18, VPS25, VPS26A, VPS26B, VPS28, VPS29, VPS33A, VPS33B, VPS35, VPS36, VPS37A, VPS37B, VPS37C, VPS37D, VPS39, VPS41, VPS45, VPS4A, VPS4B, VPS50, VPS51, VPS52, VPS53, VPS54, VPS72, VPS8, VPS9D1, VRK1, VRK2, VRK3, VRTN, VSIG1, VSIG10, VSIG1OL, VSIG10L2, VSIG2, VSIG4, VSIG8, VSIR, VSNL1, VSTM1, VSTM2A, VSTM2B, VSTM2L, VSTM4, VSTM5, VSX1, VSX2, VTA1, VTCN1, VTI1A, VTI1B, VTN, VWA1, VWA2, VWA3A, VWA3B, VWA5A, VWA5B1, VWA5B2, VWA7, VWA8, VWC2, VWC2L, VWCE, VWDE, VWF, WAC, WAPL, WARS, WARS2, WAS, WASF1, WASF2, WASF3, WASHC1, WASHC2A, WASHC2C, WASHC3, WASHC4, WASHC5, WASL, WBP1, WBP11, WBP1L, WBP2, WBP2NL, WBP4, WDCP, WDFY1, WDFY2, WDFY3, WDFY4, WDHD1, WDPCP, WDR1, WDR11, WDR12, WDR13, WDR17, WDR18, WDR19, WDR20, WDR24, WDR25, WDR26, WDR27, WDR3, WDR31, WDR33, WDR34, WDR35, WDR36, WDR37, WDR38, WDR4, WDR41, WDR43, WDR44, WDR45, WDR45B, WDR46, WDR47, WDR48, WDR49, WDR5, WDR53, WDR54, WDR55, WDR59, WDR5B, WDR6, WDR60, WDR61, WDR62, WDR63, WDR64, WDR66, WDR7, WDR70, WDR72, WDR73, WDR74, WDR75, WDR76, WDR77, WDR78, WDR81, WDR82, WDR83, WDR83OS, WDR86, WDR87, WDR88, WDR89, WDR90, WDR91, WDR92, WDR93, WDR97, WDSUB1, WDTC1, WDYHV1, WEE1, WEE2, WFDC1, WFDC10A, WFDC10B, WFDC11, WFDC12, WFDC13, WFDC2, WFDC3, WFDC5, WFDC6, WFDC8, WFDC9, WFIKKN1, WFIKKN2, WFS1, WHAMM, WHRN, WIF1, WIPF1, WIPF2, WIPF3, WIPI1, WIPI2, WISP1, WISP2, WISP3, WIZ, WLS, WNK1, WNK2, WNK3, WNK4, WNT1, WNT10A, WNT10B, WNT11, WNT16, WNT2, WNT2B, WNT3, WNT3A, WNT4, WNT5A, WNT5B, WNT6, WNT7A, WNT7B, WNT8A, WNT8B, WNT9A, WNT9B, WRAP53, WRAP73, WRB, WRN, WRNIP1, WSB1, WSB2, WSCD1, WSCD2, WT1, WTAP, WTH3DI, WTIP, WWC1, WWC2, WWC3, WWOX, WWP1, WWP2, WWTR1, XAB2, XAF1, XAGE1A, XAGE1B, XAGE2, XAGE3, XAGE5, XBP1, XCL1, XCL2, XCR1, XDH, XG, XIAP, XIRP1, XIRP2, XK, XKR3, XKR4, XKR5, XKR6, XKR7, XKR8, XKR9, XKRX, XPA, XPC, XPNPEP1, XPNPEP2, XPNPEP3, XPO1, XPO4, XPO5, XPO6, XPO7, XPOT, XPR1, XRCC1, XRCC2, XRCC3, XRCC4, XRCC5, XRCC6, XRN1, XRN2, XRRA1, XXYLT1, XYLB, XYLT1, XYLT2, YAE1D1, YAF2, YAP1, YARS, YARS2, YBEY, YBX1, YBX2, YBX3, YDJC, YEATS2, YEATS4, YES1, YIF1A, YIF1B, YIPF1, YIPF2, YIPF3, YIPF4, YIPF5, YIPF6, YIPF7, YJEFN3, YKT6, YLPM1, YME1L1, YOD1, YPEL1, YPEL2, YPEL3, YPEL4, YPEL5, YRDC, YTHDC1, YTHDC2, YTHDF1, YTHDF2, YTHDF3, YWHAB, YWHAE, YWHAG, YWHAH, YWHAQ, YWHAZ, YY1, YY1AP1, YY2, Z82206.1, Z83844.1, Z84492.1, Z98749.3, Z98752.3, ZACN, ZADH2, ZAN, ZAP70, ZAR1, ZAR1L, ZBBX, ZBED1, ZBED2, ZBED3, ZBED4, ZBED5, ZBED6, ZBED6CL, ZBED8, ZBED9, ZBP1, ZBTB1, ZBTB10, ZBTB11, ZBTB12, ZBTB14, ZBTB16, ZBTB17, ZBTB18, ZBTB2, ZBTB20, ZBTB21, ZBTB22, ZBTB24, ZBTB25, ZBTB26, ZBTB3, ZBTB32, ZBTB33, ZBTB34, ZBTB37, ZBTB38, ZBTB39, ZBTB4, ZBTB40, ZBTB41, ZBTB42, ZBTB43, ZBTB44, ZBTB45, ZBTB46, ZBTB47, ZBTB48, ZBTB49, ZBTB5, ZBTB6, ZBTB7A, ZBTB7B, ZBTB7C, ZBTB8A, ZBTB8B, ZBTB8OS, ZBTB9, ZC2HC1A, ZC2HC1B, ZC2HC1C, ZC3H10, ZC3H11A, ZC3H11B, ZC3H12A, ZC3H12B, ZC3H12C, ZC3H12D, ZC3H13, ZC3H14, ZC3H15, ZC3H18, ZC3H3, ZC3H4, ZC3H6, ZC3H7A, ZC3H7B, ZC3H8, ZC3HAV1, ZC3HAV1L, ZC3HC1, ZC4H2, ZCCHC10, ZCCHC11, ZCCHC12, ZCCHC13, ZCCHC14, ZCCHC17, ZCCHC18, ZCCHC2, ZCCHC24, ZCCHC3, ZCCHC4, ZCCHC6, ZCCHC7, ZCCHC8, ZCCHC9, ZCRB1, ZCWPW1, ZCWPW2, ZDBF2, ZDHHC1, ZDHHC11, ZDHHC11B, ZDHHC12, ZDHHC13, ZDHHC14, ZDHHC15, ZDHHC16, ZDHHC17, ZDHHC18, ZDHHC19, ZDHHC2, ZDHHC20, ZDHHC21, ZDHHC22, ZDHHC23, ZDHHC24, ZDHHC3, ZDHHC4, ZDHHC5, ZDHHC6, ZDHHC7, ZDHHC8, ZDHHC9, ZEB1, ZEB2, ZER1, ZFAND1, ZFAND2A, ZFAND2B, ZFAND3, ZFAND4, ZFAND5, ZFAND6, ZFAT, ZFC3H1, ZFHX2, ZFHX3, ZFHX4, ZFP1, ZFP14, ZFP2, ZFP28, ZFP3, ZFP30, ZFP36, ZFP36L1, ZFP36L2, ZFP37, ZFP41, ZFP42, ZFP57, ZFP62, ZFP64, ZFP69, ZFP69B, ZFP82, ZFP90, ZFP91, ZFP91-CNTF, ZFP92, ZFPL1, ZFPM1, ZFPM2, ZFR, ZFR2, ZFX, ZFY, ZFYVE1, ZFYVE16, ZFYVE19, ZFYVE21, ZFYVE26, ZFYVE27, ZFYVE28, ZFYVE9, ZG16, ZG16B, ZGLP1, ZGPAT, ZGRF1, ZHX1, ZHX1-C$_8$orf76, ZHX2, ZHX3, ZIC1, ZIC2, ZIC3, ZIC4, ZIC5, ZIK1, ZIM2, ZIM3, ZKSCAN1, ZKSCAN2, ZKSCAN3, ZKSCAN4, ZKSCAN5, ZKSCAN7, ZKSCAN8, ZMAT1, ZMAT2, ZMAT3, ZMAT4, ZMAT5, ZMIZ1, ZMIZ2, ZMPSTE24, ZMYM1, ZMYM2, ZMYM3, ZMYM4, ZMYM5, ZMYM6, ZMYND10, ZMYND11, ZMYND12, ZMYND15, ZMYND19, ZMYND8, ZNF10, ZNF100, ZNF101, ZNF106, ZNF107, ZNF112, ZNF114, ZNF117, ZNF12, ZNF121, ZNF124, ZNF131, ZNF132, ZNF133, ZNF134, ZNF135, ZNF136, ZNF138, ZNF14, ZNF140, ZNF141, ZNF142, ZNF143, ZNF146, ZNF148, ZNF154, ZNF155, ZNF157, ZNF16, ZNF160, ZNF165, ZNF169, ZNF17, ZNF174, ZNF175, ZNF177, ZNF18, ZNF180, ZNF181, ZNF182, ZNF184, ZNF185, ZNF189, ZNF19, ZNF195, ZNF197, ZNF2, ZNF20, ZNF200, ZNF202, ZNF205, ZNF207, ZNF208, ZNF211, ZNF212, ZNF213, ZNF214, ZNF215, ZNF217, ZNF219, ZNF22, ZNF221, ZNF222, ZNF223, ZNF224, ZNF225, ZNF226, ZNF227, ZNF229, ZNF23, ZNF230, ZNF232, ZNF233, ZNF234, ZNF235, ZNF236, ZNF239, ZNF24, ZNF248, ZNF25, ZNF250, ZNF251, ZNF253, ZNF254, ZNF256, ZNF257, ZNF26, ZNF260, ZNF263, ZNF264, ZNF266, ZNF267, ZNF268, ZNF273, ZNF274, ZNF275, ZNF276, ZNF277, ZNF28, ZNF280A, ZNF280B, ZNF280C, ZNF280D, ZNF281, ZNF282, ZNF283, ZNF284, ZNF285, ZNF286A, ZNF286B, ZNF287, ZNF292, ZNF296, ZNF3, ZNF30, ZNF300, ZNF302, ZNF304, ZNF311, ZNF316, ZNF317, ZNF318, ZNF319, ZNF32, ZNF320, ZNF322, ZNF324, ZNF324B, ZNF326, ZNF329, ZNF330, ZNF331, ZNF333, ZNF334, ZNF335, ZNF337, ZNF33A, ZNF33B, ZNF34, ZNF341, ZNF343, ZNF345, ZNF346, ZNF347, ZNF35, ZNF350, ZNF354A, ZNF354B, ZNF354C, ZNF358, ZNF362, ZNF365, ZNF366, ZNF367, ZNF37A, ZNF382, ZNF383, ZNF384, ZNF385A, ZNF385B, ZNF385C, ZNF385D, ZNF391, ZNF394, ZNF395, ZNF396, ZNF397, ZNF398, ZNF404, ZNF407, ZNF408, ZNF41, ZNF410, ZNF414, ZNF415, ZNF416, ZNF417, ZNF418, ZNF419, ZNF420, ZNF423, ZNF425, ZNF426, ZNF428, ZNF429, ZNF43, ZNF430, ZNF431, ZNF432, ZNF433, ZNF436, ZNF438, ZNF439, ZNF44, ZNF440, ZNF441, ZNF442, ZNF443, ZNF444, ZNF445, ZNF446, ZNF449, ZNF45, ZNF451, ZNF454, ZNF460, ZNF461, ZNF462, ZNF467, ZNF468, ZNF469, ZNF470, ZNF471, ZNF473, ZNF474, ZNF479, ZNF48, ZNF480, ZNF483, ZNF484, ZNF485, ZNF486, ZNF487, ZNF488, ZNF490, ZNF491, ZNF492, ZNF493, ZNF496, ZNF497, ZNF500, ZNF501, ZNF502, ZNF503, ZNF506, ZNF507, ZNF510, ZNF511, ZNF512, ZNF512B, ZNF513, ZNF514, ZNF516, ZNF517, ZNF518A, ZNF518B, ZNF519, ZNF521, ZNF524, ZNF525, ZNF526, ZNF527, ZNF528, ZNF529, ZNF530, ZNF532, ZNF534, ZNF536, ZNF540, ZNF541, ZNF543, ZNF544, ZNF546, ZNF547, ZNF548, ZNF549, ZNF550, ZNF551, ZNF552, ZNF554, ZNF555, ZNF556, ZNF557, ZNF558, ZNF559, ZNF559-ZNF177, ZNF560, ZNF561, ZNF562, ZNF563, ZNF564, ZNF565, ZNF566, ZNF567, ZNF568, ZNF569, ZNF57, ZNF570, ZNF571, ZNF572, ZNF573, ZNF574, ZNF575, ZNF576, ZNF577, ZNF578, ZNF579, ZNF580, ZNF581, ZNF582, ZNF583, ZNF584, ZNF585A, ZNF585B, ZNF586, ZNF587, ZNF587B, ZNF589, ZNF592, ZNF593, ZNF594, ZNF595, ZNF596, ZNF597, ZNF598, ZNF599, ZNF600, ZNF605, ZNF606, ZNF607, ZNF608, ZNF609, ZNF610, ZNF611, ZNF613, ZNF614, ZNF615, ZNF616, ZNF618, ZNF619, ZNF620, ZNF621, ZNF622, ZNF623, ZNF624, ZNF625, ZNF625-ZNF20, ZNF626, ZNF627, ZNF628, ZNF629, ZNF630, ZNF638, ZNF639, ZNF641, ZNF644, ZNF645, ZNF646, ZNF648, ZNF649, ZNF652, ZNF653, ZNF654, ZNF655, ZNF658, ZNF66, ZNF660, ZNF662, ZNF664, ZNF665, ZNF667, ZNF668, ZNF669, ZNF670, ZNF670-ZNF695, ZNF671, ZNF672, ZNF674, ZNF675, ZNF676, ZNF677, ZNF678, ZNF679, ZNF680, ZNF681, ZNF682, ZNF683, ZNF684, ZNF687, ZNF688, ZNF689, ZNF69, ZNF691, ZNF692, ZNF695, ZNF696, ZNF697, ZNF699, ZNF7, ZNF70, ZNF700, ZNF701, ZNF703, ZNF704, ZNF705A, ZNF705B, ZNF705D, ZNF705E, ZNF705G, ZNF706, ZNF707, ZNF708, ZNF709, ZNF71, ZNF710, ZNF711, ZNF713, ZNF714, ZNF716, ZNF717, ZNF718, ZNF720, ZNF721, ZNF724, ZNF726, ZNF727, ZNF728, ZNF729, ZNF730, ZNF732, ZNF735, ZNF736, ZNF737, ZNF738, ZNF74, ZNF740, ZNF746, ZNF747, ZNF749, ZNF750, ZNF75A, ZNF75D, ZNF76, ZNF761, ZNF763, ZNF764, ZNF765, ZNF766, ZNF768, ZNF77, ZNF770, ZNF771, ZNF772, ZNF773, ZNF774, ZNF775, ZNF776, ZNF777, ZNF778, ZNF780A, ZNF780B, ZNF781, ZNF782, ZNF783, ZNF784, ZNF785, ZNF786, ZNF787, ZNF788, ZNF789, ZNF79, ZNF790, ZNF791, ZNF792, ZNF793, ZNF799, ZNF8, ZNF80, ZNF800, ZNF804A, ZNF804B, ZNF805, ZNF808, ZNF81, ZNF813, ZNF814, ZNF816, ZNF816-ZNF321P, ZNF821, ZNF823, ZNF827, ZNF829, ZNF83, ZNF830, ZNF831, ZNF835, ZNF836, ZNF837, ZNF839, ZNF84, ZNF841, ZNF843, ZNF844, ZNF845, ZNF846, ZNF85, ZNF850, ZNF852, ZNF853, ZNF860, ZNF862, ZNF865, ZNF878, ZNF879, ZNF880, ZNF883, ZNF888, ZNF891, ZNF90, ZNF91, ZNF92, ZNF93, ZNF98, ZNF99, ZNFX1, ZNHIT1, ZNHIT2, ZNHIT3, ZNHIT6, ZNRD1, ZNRF1, ZNRF2, ZNRF3, ZNRF4, ZP1, ZP2, ZP3, ZP4, ZPBP, ZPBP2, ZPLD1, ZPR1, ZRANB1, ZRANB2, ZRANB3, ZRSR1, ZRSR2, ZSCAN1, ZSCAN10, ZSCAN12, ZSCAN16, ZSCAN18, ZSCAN2, ZSCAN20, ZSCAN21, ZSCAN22, ZSCAN23, ZSCAN25, ZSCAN26, ZSCAN29, ZSCAN30, ZSCAN31, ZSCAN32, ZSCAN4, ZSCAN5A, ZSCAN5B, ZSCAN5C, ZSCAN9, ZSWIM1, ZSWIM2, ZSWIM3, ZSWIM4, ZSWIM5, ZSWIM6, ZSWIM7, ZSWIM8, ZUFSP, ZW10, ZWILCH, ZWINT, ZXDA, ZXDB, ZXDC, ZYG11A, ZYG11B, ZYX, ZZEF1, and ZZZ3.

Furthermore, the invention provides the use of a compound according to the definitions herein, or a pharmaceutically acceptable salt, or a hydrate or solvate thereof for the preparation of a medicament for the treatment of an autoimmune disorder, an inflammatory disorder, or a proliferative disorder, or a disorder commonly occurring in connection with transplantation.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I, formula I', formula I-i, formula II, formula II' or formula II-i and one or more additional therapeutic agents. The therapeutic agent may be administered together with a compound of formula I, formula I', formula I-i, formula II, formula II' or formula II-i, or may be administered prior to or following administration of a compound of formula I, formula I', formula I-i, formula II, formula II' or formula I-i. Suitable therapeutic agents are described in further detail below. In certain embodiments, a compound of formula I, formula I', formula I-i, formula II, formula II' or formula II-i may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I, formula I', formula I-i, formula II, formula II' or formula II-i may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I, formula I', formula I-i, formula II, formula II' or formula II-i and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I, formula I', formula I-i, formula II, formula II' or formula II-i and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I, formula I', formula I-i, formula II, formula II' or formula I-i and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating systemic lupus erythematosus comprising administering to a patient in need thereof a compound of formula I, formula I', formula I-i, formula II, formula II' or formula I-i and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I, formula I', formula I-i, formula II, formula II' or formula I-i and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I, formula I', formula I-i, formula II, formula II' or formula II-i and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I, formula I', formula I-i, formula II, formula II' or formula II-i and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theo-lair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®.

In another embodiment, the present invention provides a method of treating a hematological malignancy comprising administering to a patient in need thereof a compound of formula I, formula I', formula I-i, formula II, formula II' or formula II-i and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I, formula I', formula I-i, formula II, formula II' or formula II-i and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I, formula I', formula I-i, formula II, formula II' or formula II-i and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I, formula I', formula I-i, formula II, formula II' or formula II-i and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I, formula I', formula I-i, formula II, formula II' or formula II-i and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I, formula I', formula I-i, formula II, formula II' or formula II-i and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I, formula I', formula I-i, formula II, formula II' or formula II-i and a PI3K inhibitor, wherein the disease is selected from a cancer, a neurodegenative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I, formula I', formula I-i, formula II, formula II' or formula II-i and a PI3K inhibitor, wherein die disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treading or lessening the severity of a disease comprising administering to a patient in need thereof a compound of formula I, formula I', formula I-i, formula II, formula II' or formula II-i and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lyrphocytic leukemia, diffuse large B-cell lymphoma, Hodgkin's disease, small-cell lung cancer, non-small-cell lung cancer, Myelodysplastic syndrome, lymphoma, a hematological neoplasm, or solid tumor.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of modulating CRBN activity in a biological sample comprising the step of contacting said biological sample with a compound of this invention, or a composition comprising said compound.

According to another embodiment, the invention relates to a method of binding CRBN, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof, and blood, saliva, urine, feces, semen, tears, or other body fluids or extracts thereof.

Binding CRBN (or a mutant thereof) activity in a biological sample is useful for a variety of purposes that are known to one of skill in the art. Examples of such purposes include, but are not limited to, biological specimen storage and biological assays.

Another embodiment of the present invention relates to a method of modulating CRBN activity in a patient comprising the step of administering to said patient a compound of the present invention, or a composition comprising said compound.

According to another embodiment, the invention relates to a method of modulating the activity of CRBN, or a mutant thereof, in a patient comprising the step of administering to said patient a compound of the present invention, or a composition comprising said compound. According to certain embodiments, the invention relates to a method of reversibly or irreversibly modulating one or more of CRBN, or a mutant thereof, activity in a patient comprising the step of administering to said patient a compound of the present invention, or a composition comprising said compound. In other embodiments, the present invention provides a method for treating a disorder mediated by CRBN, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal©); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxo™ Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-R, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, P3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; sis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFRi ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, $C_{1-1033}$, EKB-569, GW-2016, E1.1, E2.4, E2.5, E6.2, E6.4, E2.11, E6.3 or E7.6.3, and 7H-pyrrolo-[2, 3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™.

Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl] phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)$_{0-4}$-(4-pyridylmethyl)phthalazine or a pharmaceutically acceptable salt thereof, 1-(4-chloroanilino)$_{0-4}$-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl]tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 pg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Example 1. Synthesis of 3-(2-Oxo-2,3-dihydro-1H-indol-1-yl)piperidine-2,6-dione, I-3

Scheme 1

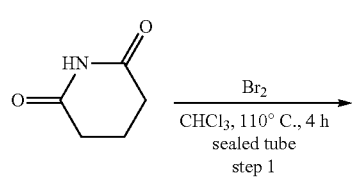

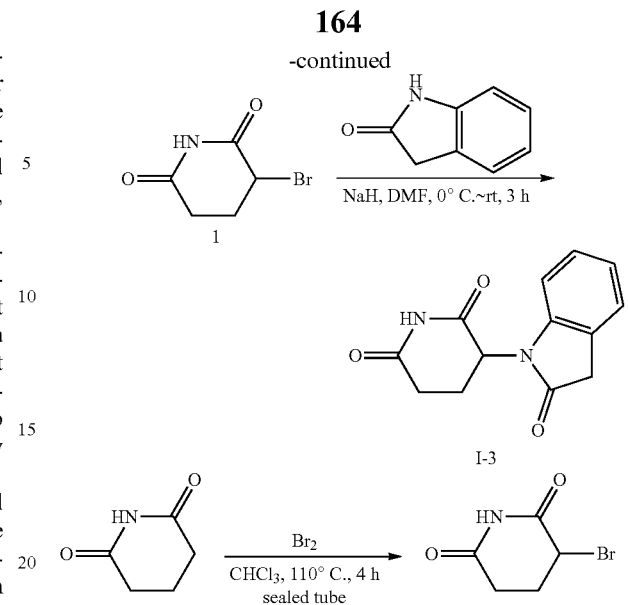

3-Bromopiperidine-2,6-dione

To a stirred solution of piperidine-2,6-dione (5 g, 44.20 mmol) in CHCl$_3$ (10 mL) was added Br$_2$ (2.25 mL) in one portion at room temperature under nitrogen atmosphere. The reaction mixture was sealed in a tube and stirred for 4 hours at 110° C. The resulting mixture was cooled to room temperature and concentrated under reduced pressure. The residue was purified by silica gel column chromatography, eluted with 50% ethyl acetate in petroleum ether to afford 3-bromopiperidine-2,6-dione as a pink solid (3.2 g, 38%): $^1$H NMR (300 MHz, DMSO-d$_6$) δ 11.05 (br s, 1H), 4.89 (dd, J=5.2, 3.9 Hz, 1H), 2.60 (dt, J=9.8, 4.7 Hz, 2H), 2.46 (ddd, J=9.6, 5.1, 3.9 Hz, 1H), 2.15 (dq, J=14.9, 4.9 Hz, 1H); LC/MS (ESI, m/z): [(M+1)]$^+$=192.1, 194.1.

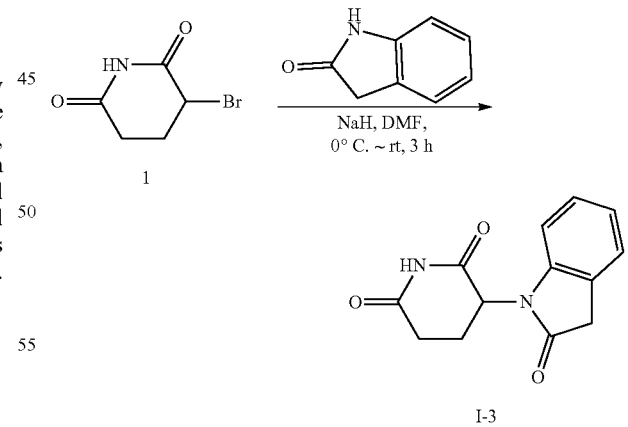

3-(2-Oxo-2,3-dihydro-1H-indol-1-yl)piperidine-2,6-dione

To a stirred solution of 2,3-dihydro-1H-indol-2-one (228 mg, 1.71 mmol) in DMF (2 mL) was added NaH (75.3 mg, 1.88 mmol, 60% w/w dispersed into mineral oil) at 0° C. under nitrogen atmosphere. The reaction mixture was stirred for 20 min at 0° C. To the above mixture was added dropwise a solution of 3-bromopiperidine-2,6-dione (164.4 mg, 0.86 mmol) in DMF (0.5 mL) at 0° C. The resulting mixture was stirred for additional 3 hours at room temperature. The resulting mixture was quenched with AcOH (0.5 mL) and was concentrated under reduced pressure. The residue was purified by prep-TLC, eluted with 50% ethyl acetate in petroleum ether to afford 3-(2-oxo-2,3-dihydro-1H-indol-1-yl)piperidine-2,6-dione, I-3, as a light yellow solid (14.2 mg, 4%): $^1$H NMR (400 MHz, DMSO-d$_6$) δ 10.55-10.43 (m, 1H), 7.33-7.11 (m, 1H), 7.01-6.90 (m, 2H), 6.84 (t, J=9.0 Hz, 1H), 4.09-3.94 (m, 1H), 2.67-2.59 (m, 1H), 2.47-2.36 (m, 1H), 2.02-1.72 (m, 1H), 1.62-1.35 (m, 1H); LC/MS (ESI, m/z): [(M+1)]$^+$=245.2.

Example 2. Synthesis of 3-(2oxobenzo[d]oxazol-3(2H)-yl)piperidine-2,6-dione, I-1

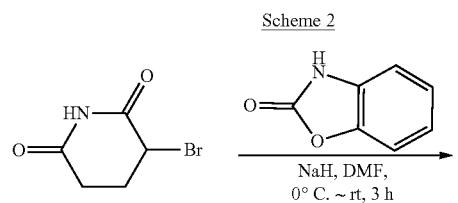

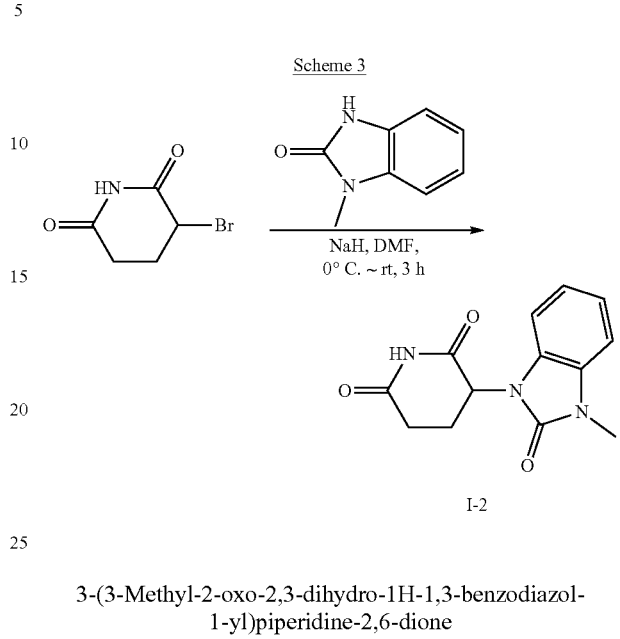

3-(2-oxobenzo[d]oxazol-3(2H)-yl)piperidine-2,6-dione

To a stirred solution of 2,3-dihydro-1,3-benzoxazol-2-one (210 mg, 1.55 mmol) in DMF (3 mL) was added NaH (68.3 mg, 1.71 mmol, 60% w/w dispersed into mineral oil) at 0° C. under nitrogen atmosphere. The reaction mixture was stirred for 20 min at 0° C. To the above mixture was added dropwise a solution of 3-bromopiperidine-2,6-dione (149.2 mg, 0.78 mmol) in DMF (0.5 mL) at 0° C. The resulting mixture was stirred for additional 3 hours at room temperature. The resulting mixture was quenched with AcOH (0.2 mL) and was concentrated under reduced pressure. The residue was purified by prep-TLC, eluted with 50% ethyl acetate in petroleum ether to afford 3-(2-oxo-2,3-dihydro-1,3-benzoxazol-3-yl)piperidine-2,6-dione, I-1, as a light yellow solid (30.2 mg, 8%): $^1$H NMR (400 MHz, DMSO-d$_6$) δ 11.23 (br s, 1H), 7.42-7.38 (m, 1H), 7.32-7.14 (m, 3H), 5.39 (dd, J=12.8, 5.2 Hz, 1H), 2.98-2.80 (m, 1H), 2.78-2.60 (m, 2H), 2.24-2.11 (m, 1H); LC/MS (ESI, m/z): [(M+1)]+= 247.1.

Example 3. Synthesis of 3-(3-Methyl-2-oxo-2,3-dihydro-1H-1,3-benzodiazol-1-yl)piperidine-2,6-dione, I-2

3-(3-Methyl-2-oxo-2,3-dihydro-1H-1,3-benzodiazol-1-yl)piperidine-2,6-dione

To a stirred solution of 1-methyl-2,3-dihydro-1H-1,3-benzodiazol-2-one (217 mg, 1.46 mmol) in DMF (2 mL) was added NaH (64.5 mg, 1.61 mmol, 60% w/w dispersed into mineral oil) at 0° C. under nitrogen atmosphere. The reaction mixture was stirred for 20 min at 0° C. To the above mixture was added dropwise a solution of 3-bromopiperidine-2,6-dione(140.6 mg, 0.73 mmol) in DMF (0.5 mL) at 0° C. The resulting mixture was stirred for additional 3 hours at room temperature. The resulting mixture was quenched with AcOH (0.5 mL) and was concentrated under reduced pressure. The crude product was purified by prep-HPLC with the following conditions: Column: XBridge Shield RP18 EVO Column, 5 um, 19×150 mm; Mobile Phase A: water (plus 0.05% FA), Mobile Phase B: ACN; Flow rate: 20 mL/min; Gradient: 10% B to 35% B in 7 min; Detector: UV 220 nm; Rt: 6.30 min. Desired fractions were collected and concentrated under reduced pressure. The residue was lyophilized to afford 3-(3-methyl-2-oxo-2,3-dihydro-1H-1,3-benzodiazol-1-yl)piperidine-2,6-dione, I-2, as a white solid (30.4 mg, 21%): $^1$H NMR (400 MHz, DMSO-d$_6$) δ 11.03 (br s, 1H), 7.13-6.97 (m, 4H), 5.30 (dd, J=12.7, 5.4 Hz, 1H), 3.35 (s, 3H), 2.90-2.78 (m, 1H), 2.73-2.49 (m, 2H), 2.03-1.90 (m, 1H); LC/MS (ESI, m/z): [(M+1)]$^+$=260.2.

Example 4. Synthesis of 3-(2-Oxo-4-phenylpyrrolidin-1-yl)piperidine-2,6-dione, I-29

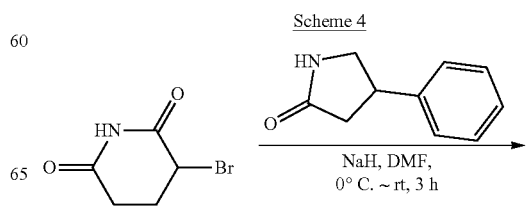

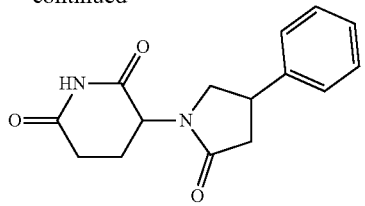

I-29

3-(2-Oxo-4-phenylpyrrolidin-1-yl)piperidine-2,6-dione

To a stirred solution of 4-phenylpyrrolidin-2-one (211 mg, 1.31 mmol) in DMF (2 mL) was added NaH (57.6 mg, 1.44 mmol, 60% w/w dispersed into mineral oil) at 0° C. under nitrogen atmosphere. The reaction mixture was stirred for 20 min at 0° C. To the above mixture was added dropwise a solution of 3-bromopiperidine-2,6-dione (125.7 mg, 0.65 mmol) in DMF (0.5 mL) at 0° C. The resulting mixture was stirred for additional 3 hours at room temperature. The resulting mixture was quenched with AcOH (0.5 mL) and concentrated under reduced pressure. The crude product was purified by prep-HPLC with the following conditions: Column: XBridge Shield RP18 EVO Column, 5 um, 19×150 mm; Mobile Phase A: water (plus 0.05% FA), Mobile Phase B: ACN; Flow rate: 20 mL/min; Gradient: 15% B to 45% B in 7 min; Detector: UV 220 nm; Rt: 5.72 min). Desired fractions were collected and concentrated under reduced pressure. The residue was lyophilized to afford 3-(2-oxo-4-phenylpyrrolidin-1-yl)piperidine-2,6-dione, I-29, as a white solid (29.4 mg, 9%): $^1$H NMR (400 MHz, DMSO-$d_6$) δ 10.94 (br s, 1H), 7.40-7.31 (m, 4H), 7.27 (dt, J=5.9, 2.8 Hz, 1H), 4.93-4.86 (m, 1H), 3.79-3.56 (m, 2H), 3.33-3.15 (m, 1H), 2.90-2.69 (m, 2H), 2.60-2.50 (m, 1H), 2.48-2.36 (m, 1H), 2.35-2.16 (m, 1H), 1.92-1.80 (m, 1H); LC/MS (ESI, m/z): [(M+1)]$^+$=273.2.

Example 5. Time-Resolved Fluorescence Resonance Energy Transfer (TR-FRET) Assay Equal volumes of His-tagged CRBN-DDB1 complex (56 nM) was mixed with Eu-cryptate labeled Anti-6HIS-monoclonal antibody (50× dilution from the commercial stock solution, Vender: Cisbio, Cat. #61HI2KLA) in a final buffer containing 20 mM HEPES pH 7.0, 150 mM NaCl, 0.005% Tween-20. The solution was then mixed with Cy5-labeled thalidomide (final 8 nM) and various concentrations of compounds (a serial 3-fold dilution with the top concentration 200 uM). The mixture were incubated at room temperature for 1 hour. FRET signals were measured on an EnVision plate reader (Perkin Elmer) by exciting at 340 nm and recording emission at both 615 nm as no FRET control and 665 nm as the FRET signals with a 60 microsecond delay. FRET efficiency was calculated as the ratio of fluorescent signals at 665 nM/615 nM. Quantitative loss of FRET efficiency as a function of compound concentrations was fitted by a four-parameter Logistic Function using GraphPad Prism 7.0 and the IC50 values were reported for each compound.

Table 2 shows the results for selected compounds in the time-resolved fluorescence resonance energy transfer (TR-FRET) assay. The compound numbers correspond to the compound numbers in Table 1. Compounds having an activity designated as "A" provided an IC$_{50}$ of <1 μM; compounds having an activity designated as "B" provided an IC$_{50}$ of 1-10 μM; compounds having an activity designated as "C" provided an IC$_{50}$ of 10-100 μM; and compounds having an activity designated as "D" provided an IC$_{50}$ of >100 μM. For reference, the known CRBN binders provided the following IC$_{50}$ values in the TR-FRET assay: thalidomide (IC$_{50}$=2.9 μM), lenalidomide (IC$_{50}$=1.17 μM) and pomalidomide (IC$_{50}$=1.28 μM).

TABLE 2

TR-FRET Assay Results

| Compound Number | CRBN HTRF IC$_{50}$ (μM) |
|---|---|
| I-1 | A |
| I-2 | A |
| I-3 | C |
| I-29 | B |
| I-61 | B |
| I-62 | A |
| I-63 | A |
| I-64 | A |
| I-65 | A |
| I-66 | A |
| I-67 | A |
| I-68 | A |
| I-69 | A |
| I-70 | B |
| I-71 | A |
| I-72 | A |
| I-73 | C |
| I-74 | A |
| I-75 | A |
| I-76 | A |
| I-77 | A |
| I-78 | A |
| I-79 | A |
| I-80 | A |
| I-81 | A |
| I-82 | A |
| I-83 | A |
| I-84 | A |
| I-85 | A |
| I-86 | A |
| I-90 | D |

Example 6. Fluorescence Polarization (FP) Assay

Untagged CRBN-DDB1 complex (final 50 nM) was mixed with Cy5-labeled thalidomide (final 20 nM) and various concentrations of compounds (a serial 3-fold dilution with the top concentration of 200 uM). The final solution contained 50 mM HEPES, 200 mM NaCl and 2 mM DTT, pH 7.5. The mixtures were incubated at room temperature for 10 min. The FP signals were recorded on an EnVision plate reader (Perkin Elmer) using the following settings: Excitation Light (%): 100; Measurement Height: 12; G-Factor: 1; Detector Gain 1: 500; Detector Gain 2: 500; Flash Number: 100. Dose-dependent loss of FP signals was fitted by four-parameter Logistic Function using GraphPad Prism 7.0 and the IC50 values were reported for each compound.

Table 3 shows the results for selected compounds in the fluorescence polarization (FP) assay. The compound numbers correspond to the compound numbers in Table 1. Compounds having an activity designated as "A" provided an IC$_{50}$ of <1 μM; compounds having an activity designated as "B" provided an IC$_{50}$ of 1-10 μM; compounds having an activity designated as "C" provided an IC$_{50}$ of 10-100 μM; and compounds having an activity designated as "D" provided an IC$_{50}$ of >100 μM. For reference, the known CRBN binders provided the following IC$_{50}$ values in the FP assay: thalidomide (IC$_{50}$=2.4 μM) and pomalidomide (IC$_{50}$=1.15 μM).

TABLE 3

Fluorescence Polarization (FP) Assay Results

| Compound Number | CRBN FP IC$_{50}$ (μM) |
|---|---|
| I-1 | A |
| I-2 | A |
| I-3 | D |
| I-29 | C |

Example 7. Synthesis of 3-(5-((dimethylamino)methyl)-3-methyl-2-oxo-2,3-dihydro-1H-benzo[d]imidazol-1-yl)piperidine-2,6-dione (I-61)

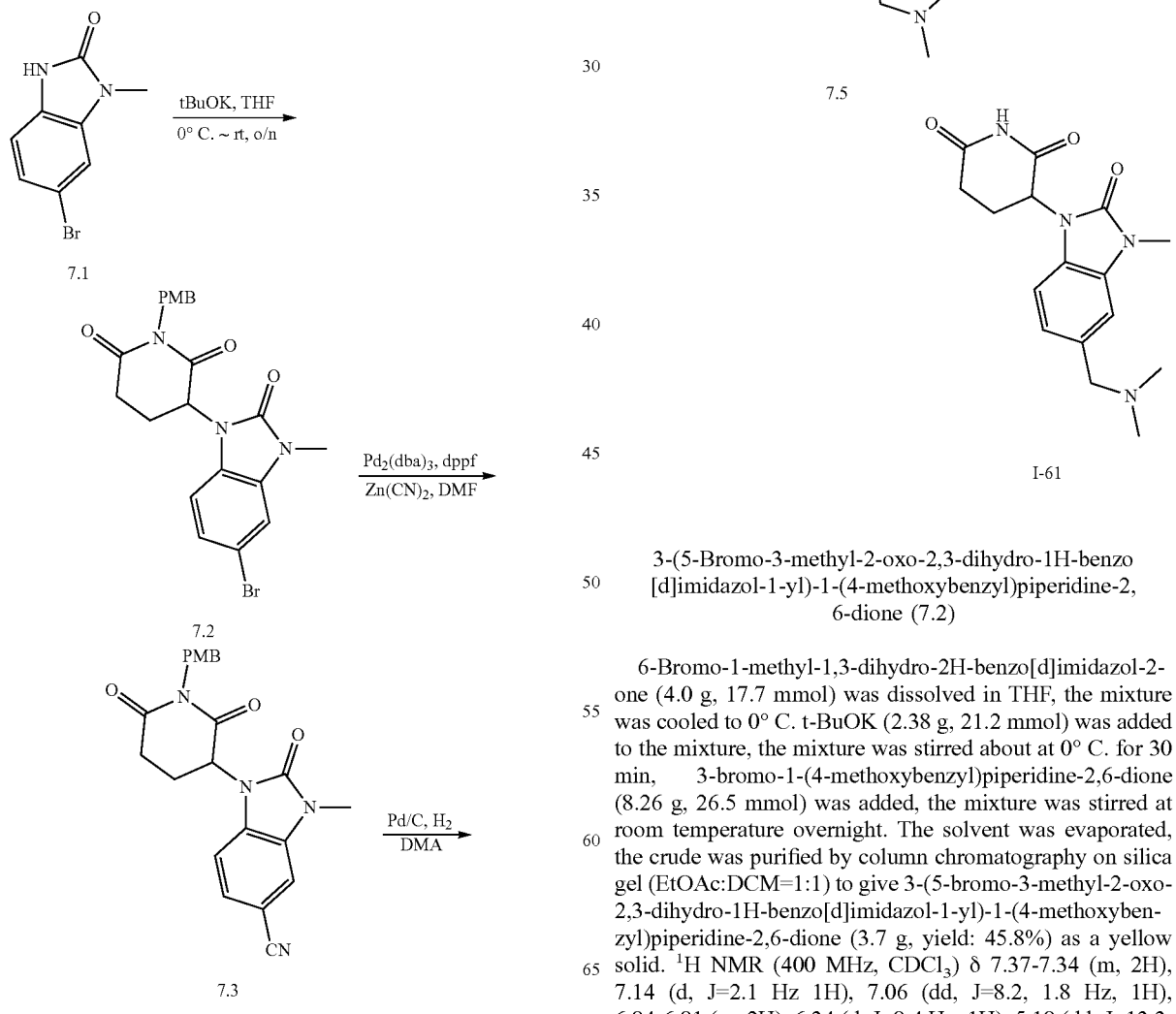

3-(5-Bromo-3-methyl-2-oxo-2,3-dihydro-1H-benzo[d]imidazol-1-yl)-1-(4-methoxybenzyl)piperidine-2,6-dione (7.2)

6-Bromo-1-methyl-1,3-dihydro-2H-benzo[d]imidazol-2-one (4.0 g, 17.7 mmol) was dissolved in THF, the mixture was cooled to 0° C. t-BuOK (2.38 g, 21.2 mmol) was added to the mixture, the mixture was stirred about at 0° C. for 30 min, 3-bromo-1-(4-methoxybenzyl)piperidine-2,6-dione (8.26 g, 26.5 mmol) was added, the mixture was stirred at room temperature overnight. The solvent was evaporated, the crude was purified by column chromatography on silica gel (EtOAc:DCM=1:1) to give 3-(5-bromo-3-methyl-2-oxo-2,3-dihydro-1H-benzo[d]imidazol-1-yl)-1-(4-methoxybenzyl)piperidine-2,6-dione (3.7 g, yield: 45.8%) as a yellow solid. $^1$H NMR (400 MHz, CDCl$_3$) δ 7.37-7.34 (m, 2H), 7.14 (d, J=2.1 Hz 1H), 7.06 (dd, J=8.2, 1.8 Hz, 1H), 6.84-6.81 (m, 2H), 6.34 (d, J=8.4 Hz, 1H), 5.18 (dd, J=13.3, 5.5 Hz, 1H), 4.96 (s, 2H), 3.80 (s, 3H), 3.41 (s, 3H), 3.01 (ddd, J=17.5, 4.4, 2.6 Hz, 1H), 2.87-2.78 (m, 1H), 2.56 (ddd, J=26.8, 13.4, 4.5 Hz, 1H), 2.20-2.14 (m, 1H); LC/MS (ESI, m/z): [M+1]+=458.3.

1-(1-(4-Methoxybenzyl)-2,6-dioxopiperidin-3-yl)-3-methyl-2-oxo-2,3-dihydro-1H-benzo[d]imidazole-5-carbonitrile (7.3)

A mixture of 3-(5-bromo-3-methyl-2-oxo-2,3-dihydro-1H-benzo[d]imidazol-1-yl)-1-(4-methoxybenzyl)piperidine-2,6-dione (2.4 g, 5.25 mmol), Zinc cyanide (2.5 g, 21.0 mmol), Tris(dibenzylideneacetone)dipalladium (0.48 g, 0.53 mmol) and 1,1'-Ferrocenebis(diphenylphosphine) (0.58 g, 1.05 mmol) in DMF (40 mL) was heated to 120° C. in sealed tube under nitrogen atmosphere and stirred at 120° C. for 19 hours. The reaction mixture was cooled to room temperature, diluted with water and filtered. The crude solid was washed with water and purified by silica gel column chromatography (DCM: CH$_3$CN=1:1) to give target compound (1.5 g, 70.8%) as a yellow solid. $^1$H NMR (400 MHz, CDCl$_3$) δ 7.36-7.33 (m, 2H), 7.28-7.25 (m, 2H), 6.85-6.81 (m, 2H), 6.52 (d, J=8.0 Hz, 1H), 5.21 (dd, J=13.2, 5.4 Hz, 1H), 4.96 (s, 2H), 3.80 (s, 3H), 3.46 (s, 3H), 3.04 (ddd, J=17.6, 4.4, 2.6 Hz, 1H), 2.89-2.80 (m, 1H), 2.57 (ddd, J=26.9, 13.4, 4.4 Hz, 1H), 2.24-2.17 (m, 1H); LC/MS (ESI, m/z): [M+1]f=405.3.

3-(5-(Aminomethyl)-3-methyl-2-oxo-2,3-dihydro-1H-benzo[d]imidazol-1-yl)-1-(4-methoxybenzyl)piperidine-2,6-dione (7.4)

A mixture of 1-(1-(4-methoxybenzyl)-2,6-dioxopiperidin-3-yl)-3-methyl-2-oxo-2,3-dihydro-1H-benzo[d]imidazole-5-carbonitrile (1.5 g, 3.7 mmol), 10 percent Pd—C (0.15 g) and 4N HCl (5.0 mL) in Dimethylacetamide (20 mL) was hydrogenated at 70° C. overnight. The crude reaction mixture was filtered through Celite, and the catalyst washed with water. The combined filtrate was concentrated in vacuo and purified via reverse phase column chromatography (CH$_3$CN/H$_2$O=5%-80%) to give 3-(5-(aminomethyl)-3-methyl-2-oxo-2,3-dihydro-1H-benzo[d]imidazol-1-yl)-1-(4-methoxybenzyl)piperidine-2,6-dione hydrochloride (0.95 g, 62.9%) as a white solid. $^1$H NMR (400 MHz, DMSO-d$_6$) δ 8.06 (br s, 3H), 7.30 (s, 1H), 7.22-7.18 (m, 2H), 7.12-7.07 (m, 2H), 6.87-6.84 (m, 2H), 5.55 (dd, J=13.2, 5.4 Hz, 1H), 4.78 (dd, J=32.9, 14.4 Hz, 2H), 4.08-4.03 (m, 2H), 3.73 (s, 3H), 3.36 (s, 3H), 3.12-3.03 (m, 1H), 2.86-2.70 (m, 2H), 2.10-2.03 (m, 1H); LC/MS (ESI, m/z): [M+1]f=409.3.

3-(5-((Dimethylamino)methyl)-3-methyl-2-oxo-2,3-dihydro-1H-benzo[d]imidazol-1-yl)-1-(4-methoxybenzyl)piperidine-2,6-dione (7.5)

To a mixture of 3-(5-(aminomethyl)-3-methyl-2-oxo-2,3-dihydro-1H-benzo[d]imidazol-1-yl)-1-(4-methoxybenzyl)piperidine-2,6-dione (250 mg, 0.613 mol) and paraformaldehyde (184 mg, 6.13 mmol) in THF (5 mL) was added AcOH (5 drops). The mixture was stirred at room temperature for 1 h, then NaCNBH$_3$ (116 mg, 1.839 mmol) was added into the mixture. The resulting mixture was warmed to 40° C. and stirred overnight. The reaction mixture was cooled to room temperature and concentrated in vacuo, the residue was purified by prep-HPLC eluting with CH$_3$CN/H$_2$O to get the title compound 50 mg as a white solid. (yield: 18.7%); LC/MS (ESI, m/z): [M+1]+=437.32.

3-(5-((Dimethylamino)methyl)-3-methyl-2-oxo-2,3-dihydro-1H-benzo[d]imidazol-1-yl)piperidine-2,6-dione (I-61)

To a solution of 3-(5-((dimethylamino)methyl)-3-methyl-2-oxo-2,3-dihydro-1H-benzo[d]imidazol-1-yl)-1-(4-methoxybenzyl)piperidine-2,6-dione (72 mg, 0.165 mmol) in toluene (5 mL) was added methanesulfonic acid (1 mL). The reaction mixture was warmed to 110° C. and stirred for 3 h. Then the mixture was cooled to room temperature and concentrated in vacuo, the residue was poured into ice water, basified with 1 M NaHCO$_3$ to pH=8-10, then extracted with EtOAc (3*20 mL), the combined organic layers were concentrated in vacuo. The residue was purified by prep HPLC to get the title compound 2 mg as a white solid. (yield: 3.8%). $^1$H NMR (400 MHz, DMSO-d$_6$) δ 11.13 (s, 1H), 9.66 (s, 1H), 7.31 (s, 1H), 7.23 (d, J=8.0 Hz, 1H), 7.17 (d, J=8.0 Hz, 1H), 5.41 (dd, J=12.7, 5.3 Hz, 1H), 4.29 (br. s., 2H), 3.36 (s, 3H), 2.86-2.96 (m, 1H), 2.71-2.77 (m, 6H), 2.60-2.71 (m, 2H), 1.98-2.09 (m, 1H); LC/MS (ESI, m/z): [M+1]+=317.1.

Example 8. Synthesis of N-(1-(2,6-dioxopiperidin-3-yl)-3-methyl-2-oxo-2,3-dihydro-1H-benzo[d]imidazol-5-yl)acetamide (I-62)

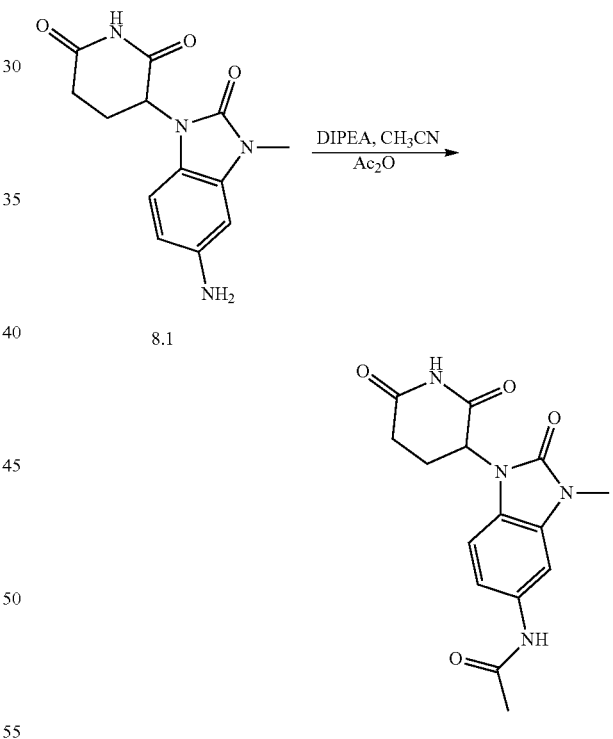

A suspension of 3-(5-amino-3-methyl-2-oxo-2,3-dihydro-1H-benzo[d]imidazol-1-yl)piperidine-2,6-dione (0.073 mmol, 20 mg) in 5 mL CH$_3$CN was added Ac$_2$O (3 drops) and DIPEA (10 drops) was stirred at room temperature for 6 h. LC-MS showed complete consumption of the starting material. The reaction mixture concentrated to give crude product which was purified by prep-HPLC to give desired compound N-(1-(2,6-dioxopiperidin-3-yl)-3-methyl-2-oxo-2,3-dihydro-1H-benzo[d]imidazol-5-yl)acetamide (12.5 mg, yield 54%) as white solid. $^1$H NMR (400 MHz, DMSO-d$_6$)

δ 11.08 (s, 1H), 9.91 (s, 1H), 7.54 (d, J=1.8 Hz, 1H), 7.09 (dd, J=8.4, 1.8 Hz, 1H), 7.02 (d, J=8.5 Hz, 1H), 5.33 (dd, J=12.9, 5.3 Hz, 1H), 3.30 (s, 3H), 2.96-2.84 (m, 1H), 2.75-2.56 (m, 2H), 2.03 (s, 3H), 2.02-1.98 (m, 1H); LC/MS (ESI, m/z): [M+1]$^+$=317.0.

Example 9. Synthesis of 3-(3,5-dimethyl-2-oxo-2,3-dihydro-1H-benzo[d]imidazol-1-yl)piperidine-2,6-dione (I-63)

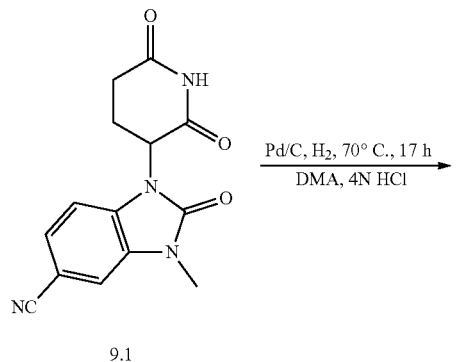

9.1

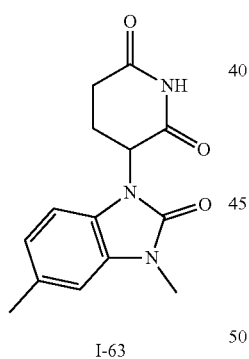

I-63

A mixture of 1-(2,6-dioxopiperidin-3-yl)-3-methyl-2-oxo-2,3-dihydro-1H-benzo[d]imidazole-5-carbonitrile (50 mg, 0.18 mmol), 10 percent Pd—C (10 mg) and 4 N HCl (0.1 mL) in dimethylacetamide (4 mL) was hydrogenated at 70° C. overnight. The crude reaction mixture was filtered through Celite, and the catalyst washed with water. The combined filtrate was concentrated in vacuo and purified via reverse phase column chromatography (CH$_3$CN/H$_2$O=5%-80%) to give the desired compound (13.0 mg, 27.1%) as a white solid. $^1$H NMR (400 MHz, DMSO-d$_6$) δ 11.07 (s, 1H), 7.07-6.92 (m, 2H), 6.85 (d, J=7.9 Hz, 1H), 5.40-5.23 (m, 1H), 3.31 (s, 3H), 2.98-2.81 (m, 1H), 2.77-2.55 (m, 2H), 2.35 (s, 3H), 2.03-1.93 (m, 1H); LC/MS (ESI, m/z): [M+1]+= 274.0.

Example 10. Synthesis of 1-(2,6-dioxopiperidin-3-yl)-3-methyl-2-oxo-2,3-dihydro-1H-benzo[d]imidazole-5-carbonitrile (I-64)

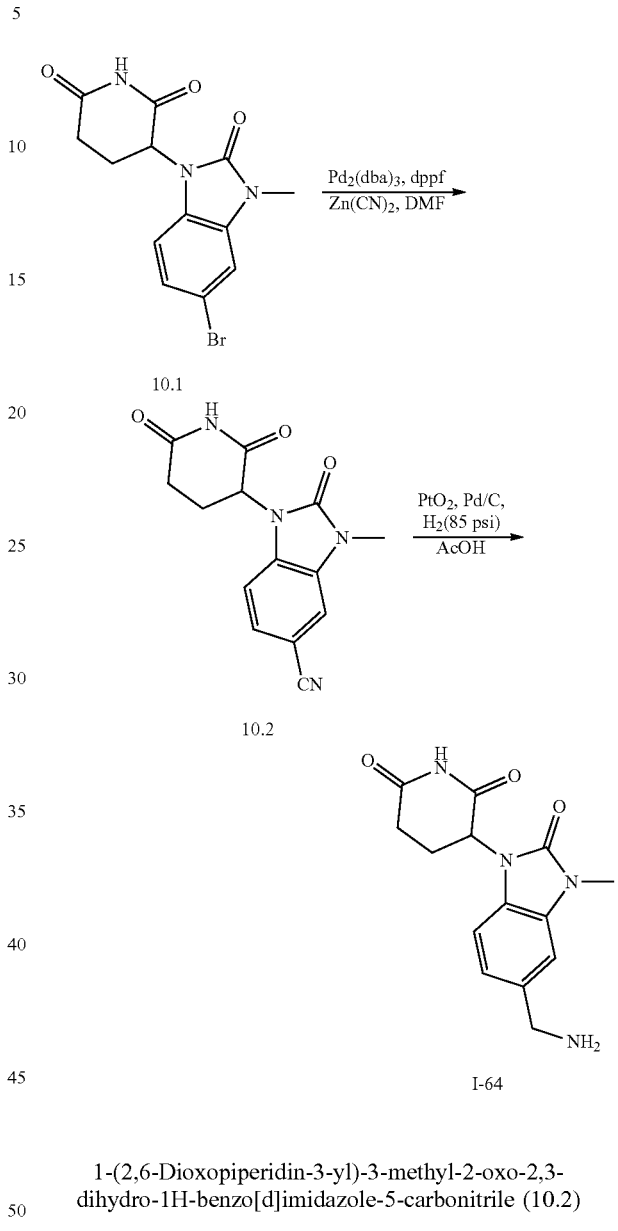

I-64

1-(2,6-Dioxopiperidin-3-yl)-3-methyl-2-oxo-2,3-dihydro-1H-benzo[d]imidazole-5-carbonitrile (10.2)

A mixture of 3-(5-bromo-3-methyl-2-oxo-2,3-dihydro-1H-benzo[d]imidazol-1-yl)piperidine-2,6-dione (5 g, 14.8 mmol), zinc cyanide (6.9 g, 59.2 mmol), tris(dibenzylideneacetone)dipalladium (1.4 g, 1.5 mmol) and 1,1'-Ferrocenebis(diphenylphosphine) (1.6 g, 3.0 mmol) in DMF (100 mL) was heated to 120° C. under nitrogen atmosphere in sealed tube and stirred at this temperature for 19 hours. The reaction mixture was cooled to room temperature, filtered and concentrated in vacuo. The residue was purified by silica gel column chromatography (EA/DCM=2/1) to give product (3 g, 71.4%) as a white solid. $^1$H NMR (400 MHz, DMSO-d$_6$) δ 11.16 (s, 1H), 7.75 (d, J=1.50 Hz, 1H), 7.55 (dd, J=8.25, 1.50 Hz, 1H), 7.34 (d, J=8.25 Hz, 1H), 5.46 (dd, J=12.76, 5.38 Hz, 1H), 3.38 (s, 3H), 2.94-2.83 (m, 1H), 2.78-2.59 (m, 2H), 2.09-2.01 (m, 1H); LC/MS (ESI, m/z): [M+1]$^+$=284.9.

3-(5-(Aminomethyl)-3-methyl-2-oxo-2,3-dihydro-1H-benzo[d]imidazol-1-yl)piperidine-2,6-dione (I-64)

To a solution of 1-(2,6-dioxopiperidin-3-yl)-3-methyl-2-oxo-2,3-dihydro-1H-benzo[d]imidazole-5-carbonitrile (2.3 g, 8.1 mmol) in AcOH (20 mL) was added PtO$_2$ (98.8 mg, 0.41 mmol) and 10 wt. % palladium on activated carbon (850 mg, 0.81 mmol). The mixture was hydrogenated for 1 h at 85 psi at room temperature. The catalyst is filtered off, the filtrate is concentrated and dried to get the title compound 2.8 g crude as a salt with AcOH. (yield: quant.) H NMR (400 MHz, DMSO-d$_6$) δ 7.24 (s, 1H), 7.10-7.01 (m, 2H), 5.36 (dd, J=12.76, 5.38 Hz, 1H), 3.84 (br s, 2H), 3.33 (s, 3H), 2.96-2.83 (m, 1H), 2.78-2.57 (m, 2H), 2.05-1.97 (m, 1H), 1.85 (br s, 6H); LC/MS (ESI, m/z): [M−NH2]$^+$= 272.17.

Example 11. Synthesis of 3-(5-Amino-3-methyl-2-oxo-2,3-dihydro-1H-1,3-benzodiazol-1-yl)piperidine-2,6-dione Hydrochloride (I-65)

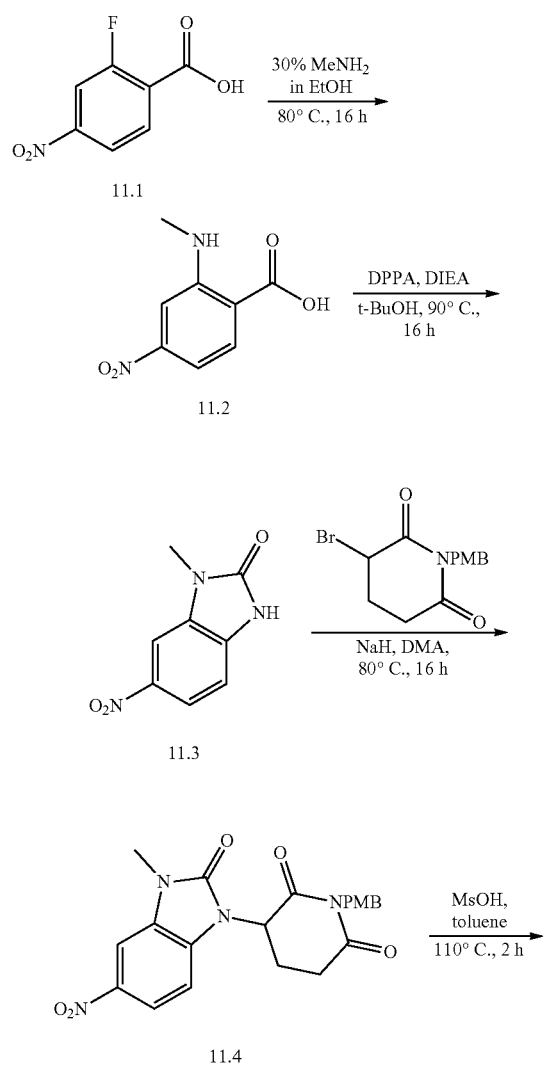

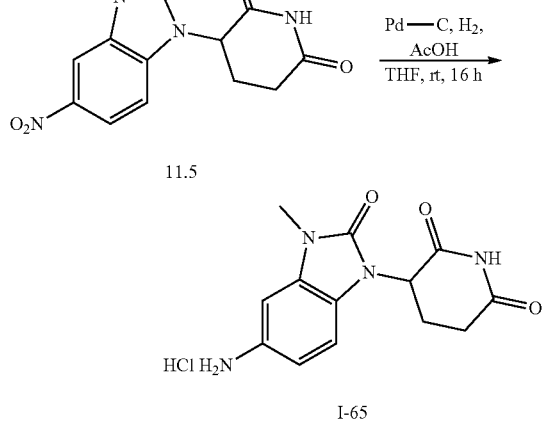

2-(Methylamino)$_{0-4}$-nitrobenzoic Acid (11.2)

A reaction solution of 2-fluoro-4-nitrobenzoic acid (80 g, 432.175 mmol) in a solution of CH$_3$NH2 in EtOH (300 mL) was sealed and was stirred for overnight at 80° C. The mixture was allowed to cool down to room temperature and diluted with water (500 mL). The solution was acidified to pH 6 with aq. HCl (2 M). The resulting mixture was filtered. The filter cake was washed with water (3×50 mL). The filter cake was dried under reduced pressure to afford 2-(methylamino)$_{0-4}$-nitrobenzoic acid (76.8 g, 91%) as an orange solid: $^1$H NMR (400 MHz, DMSO-d$_6$) δ 13.36 (br s, 1H), 8.01 (d, J=8.6 Hz, 1H), 7.39 (d, J=2.3 Hz, 1H), 7.32 (dd, J=8.6, 2.3 Hz, 1H), 2.93 (s, 3H); LC/MS (ESI, m/z): [M+1]=197.15.

1-Methyl-6-nitro-2,3-dihydro-1H-1,3-benzodiazol-2-one (11.3)

To a stirred solution of 2-(methylamino)$_{0-4}$-nitrobenzoic acid (8 g, 40.783 mmol) and DIPEA (15.81 g, 122.348 mmol) in t-BuOH (200 mL) was added DPPA (13.47 g, 48.939 mmol) at room temperature under nitrogen atmosphere. The resulting mixture was stirred for 16 h at 90° C. under nitrogen atmosphere. The reaction was monitored by LCMS. The resulting mixture was cooled and concentrated under reduced pressure. The residue was diluted with water (300 mL). The resulting mixture was filtered. The filter cake was washed with water (3×50 mL) and was purified by reverse flash chromatography with the following conditions (column, C18 silica gel; mobile phase, ACN in water, 15% to 40% gradient in 25 min; detector, UV 254 nm) to afford 1-methyl-6-nitro-2,3-dihydro-1H-1,3-benzodiazol-2-one (2.6 g, 32%) as a light yellow solid: 1H NMR (400 MHz, DMSO-d$_6$) δ 11.62 (s, 1H), 7.97 (s, 1H), 7.95 (d, J=8.0 Hz, 1H), 7.12 (d, J=8.0 Hz, 1H), 3.36 (s, 3H); LC/MS (ESI, m/z): [M+1]f=194.15.

1-[(4-Methoxyphenyl)methyl]-3-(3-methyl-5-nitro-2-oxo-2,3-dihydro-1H-1,3-benzodiazol-1-yl)piperidine-2,6-dione (11.4)

To a solution of 1-methyl-6-nitro-2,3-dihydro-1H-1,3-benzodiazol-2-one (5.5 g, 28.474 mmol) in DMF (80 mL) was added sodium hydride (60% in oil, 2.05 g, 51.252 mmol) at 0° C. The mixture was stirred for 15 min. A solution of 3-bromo-1-[(4-methoxyphenyl)methyl]piperidine-2,6-dione (6.84 g, 21.925 mmol) in DMF (50 mL) was added and the mixture was allowed to warm to room temperature and stirred for 16 h. The reaction was monitored by LCMS. The mixture was acidified to pH 6 with acetic acid. The resulting mixture was diluted with water (600 mL) and extracted with EtOAc (3×150 mL). The combined organic layers was washed with brine (200 mL), dried over anhydrous Na₂SO₄. After filtration, the filtrate was concentrated under reduced pressure. The residue was purified by silica gel column chromatography, eluted with Petroleum ether/EtOAc (2:1) to afford crude product, which was purified by reverse phase flash chromatography with the following conditions: Column: WelFlash™ C18-I, 20-40 μm, 330 g; Eluent A: Water (plus 10 mmol/L FA); Eluent B: ACN; Gradient: 40%-60% B in 25 min; Flow rate: 80 mL/min; Detector: 220/254 nm; desired fractions were collected at 54% B and concentrated under reduced pressure to afford the product. 1-[(4-methoxyphenyl)methyl]-3-(3-methyl-5-nitro-2-oxo-2,3-dihydro-1H-1,3-benzodiazol-1-yl)piperidine-2,6-dione (2.5 g, 21%) as a light yellow solid: ¹H NMR (400 MHz, DMSO-d₆) δ 8.14 (d, J=2.2 Hz, 1H), 8.03 (dd, J=8.7, 2.3 Hz, 1H), 7.30 (d, J=8.7 Hz, 1H), 7.25-7.18 (m, 2H), 6.92-6.81 (m, 2H), 5.69 (dd, J=12.9, 5.4 Hz, 1H), 4.81 (q, J=14.4 Hz, 2H), 3.73 (s, 3H), 3.46 (s, 3H), 3.07 (ddd, J=17.7, 13.6, 5.2 Hz, 1H), 2.92-2.70 (m, 2H), 2.14 (ddd, J=12.6, 5.6, 3.3 Hz, 1H); LC/MS (ESI, m/z): [M+1]*=425.25.

3-(3-Methyl-5-nitro-2-oxo-2,3-dihydro-1H-1,3-benzodiazol-1-yl)piperidine-2,6-dione (11.5)

To a stirred mixture of 1-[(4-methoxyphenyl)methyl]-3-(3-methyl-5-nitro-2-oxo-2,3-dihydro-1H-1,3-benzodiazol-1-yl)piperidine-2,6-dione (5 g, 11.781 mmol) in toluene (25 mL) was added methanesulfonic acid (25 mL) at room temperature under nitrogen atmosphere. The resulting mixture was stirred for 2 h at 110° C. under nitrogen atmosphere. The mixture was allowed to cool down to room temperature. The resulting mixture was concentrated under reduced pressure. The resulting solution was diluted with ice-water (300 mL). The precipitated solids were collected by filtration, washed with water (3×20 mL) and purified by reverse phase flash chromatography with the following conditions: Column: WelFlash™ C18-I, 20-40 μm, 330 g; Eluent A: water (plus 10 mmol/L FA); Eluent B: ACN; Gradient: 40%-70% B in 30 min; Flow rate: 80 mL/min; Detector: 220/254 nm; desired fractions were collected at 58% B and concentrated under reduced pressure to afford 3-(3-methyl-5-nitro-2-oxo-2,3-dihydro-1H-1,3-benzodiazol-1-yl)piperidine-2,6-dione (1.7 g, 46%) as a light brown solid: ¹H NMR (400 MHz, DMSO-d₆) δ 11.22 (s, 1H), 8.15 (d, J=2.2 Hz, 1H), 8.07 (d, J=8.5 Hz, 1H), 7.39 (d, J=8.7 Hz, 1H), 5.53 (dd, J=12.9, 5.4 Hz, 1H), 3.46 (s, 3H), 2.95-2.80 (m, 1H), 2.75 (td, J=12.9, 4.2 Hz, 1H), 2.66 (d, J=18.3 Hz, 1H), 2.09 (dq, J=8.6, 4.8 Hz, 1H); LC/MS (ESI, m/z): [M+1]f=305.25.

3-(5-Amino-3-methyl-2-oxo-2,3-dihydro-1H-1,3-benzodiazol-1-yl)piperidine-2,6-dione Hydrochloride (I-65)

To a solution of 3-(3-methyl-5-nitro-2-oxo-2,3-dihydro-1H-1,3-benzodiazol-1-yl)piperidine-2,6-dione (1.4 g, 4.601 mmol) in AcOH (200 mL) was added palladium on charcoal (200 mg, 10% w/w) under nitrogen atmosphere. The mixture was hydrogenated at room temperature for 4 h under hydrogen atmosphere using a hydrogen balloon. After the reaction was completed, it was filtered through a Celite pad and concentrated under reduced pressure. The residue was purified by reverse phase flash chromatography with the following conditions: Column: WelFlash™ C18-I, 20-40 μm, 330 g; Eluent A: water (plus 10 mmol/L NH₄HCO₃); Eluent B: ACN; Gradient: 10%-30% B in 20 min; Flow rate: 80 mL/min; Detector: 220/254 nm; desired fractions were collected at 15% B, acidified to pH 3 with aq. HCl (1 M) and concentrated under reduced pressure to afford 3-(5-amino-3-methyl-2-oxo-2,3-dihydro-1H-1,3-benzodiazol-1-yl)piperidine-2,6-dione hydrochloride (269.9 mg, 19%) as a white solid: ¹H NMR (400 MHz, Methanol-d₄) δ 7.31-7.26 (m, 2H), 7.19 (dd, J=8.3, 2.1 Hz, 1H), 5.41 (dd, J=12.9, 5.4 Hz, 1H), 3.49 (s, 3H), 2.99 (ddd, J=18.4, 13.7, 5.3 Hz, 1H), 2.91-2.74 (m, 2H), 2.30-2.20 (m, 1H); LC/MS (ESI, m/z): [M+1]⁺=275.05.

Example 12. Synthesis of N-((1-(2,6-dioxopiperidin-3-yl)-3-methyl-2-oxo-2,3-dihydro-1H-benzo[d]imidazol-5-yl)methyl)acetamide (I-66)

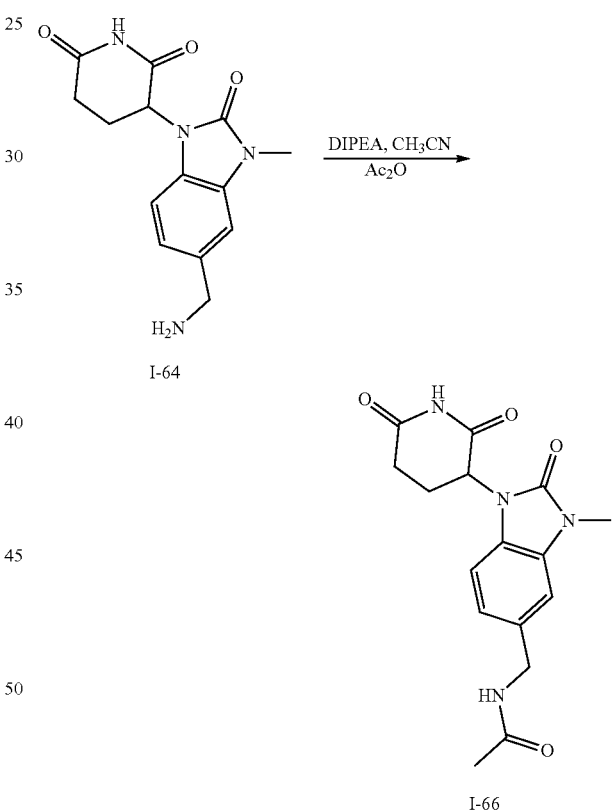

To a solution of 3-(5-(aminomethyl)-3-methyl-2-oxo-2,3-dihydro-1H-benzo[d]imidazol-1-yl)piperidine-2,6-dione (100 mg, 0.35 mmol) in CH₃CN (4 mL) was added DIPEA (3 eq) and Ac₂O (2 eq), the reaction mixture was stirred at room temperature for 6 h. The solvent was removed and the residue was purified by prep-HPLC to give the product N-((1-(2,6-dioxopiperidin-3-yl)-3-methyl-2-oxo-2,3-dihydro-1H-benzo[d]imidazol-5-yl)methyl)acetamide (25 mg, yield 22%). ¹H NMR (400 MHz, DMSO-d₆) δ 11.08 (s, 1H), 8.29 (t, J=5.5 Hz, 1H), 7.07-7.04 (m, 2H), 6.94 (d, J=7.9 Hz, 1H), 5.35 (dd, J=1.27, 5.4 Hz, 1H), 4.26 (d, J=5.8 Hz, 2H), 3.33 (s, 3H), 2.91-2.86 (m, 1H), 2.72-2.60 (m, 2H), 2.01-1.97 (m, 1H), 1.86 (s, 3H); LC/MS (ESI, m/z): [M+1]+=331.1.

Example 13. Synthesis of 1-(1-(2,6-dioxopiperidin-3-yl)-3-methyl-2-oxo-2,3-dihydro-1H-benzo[d]imidazol-5-yl)-3-ethylurea (I-67)

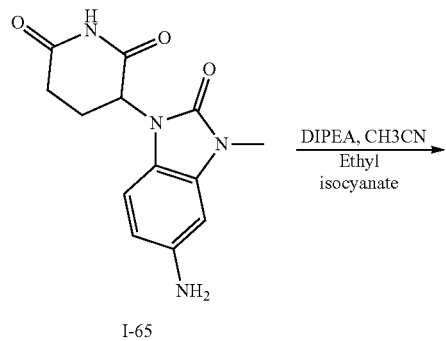

I-65

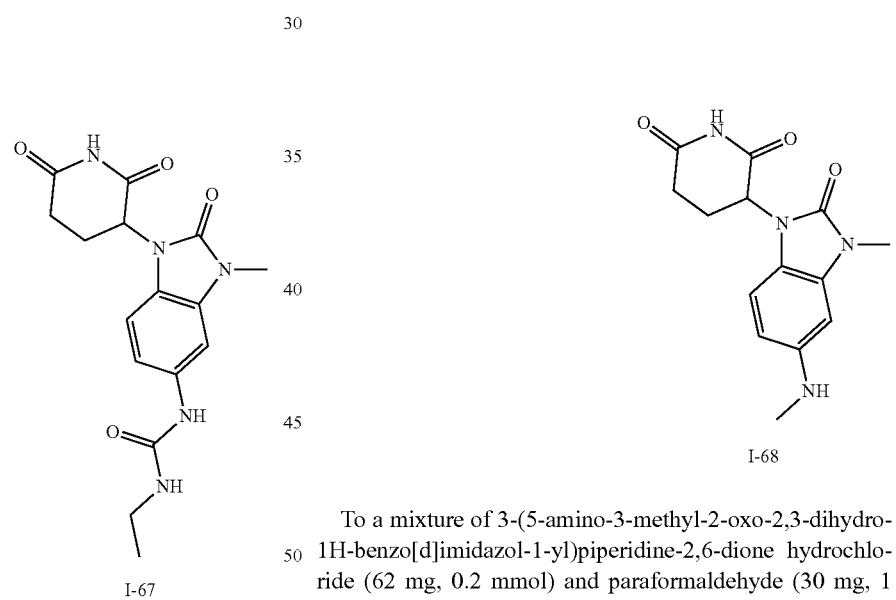

I-67

A suspension of 3-(5-amino-3-methyl-2-oxo-2,3-dihydro-1H-benzo[d]imidazol-1-yl)piperidine-2,6-dione (0.073 mmol, 20 mg) in 5 mL CH₃CN was added Ethyl isocyanate (3 drops) and DIPEA (10 drops) was stirred at room temperature for 6 h. LC-MS showed complete consumption of the starting material. The reaction mixture was concentrated to give crude product which was purified by Prep-HPLC to give desired compound (2.7 mg) as white solid as white solid. (yield, 11%). $^1$H NMR (400 MHz, DMSO-d₆) δ 11.07 (s, 1H), 8.35 (s, 1H), 7.40 (d, J=2.0 Hz, 1H), 7.02-6.79 (m, 2H), 6.03 (t, J=5.6 Hz, 1H), 5.30 (dd, J=12.8, 5.4 Hz, 1H), 3.28 (s, 3H), 3.10 (qd, J=7.2, 5.5 Hz, 2H), 2.96-2.84 (m, 1H), 2.72-2.57 (m, 2H), 2.08-1.94 (m, 1H), 1.05 (t, J=7.2 Hz, 3H); LC/MS (ESI, m/z): [M+1]+=346.0.

Example 14. Synthesis of 3-(3-methyl-5-(methylamino)-2-oxo-2,3-dihydro-1H-benzo[d]imidazol-1-yl)piperidine-2,6-dione (I-68)

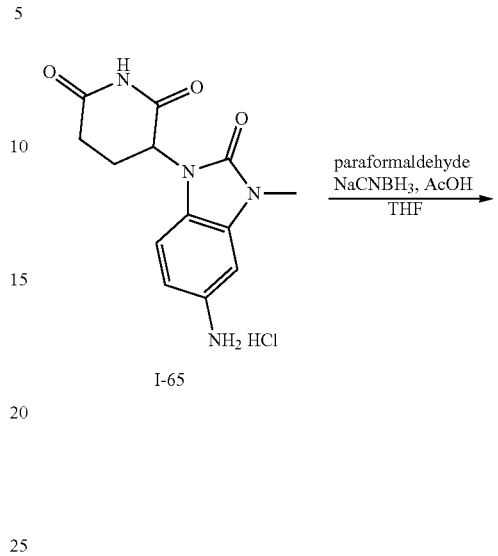

To a mixture of 3-(5-amino-3-methyl-2-oxo-2,3-dihydro-1H-benzo[d]imidazol-1-yl)piperidine-2,6-dione hydrochloride (62 mg, 0.2 mmol) and paraformaldehyde (30 mg, 1 mmol) in THF (5 mL) was added AcOH (3 drops). The mixture was stirred at room temperature for 1 h, then NaCNBH₃ (30 mg, 0.48 mmol) was added into the mixture. The resulting mixture was warmed to 40° C. and stirred for 2 h. The reaction mixture was poured into water, extracted with EtOAc (3*20 mL), the combined organic layers were concentrated in vacuo, the residue was purified by prep-HPLC eluting with CH₃CN/H₂O to get the title compound 13.7 mg as a white solid. (yield: 22.6%). $^1$H NMR (400 MHz, DMSO-d₆) δ11.12 (s, 1H), 8.96 (br. s., 1H), 7.25 (d, J=1.88 Hz, 1H), 7.15 (d, J=8.38 Hz, 1H), 7.07 (dd, J=8.38, 1.94 Hz, 1H), 5.39 (dd, J=12.76, 5.38 Hz, 1H), 3.36 (s, 3H), 2.96-2.85 (m, 1H), 2.83 (s, 3H), 2.77-2.59 (m, 2H), 2.07-1.99 (m, 1H); LC/MS (ESI, m/z): [M+1]+=289.1.

Example 15. Synthesis of 3-(5-(dimethylamino)-3-methyl-2-oxo-2,3-dihydro-1H-benzo[d]imidazol-1-yl)piperidine-2,6-dione (I-69)

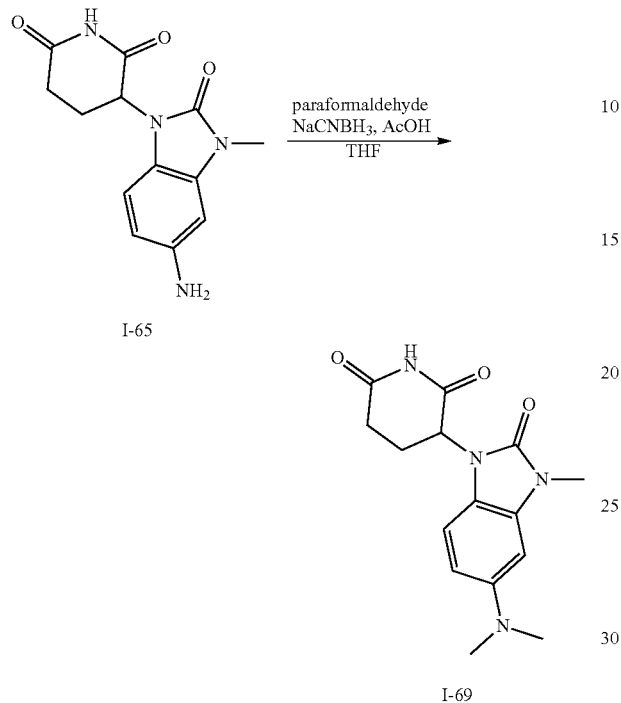

To a mixture of 3-(5-amino-3-methyl-2-oxo-2,3-dihydro-1H-benzo[d]imidazol-1-yl)piperidine-2,6-dione (85 mg, 0.274 mol) and paraformaldehyde (82 mg, 2.74 mmol) in THF (5 mL) was added AcOH (3 drops). The mixture was stirred at room temperature for 1 h, then NaCNBH$_3$ (51.6 mg, 0.822 mmol) was added into the mixture. The resulting mixture was warmed to 40° C. and stirred overnight. The reaction mixture was concentrated in vacuo, the residue was purified by prep-HPLC eluting with CH$_3$CN/H$_2$O to get the title compound 18 mg as a white solid. (yield: 21.6%). $^1$H NMR (400 MHz, DMSO-d$_6$) δ 11.05 (s, 1H), 6.91 (d, J=8.63 Hz, 1H), 6.61 (d, J=2.25 Hz, 1H), 6.44 (dd, J=8.63, 2.38 Hz, 1H), 5.27 (dd, J=12.88, 5.38 Hz, 1H), 3.30 (s, 3H), 2.95-2.81 (m, 7H), 2.73-2.56 (m, 2H), 2.02-1.94 (m, 1H); LC/MS (ESI, m/z): [M+1]$^+$=303.1.

Example 16. Synthesis of 1-(2,6-Dioxopiperidin-3-yl)-N,3-dimethyl-2-oxo-2,3-dihydro-1H-benzo[d]imidazole-5-carboxamide (I-70)

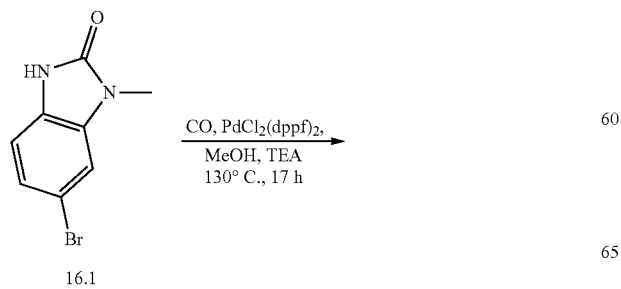

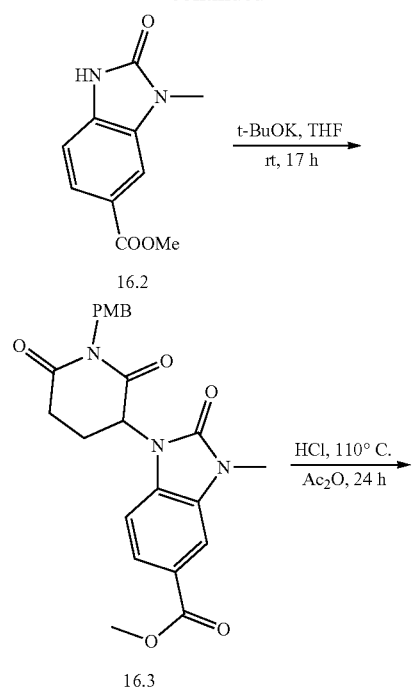

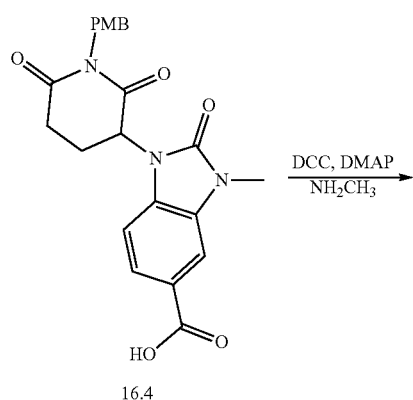

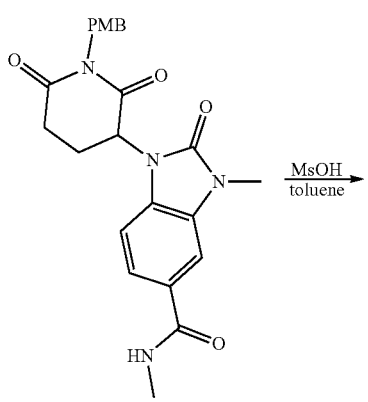

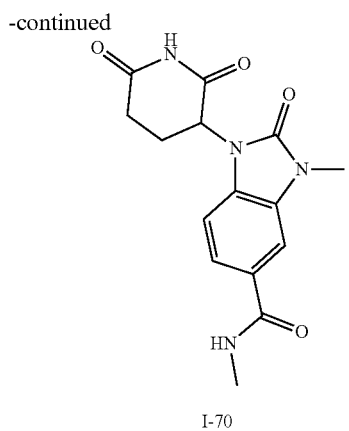

I-70

Methyl 3-methyl-2-oxo-2,3-dihydro-1H-benzo[d]imidazole-5-carboxylate (16.2)

A mixture of 6-bromo-1-methyl-1,3-dihydro-2H-benzo[d]imidazol-2-one (10.0 g, 44.2 mmol), 1,1'-Bis(diphenylphosphino)ferrocene-palladium(II)dichloride dichloromethane complex (3.6 g, 4.42 mmol), TEA (9.0 g, 88.5 mmol) in MeOH (200 mL) and DMF (10 mL) was sparged with carbon monoxide for about 10 min, placed under 4 atm carbon monoxide atmosphere, and heated to 130° C. for 17 hours. The reaction mixture was cooled down to room temperature, filtered and concentrated in vacuo. The residue was purified by silica gel column chromatography (PE:EA=2:1) to give product (7.0 g, 76.9%) as a yellow solid. $^1$H NMR (400 MHz, DMSO-$d_6$) δ 11.27 (s, 1H), 7.77-7.53 (m, 2H), 7.07 (d, J=8.1 Hz, 1H), 3.84 (s, 3H), 3.33 (s, 3H); LC/MS (ESI, m/z): [M+1]+=207.1.

Methyl-1-(1-(4-methoxybenzyl)-2,6-dioxopiperidin-3-yl)-3-methyl-2-oxo-2,3-dihydro-1H-benzo[d]imidazole-5-carboxylate (16.3)

To a solution of methyl 3-methyl-2-oxo-2,3-dihydro-1H-benzo[d]imidazole-5-carboxylate (2.0 g, 9.71 mmol) in DMF (10 mL) and THF (40 mL) was added t-BuOK (1.2 g, 10.7 mmol) at 0° C. The mixture was stirred at 0-10° C. for 30 min under $N_2$. Then a solution of 3-bromo-1-(4-methoxybenzyl)piperidine-2,6-dione (3.6 g, 11.7 mmol) in DMF (10 mL) was added to the reaction mixture at 0-10° C. during 20 minutes. After addition, the reaction mixture was warmed to r.t and stirred for 17 hours under $N_2$. The reaction was quenched by water (80 mL) and extracted with EA (3×100 mL). The combined organic layer was washed with water (3×50 mL) and brine (3×50 mL), dried over anhydrous $Na_2SO_4$, filtered and concentrated in vacuo. The residue was purified by column chromatography (PE:EA=1:1) to give product (0.68 g, 16.0% yield) as a yellow solid. $^1$H NMR (400 MHz, DMSO) δ 7.75 (d, J=1.4 Hz, 1H), 7.71 (d, J=7.9 Hz, 1H), 7.21 (d, J=8.7 Hz, 2H), 7.16 (d, J=7.9 Hz, 1H), 6.87 (d, J=8.7 Hz, 2H), 5.61 (dd, J=13.0, 5.4 Hz, 1H), 4.80 (q, J=14.3 Hz, 2H), 3.87 (s, 3H), 3.73 (s, 3H), 3.41 (s, 3H), 3.17-2.97 (m, 1H), 2.93-2.63 (m, 2H), 2.16-2.05 (m, 1H); LC/MS (ESI, m/z): [M+1]+=438.3.

1-(1-(4-Methoxybenzyl)-2,6-dioxopiperidin-3-yl)-3-methyl-2-oxo-2,3-dihydro-1H-benzo[d]imidazole-5-carboxylic Acid (16.4)

methyl 1-(1-(4-methoxybenzyl)-2,6-dioxopiperidin-3-yl)-3-methyl-2-oxo-2,3-dihydro-1H-benzo[d]imidazole-5-carboxylate (1.0 g, 2.29 mmol) in HCl/$Ac_2O$ (20 mL, V:V=1:3.3) was heated to 110° C. and stirred for 24 hours. Then the reaction mixture was cooled down to r.t and powered into ice-water (100 mL), filtered to give product (0.5 g, 51.7% yield) as a yellow solid. LC/MS (ESI, m/z): [M+1]+=424.3.

1-(1-(4-methoxybenzyl)-2,6-dioxopiperidin-3-yl)-N,3-dimethyl-2-oxo-2,3-dihydro-1H-benzo[d]imidazole-5-carboxamide (16.5)

To a solution of 1-(1-(4-methoxybenzyl)-2,6-dioxopiperidin-3-yl)-3-methyl-2-oxo-2,3-dihydro-1H-benzo[d]imidazole-5-carboxylic acid (0.15 g, 0.35 mmol) in DCM (5 mL) was added methylamine (0.2 mL, 0.43 mmol, 2N in THF solution), DMAP (8.7 mg, 0.07 mmol) and DCC (0.11 g, 0.53 mmol). The reaction mixture was stirred at r.t for 2 hours and filtered. The filtrate was concentrated in vacuo and purified by column chromatography (PE:EA=1:1) to give product (85 mg, 55.2% yield) as a yellow solid. LC/MS (ESI, m/z): [M+1]+=437.3.

1-(2,6-Dioxopiperidin-3-yl)-N,3-dimethyl-2-oxo-2,3-dihydro-1H-benzo[d]imidazole-5-carboxamide (I-70)

To a stirred solution of 1-(1-(4-methoxybenzyl)-2,6-dioxopiperidin-3-yl)-N,3-dimethyl-2-oxo-2,3-dihydro-1H-benzo[d]imidazole-5-carboxamide (70 mg, 0.16 mol) in toluene (4 mL), methanesulfonic acid (2 mL) was added. The reaction mixture was heated to 110° C. and stirred for 2 hours. The reaction mixture was cooled to r.t and concentrated to remove toluene. The residue was diluted with $CH_3CN$ and purified via reverse phase column chromatography ($CH_3CN$/$H_2O$=5%-80%) to give the desired compound (6.0 mg, 11.8%) as a white solid. $^1$H NMR (400 MHz, DMSO-$d_6$) δ 11.12 (s, 1H), 8.37-8.34 (m, 1H), 7.74-7.46 (m, 2H), 7.19 (d, J=8.3 Hz, 1H), 5.41 (dd, J=12.8, 5.4 Hz, 1H), 3.35 (s, 3H), 2.95-2.85 (m, 1H), 2.80 (d, J=4.5 Hz, 3H), 2.76-2.58 (m, 2H), 2.07-2.00 (m, 1H); LC/MS (ESI, m/z): [M+1]f=317.0.

Example 17. Synthesis of 1-((1-(2,6-dioxopiperidin-3-yl)-3-methyl-2-oxo-2,3-dihydro-1H-benzo[d]imidazol-5-yl)methyl)-3-ethylurea (I-71)

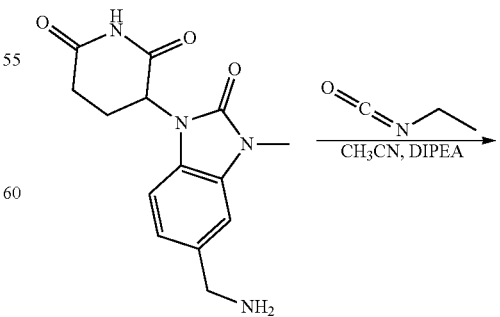

I-64

-continued

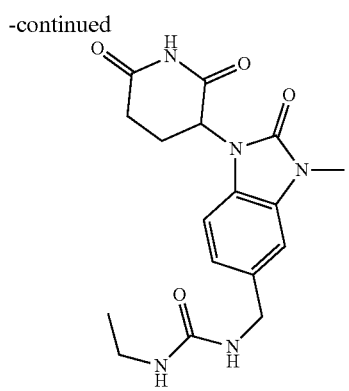

I-71

To a stirred solution of 3-(5-(aminomethyl)-3-methyl-2-oxo-2,3-dihydro-1H-benzo[d]imidazol-1-yl)piperidine-2,6-dione (30 mg, 0.10 mmol) in MeCN (2 mL) was added isocyanatoethane (15 mg, 0.21 mmol) and DIPEA (27 mg, 0.21 mmol). The reaction mixture was stirred at r.t for 2 hours. The reaction mixture was concentrated in vacuo and purified via reverse phase column chromatography (CH$_3$CN/H$_2$O=5%-80%) to give the desired compound (7.2 mg, 19.3%) as a white solid. $^1$H NMR (400 MHz, DMSO-d$_6$) δ 11.08 (s, 1H), 7.09-6.99 (m, 2H), 6.94 (d, J=8.1 Hz, 1H), 6.24 (t, J=5.6 Hz, 1H), 5.84 (t, J=5.6 Hz, 1H), 5.35 (dd, J=12.7, 5.6 Hz, 1H), 4.21 (d, J=5.9 Hz, 2H), 3.29 (s, 3H), 3.07-2.98 (m, 2H), 2.95-2.84 (m, 1H), 2.73-2.60 (m, 2H), 2.04-1.95 (m, 1H), 0.99 (t, J=7.2 Hz, 3H); LC/MS (ESI, m/z): [M+1]$^+$=360.3.

Example 18. Synthesis of (R)-3-((S)-5-(4-bromophenyl)-2-oxooxazolidin-3-yl)piperidine-2,6-dione (I-72) and (S)-3-((S)-5-(4-bromophenyl)-2-oxooxazolidin-3-yl)piperidine-2,6-dione (I-73)

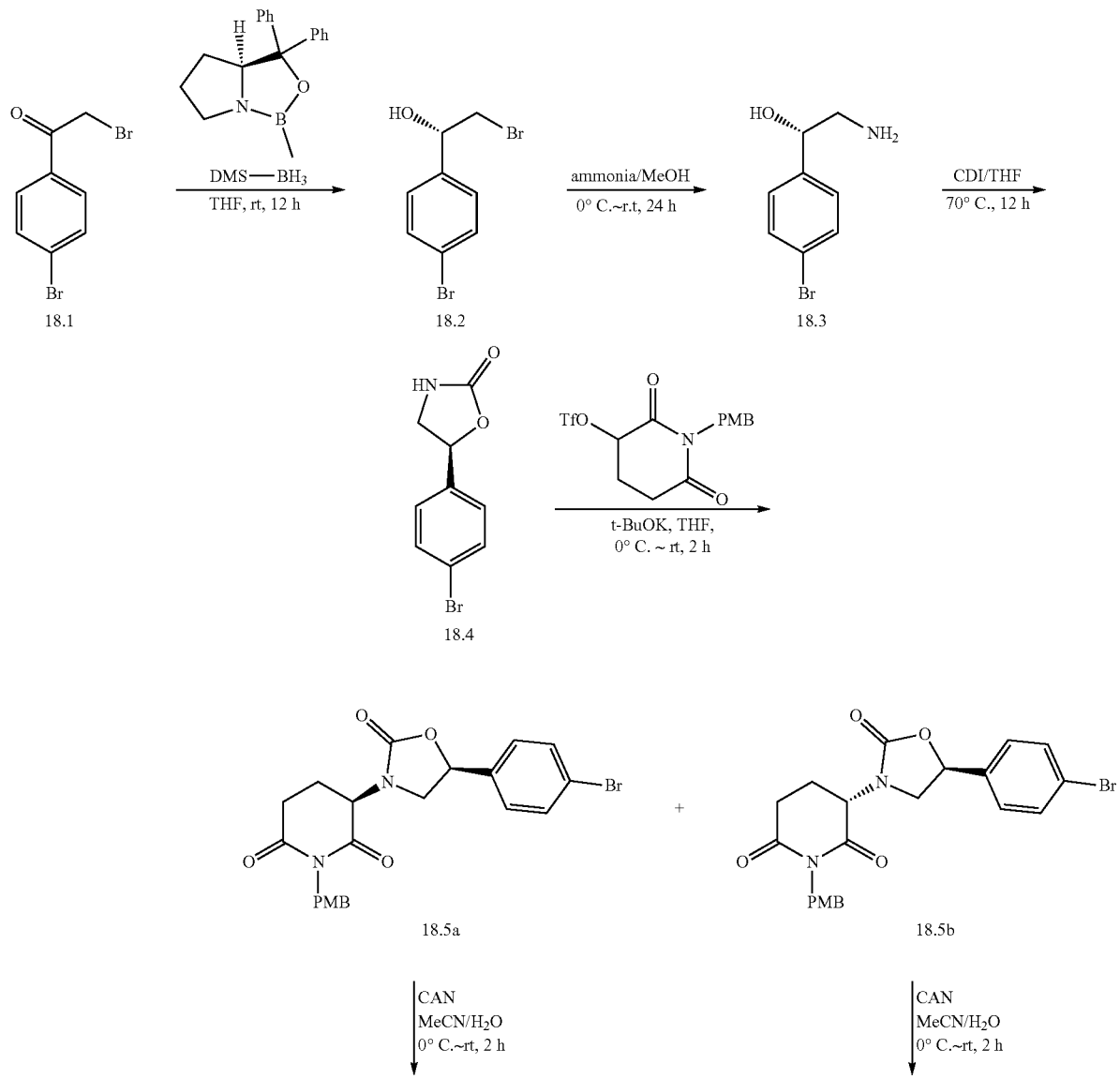

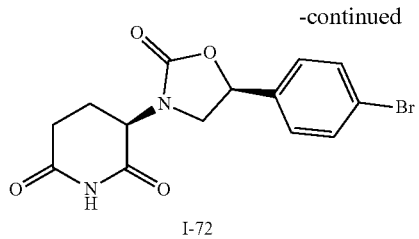

I-72

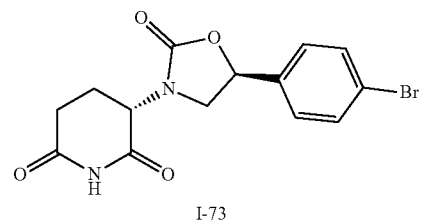

I-73

(S)-2-Bromo-1-(4-bromophenyl)ethanol (18.2)

To a stirred solution of (S)-1-methyl-3,3-diphenylhexahydropyrrolo[1,2-c][1,3,2]oxazaborole (0.5 g, 1.81 mmol) in THF (25 mL) was added $BH_3.DMS$ (10 M, 1.3 mL, 12.7 mmol) at 0° C. The mixture was stirred for 0.5 h at 0° C. To the reaction mixture was added a solution of 2-bromo-1-(4-bromophenyl)ethanone (5 g, 18.1 mmol) in THF (15 mL) dropwise at 0° C. The mixture was stirred for 12 h at rt. To the mixture was added MeOH (the mixture was bubbled) dropwise. The MeOH was stopped to add after the mixture didn't bubble. The mixture was concentrated and purified by column chromatography on silica gel (PE/EA=50/1 to 20/1 to 10/1 to 5/1) to give (S)-2-bromo-1-(4-bromophenyl)ethanol (5 g, 100% yield) as a white solid. $^1H$ NMR (400 MHz, DMSO-$d_6$) δ 7.55-7.52 (m, 2H), 7.38-7.34 (m, 2H), 5.89 (d, J=4.9 Hz, 1H), 4.82-4.78 (m, 1H), 3.66 (dd, J=10.2, 4.6 Hz, 1H), 3.57 (dd, J=10.2, 6.8 Hz, 1H).

(S)-2-Amino-1-(4-bromophenyl)ethanol (18.3)

To a solution of (S)-2-bromo-1-(4-bromophenyl)ethanol (15 g, 123 mmol) in MeOH (100 mL) was added $NH_3.H_2O$ (25%, 250 mL) at 0° C. under $N_2$. The reaction mixture was stirred at room temperature for 12 h under $N_2$. The mixture was concentrated. The solid was washed with EA to give (S)-2-amino-1-(4-bromophenyl)ethanol (8.4 g, 74% yield) as a white solid. $^1H$ NMR (400 MHz, DMSO-$d_6$) δ 7.54 (d, J=8.4 Hz, 2H), 7.32 (d, J=8.4 Hz, 2H), 5.51 (br s, 3H), 4.64 (dd, J=8.4, 3.6 Hz, 1H), 2.83 (dd, J=12.8, 3.4 Hz, 1H), 2.69 (dd, J=12.6, 6.8 Hz, 1H).

(S)-5-(4-Bromophenyl)oxazolidin-2-one (18.4)

A mixture of (S)-2-amino-1-(4-bromophenyl)ethanol (22 g, 102 mmol), CDI (24.2 g, 153 mmol) and THF (500 mL) was heated to 80° C. and stirred for overnight at 80° C. under $N_2$. To the mixture was added $H_2O$ (200 mL), extracted with EA (300 mL). The organic layer was concentrated and purified by column (PE/EA=2/1 to 1/1) to give (S)-5-(4-bromophenyl)oxazolidin-2-one (8.0 g, 33% yield) as a yellow solid.

(R)-3-((S)-5-(4-Bromophenyl)-2-oxooxazolidin-3-yl)-1-(4-methoxybenzyl)piperidine-2,6-dione (18.5a) and (S)-3-((S)-5-(4-Bromophenyl)-2-oxooxazolidin-3-yl)-1-(4-methoxybenzyl)piperidine-2,6-dione (18.5b)

To a solution of (S)-5-(3-bromophenyl)oxazolidin-2-one (8.0 g, 30.2 mmol) in THF (100 mL) was added t-BuOK (5.5 g, 49.8 mmol) at 0° C. under $N_2$. The mixture was stirred for 1 h at 0° C. Then to the mixture was added 1-(4-methoxybenzyl)-2,6-dioxopiperidin-3-yl trifluoromethanesulfonate (13.9 g, 36.8 mmol) at 0° C. under $N_2$. The mixture was stirred at 0° C.~10° C. for 2 h. To the mixture was added EA (100 mL), washed with $H_2O$ (100 mL), brine (50 mL), dried over $Na_2SO_4$, filtered, concentrated and purified by column chromatography on silica gel (PE/EA=2/1) followed by flash (210 nm, 30% MeCN in $H_2O$) to give (R)-3-((S)-5-(4-bromophenyl)-2-oxooxazolidin-3-yl)-1-(4-methoxybenzyl)piperidine-2,6-dione (4.5 g, 28% yield) as a white solid and (S)-3-((S)-5-(4-bromophenyl)-2-oxooxazolidin-3-yl)-1-(4-methoxybenzyl)piperidine-2,6-dione. $^1H$ NMR (400 MHz, CDCl$_3$) δ 7.57-7.52 (m, 2H), 7.34-7.29 (m, 2H), 7.26-7.24 (m, 2H), 6.86-6.80 (m, 2H), 5.89 (dd, J=8.7, 7.1 Hz, 1H), 4.89 (s, 2H), 4.58 (dd, J=12.8, 6.0 Hz, 1H), 3.94 (t, J=8.4 Hz, 1H), 3.78 (s, 3H), 3.80 (dd, J=17.9, 7.1 Hz, 1H), 2.97-2.90 (m, 1H), 2.79-2.70 (m, 1H), 2.20-2.04 (m, 2H).

(R)-3-((S)-5-(4-bromophenyl)-2-oxooxazolidin-3-yl)piperidine-2,6-dione (I-72)

To a solution of (R)-3-((S)-5-(4-bromophenyl)-2-oxooxazolidin-3-yl)-1-(4-methoxybenzyl)piperidine-2,6-dione (50 mg, 0.106 mmol) in MeCN (5 mL) was added dropwise a solution of CAN (232 mg, 0.424 mmol) in $H_2O$ (1 mL) at 0° C. The mixture was stirred for 3 h at 0° C.~10° C. To the mixture was added $H_2O$ (100 mL), extracted with EA (200 mL). The organic layer was washed with brine (50 mL), dried over $Na_2SO_4$, filtered, concentrated and purified by column (PE/EA=1/1) to give (R)-3-((S)-5-(4-bromophenyl)-2-oxooxazolidin-3-yl)piperidine-2,6-dione (5 mg, 14% yield) as a white solid. $^1H$ NMR (400 MHz, CDCl$_3$) δ 8.20 (s, 1H), 7.56 (d, J=8.0 Hz, 2H), 7.35 (d, J=8.0 Hz, 2H), 5.49 (t, J=8.2 Hz, 1H), 4.74 (dd, J=13.0, 5.2 Hz, 1H), 3.84 (t, J=8.4 Hz, 1H), 3.48 (t, J=7.8 Hz, 1H), 2.91-2.87 (m, 1H), 2.82-2.73 (m, 1H), 2.22-2.11 (m, 2H); LC/MS (ESI, m/z): [M+1]f=355.0.

(S)-3-((S)-5-(4-bromophenyl)-2-oxooxazolidin-3-yl)piperidine-2,6-dione (I-73)

To a solution of (S)-3-((S)-5-(4-bromophenyl)-2-oxooxazolidin-3-yl)-1-(4-methoxybenzyl)piperidine-2,6-dione (80 mg, 0.169 mmol) in MeCN (10 mL) was added dropwise a solution of CAN (372 mg, 0.678 mmol) in $H_2O$ (2 mL) at 0° C. The mixture was stirred for 3 h at 0° C.~10° C. To the mixture was added $H_2O$ (100 mL), extracted with EA (200 mL). The organic layer was washed with brine (50 mL), dried over $Na_2SO_4$, filtered, concentrated and purified by column (PE/EA=1/1) to give (S)-3-((S)-5-(4-bromophenyl)-2-oxooxazolidin-3-yl)piperidine-2,6-dione (1.5 mg, 3% yield) as a white solid. $^1H$ NMR (400 MHz, CDCl$_3$) δ 7.86 (s, 1H), 7.56 (d, J=8.2 Hz, 2H), 7.26-7.22 (m, 2H), 5.60 (t, J=7.8 Hz, 1H), 4.64 (dd, J=12.0, 5.2 Hz, 1H), 4.00 (t, J=8.2 Hz, 1H), 3.41 (t, J=7.4 Hz, 1H), 2.91-2.86 (m, 1H), 2.78-2.73 (m, 1H), 2.24-2.20 (m, 2H); LC/MS (ESI, m/z): [M+1]$^+$=355.0.

Example 19. Synthesis of 1-((1-(2,6-dioxopiperidin-3-yl)-3-methyl-2-oxo-2,3-dihydro-1H-benzo[d]imidazol-5-yl)methyl)urea (I-74)

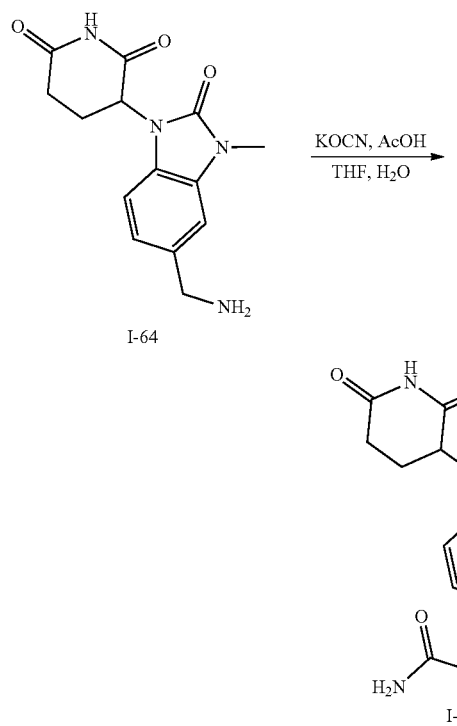

To a stirred solution of 3-(5-(aminomethyl)-3-methyl-2-oxo-2,3-dihydro-1H-benzo[d]imidazol-1-yl)piperidine-2,6-dione (30 mg, 0.10 mol) in THF (2 mL) and H$_2$O (0.2 mL) was added potassium cyanate (13 mg, 0.16 mol) and AcOH (9 mg, 0.16 mol). The reaction mixture was heated to 60° C. and stirred for 2 hours. Then the reaction was cooled down to r.t and concentrated in vacuo. The residue was purified via reverse phase column chromatography (CH$_3$CN/H$_2$O=5%-80%) to give the desired compound (6.4 mg, 18.6%) as a white solid. $^1$H NMR (400 MHz, DMSO-d$_6$) δ 11.09 (s, 1H), 7.07-7.04 (m, 2H), 7.00-6.84 (m, 1H), 6.40 (s, 1H), 5.35 (dd, J=12.8, 5.4 Hz, 1H), 4.22 (s, 2H), 3.29 (s, 3H), 2.99-2.83 (m, 1H), 2.75-2.59 (m, 2H), 2.04-1.90 (m, 1H); LC/MS (ESI, m/z): [M+1]f=332.27.

Example 20. Synthesis of 3-(3-methyl-4-nitro-2-oxo-2,3-dihydro-1H-1,3-benzodiazol-1-yl)piperidine-2,6-dione (I-75)

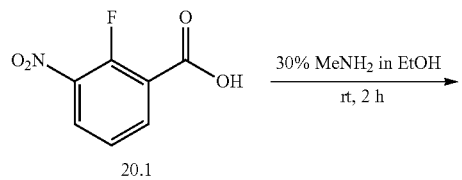

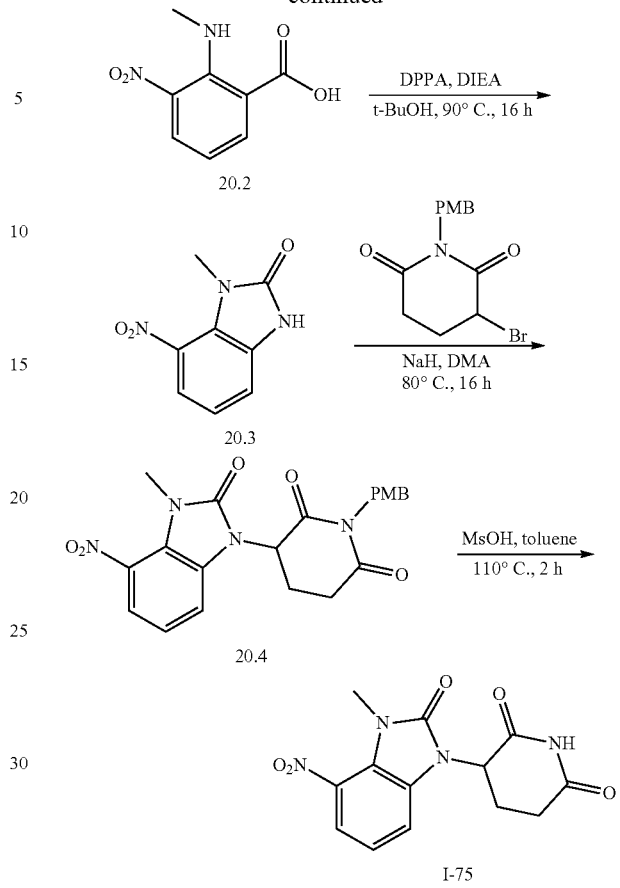

2-(Methylamino)-3-nitrobenzoic Acid (20.2)

To stirred solution of methanamine (30% in EtOH, w/w, 500 mL) was added 2-fluoro-3-nitrobenzoic acid (23.5 g, 0.13 mol) in portions at 0° C. The resulting mixture was stirred for 2 h at room temperature under nitrogen atmosphere and then concentrated under reduced pressure. The residue was dissolved in water (200 mL) and the resulting solution was acidified to pH=56 by addition of 1 M hydrochloric acid at 0° C. The precipitated solids were collected by filtration and dried in a vacuum oven to afford 2-(methylamino)-3-nitrobenzoic acid (23 g, 92%) as a yellow solid: $^1$H NMR (400 MHz, CDCl$_3$) δ 8.21 (d, J=7.8 Hz, 1H), 8.04 (d, J=8.1 Hz, 1H), 6.77 (t, J=8.0 Hz, 1H), 2.86 (s, 3H); LC/MS (ESI, m/z): [M+1]f=197.2.

1-Methyl-7-nitro-2,3-dihydro-1H-1,3-benzodiazol-2-one (20.3)

To a stirred suspension of 2-(methylamino)-3-nitrobenzoic acid (13 g, 66.3 mmol) in t-BuOH (300 mL) were added N-ethyldiisopropylamine (25.7 g, 198.8 mmol) and diphenylphosphoryl azide (17.2 mL, 62.5 mmol) dropwise at 0° C. under nitrogen atmosphere. The resulting mixture was stirred for 16 h at 90° C. The resulting mixture was cooled down to room temperature and filtered. The filter cake was triturated with MeOH (200 mL) and filtered. The filter cake was dried in a vacuum oven to afford 1-methyl-7-nitro-2,3-dihydro-1H-1,3-benzodiazol-2-one (9.5 g, 74%) as a yellow solid: $^1$H NMR (400 MHz, DMSO-d$_6$) δ 11.64 (s, 1H), 7.61

(dd, J=8.4, 1.1 Hz, 1H), 7.33 (dd, J=7.8, 1.1 Hz, 1H), 7.15 (t, J=8.1 Hz, 1H), 3.36 (s, 3H); LC/MS (ESI, m/z): [M−H]⁻= 192.1.

1-[(4-Methoxyphenyl)methyl]-3-(3-methyl-4-nitro-2-oxo-2,3-dihydro-1H-1,3-benzodiazol-1-yl)piperidine-2,6-dione (20.4)

A solution of 1-methyl-7-nitro-2,3-dihydro-1H-1,3-benzodiazol-2-one (10.46 g, 54.14 mmol) in DMA (250 mL) was treated with NaH (60% in mineral oil, 2.18 g, 90.78 mmol) for 1 h at 0° C. under nitrogen atmosphere followed by the addition of 3-bromo-1-[(4-methoxyphenyl)methyl]piperidine-2,6-dione (13 g, 41.64 mmol) at 0° C. The resulting mixture was stirred for 16 h at 80° C. The resulting mixture was cooled down to room temperature, acidified to pH=5 by addition of AcOH and diluted with water (500 mL). The resulting mixture was extracted with ethyl acetate (3×400 mL). The combined organic layers was washed with brine (600 mL) and dried over anhydrous Na₂SO₄. After filtration, the filtrate was concentrated under reduced pressure. The residue was purified by reverse phase flash chromatography with the following conditions: Column: WelFlash™ C18-I, 20-40 μm, 330 g; Eluent A: Water (plus 10 mmol/L formic acid); Eluent B: ACN; Gradient: 45%-70% B in 20 min; Flow rate: 100 mL/min; Detector: 220/254 nm; desired fractions were collected at 65% B and concentrated under reduced pressure to afford 1-[(4-methoxyphenyl)methyl]-3-(3-methyl-4-nitro-2-oxo-2,3-dihydro-1H-1,3-benzodiazol-1-yl)piperidine-2,6-dione (3.6 g, 20%) as a yellow solid: ¹H NMR (400 MHz, DMSO-d₆) δ 7.69 (dd, J=8.4, 1.0 Hz, 1H), 7.47 (d, J=7.8 Hz, 1H), 7.25-7.16 (m, 3H), 6.90-6.82 (m, 2H), 5.68 (dd, J=12.9, 5.4 Hz, 1H), 4.83 (d, J=14.3 Hz, 1H), 4.76 (d, J=14.3 Hz, 1H), 3.72 (s, 3H), 3.41 (s, 3H), 3.13-2.99 (m, 1H), 2.90-2.70 (m, 2H), 2.17-2.05 (m, 1H); LC/MS (ESI, m/z): [M+1]+=425.25.

3-(3-Methyl-4-nitro-2-oxo-2,3-dihydro-1H-1,3-benzodiazol-1-yl)piperidine-2,6-dione (I-75)

To a suspension of 1-[(4-methoxyphenyl)methyl]-3-(3-methyl-4-nitro-2-oxo-2,3-dihydro-1H-1,3-benzodiazol-1-yl)piperidine-2,6-dione (3.7 g, 8.7 mmol) in toluene (20 mL) was added methanesulfonic acid (20 mL). The resulting mixture was stirred for 2 h at 110° C. After cooling down to room temperature, the resulting mixture was added dropwise to ice water (500 mL) at 0° C. The precipitated solids were collected by filtration and washed with water (3×100 mL). The collected solids were taken up with DMF (50 mL) and purified by reverse phase flash chromatography with the following conditions: Column: WelFlash™ C18-I, 20-40 μm, 330 g; Eluent A: Water (plus 10 mmol/L formic acid); Eluent B: ACN; Gradient: 40%-60% B in 15 min; Flow rate: 100 mL/min; Detector: 220/254 nm; desired fractions were collected at 55% B and concentrated under reduced pressure to afford 3-(3-methyl-4-nitro-2-oxo-2,3-dihydro-1H-1,3-benzodiazol-1-yl)piperidine-2,6-dione (1.4 g, 53%) as a yellow solid: ¹H NMR (400 MHz, DMSO-d₆) δ 11.19 (s, 1H), 7.69 (d, J=8.5 Hz, 1H), 7.56 (d, J=7.9 Hz, 1H), 7.24 (t, J=8.2 Hz, 1H), 5.52 (dd, J=12.7, 5.3 Hz, 1H), 3.42 (s, 3H), 3.01-2.84 (m, 1H), 2.82-2.60 (m, 2H), 2.10 (d, J=11.0 Hz, 1H); LC/MS (ESI, m/z): [M−H]⁻=303.10.

Example 21. Synthesis of ethyl ((1-(2,6-dioxopiperidin-3-yl)-3-methyl-2-oxo-2,3-dihydro-1H-benzo[d]imidazol-5-yl)methyl)carbamate (I-76)

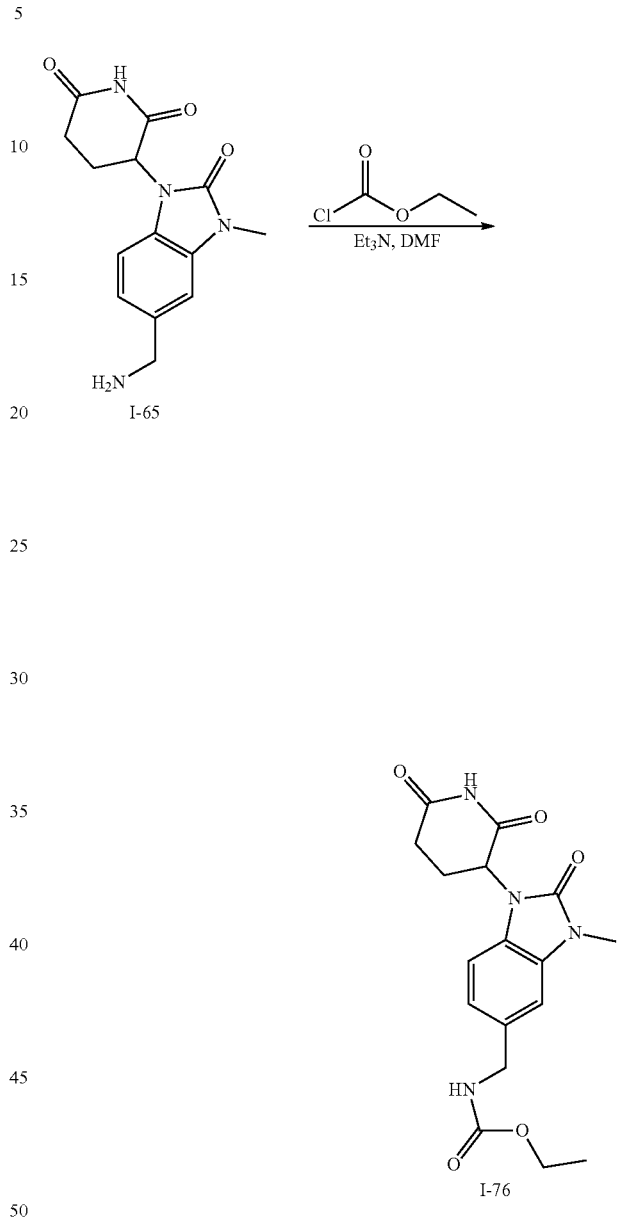

A suspension of 3-(5-amino-3-methyl-2-oxo-2,3-dihydro-1H-benzo[d]imidazol-1-yl)piperidine-2,6-dione (0.18 mmol, 50 mg) in 5 mL DMF was added ethyl carbonochloridate (3 drops) and Et₃N (10 drops) was stirred at room temperature for 16 h. LC-MS showed complete consumption of the starting material. The reaction mixture was concentrated to give crude product which was purified by Prep-HPLC to give desired compound ethyl ((1-(2,6-dioxopiperidin-3-yl)-3-methyl-2-oxo-2,3-dihydro-1H-benzo[d]imidazol-5-yl)methyl)carbamate (16.8 mg, yield 25%) as white solid. ¹H NMR (400 MHz, DMSO-d₆) δ 11.09 (s, 1H), 7.61 (t, J=6.0 Hz, 1H), 7.09-7.02 (m, 2H), 6.94 (dd, J=8.1, 1.6 Hz, 1H), 5.35 (dd, J=12.7, 5.4 Hz, 1H), 4.19 (d, J=6.1 Hz, 2H), 4.00 (q, J=7.1 Hz, 2H), 2.89 (dd, J=16.8, 5.5 Hz, 1H), 2.74-2.58 (m, 2H), 2.05-1.96 (m, 1H), 1.16 (t, J=7.1 Hz, 3H); LC/MS (ESI, m/z): [M+1]f=361.0.

Example 22. Synthesis of tert-butyl (15-(4-((S)-3-((S)-2,6-dioxopiperidin-3-yl)-2-oxooxazolidin-5-yl)phenyl)-3,6,9,12-tetraoxapentadec-14-yn-1-yl)carbamate (I-77)

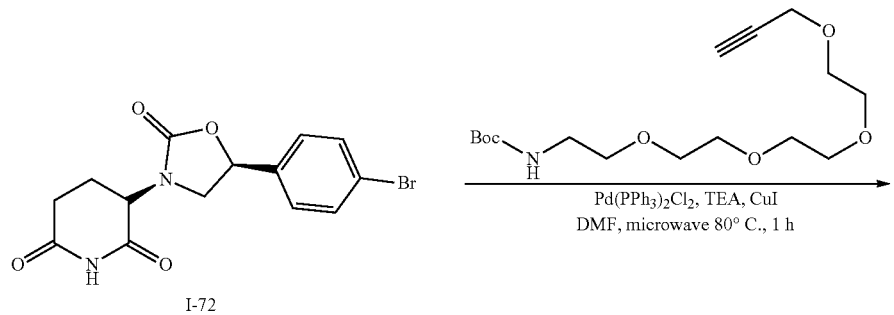

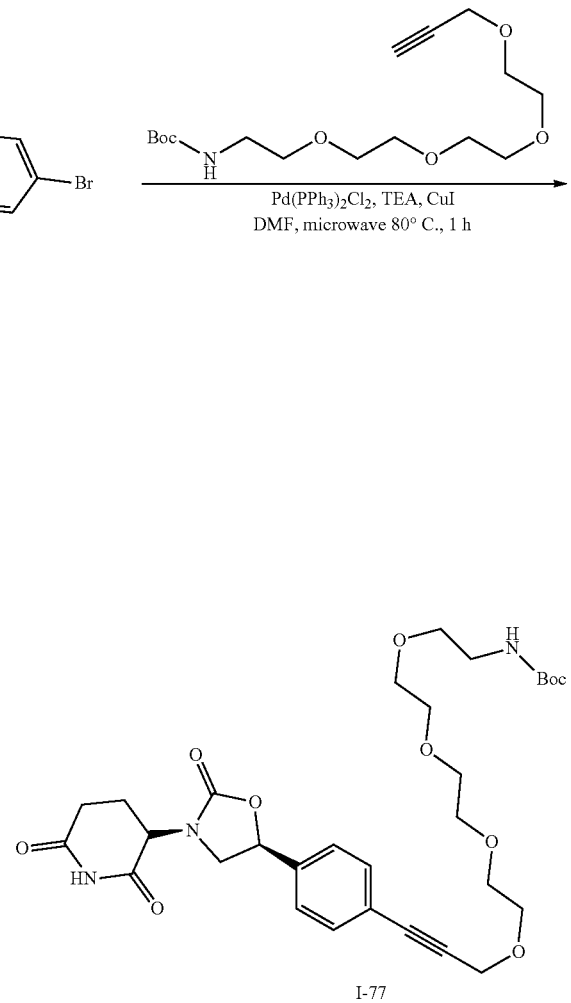

A mixture of (S)-3-((S)-5-(4-bromophenyl)-2-oxooxazolidin-3-yl)piperidine-2,6-dione (200 mg, 0.568 mmol), tert-butyl 3,6,9,12-tetraoxapentadec-14-yn-1-ylcarbamate (469 mg, 1.42 mmol), Pd(PPh$_3$)$_2$C$_2$ (60 mg, 0.0852 mmol), TEA (574 mg, 5.68 mmol), CuI (9 mg, 0.0454 mmol) and DMF (5 mL) was heated with microwave to 80° C. and stirred for 1 h under N$_2$. To the mixture was added H$_2$O (30 mL), extracted with EA (50 mL). The combined organic layer was washed with brine (50 mL), dried over Na$_2$SO$_4$, filtered, concentrated and purified by flash (30% MeCN in H$_2$O) to give tert-butyl (15-(4-((S)-3-((S)-2,6-dioxopiperidin-3-yl)-2-oxooxazolidin-5-yl)phenyl)-3,6,9,12-tetraoxapentadec-14-yn-1-yl)carbamate (80 mg, 23% yield) as a yellow oil. $^1$H NMR (400 MHz, CDCl$_3$) δ 8.00 (br s, 1H), 7.49 (d, J=8.2 Hz, 2H), 7.42 (d, J=8.1 Hz, 2H), 5.53 (t, J=8.3 Hz, 1H), 4.74 (dd, J=13.2, 5.4 Hz, 1H), 4.43 (s, 2H), 3.85 (t, J=8.4 Hz, 1H), 3.78-3.61 (m, 13H), 3.54-3.49 (m, 3H), 3.30 (t, J=4.6 Hz, 2H), 2.93-2.88 (m, 1H), 2.81-2.72 (m, 1H), 2.28-2.16 (m, 2H), 1.44 (s, 9H); LC/MS (ESI, m/z): [M−Boc+1]$^+$=504.8.

Example 23. Synthesis of 1-(2,6-dioxopiperidin-3-yl)-3-methyl-2-oxo-2,3-dihydro-1H-benzo[d]imidazole-4-carbonitrile (I-63)

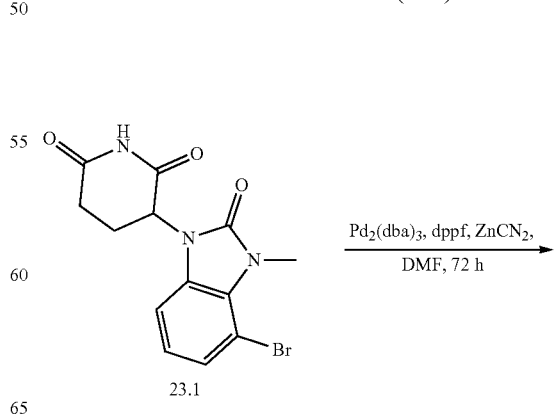

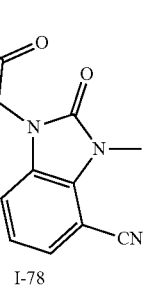

I-78

A mixture of 3-(4-bromo-3-methyl-2-oxo-2,3-dihydro-1H-benzo[d]imidazol-1-yl)piperidine-2,6-dione (1.33 mmol, 450 mg), Pd$_2$(dba)$_3$ (0.13 mmol, 119 mg), dppf (0.26 mmol, 156 mg) and ZnCN$_2$ (5.32 mmol, 622 mg) in 15 mL DMF was stirred under N$_2$ with sealed tube 48 h. LC-MS showed the starting material was consumed. The reaction mixture was concentrated to give crude product which was purified by Prep-HPLC to give desired compound 1-(2,6-dioxopiperidin-3-yl)-3-methyl-2-oxo-2,3-dihydro-1H-benzo[d]imidazole-4-carbonitrile (200 mg, yield 53%) as white solid. $^1$H NMR (400 MHz, DMSO-d$_6$) δ 11.16 (s, 1H), 7.48 (d, J=8.0 Hz, 2H), 7.19 (t, J=8.0 Hz, 1H), 5.46 (dd, J=12.8, 5.2 Hz, 1H), 3.61 (s, 3H), 2.92-2.85 (m, 1H), 2.78-2.60 (m, 2H), 2.05 (dd, J=12.4, 5.4 Hz, 1H); LC/MS (ESI, m/z): [M+1]*=285.0.

Example 24. Synthesis of 3-(3-methyl-5-(3-methyl-1H-pyrazol-5-yl)-2-oxo-2,3-dihydro-1H-benzo[d]imidazol-1-yl)piperidine-2,6-dione (I-79)

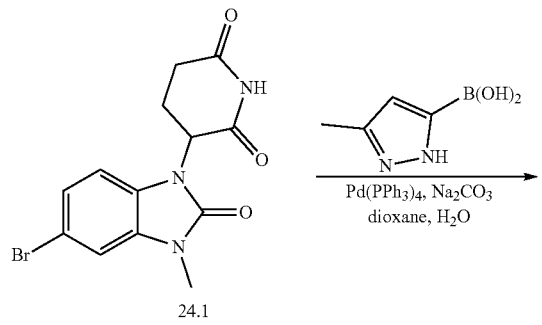

24.1

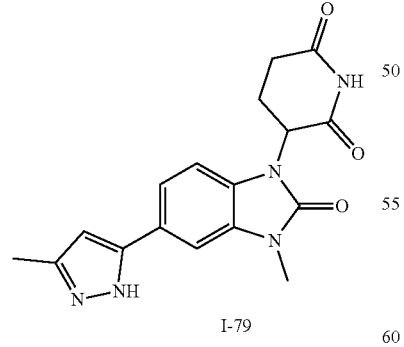

I-79

A mixture of 3-(5-bromo-3-methyl-2-oxo-2,3-dihydro-1H-benzo[d]imidazol-1-yl)piperidine-2,6-dione (100 mg, 0.306 mmol), Na$_2$CO$_3$ (65 mg, 0.612 mmol), (3-methyl-1H-pyrazol-5-yl)boronic acid (58 mg, 0.459 mmol), Pd(PPh$_3$)$_4$ (35.3 mg, 0.0306 mmol) in dioxane (5 mL) and water (1 mL) was stirred at 110° C. under nitrogen in microwave for 1 h.

The mixture was cooled to room temperature, poured into water and extracted with EtOAc (3×20 mL), the combined organic layers were concentrated under reduced pressure, the residue was purified by prep HPLC eluting with CH$_3$CN/H$_2$O to get the title compound (10 mg) as a white solid. (yield: 9.6%). $^1$H NMR (400 MHz, DMSO-d$_6$) δ 12.48 (br. s., 1H), 11.11 (s, 1H), 7.61-7.52 (m, 1H), 7.45 (d, J=8.13 Hz, 1H), 7.12 (d, J=8.25 Hz, 1H), 6.51-6.37 (m, 1H), 5.38 (dd, J=12.82, 5.44 Hz, 1H), 3.38 (s, 3H), 2.97-2.84 (m, 1H), 2.79-2.69 (m, 1H), 2.69-2.59 (m, 1H), 2.25 (s, 3H), 2.10-1.99 (m, 1H); LC/MS (ESI, m/z): [M+1]f=340.1.

Example 25. Synthesis of 3-(3-methyl-5-(2-methyl-1H-imidazol-5-yl)-2-oxo-2,3-dihydro-1H-benzo[d]imidazol-1-yl)piperidine-2,6-dione (I-80)

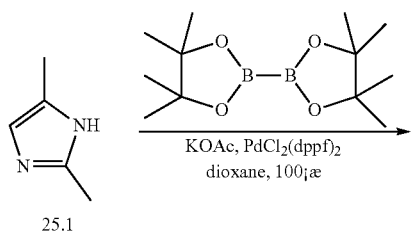

25.1

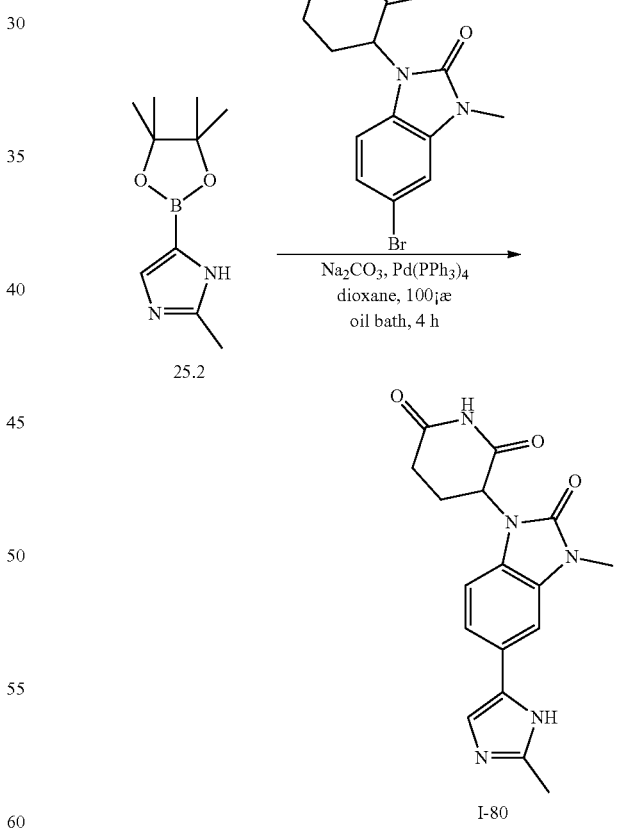

25.2

I-80

2-Methyl-5-(4,4,5,5-tetramethyl-1,3,2-dioxaborolan-2-yl)-1H-imidazole (25.2)

A mixture of 5-iodo-2-methyl-1H-imidazole (0.4 g, 1.92 mmol), 1,1'-Bis(diphenylphosphino)ferrocene-palladium(II)

dichloride dichloromethane complex (0.31 g, 0.38 mmol), 4,4,4',4',5,5,5',5'-octamethyl-2,2'-bi(1,3,2-dioxaborolane) (0.98 g, 3.85 mmol) and palladium(II)acetate (0.57 g, 5.77 mmol) in 1,4-dioxane (15 mL) was sparged with argon for about 10 min, placed under an argon atmosphere, and heated to 110° C. for 17 hours. The reaction mixture was cooled down to room temperature, filtered and concentrated in vacuo. The residue was purified by silica gel column chromatography (PE:EA=1:1) to give product (0.3 g, 75.0%) as a yellow solid. LC/MS (ESI, m/z): [M+1]$^+$=209.3.

3-(3-Methyl-5-(2-methyl-1H-imidazol-5-yl)-2-oxo-2,3-dihydro-1H-benzo[d]imidazol-1-yl)piperidine-2,6-dione (I-80)

A mixture of 3-(5-bromo-3-methyl-2-oxo-2,3-dihydro-1H-benzo[d]imidazol-1-yl)piperidine-2,6-dione (0.25 g, 0.74 mmol), 2-methyl-5-(4,4,5,5-tetramethyl-1,3,2-dioxaborolan-2-yl)-1H-imidazole (0.30 g, 1.48 mmol), sodium carbonate (0.16 g, 1.48 mmol) and tetrakis(triphenylphosphine)palladium (86 mg, 0.074 mmol) in 1,4-dioxane (5 mL) was sparged with argon for about 10 min, placed under an argon atmosphere, and heated to 100° C. for 4 hours. The reaction mixture was cooled down to room temperature, filtered and concentrated in vacuo. The residue was purified by silica gel column chromatography (DCM: CH$_3$CN=2:1) firstly, then purified via reverse phase column chromatography (CH$_3$CN/H$_2$O=5%-80%) to give the desired compound (2.5 mg, 1.0%) as a white solid. $^1$H NMR (400 MHz, DMSO-d$_6$) δ 11.96 (s, 1H), 11.12 (s, 1H), 7.47 (d, J=1.8 Hz, 1H), 7.31-7.00 (m, 3H), 5.47-5.24 (m, 1H), 3.34 (s, 3H), 2.95-2.81 (m, 1H), 2.78-2.55 (m, 2H), 2.25 (s, 3H), 2.07-1.97 (m, 1H); LC/MS (ESI, m/z): [M+1]$^+$=340.3.

Example 26. Synthesis of 3-(4-amino-3-methyl-2-oxo-2,3-dihydro-1H-benzo[d]imidazol-1-yl)piperidine-2,6-dione (I-81)

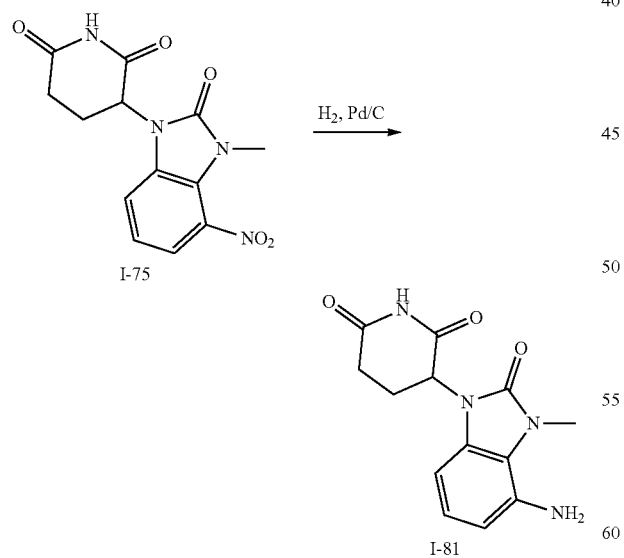

To a stirred solution of 3-(3-methyl-4-nitro-2-oxo-2,3-dihydro-1H-benzo[d]imidazol-1-yl)piperidine-2,6-dione (150 mg, 0.493 mmol) in THF (5 mL) and H$_2$O (1 mL) were added Zn (320.7 mg, 4.93 mmol) and NH$_4$Cl (263.8 mg, 4.93 mmol) at room temperature. The reaction mixture was heated at 60° C. for 12 h. The reaction mixture was cooled to room temperature and filtered. The filtrate was concentrated in vacuum. The residue was purified via reverse phase column chromatography (CH$_3$CN/H$_2$O=5%-90%) to give the desired compound (69.8 mg, 51.7%) as a yellow solid. $^1$H NMR (400 MHz, DMSO-d$_6$) δ 11.04 (s, 1H), 6.74 (t, J=7.9 Hz, 1H), 6.42 (t, J=8.7 Hz, 2H), 5.25 (dd, J=12.7, 5.4 Hz, 1H), 4.96 (s, 2H), 3.57 (s, 3H), 2.90-2.83 (m, 1H), 2.71-2.58 (m, 2H), 2.02-1.89 (m, 1H); LC/MS (ESI, m/z): [M+1]$^+$=275.0.

Example 27. Synthesis of tert-butyl (2-(2-(2-(2-(4-(1-(2,6-dioxopiperidin-3-yl)-3-methyl-2-oxo-2,3-dihydro-1H-benzo[d]imidazol-5-yl)-1H-1,2,3-triazol-1-yl)ethoxy)ethoxy)ethoxy)ethyl)carbamate (I-82)

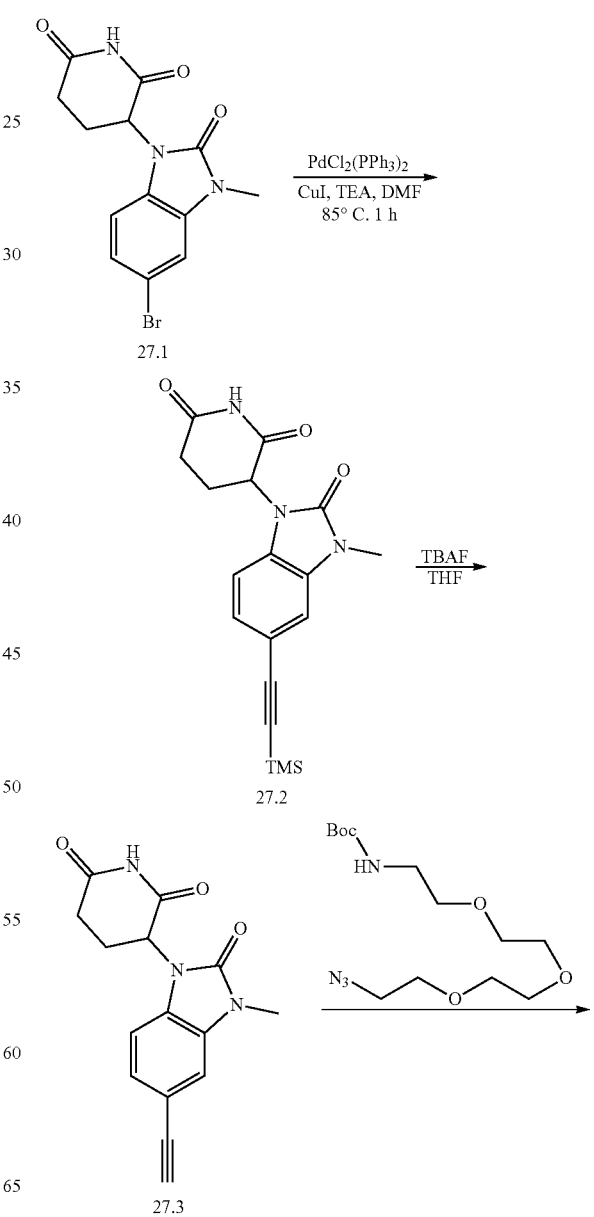

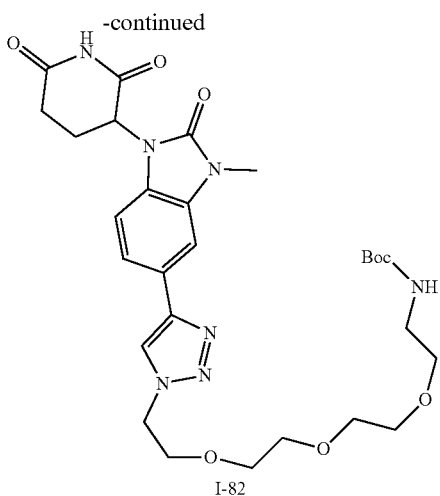

I-82

3-(3-Methyl-2-oxo-5-((trimethylsilyl)ethynyl)-2,3-dihydro-1H-benzo[d]imidazol-1-yl)piperidine-2,6-dione (27.2)

To a solution of 3-(5-bromo-3-methyl-2-oxo-2,3-dihydro-1H-benzo[d]imidazol-1-yl)piperidine-2,6-dione (200 mg, 0.594 mmol) in DMF (5 mL) were added ethynyltrimethylsilane (175 mg, 1.782 mmol), Pd(PPh$_3$)C$_2$ (84.35 mg, 0.119 mmol) and CuI (11.52 mg, 0.06 mmol) at room temperature under nitrogen. The reaction mixture was degassed and purged with nitrogen 3 times at −78° C. Then TEA (600 mg, 5.94 mmol) was added to the reaction mixture under nitrogen. The reaction mixture was heated at 85° C. in microwave for 1.5 h. The reaction mixture was concentrated in vacuum. The residue was purified via reverse phase column chromatography (CH$_3$CN/H$_2$O=5%-90%) to give the desired product 3-(3-methyl-2-oxo-5-((trimethylsilyl)ethynyl)-2,3-dihydro-1H-benzo[d]imidazol-1-yl)piperidine-2,6-dione (125 mg, 59.3%) as a yellow solid. LC/MS (ESI, m/z): [M+1]f=356.3.

3-(5-Ethynyl-3-methyl-2-oxo-2,3-dihydro-1H-benzo[d]imidazol-1-yl)piperidine-2,6-dione (27.3)

To a solution of 3-(3-methyl-2-oxo-5-((trimethylsilyl)ethynyl)-2,3-dihydro-1H-benzo[d]imidazol-1-yl)piperidine-2,6-dione (130 mg, 0.3662 mmol) in THF (2 mL) was added TBAF (2 mL, 1 N TBAF in THF) at room temperature under nitrogen. The reaction mixture was stirred at room temperature for 0.5 h. TLC (Petroleum ether/EtOAc=1/1, silica gel plate) showed complete consumption of the starting material after this time. The reaction mixture was concentrated in vacuum. The residue was purified via column chromatography (PE/EA=5%-90%) to give the desired product 3-(5-ethynyl-3-methyl-2-oxo-2,3-dihydro-1H-benzo[d]imidazol-1-yl)piperidine-2,6-dione (100.1 mg, yield 96.1%) as a yellow solid. LC/MS (ESI, m/z): [M+1]$^+$=284.2.

tert-Butyl (2-(2-(2-(2-(4-(1-(2,6-dioxopiperidin-3-yl)-3-methyl-2-oxo-2,3-dihydro-1H-benzo[d]imidazol-5-yl)-1H-1,2,3-triazol-1-yl)ethoxy)ethoxy)ethoxy)ethyl)carbamate (I-82)

To a solution of 3-(5-ethynyl-3-methyl-2-oxo-2,3-dihydro-1H-benzo[d]imidazol-1-yl)piperidine-2,6-dione (30 mg, 0.106 mmol) in THF (5 mL) were added tert-butyl (2-(2-(2-(2-azidoethoxy)ethoxy)ethoxy)ethyl)carbamate (101.1 mg, 0.318 mmol) and CuCl (10.5 mg, 0.106 mmol) at room temperature under nitrogen. The reaction mixture was degassed and purged with nitrogen 3 times. The reaction mixture was stirred at 65° C. for 3 h. TLC (Petroleum ether/EtOAc=1/1, silica gel plate) showed complete consumption of the starting material after this time. The reaction mixture was concentrated in vacuum. The residue was purified via reverse phase column chromatography (CH$_3$CN/H$_2$O=5%-90%) to give the desired product tert-butyl (2-(2-(2-(2-(4-(1-(2,6-dioxopiperidin-3-yl)-3-methyl-2-oxo-2,3-dihydro-1H-benzo[d]imidazol-5-yl)-1H-1,2,3-triazol-1-yl)ethoxy)ethoxy)ethoxy)ethyl)carbamate (48.1 mg, yield 75.5%) as a white solid. $^1$H NMR (400 MHz, CDCl$_3$) δ 8.39 (s, 1H), 8.01 (s, 1H), 7.71 (s, 1H), 7.43 (dd, J=8.1, 1.2 Hz, 1H), 6.83 (d, J=8.2 Hz, 1H), 5.26 (dd, J=12.7, 5.3 Hz, 1H), 5.02 (br s, 1H), 4.70-4.54 (m, 2H), 3.93 (dd, J=7.9, 3.3 Hz, 2H), 3.67-3.61 (m, 4H), 3.60-3.52 (m, 8H), 3.50 (s, 3H), 3.47 (t, J=5.1 Hz, 2H), 3.28 (br s, 2H), 2.99-2.94 (m, 1H), 2.89-2.81 (m, 1H), 2.79-2.68 (m, 1H), 2.31-2.22 (m, 1H), 1.44 (s, 9H); LC/MS (ESI, m/z): [M+1]f=602.5.

Example 28. Synthesis of tert-butyl (15-(4-((5S)-3-(2,6-dioxopiperidin-3-yl)-2-oxooxazolidin-5-yl)phenyl)-3,6,9,12-tetraoxapentadecyl)carbamate (I-83)

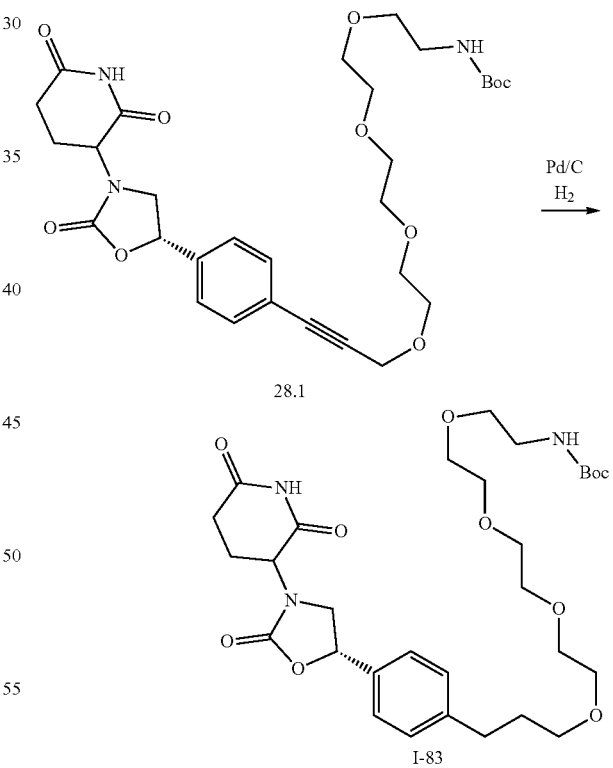

To a stirred solution of tert-butyl (15-(4-((5S)-3-(2,6-dioxopiperidin-3-yl)-2-oxooxazolidin-5-yl)phenyl)-3,6,9,12-tetraoxapentadec-14-yn-1-yl)carbamate (70 mg, 0.116 mmol) in THF (5 mL) and H$_2$O (1 mL) was added Pd/C (70 mg) at room temperature under nitrogen. The reaction mixture was degassed and purged with hydrogen 3 times. The reaction mixture was stirred at room temperature for 3 h. The reaction mixture was filtered. The filtrate was concentrated in vacuum. The residue was purified via column chromatography to give (DCM/CH₃OH=0%-10%) to give the desired product tert-butyl (15-(4-((5S)-3-(2,6-dioxopiperidin-3-yl)-2-oxooxazolidin-5-yl)phenyl)-3,6,9,12-tetraoxapentadecyl)carbamate (8.1 mg, 12.2%) as a white solid. ¹H NMR (400 MHz, CDCl₃) δ 8.16 (s, 1H), 7.39 (d, J=8.1 Hz, 2H), 7.25 (d, J=8.1 Hz, 2H), 5.51 (t, J=8.4 Hz, 1H), 5.13 (br s, 1H), 4.75 (dd, J=13.1, 5.5 Hz, 1H), 3.82 (t, J=8.4 Hz, 1H), 3.73-3.63 (m, 8H), 3.63-3.51 (m, 7H), 3.46 (t, J=6.4 Hz, 2H), 3.33-3.29 (m, 2H), 2.93-2.86 (m, 1H), 2.82-2.75 (m, 1H), 2.72 (t, J=7.5 Hz, 2H), 2.31-2.14 (m, 2H), 1.93-1.85 (m, 2H), 1.44 (s, 9H); LC/MS (ESI, m/z): [M+1]⁺=608.4.

Example 29. Synthesis of (R)-3-((S)-5-(3-bromophenyl)-2-oxooxazolidin-3-yl)piperidine-2,6-dione or (S)-3-((S)-5-(3-bromophenyl)-2-oxooxazolidin-3-yl)piperidine-2,6-dione (I-84)

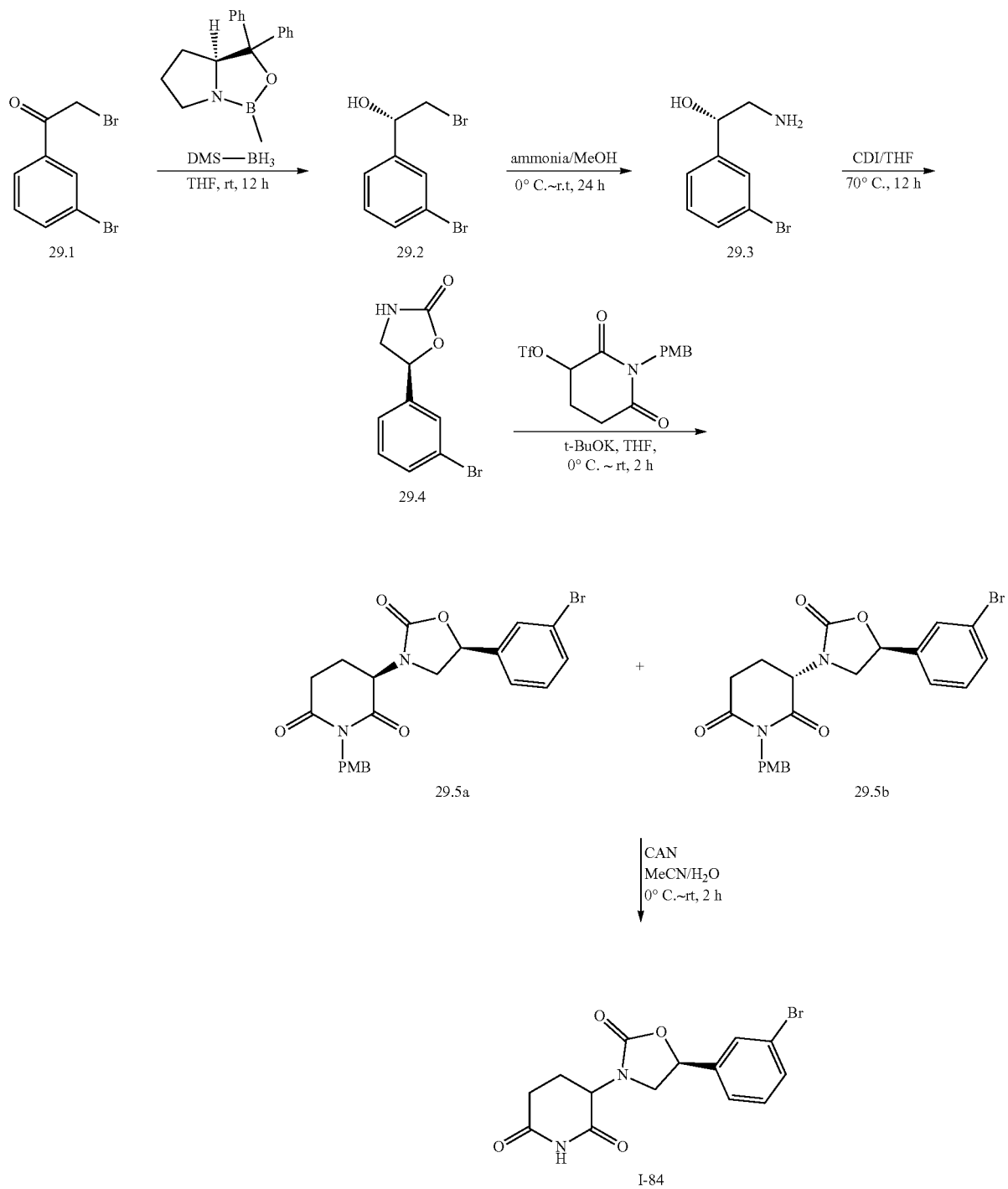

(S)-2-Bromo-1-(3-bromophenyl)ethanol (29.2)

To a stirred solution of (S)-1-methyl-3,3-diphenylhexahydropyrrolo[1,2-c][1,3,2]oxazaborole (1 g, 3.61 mmol) in THF (50 mL) was added $BH_3$-DMS (10 M, 2.5 mL, 25.3 mmol) at 0° C. The mixture was stirred for 0.5 h at 0° C. To the reaction mixture was added a solution of 2-bromo-1-(3-bromophenyl)ethanone (10 g, 36.1 mmol) in THF (30 mL) dropwise at 0° C. The mixture was stirred for 12 h at rt. To the mixture was added MeOH dropwise (the mixture was bubbled). Stop the adding of MeOH after the mixture didn't bubble. Then the mixture was concentrated and purified by column (PE/EA=50/1 to 20/1 to 10/1 to 5/1) to give (S)-2-bromo-1-(3-bromophenyl)ethanol (10 g, 100% yield) as a white solid. $^1$H NMR (400 MHz, $CDCl_3$) δ 7.56 (t, J=1.8 Hz, 1H), 7.47-7.45 (m, 1H), 7.32-7.30 (m, 1H), 7.26-7.22 (m, 1H), 4.90 (d, J=8.7 Hz, 1H), 3.63 (dd, J=10.5, 3.4 Hz, 1H), 3.51 (dd, J=10.5, 8.8 Hz, 1H), 2.68 (d, J=1.6 Hz, 1H).

(S)-2-Amino-1-(3-bromophenyl)ethanol (29.3)

To a solution of (S)-2-bromo-1-(3-bromophenyl)ethanol (11 g, 90.3 mmol) in MeOH (80 mL) was added $NH_3 \cdot H_2O$ (25%, 200 mL) at 0° C. under $N_2$. The reaction mixture was stirred for 12 h under $N_2$ at room temperature. The mixture was concentrated. The solid was washed with EA to give (S)-2-amino-1-(3-bromophenyl)ethanol (6.2 g, 74% yield) as a white solid. $^1$H NMR (400 MHz, DMSO-$d_6$) δ 7.70 (br s, 2H), 7.60 (t, J=1.9 Hz, 1H), 7.54-7.51 (m, 1H), 7.42-7.34 (m, 2H), 6.17 (d, J=3.8 Hz, 1H), 4.81-4.79 (m, 1H), 3.09 (dd, J=12.8, 3.2 Hz, 1H), 2.87 (dd, J=12.8, 9.6 Hz, 1H).

(S)-5-(3-Bromophenyl)oxazolidin-2-one (29.4)

A mixture of (S)-2-amino-1-(3-bromophenyl)ethanol (1 g, 4.63 mmol), CDI (1.1 g, 6.94 mmol) and THF (30 mL) was heated to 80° C. and stirred for overnight at 80° C. under $N_2$. To the mixture was added $H_2O$ (20 mL), extracted with EA (50 mL). The organic layer was concentrated and purified by column chromatography on silica gel (PE/EA=2/1 to 1/1) to give (S)-5-(3-bromophenyl)oxazolidin-2-one (300 mg, 27% yield) as a yellow solid. $^1$H NMR (400 MHz, $CDCl_3$) δ 7.55-7.54 (m, 1H), 7.51 (dt, J=6.9, 2.0 Hz, 1H), 7.32-7.29 (m, 2H), 5.60 (t, J=8.0 Hz, 1H), 5.09 (br s, 1H), 4.00 (dt, J=0.6, 8.7 Hz, 1H), 3.53-3.49 (m, 1H).

(R)-3-((S)-5-(3-Bromophenyl)-2-oxooxazolidin-3-yl)-1-(4-methoxybenzyl)piperidine-2,6-dione (29.5a) and (R)-3-((S)-5-(3-Bromophenyl)-2-oxooxazolidin-3-yl)-1-(4-methoxybenzyl)piperidine-2,6-dione (29.5b)

To a solution of (S)-5-(3-bromophenyl)oxazolidin-2-one (8.1 g, 33.5 mmol) in THF (100 mL) was added t-BuOK (5.6 g, 50.3 mmol) at 0° C. under $N_2$. The mixture was stirred for 1 h at 0° C. Then to the mixture was added 1-(4-methoxybenzyl)-2,6-dioxopiperidin-3-yl trifluoromethanesulfonate (14 g, 36.8 mmol) at 0° C. under $N_2$. The mixture was stirred for 2 h at 0° C.~10° C. To the mixture was added EA (100 mL), washed with $H_2O$ (100 mL), brine (50 mL), dried over $Na_2SO_4$, filtered, concentrated and purified by column chromatography on silica gel (PE/EA=2/1) followed by flash (210 nm, 30% MeCN in $H_2O$) to give fraction A and fraction B. Fr-A was concentrated to afford a white solid (4.0 g, 25% yield). $^1$H NMR (400 MHz, $CDCl_3$) δ 7.60-7.57 (m, 2H), 7.39-7.36 (m, 2H), 7.32-7.28 (m, 2H), 6.81-6.77 (m, 2H), 5.48 (t, J=8.4 Hz, 1H), 4.87 (s, 2H), 4.69 (dd, J=13.5, 5.2 Hz, 1H), 3.79 (t, J=8.4 Hz, 1H), 3.76 (s, 3H), 3.42 (t, J=8.0 Hz, 1H), 2.95 (ddd, J=17.8, 4.5, 2.4 Hz, 1H), 2.77 (ddd, J=17.8, 13.5, 5.5 Hz, 1H), 2.24-2.07 (m, 2H).

(R)-3-((S)-5-(3-Bromophenyl)-2-oxooxazolidin-3-yl)piperidine-2,6-dione or (S)-3-((S)-5-(3-Bromophenyl)-2-oxooxazolidin-3-yl)piperidine-2,6-dione (I-84)

To a solution of Fr-A (4.0 g, 8.47 mmol) in MeCN (90 mL) was added dropwise a solution of CAN (18.6 g, 33.9 mmol) in $H_2O$ (20 mL) at 0° C. The mixture was stirred for 3 h at 0° C.~10° C. To the mixture was added $H_2O$ (50 mL), extracted with EA (100 mL). The organic layer was washed with brine (30 mL), dried over $Na_2SO_4$, filtered, concentrated to give a yellow solid. The solid was washed with EA (30 mL) to give (R)-3-((S)-5-(3-bromophenyl)-2-oxooxazolidin-3-yl)piperidine-2,6-dione or (S)-3-((S)-5-(3-Bromophenyl)-2-oxooxazolidin-3-yl)piperidine-2,6-dione (1.2 g, 40% yield) as a white solid. The filtrate was concentrated and purified by flash (210 nm, 30% MeCN in $H_2O$) to give another portion of product (0.2 g, 7% yield). $^1$H NMR (400 MHz, DMSO-$d_6$) δ 11.00 (s, 1H), 7.72 (t, J=1.6 Hz, 1H), 7.63-7.60 (m, 1H), 7.50-7.49 (m, 1H), 7.42 (t, J=8 Hz, 1H), 5.63 (dd, J=7.6, 8.8 Hz, 1H), 4.71 (dd, J=5.2, 13.2 Hz, 1H), 3.94 (t, J=8.8 Hz, 1H), 3.29-3.25 (m, 1H), 2.92-2.82 (m, 1H), 2.59-2.57 (m, 1H), 2.25-2.14 (m, 1H), 2.03-2.01 (m, 1H); LC/MS (ESI, m/z): [M+1]f=355.0.

Example 30. Synthesis of tert-butyl (15-(1-(2,6-dioxopiperidin-3-yl)-3-methyl-2-oxo-2,3-dihydro-1H-benzo[d]imidazol-5-yl)-3,6,9,12-tetraoxapentadecyl)carbamate (I-85)

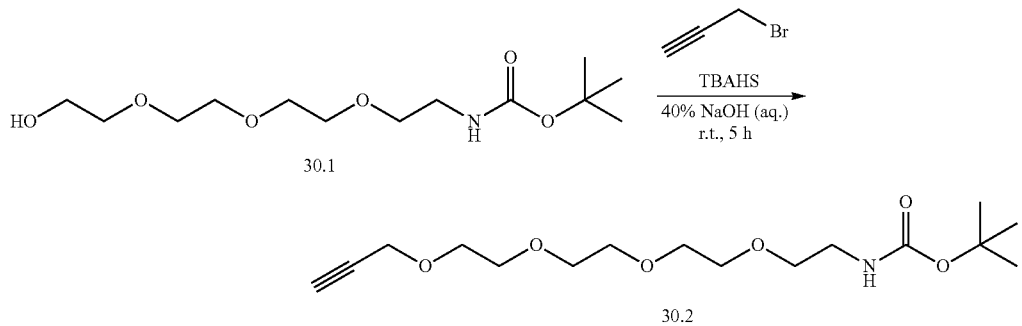

-continued
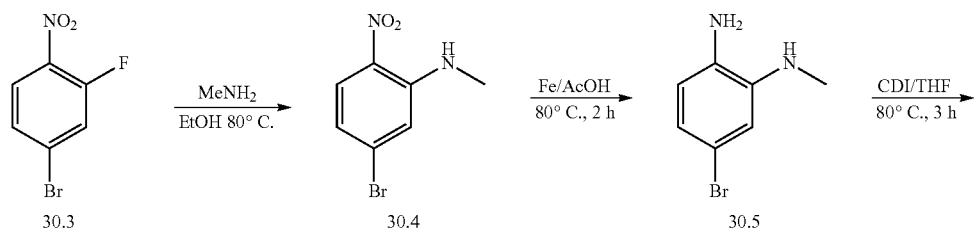
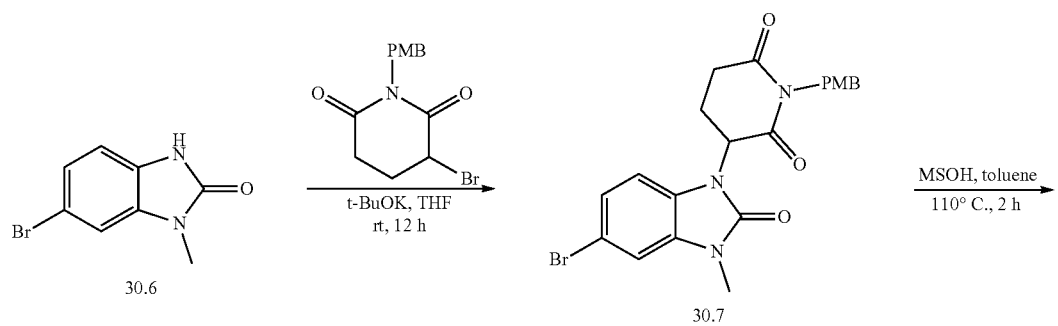
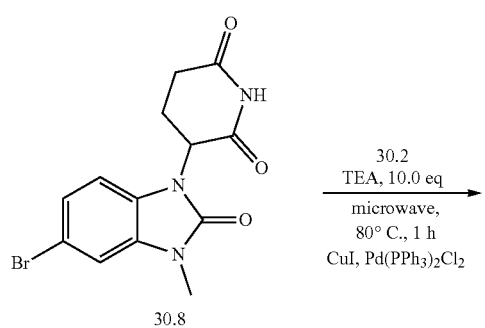
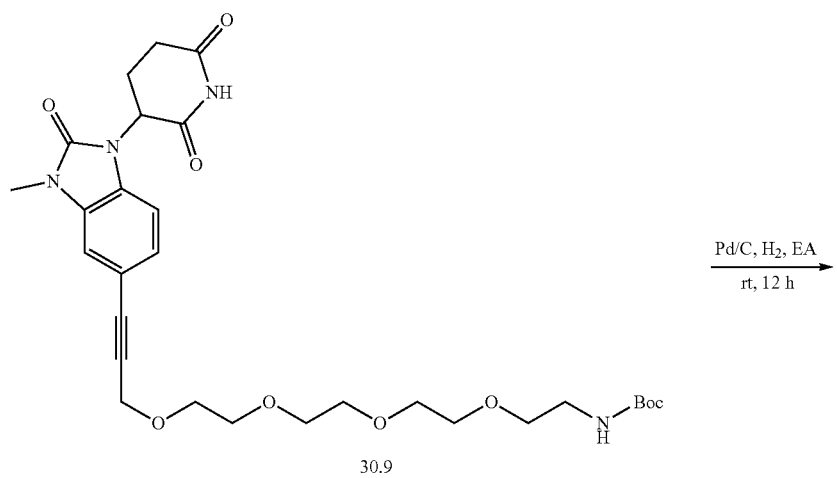

-continued

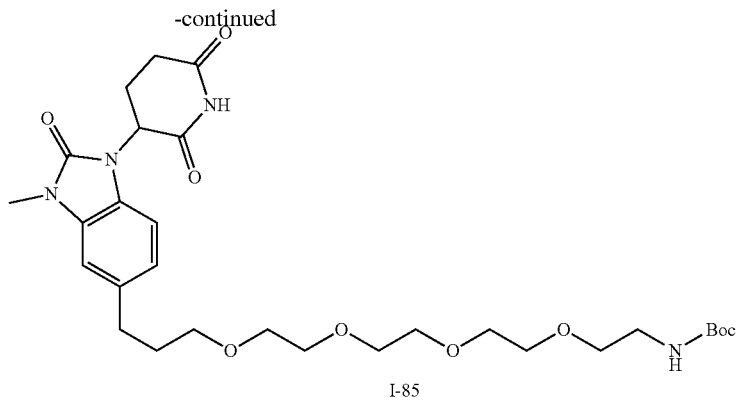

I-85 tert-Butyl 3,6,9,12-tetraoxapentadec-14-yn-1-ylcarbamate (30.2)

tert-Butyl (2-(2-(2-(2-hydroxyethoxy)ethoxy)ethoxy)ethyl)carbamate (9.0 g, 30.8 mmol) was dissolved in NaOH (40% aq.) (61.2 mL). Then TBAHS (522 mg, 1.54 mmol) was added into the mixture and followed with 3-bromoprop-1-yne (4.21 g, 35.4 mmol) at 0° C., then warmed to r.t. for 5 hours. The reaction was monitored by TLC. When the starting material was consumed, the mixture was cooled to 0° C. EtOAc (300 mL) and H$_2$O (300 mL) were added, the organic phase was washed with H$_2$O (200 mL×2), evaporated the solvent, the crude was purified with column (DCM:EA=3:1), 8.1 g of product was obtained as a light yellow oil. (79.4% yield.) H NMR (400 MHz, CDCl$_3$) δ 4.20 (t, J=4.6 Hz, 2H), 3.71-3.60 (m, 12H), 3.54 (t, J=5.2 Hz, 2H), 3.31 (t, J=5.1 Hz, 2H), 2.43 (t, J=2.4 Hz, 1H), 1.45 (s, 9H).

5-Bromo-N-methyl-2-nitroaniline (30.4)

4-Bromo-2-fluoro-1-nitrobenzene (23 g, 105 mmol) was dissolved in EtOH (20 mL), MeNH$_2$ (250 mL, 33%, in EtOH) was added, the mixture was stirred at R.T overnight, The mixture was detected by LC-MS, the starting material was consumed, evaporated the solvent, the crude was dissolved in EtOAc (300 mL) and washed with water (200 mL×2) and brine (200 mL), dried with Na$_2$SO$_4$, filtered and the organic phase was evaporated the solvent, 23 g of the target compound was obtained as yellow solid (95% yield). $^1$H NMR (400 MHz, CDCl$_3$) δ 8.03 (d, J=9.2 Hz, 2H), 7.01 (s, 1H), 6.76 (d, J=9.2 Hz, 1H), 3.02 (s, 3H); LC-MS (ESI$^+$): m/z 232.1 (M+H)$^+$.

5-Bromo-N1-methylbenzene-1,2-diamine (30.5)

5-Bromo-N-methyl-2-nitroaniline (23.0 g, 0.10 mol) was dissolved in AcOH (230 mL), then EtOAc (230 mL) and H$_2$O (50 mL) were added, the mixture was warmed to 50° C., Fe (20 g, 0.36 mol) was added, the mixture was heated to 80° C. about 30 min, the starting material was consumed, the mixture was cooled to R.T, EtOAc (300 mL) and H$_2$O (300 mL) were added, the organic phase was washed with H$_2$O (500 mL×2), evaporated the solvent, the crude was purified with column (EA:PE=1:2), 14 g of product was obtained (70% yield). LC-MS (ESI$^+$): m/z 202.1 (M+H)$^+$.

6-Bromo-1-methyl-1H-benzo[d]imidazol-2(3H)-one (30.6)

5-Bromo-N1-methylbenzene-1,2-diamine (14 g, 69.3 mmol) was dissolved in THF (200 mL), CDI (13.4 g, 83.2 mmol) was added, the mixture was reflux about 2 hours under N$_2$. The staring material was consumed, evaporated the solvent, the crude was purified with column (EA:PE=1:2), 10 g of target compound was obtained (63% yield). $^1$H NMR (400 MHz, DMSO-d$_6$) δ 11.0 (s, 1H), 7.33 (s, 1H), 7.13 (t, J=8.0 Hz, 1H), 6.92 (d, J=8.0 Hz, 1H), 3.26 (s, 3H); LC-MS (ESI$^+$): m/z 228.1 (M+H)$^+$

3-(5-Bromo-3-methyl-2-oxo-2,3-dihydro-1H-benzo[d]imidazol-1-yl)-1-(4-methoxybenzyl)piperidine-2,6-dione (30.7)

6-Bromo-1-methyl-1H-benzo[d]imidazol-2(3H)-one (5.0 g, 22.1 mmol) was dissolved in THF, the mixture was cooled to 0° C., t-BuOK (2.48 g, 22.1 mmol) was added, the mixture was stirred about 30 min, 3-bromo-1-(4-methoxybenzyl) piperidine-2,6-dione (6.9 g, 22.1 mmol) was added, the mixture was stirred overnight, evaporated the solvent, the crude was purified with column (EtOAc:DCM=1:1), 3.7 g of target compound was obtained (37% yield). $^1$H NMR (400 MHz, DMSO-d$_6$) δ 7.48-7.47 (d, J=2.0 Hz, 1H), 7.21-7.16 (m, 3H), 7.02-6.99 (d, J=8.4 Hz, 1H), 6.87-6.84 (m, 2H), 5.55-5.51 (dd, J$_1$=6.4 Hz, J$_2$=14.2 Hz, 1H), 4.84-4.73 (q, J=14.4 Hz, 2H), 3.72 (s, 3H), 3.34 (s, 3H), 3.08-3.00 (m, 1H), 2.84-2.67 (m, 2H), 2.09-2.04 (m, 1H); LC-MS (ESI$^+$): m/z 459.4 (M+H)$^+$

3-(5-Bromo-3-methyl-2-oxo-2,3-dihydro-1H-benzo[d]imidazol-1-yl)piperidine-2,6-dione (30.8)

3-(5-bromo-3-methyl-2-oxo-2,3-dihydro-1H-benzo[d]imidazol-1-yl)-1-(4-methoxybenzyl)piperidine-2,6-dione (1.5 g, 3.28 mmol) was added to toluene (30 mL), the Methanesulfonic acid (10 mL) was added, the mixture was heated to 110° C. about 2 hours under N$_2$. The starting material was consumed, evaporated the solvent, the mixture was cooled to R.T, 20 mL of EtOAc was added, the organic phase was washed with H$_2$O (10 mL), dried with Na$_2$SO$_4$, evaporated the solvent, the crude was purified with column (EtOAc:DCM=1:1), 0.8 g (yield: 72%) of product was obtained. $^1$H NMR (400 MHz, DMSO-d$_6$) δ 11.13 (s, 1H), 7.47 (d, J=1.6 Hz, 1H), 7.22 (dd, J=10.4, 2.0 Hz, 1H), 7.11 (d, J=8.4 Hz, 1H), 5.41-5.36 (m, 3H), 3.34 (s, 3H), 2.92-2.85 (m, 1H), 2.74-2.60 (m, 2H), 2.05-1.99 (m, 1H); LC-MS (ESI$^+$): m/z 339.2 (M+H)$^+$ tert-Butyl (15-(1-(2,6-dioxopiperidin-3-yl)-3-methyl-2-oxo-2,3-dihydro-1H-benzo[d]imidazol-5-yl)-3,6,9,12-tetraoxapentadec-14-yn-1-yl)carbamate (30.9)

A mixture of 3-(5-bromo-3-methyl-2-oxo-2,3-dihydro-1H-benzo[d]imidazol-1-yl)piperidine-2,6-dione (100 mg, 0.296 mmol), tert-butyl 3,6,9,12-tetraoxapentadec-14-yn-1-ylcarbamate (196 mg, 0.592 mmol), Pd(PPh₃)₂C₂ (17 mg, 0.0237 mmol), TEA (299 mg, 2.96 mmol), CuI (9 mg, 0.0474 mmol) and DMF (5 mL) was heated with microwave to 80° C. and stirred for 1 h under N₂. To the cooled mixture was added H₂O (30 mL), extracted with EA (50 mL×3). The combined organic layer was washed with brine (20 mL×3), dried over Na₂SO₄, filtered, concentrated, purified by flash (ACN/H₂O) to give ert-butyl(15-(1-(2,6-dioxopiperidin-3-yl)-3-methyl-2-oxo-2,3-dihydro-1H-benzo[d]imidazol-5-yl)-3,6,9,12-tetraoxapentadec-14-yn-1-yl)carbamate (50 mg, 29% yield). LC-MS (ESI⁺): m/z 589.7 (M+H)⁺ tert-Butyl (15-(1-(2,6-dioxopiperidin-3-yl)-3-methyl-2-oxo-2,3-dihydro-1H-benzo[d]imidazol-5-yl)-3,6,9,12-tetraoxapentadecyl)carbamate (I-85)

A mixture of tert-butyl (15-(1-(2,6-dioxopiperidin-3-yl)-3-methyl-2-oxo-2,3-dihydro-1H-benzo[d]imidazol-5-yl)-3,6,9,12-tetraoxapentadec-14-yn-1-yl)carbamate (750 mg, 1.28 mmol), Pd/C (150 mg) and EA (30 mL) was stirred for overnight at rt under H₂. The mixture was filtered, concentrated and purified by flash (H₂O/ACN=½) to give tert-butyl (15-(1-(2,6-dioxopiperidin-3-yl)-3-methyl-2-oxo-2,3-dihydro-1H-benzo[d]imidazol-5-yl)-3,6,9,12-tetraoxapentadecyl)carbamate (600 mg, 80% yield). ¹H NMR (400 MHz, CDCl₃) δ 8.20 (s, 1H), 6.91-6.87 (m, 2H), 6.72-6.70 (d, J=8 Hz, 1H), 5.23-5.19 (dd, J=5.6 Hz, J=12.8 Hz, 1H), 3.70-3.58 (m, 12H), 3.53 (t, J=5.2 Hz, 2H), 3.47 (t, J=6.4 Hz, 2H), 3.42 (s, 3H), 3.30 (t, J=4.8 Hz, 2H), 2.97-2.68 (m, 5H), 2.26-2.21 (m, 1H), 1.94-1.87 (m, 2H), 1.44 (s, 9H); LC-MS (ESI⁺): m/z 493.1 (M+H)⁺.

Example 31. Synthesis of tert-butyl (2-(2-((3-(1-(2,6-dioxopiperidin-3-yl)-3-methyl-2-oxo-2,3-dihydro-1H-benzo[d]imidazol-4-yl)prop-2-yn-1-yl)oxy)ethoxy)ethyl)carbamate (I-86)

I-86 was synthesized according to the same method as I-85 replacing 30.2 with the appropriate length polyether derivative. ¹H NMR (400 MHz, CDCl₃) δ 8.10 (s, 1H), 7.18 (d, J=7.9 Hz, 1H), 7.00 (t, J=7.9 Hz, 1H), 6.77 (d, J=7.9 Hz, 1H), 5.21 (dd, J=12.6, 5.4 Hz, 1H), 5.00 (s, 1H), 4.48 (s, 2H), 3.81-3.74 (m, 5H), 3.69-3.66 (m, 2H), 3.57-3.55 (m, 2H), 3.35-3.33 (m, 2H), 2.99-2.93 (m, 1H), 2.86 (dd, J=13.3, 5.0 Hz, 1H), 2.81-2.67 (m, 1H), 2.28-2.21 (m, 1H), 1.44 (s, 9H); LC/MS (ESI, m/z): [M-Boc+1]+=401.1.

Example 32. Synthesis of tert-butyl (2-(2-(3-(1-(2,6-dioxopiperidin-3-yl)-3-methyl-2-oxo-2,3-dihydro-1H-benzo[d]imidazol-5-yl)propoxy)ethoxy)ethyl)carbamate (I-87)

I-87 was synthesized according to the same method as I-85 replacing 30.2 with the appropriate length polyether derivative. ¹H NMR (400 MHz, CDCl₃) δ 8.14 (s, 1H), 6.95-6.85 (m, 2H), 6.72 (d, J=7.9 Hz, 1H), 5.22 (dd, J=12.5, 5.3 Hz, 1H), 5.06 (s, 1H), 3.66-3.53 (m, 6H), 3.48 (t, J=6.4 Hz, 2H), 3.43 (s, 3H), 3.34-3.30 (m, 2H), 2.97-2.92 (m, 1H), 2.86 (dd, J=13.2, 4.8 Hz, 1H), 2.80-2.69 (m, 3H), 2.26-2.21 (m, 1H), 1.95-1.90 (m, 2H), 1.43 (s, 9H); LC/MS (ESI, m/z): [M-Boc+1]+=405.2.

Example 33. Synthesis of tert-Butyl (2-(2-(2-(3-(1-(2,6-dioxopiperidin-3-yl)-3-methyl-2-oxo-2,3-dihydro-1H-benzo[d]imidazol-5 yl)propoxy)ethoxy)ethoxy)ethyl)carbamate (I-88)

I-88 was synthesized according to the same method as I-85 replacing 30.2 with the appropriate length polyether derivative. ¹H NMR (400 MHz, DMSO-d₆) δ 11.08 (s, 1H), 6.94-7.07 (m, 2H), 6.81-6.93 (m, 1H), 6.74 (br. s., 1H), 5.33 (dd, J=12.76, 5.38 Hz, 1H), 3.44-3.57 (m, 8H), 3.35-3.44 (m, 4H), 3.32 (s, 3H), 3.06 (q, J=5.88 Hz, 2H), 2.83-2.98 (m, 1H), 2.55-2.76 (m, 4H), 1.98-2.08 (m, 1H),1.74-1.89 (m, 2H), 1.36 (s, 9H); LC-MS (ESI⁺): m/z 549.1 (M+H)⁺.

Example 34. Synthesis of tert-Butyl (18-(1-(2,6-dioxopiperidin-3-yl)-3-methyl-2-oxo-2,3-dihydro-1H-benzo[d]imidazol-5-yl)-3,6,9,12,15-pentaoxaoctadecyl)carbamate (I-89)

I-89 was synthesized according to the same method as I-85 replacing 30.2 with the appropriate length polyether derivative. ¹H NMR (400 MHz, DMSO-d₆) δ 8.25 (s, 1H), 6.94-6.84 (m, 2H), 6.71 (d, J=8.0 Hz, 1H), 5.21 (dd, J=12.6, 5.3 Hz, 1H), 3.74-3.56 (m, 16H), 3.53 (t, J=5.2 Hz, 2H), 3.47 (t, J=6.4 Hz, 2H), 3.42 (s, 3H), 3.30 (t, J=5.1 Hz, 2H), 2.98-2.64 (m, 5H), 2.29-2.18 (m, 1H), 1.90 (tt, J=13.1, 6.4 Hz, 2H), 1.44 (s, 9H); LC-MS (ESI⁺): m/z 637.4 (M+H)⁺.

Example 35. Synthesis of 1-(2,6-dioxopiperidin-3-yl)-3-methyl-2-oxo-2,3-dihydro-1H-benzo[d]imidazole-5-carboxamide (I-90)

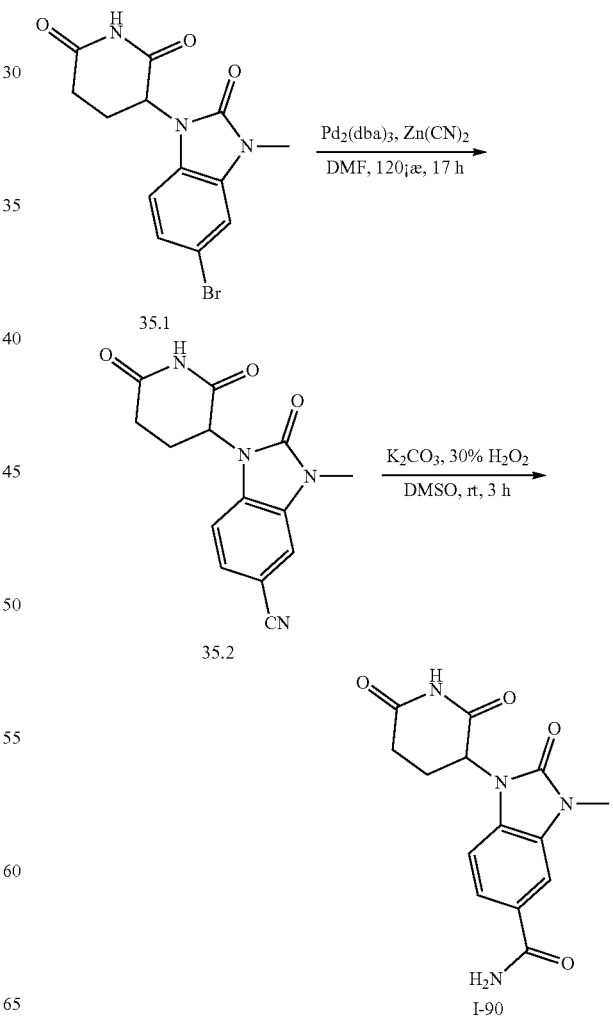

1-(2,6-Dioxopiperidin-3-yl)-3-methyl-2-oxo-2,3-dihydro-1H-benzo[d]imidazole-5-carbonitrile (35.2)

A mixture of 3-(5-bromo-3-methyl-2-oxo-2,3-dihydro-1H-benzo[d]imidazol-1-yl)piperidine-2,6-dione (0.5 g, 1.48 mmol), Zinc cyanide (0.69 g, 5.92 mmol), Tris(dibenzylideneacetone)dipalladium (0.14 g, 0.15 mmol) and 1,1'-Ferrocenebis(diphenylphosphine) (0.16 g, 0.30 mmol) in DMF (10 mL) was heated to 120° C. under nitrogen atmosphere in sealed tube, stirred at this temperature for 19 hours. The reaction mixture was cooled to room temperature, filtered and concentrated in vacuo. The residue was purified by silica gel column chromatography ($H_2O:CH_3CN$=100/1 to 1/1) to give product (0.3 g, 71.4%) as a white solid. $^1$H NMR (400 MHz, DMSO) δ 11.15 (s, 1H), 7.75 (s, 1H), 7.64-7.46 (m, 1H), 7.36 (m, 1H), 5.49-5.35 (m, 1H), 3.38 (s, 3H), 2.95-2.82 (m, 1H), 2.72-2.57 (m, 2H), 2.12-1.97 (m, 1H).

1-(2,6-Dioxopiperidin-3-yl)-3-methyl-2-oxo-2,3-dihydro-1H-benzo[d]imidazole-5-carboxamide (I-90)

To a stirred solution of 1-(2,6-dioxopiperidin-3-yl)-3-methyl-2-oxo-2,3-dihydro-1H-benzo[d]imidazole-5-carbonitrile (70 mg, 0.40 mol) in DMSO (2 mL) was added $K_2CO_3$ (56 mg, 0.40 mol) and 30% $H_2O_2$ (0.1 mL, 0.80 mol). The reaction mixture was stirred at r.t. for 4 hours. Then the reaction mixture was directly purified via reverse phase column chromatography ($CH_3CN/H_2O$=5%-80%) to give the desired compound (6.5 mg, 5.4%) as a white solid. $^1$H NMR (400 MHz, DMSO-d$_6$) δ 7.72 (m, 1H), 7.63-7.46 (m, 2H), 7.30 (s, 1H), 7.22 (d, J=8.2 Hz, 1H), 4.96-4.91 (m, 1H), 3.37 (s, 3H), 2.48-2.32 (m, 1H), 2.26-1.96 (m, 3H); LC-MS (ESI$^+$): m/z 303.2 (M+H)$^+$.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of formula I:

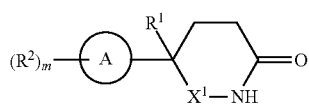

or a pharmaceutically acceptable salt thereof, wherein:
  $X^1$ is a bivalent moiety selected from a covalent bond, —CH$_2$—, —C(O)—, —C(S)—, or

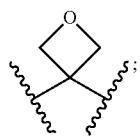 [SMILES: *C1(*)COC1]

$R^1$ is hydrogen, deuterium, halogen, —CN, —OR, —SR, —S(O)R, —S(O)$_2$R, —NR$_2$, or an optionally substituted C$_{1-4}$ aliphatic;

each $R^2$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
  Ring A is a bi- or tricyclic ring selected from

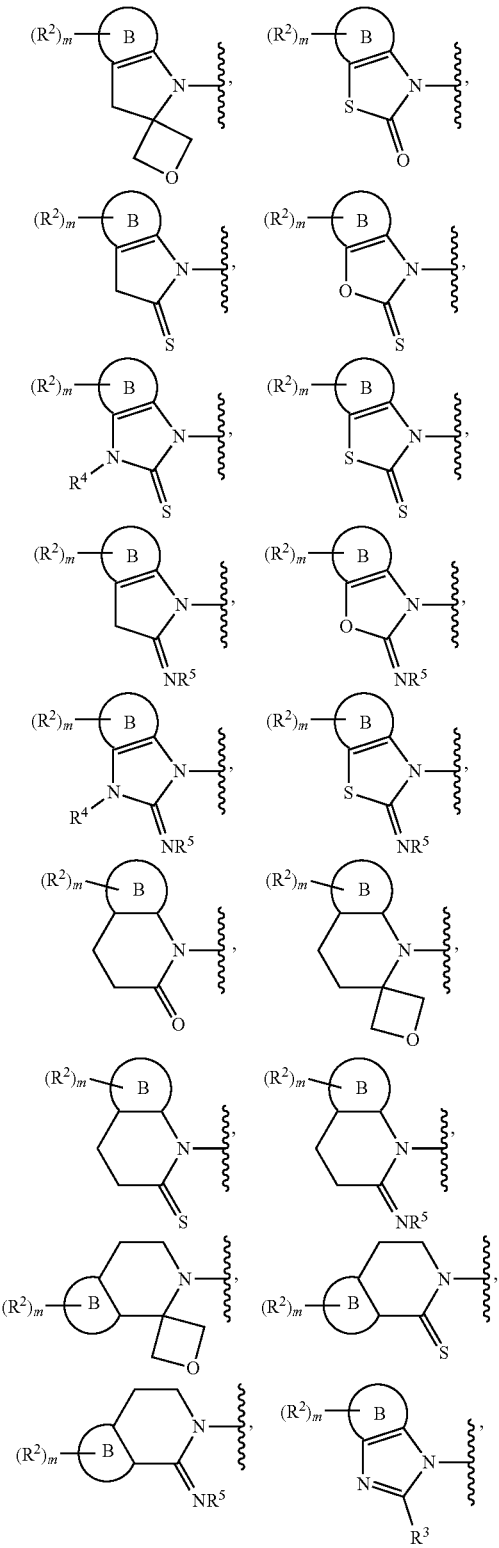

-continued

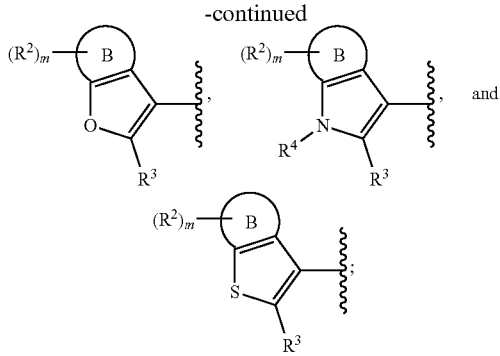

Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

2. The compound of claim 1, wherein $X^1$ is selected from a covalent bond, —CH$_2$—, —C(O)—, and

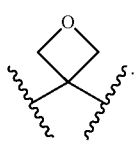 [SMILES: *C1(*)COC1]

3. The compound of claim 1, wherein $R^1$ is hydrogen, deuterium, halogen, —OR, —SR, —S(O)R, —S(O)$_2$R, —NR$_2$, or an optionally substituted $C_{1-4}$ aliphatic.

4. The compound of claim 1, wherein Ring A is selected from

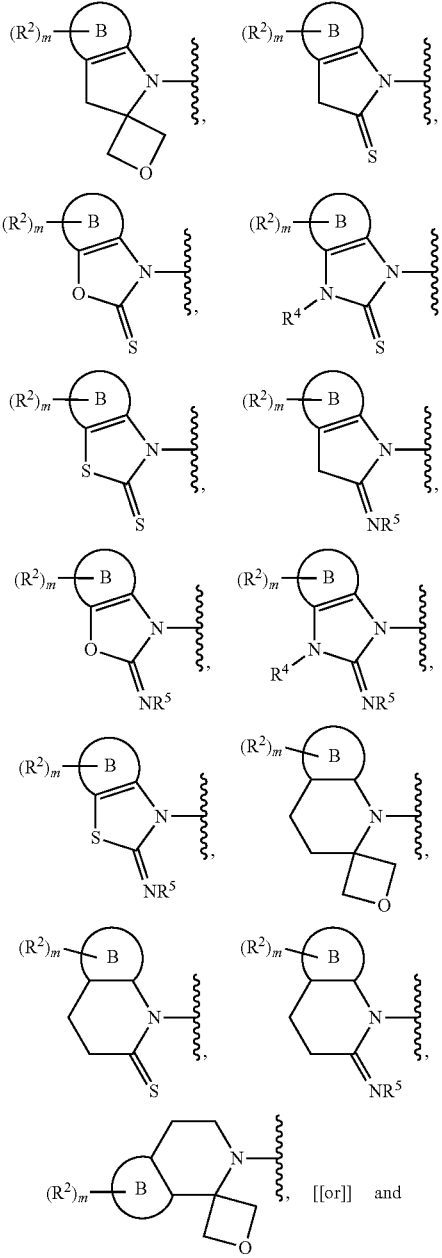

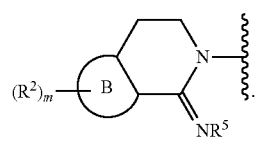

5. The compound of claim 1, wherein Ring B is selected from 6-membered aryl containing 0-2 nitrogen atoms, 5 to 7-membered partially saturated carbocyclyl, and 5 to 7-membered partially saturated heterocyclyl with 1-2 heteroatoms independently selected from nitrogen, oxygen or sulfur.

6. A compound selected from:
I-4
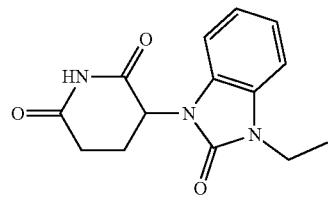
I-5
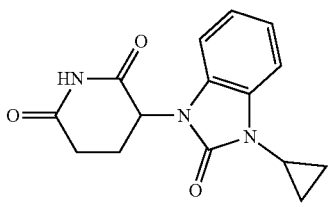
I-7
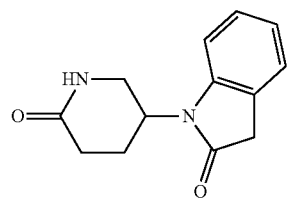
I-8
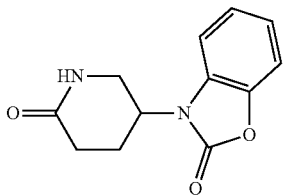
I-9
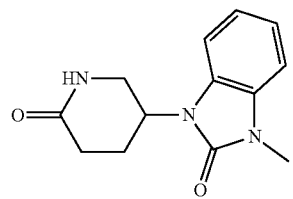
I-10
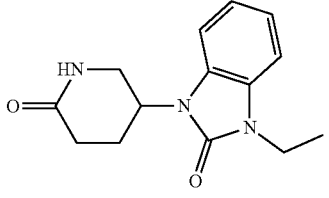
I-11
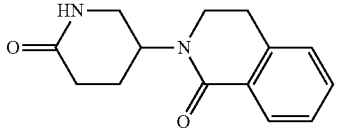
I-12
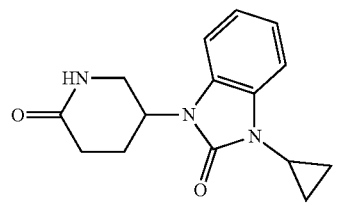
I-13
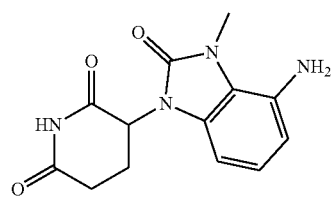
I-14
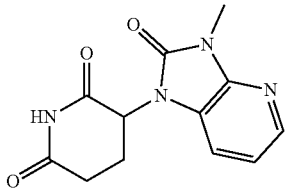
I-15
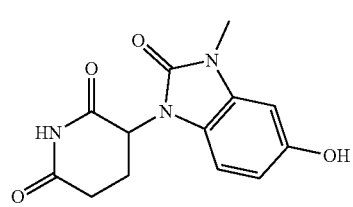
I-16
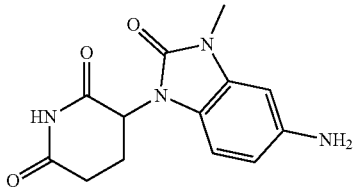
I-17
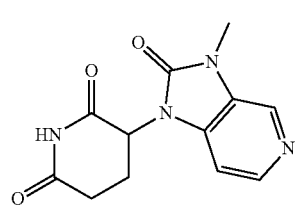
I-18
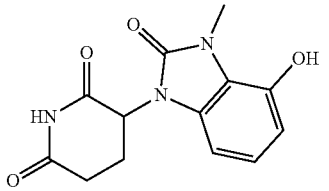

-continued
I-19
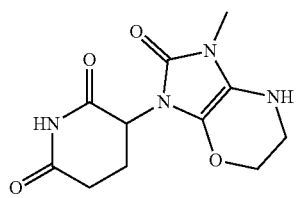
I-20
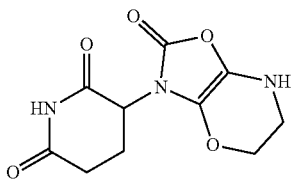
I-21
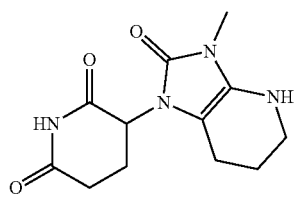
I-24
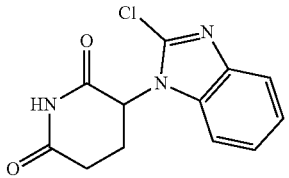
I-25
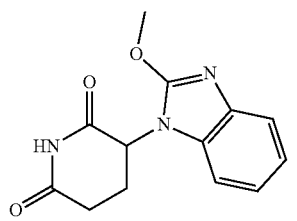
I-26
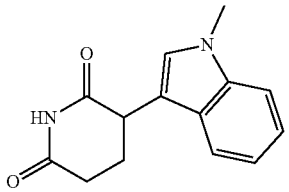
I-61
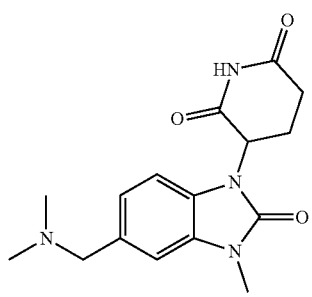
I-62
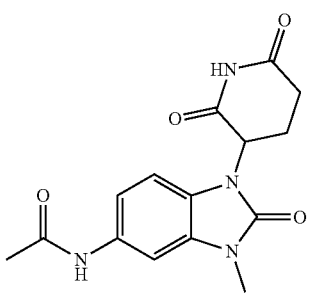
I-63
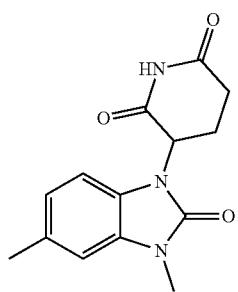
I-64
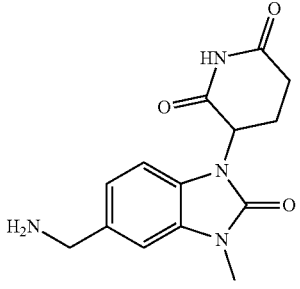
I-65
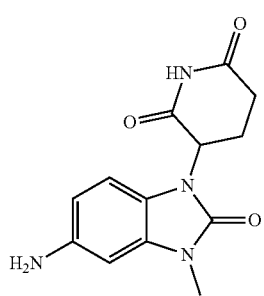
I-66
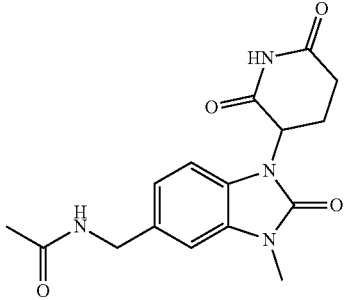

-continued
| I-67 | I-68 |
|---|---|
| 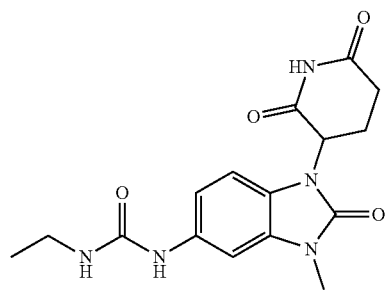 | 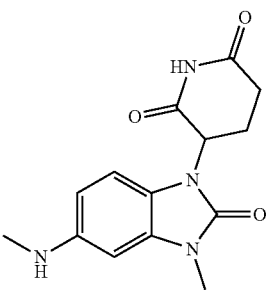 |
| I-69 | I-70 |
|---|---|
| 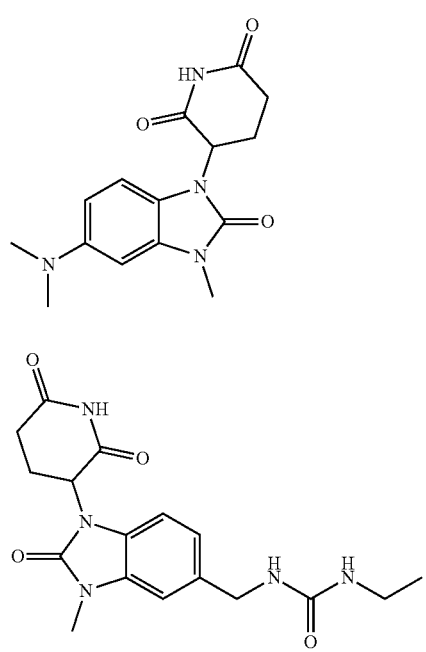 | 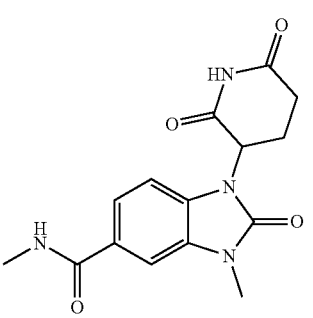 |
I-71
I-74
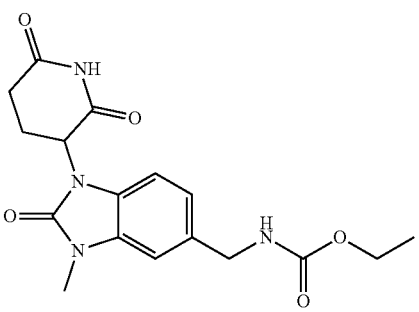
I-75
I-76
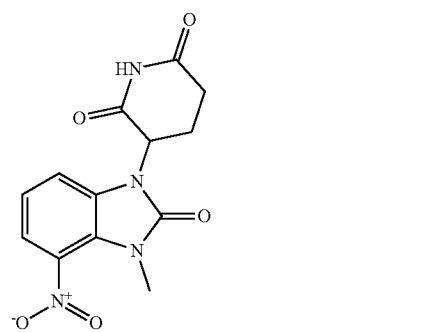
I-78
I-79
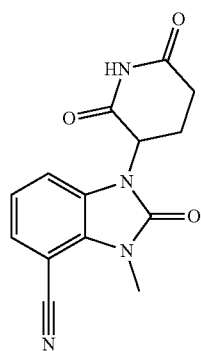
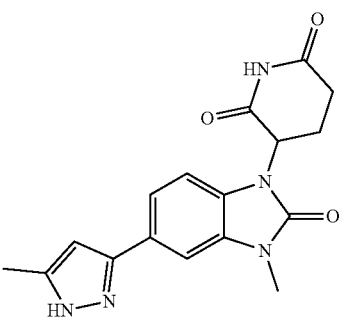

I-80
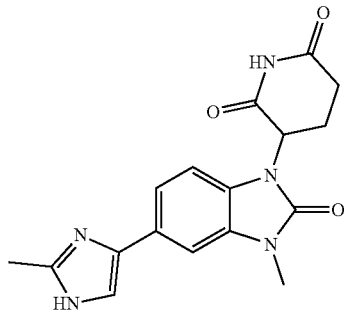
I-82
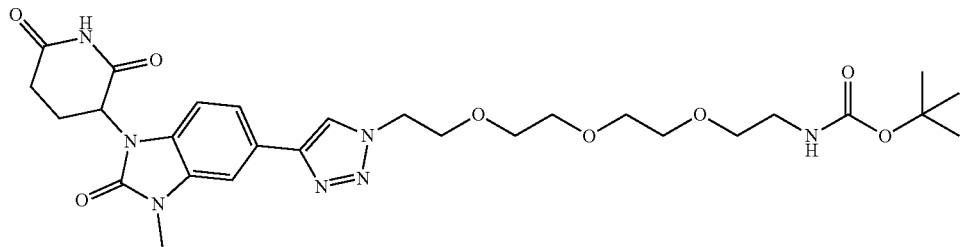
I-85
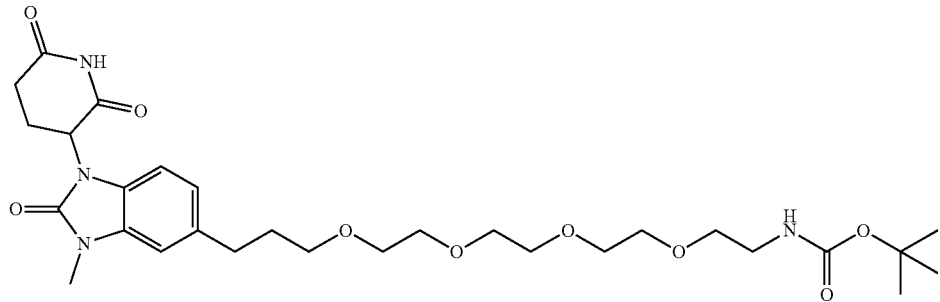
I-86
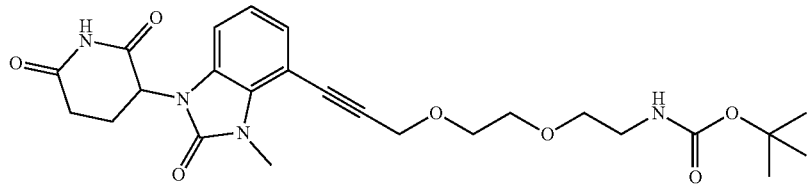
I-87
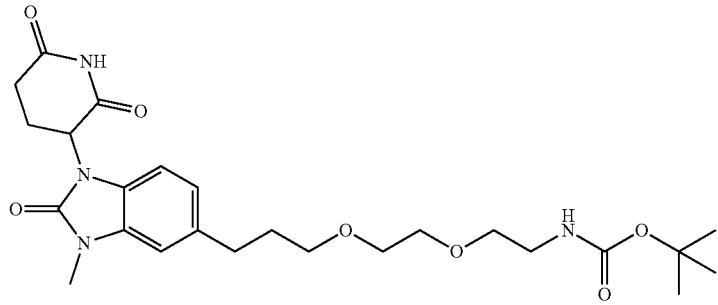

I-88

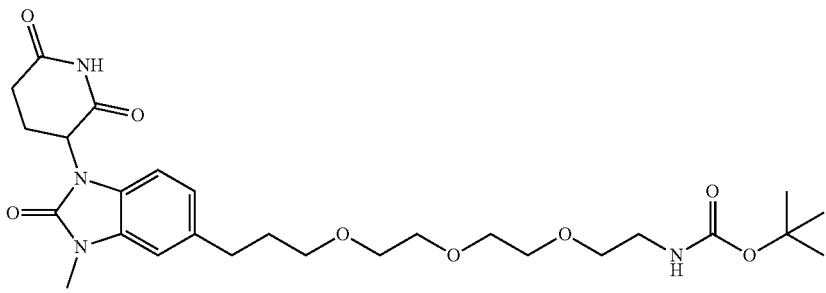

I-89

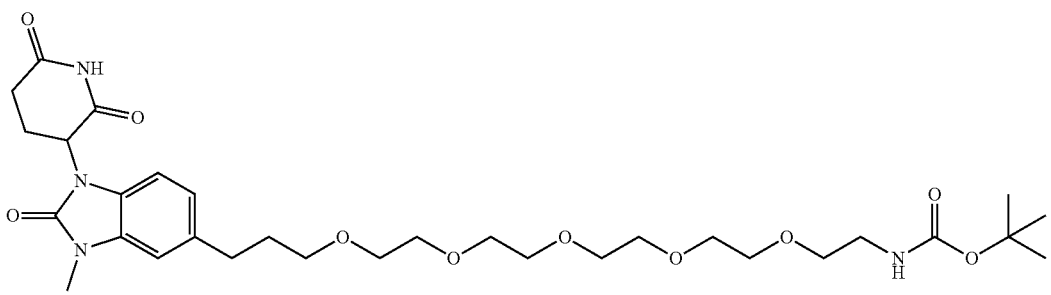

I-90

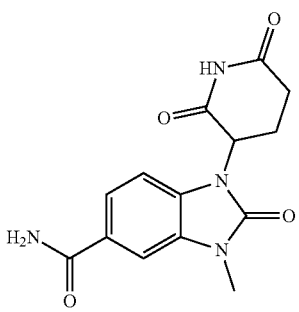

or a pharmaceutically acceptable salt thereof.

7. A pharmaceutical composition comprising the compound of claim 1, or a pharmaceutically acceptable salt thereof, and a pharmaceutically acceptable carrier, adjuvant, or vehicle.

8. The compound of claim 1, wherein $R^3$ is selected from, —OR and —N(R)$_2$.

9. The compound of claim 1, wherein each $R^4$ is independently hydrogen or —$R^6$.

10. The compound of claim 1, wherein $R^5$ is hydrogen or $C_{1-4}$ aliphatic.

11. The compound of claim 1, wherein each $R^6$ is independently an optionally substituted group selected from $C_{1-6}$ aliphatic, phenyl, and a 5-6 membered heteroaryl ring having 1-4 heteroatoms independently selected from nitrogen, oxygen, and sulfur.

12. A pharmaceutical composition comprising the compound of claim 6, or a pharmaceutically acceptable salt thereof, and a pharmaceutically acceptable carrier, adjuvant, or vehicle.

13. A method of inhibiting CRBN in a biological sample comprising contacting the sample with the compound of claim 6, or a pharmaceutically acceptable salt thereof.

14. A method of binding to and altering specificity of a cereblon complex to induce ubiquitination and degradation of a complex-associated protein in a biological sample, comprising contacting the sample with the compound of claim Y, or a pharmaceutically acceptable salt thereof.

15. A method of alleviating a CRBN-mediated disorder, disease, or condition in a patient comprising administering to said patient the compound of claim 6, or a pharmaceutically acceptable salt thereof.

16. The method of claim 15, wherein the disorder is selected from proliferative disorders, neurological disorders and disorders associated with transplantation.

* * * * *